US008333968B2

(12) United States Patent
Lewis et al.

(10) Patent No.: US 8,333,968 B2
(45) Date of Patent: Dec. 18, 2012

(54) METHODS OF INHIBITING INFLAMMATION WITH ANTAGONISTS TO IL-17A, IL-17F, AND IL-23P19

(75) Inventors: Katherine E. Lewis, Lake Forest Park, WA (US); Scott R. Presnell, Tacoma, WA (US); Steven D. Levin, Seattle, WA (US); George Robert Mabry, III, Seattle, WA (US); Stephen R. Jaspers, Edmonds, WA (US); Monica J. Huber, Mill Creek, WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 13/032,501

(22) Filed: Feb. 22, 2011

(65) Prior Publication Data

US 2011/0159589 A1 Jun. 30, 2011

Related U.S. Application Data

(60) Division of application No. 12/111,117, filed on Apr. 28, 2008, now Pat. No. 7,910,703, and a continuation-in-part of application No. 11/762,738, filed on Jun. 13, 2007, now Pat. No. 7,790,862, said application No. 12/111,117 is a continuation-in-part of application No. 11/741,189, filed on Apr. 27, 2007, now Pat. No. 7,790,163, which is a continuation-in-part of application No. 11/684,907, filed on Mar. 12, 2007, now abandoned.

(60) Provisional application No. 60/914,681, filed on Apr. 27, 2007, provisional application No. 60/914,663, filed on Apr. 27, 2007, provisional application No. 60/804,602, filed on Jun. 13, 2006, provisional application No. 60/824,665, filed on Sep. 6, 2006, provisional application No. 60/828,277, filed on Oct. 5, 2006, provisional application No. 60/891,410, filed on Feb. 23, 2007, provisional application No. 60/781,121, filed on Mar. 10, 2006, provisional application No. 60/828,271, filed on Oct. 5, 2006, provisional application No. 60/862,501, filed on Oct. 23, 2006.

(51) Int. Cl.
*A61K 39/395* (2006.01)

(52) U.S. Cl. .............. 424/133.1; 424/135.1; 424/136.1; 424/141.1; 530/388.23; 530/388.1; 530/351

(58) Field of Classification Search .................. None
See application file for complete search history.

(56) References Cited

U.S. PATENT DOCUMENTS

| 6,274,711 | B1 | 8/2001 | Golstein et al. |
| 6,495,667 | B1 | 12/2002 | Bazan |
| 7,282,204 | B2 | 10/2007 | Oft et al. |
| 7,422,743 | B2 | 9/2008 | Chirica et al. |
| 7,427,402 | B2 | 9/2008 | Kastelein et al. |
| 7,485,297 | B2 | 2/2009 | Wood et al. |
| 7,491,391 | B2 | 2/2009 | Benson et al. |
| 7,608,690 | B2 | 10/2009 | Bazan |
| 7,790,163 | B2 | 9/2010 | Jaspers et al. |
| 7,790,862 | B2 | 9/2010 | Lewis et al. |
| 7,910,703 | B2 | 3/2011 | Lewis et al. |
| 2004/0219150 | A1 | 11/2004 | Cua et al. |
| 2005/0158750 | A1 | 7/2005 | Bazan |
| 2005/0208052 | A1 | 9/2005 | Katsikis et al. |
| 2005/0244874 | A1 | 11/2005 | Kastelein et al. |
| 2006/0134112 | A1 | 6/2006 | Cua et al. |
| 2007/0009526 | A1 | 1/2007 | Benson et al. |
| 2007/0048315 | A1 | 3/2007 | Presta |
| 2007/0098727 | A1 | 5/2007 | Kastelein et al. |
| 2007/0166795 | A1 | 7/2007 | Hirata |
| 2007/0212362 | A1 | 9/2007 | Filvaroff et al. |
| 2007/0218065 | A1 | 9/2007 | Jaspers et al. |
| 2007/0269428 | A1 | 11/2007 | Christie et al. |
| 2008/0269467 | A1 | 10/2008 | Allan et al. |
| 2008/0299129 | A1 | 12/2008 | Lewis et al. |
| 2008/0317748 | A1 | 12/2008 | Chirica et al. |
| 2009/0004199 | A1 | 1/2009 | Jaspers et al. |
| 2010/0041144 | A1 | 2/2010 | Bazan |
| 2010/0310565 | A1 | 12/2010 | Jaspers et al. |
| 2011/0159589 | A1 | 6/2011 | Lewis et al. |
| 2011/0318350 | A1 | 12/2011 | Jaspers et al. |

FOREIGN PATENT DOCUMENTS

| WO | 99/05280 | 2/1999 |
| WO | 99/54357 | 10/1999 |
| WO | 01/18051 | 3/2001 |
| WO | 2004/042009 | 5/2004 |
| WO | 2004/058178 | 7/2004 |

(Continued)

OTHER PUBLICATIONS

Bowman et al., "Rationale and safety of anti-interleukin-23 and anti-interleukin-17A therapy," Current Opinion in Infectious Diseases, 19(3): 245-252, Jun. 2006. Chen et al., "Anti-IL-23 therapy inhibits multiple inflammatory pathways and ameliorates autoimmune encephalomyelitis," Journal of Clinical Investigation, 116(5): 1317-1326, May 2006.
Iwakura and Ishigame, "The IL-23/IL-17 axis in inflammation," J Clin Invest 116(5): 1218-1222, May 2006.
McKenzie et al., "Understanding the IL-23-IL-17 immune pathway," Trends in Immunology, 27(1): 17-23, Jan. 2006, Elsevier, Rahway, NJ.
Wright et al., "Identification of an interleukin 17F/17A heterodimer in activated human CD4+ T cells," J Biol Chem 282(18):13447-13455, May 4, 2007. Epub Mar. 13, 2007.
Sequence alignment between SEQ ID No. 2 and SEQ ID No. 6. Accessed Jul. 16, 2009.

(Continued)

*Primary Examiner* — Dong Jiang
(74) *Attorney, Agent, or Firm* — Brian J. Walsh; Robyn Adams

(57) ABSTRACT

The present invention relates to blocking, inhibiting, reducing, antagonizing or neutralizing the activity of IL-17A, IL-17F, and IL-23. Antagonists include antibodies and antibody fragments that bind IL-23 and that bind IL-17A or IL-17F, such as antibodies that are cross-reactive for IL-17A and Il-17F. Antagonists that include an antibody or antibody fragment that binds IL-23 and an antibody or antibody fragment that binds IL-17A or IL-17F on one molecule are also disclosed. Antibodies and antibody fragments that bind IL-23 and IL-17F but that do not bind IL-17A are also disclosed. IL-17 and IL-23 are cytokines that are involved in inflammatory processes and human disease.

14 Claims, No Drawings

FOREIGN PATENT DOCUMENTS

| | | |
|---|---|---|
| WO | 2004/071517 | 8/2004 |
| WO | 2004/081190 | 9/2004 |
| WO | 2004/106377 | 12/2004 |
| WO | 2005/010044 | 2/2005 |
| WO | 2005/051422 | 6/2005 |
| WO | 2006/013107 | 2/2006 |
| WO | 2006/020706 | 2/2006 |
| WO | 2006/054059 | 5/2006 |
| WO | 2007/005955 | 1/2007 |
| WO | 2007/024846 | 3/2007 |
| WO | 2007/027714 | 3/2007 |
| WO | 2007/027761 | 3/2007 |
| WO | 2007/051169 | 5/2007 |
| WO | 2007/070750 | 6/2007 |
| WO | 2007/076523 | 7/2007 |
| WO | 2007/076524 | 7/2007 |
| WO | 2007/106769 | 9/2007 |
| WO | 2007/147019 | 12/2007 |
| WO | 2007/149032 | 12/2007 |
| WO | 2008/001063 | 1/2008 |
| WO | 2008/021156 | 2/2008 |
| WO | 2008/047134 | 4/2008 |
| WO | 2008/103432 | 8/2008 |
| WO | 2008/103473 | 8/2008 |
| WO | 2008/106131 | 9/2008 |
| WO | 2008/133684 | 11/2008 |
| WO | 2009/082624 | 7/2009 |

OTHER PUBLICATIONS

Zhang et al., "After interleukin-12p40, are interleukin-23 and interleukin-17 the next therapeutic targets for inflammatory bowel disease," International Immunopharmacology 7(4): 409-416, Feb. 21, 2007. Elsevier, Amsterdam, NL.

Chan et al., "IL-23 stimulates epidermal hyperplasia via TNF and IL-20R2-dependent mechanisms with implications for psoriasis pathogenesis," Journal of Experimental Medicine 203(12): 2577-2587, Nov. 27, 2006. Rockefeller University Press, JP.

Jaspers and Presnell, U.S. Appl. No. 12/617,078, filed Nov. 12, 2009.

Mabry et al., "Engineering of stable bispecific antibodies targeting IL-17A and IL-23," Protein Eng Des Sel, 23(3): 115-127, Mar. 2010.

Kuestner et al., "Humane and mouse IL-17A and IL-17F differentially bind IL-17RA and IL-17RC," Keystone Cymposia—Cytokines, Disease and Therapeutic Intervention: 49, 2005.

Kuestner et al., "Identification of the IL-17 Receptor Related Molecule IL-17RC as the Receptor for IL-17F," J Immunol. 179(8): 5462-73, Oct. 15, 2007.

Lewis et al., "Soluble Interleukin-17RA-Fc Reduces Disease Severity and Inflammatory Cytokines in Murine Oxazalone Colitis," Cytokine 39(1): Jul. 24, 2007. (abstract).

METHODS OF INHIBITING INFLAMMATION WITH ANTAGONISTS TO IL-17A, IL-17F, AND IL-23P19

CROSS REFERENCE TO RELATED APPLICATIONS

This application is a divisional of U.S. application Ser. No. 12/111,117, filed Apr. 28, 2008, now U.S. Pat. No. 7,910,703 which claims the benefit of U.S. Provisional Application Ser. No. 60/914,681, filed Apr. 27, 2007, and U.S. Provisional Application Ser. No. 60/914,663, filed Apr. 27, 2007, all of which are herein incorporated by reference. U.S. application Ser. No. 12/111,117, is a continuation-in-part of U.S. application Ser. No. 11/762,738, filed Jun. 13, 2007, now U.S. Pat. No. 7,790,862 which claims the benefit of U.S. Provisional Application Ser. No. 60/804,602, filed Jun. 13, 2006, U.S. Provisional Application Ser. No. 60/824,665, filed Sep. 6, 2006, U.S. Provisional Application Ser. No. 60/828,277, filed Oct. 5, 2006, and U.S. Provisional Application Ser. No. 60/891,410, filed Feb. 23, 2007, all of which are herein incorporated by reference. U.S. application Ser. No. 12/111,117, is also a continuation-in-part of U.S. application Ser. No. 11/741,189, filed Apr. 27, 2007, now U.S. Pat. No. 7,790,163 which is a continuation-in-part of U.S. application Ser. No. 11/684,907, filed Mar. 12, 2007, now abandoned which claims the benefit of U.S. Provisional Application Ser. No. 60/781,121, filed Mar. 10, 2006, U.S. Provisional Application Ser. No. 60/828,271, filed Oct. 5, 2006, and U.S. Provisional Application Ser. No. 60/862,501, filed Oct. 23, 2006, all of which are herein incorporated by reference.

INCORPORATION-BY-REFERENCE OF THE SEQUENCE LISTING

The computer readable form of the sequence listing is being submitted electronically with this application in .txt format and is hereby incorporated-by-reference. Applicants submit herewith one file, entitled "07-09D1filed.txt", which was created on Feb. 22, 2011 and has a total file size of 269 KB (275,760 bytes).

FIELD OF THE INVENTION

The present invention relates generally to the identification and isolation of antagonists to IL-17A and IL-17F and IL-23 (via p19) and methods of using the same.

BACKGROUND OF THE INVENTION

Cytokines are soluble, small proteins that mediate a variety of biological effects, including the induction of immune cell proliferation, development, differentiation, and/or migration, as well as the regulation of the growth and differentiation of many cell types (see, for example, Arai et al., Annu. Rev. Biochem. 59:783 (1990); Mosmann, Curr. Opin. Immunol 3:311 (1991); Paul and Seder, Cell 76:241 (1994)). Cytokine-induced immune functions can also include an inflammatory response, characterized by a systemic or local accumulation of immune cells. Although they do have host-protective effects, these immune responses can produce pathological consequences when the response involves excessive and/or chronic inflammation, as in autoimmune disorders (such as multiple sclerosis) and cancer/neoplastic diseases (Oppenheim and Feldmann (eds.) Cytokine Reference, Academic Press, San Diego, Calif. (2001); von Andrian and Mackay New Engl. J. Med. 343: 1020 (2000); Davidson and Diamond, New Engl. J. Med. 345:340 (2001); Lu et al, Mol. Cancer Res. 4:221 (2006); Dalgleish and O'Byrne, Cancer Treat Res. 130:1 (2006)).

L-17A, IL-17F and IL-23 are cytokines involved in inflammation. Human interleukin-17A (also known as "IL-17A") is a cytokine which stimulates the expression of interleukin-6 (IL-6), intracellular adhesion molecule 1 (ICAM-1), interleukin-8 (IL-8), granulocyte macrophage colony-stimulating factor (GM-CSF), and prostaglandin E2 expression, and plays a role in the preferential maturation of CD34+ hematopoietic precursors into neutrophils (Yao et al., *J. Immunol.* 155:5483 (1995); Fossiez et al., *J. Exp. Med.* 183:2593 (1996)). Human interleukin-23 (also known as "IL-23") is a cytokine which has been reported to promote the proliferation of T cells, in particular memory T cells.

L-17A and IL-17F share 55% identity (Kolls and Linden, 2004). In addition to their sequence similarity, both of these cytokines seem are produced by similar cell types, most notably activated, memory CD4+ T cells. See e.g. Agarwal et al., "Interleukin-23 promotes a distinct CD4 T cell activation state characterized by the production of interleukin-17" J. Biol. Chem. 278:1910-191 (2003); see also Langrish et al. "IL-23 drives a pathogenic T cell population that induces autoimmune inflammation" J. Exp. Med. 201: 233-240 (2005); and Starnes et al. "Cutting edge: IL-17F, a novel cytokine selectively expressed in activated T cells and monocytes, regulates angiogenesis and endothelial cell cytokine production" J. Immunol. 167:4137-4140 (2001).

While IL-17F shares sequence homology with IL-17A, there are key difference between these molecules. For example, IL-17F mRNA is detected in many different tissues (such as, liver, lung, ovary, fetal liver, mast cells and basophils) while IL-17A expression is mostly restricted to T cells. See Fossiez, F., et al., "T cell IL-17 induces stromal cells to produce pro-inflammatory and hematopoietic cytokines", J. Exp. Med. 183(6):2593-2603, (1996); Toy, D. et al., "Cutting edge: IL-17 signals through a heteodimeric receptor complex", J. Immunol. 177(1):36-39 (2006). Additionally, IL-17F binds IL-17RA with a much lower affinity than IL-17A.

Moreover, both have been similarly implicated as contributing agents to progression and pathology of a variety of inflammatory and auto-immune diseases in humans and in mouse models of human diseases. Specifically, IL-17A and IL-17F have been implicated as major effector cytokines that trigger inflammatory responses and thereby contribute to a number of autoinflammatory diseases including multiple sclerosis, rheumatoid arthritis, and inflammatory bowel diseases.

Recently it has been shown that using a combination of an antagonist to IL-17A and an antagonist to IL-23, relapse was prevented in a mouse model of multiple sclerosis. See co-owned U.S. patent application Ser. No. 11/762,738, filed Jun. 13, 2007 and WIPO Publication Number 2007/147019, published Dec. 21, 2007. However, there is a need for treatment of inflammatory disorders that would antagonize not only IL-17A and IL-23, but also IL-17F. The demonstrated in vivo activities of IL-23, IL-17A and IL-17F illustrate the clinical or therapeutic potential of, and need for, antagonists of IL-23, IL-17A and IL-17F. Specifically, antibodies that bind to IL-23 and to IL-17A or IL-17F that inhibit the immunological activities of both IL-17A and IL-17F would possess such novel therapeutic qualities. The present invention serves this need by providing antagonist molecules, including antibodies and antibody fragments that bind IL-23 and IL-17A or IL-17F, including antagonists that are comprised on one molecule.

DETAILED DESCRIPTION OF THE INVENTION

The present invention addresses these needs by providing antagonists to pro-inflammatory cytokines IL-17A, IL-17F, and IL-23. Antagonists provided by the invention are antibodies, or antibody fragments that bind IL-17A and IL-17F, including antibodies that cross-react with IL-17A and IL-17F, and antibodies or antibody fragments that bind IL-23, including antibodies that bind the p19 subunit of IL-23. The polynucleotide sequence of the human IL-17A is shown in SEQ ID NO:1 and the corresponding polypeptide sequence is shown in SEQ ID NO:2. The polynucleotide sequence of the human p19 subunit of IL-23 is shown in SEQ ID NO:3 and the corresponding polypeptide sequence is shown in SEQ ID NO:4. The polynucleotide sequence of the human IL-17F is shown in SEQ ID NO:5 and the corresponding polypeptide sequence is shown in SEQ ID NO:6.

IL-17A is a cytokine which stimulates the expression of IL-6, ICAM-1, IL-8, GM-CSF, and prostaglandin E2 expression, and plays a role in the preferential maturation of CD34+ hematopoietic precursors into neutrophils (Yao et al., *J. Immunol.* 155:5483 (1995); Fossiez et al., *J. Exp. Med.* 183: 2593 (1996)).

The pro-inflammatory cytokines IL-17A and IL-17F have a high degree of sequence similarity, share many biological properties, and are both produced by activated T cells. They have both been implicated as factors that contribute to the progression of various autoimmune and inflammatory diseases including multiple sclerosis, inflammatory bowel disease, rheumatoid arthritis and asthma. In fact, reagents that negate IL-17A function significantly ameliorate disease incidence and severity in several mouse models of human disease. IL-17A mediates its effects through interaction with its cognate receptor, the IL-17 receptor (IL-17RA), and for IL-17F, IL-17RA. Thus, the present invention contemplates that a cross-reactive, also called herein cross-binding, antibody may be useful as an antagonist to both IL-17A and IL-17F, and thus to block both IL-17A and IL-17F. Accordingly, the present invention addresses this need by providing therapeutic molecules (e.g. antibodies) which may block, inhibit, reduce, antagonize or neutralize the activity of both IL-17A and IL-17F. Thus, the present invention is directed to bispecific antibodies, with one antibody portion comprising a cross-reactive antibody, or antibody fragment that binds IL-17A or IL-17F and one antibody portion comprising an antibody or antibody fragment that binds the p19 subunit of IL-23, such as the antibodies described herein. The invention further provides uses therefor in inflammatory disease, as well as related compositions and methods.

IL-23 is a heterodimeric cytokine composed of a unique subunit, p19 (herein referred to interchangeably as "IL-23", "p19" and IL23/p19"), and the p40 subunit, which is shared with interleukin-12 (IL-12) (Oppmann, *Immunity* 13:715 (2000)). IL-23 has been found to stimulate the production and/or maintenance of IL-17 from activated CD4+ T cells in what has now been termed as a "new" T-helper (Th) subset, designated Th17. A review of IL-23 cytokine and receptor biology is reviewed in Holscher, *Curr. Opin. Invest. Drugs* 6:489 (2005) and Langrish et al. *Immunol Rev.* 202:96 (2004). Similar to Th1 and Th2 lineages, Th17 cells have most likely evolved to provide adaptive immunity to specific classes of pathogens, such as extracellular bacteria. However, inappropriate Th17 responses have been strongly implicated in a growing list of autoimmune disorders, including multiple sclerosis, rheumatoid arthritis, inflammatory bowel disease, and psoriasis.

In fact, both IL-17 and IL-23 have also been reported to play important roles in many autoimmune diseases, such as multiple sclerosis, rheumatoid arthritis, Crohn's disease, and psoriasis. Both IL-23 and IL-17 are overexpressed in the central nervous system of humans with multiple sclerosis and in mice undergoing an animal model of multiple sclerosis, experimental autoimmune encephalomyelitis (EAE). The overexpression is observed in mice when the EAE is induced by either myelin oligodendrocyte glycoprotein (MOG) 35-55 peptide- or proteolipid peptide (PLP). Furthermore, neutralization of either IL-23/p19 or IL-17 results in amelioration of EAE symptoms in mice (Park et al, *Immunol.* 6:1133 (2005); Chen et al, *J Clin Invest.* 116:1317 (2006)).

It has also been demonstrated that IL-17 and Th17 cells can be produced from IL-23-independent sources, and the in vivo development of an IL-17 effector response has been shown to be IL23-independent (Mangan et al, *Nature* 441:231 (2006)). Neutralization of IL-23 would theoretically eliminate existing IL-17 producing cells, but would not prevent the development of new Th17 cells.

Co-expression of IL-17F and IL-17A in HEK293 cells has been shown to result in the production of the biologically active IL-17F/IL-17A heterodimer, in addition to the IL-17F and IL-17A homodimers and that activated human CD4+ T cells produce the IL-17F/IL-17A heterodimer along with the corresponding homodimers. See for example, Wright, J. F. et al., *J. Biol. Chem.*, Vol. 282, Issue 18: 13447-13455 2007.

The present invention concerns the inhibition of proinflammatory cytokines, IL-17A, IL-17F and IL-23/p19. This inhibition can be by administration of one or more molecules that inhibit IL-17A or IL-17F, such as a cross-reactive antibody, and one or more molecules that inhibit IL-23, such as an antibody or antibody fragment that binds the p19 subunit of IL-23. This inhibition can be by administration of one molecule that comprises a binding entity that binds IL-17A or IL-17F and that also binds the p19 subunit of IL-23. More specifically, the present invention concerns the inhibition or neutralization of IL-17A or IL-17F and IL-23 (via p19) with a single antagonistic molecule or neutralizing entity. Since the portion of the single antagonistic molecule or neutralizing entity that binds IL-17A or IL-17F can bind either IL-17A or IL-17F, administration of this molecule or entity will inhibit or neutralize IL-17A and IL-17F. As such, this portion of the molecule or entity will inhibit or neutralize IL-17A homodimers, IL-17F homodimers, and IL-17A/F heterodimers. Thus, the single antagonisitic molecule or neutralizing entity can be used to reduce, limit, neutralize, or block the proinflammatory effects of the IL-17A homodimer, the IL-17F homodimer, or the IL-17A/F heterodimer Likewise, the single antagonisitic molecule or neutralizing entity can be used to reduce, limit, neutralize, or block the pro-cancerous effects of the IL-17A homodimer, the IL-17F homodimer, or the IL-17A/F heterodimer. In such cases, the anti-IL-23p19 portion of the single antagonistic molecule or neutralizing entity is used to reduce, limit, neutralize, or block production of new T cells that would produce IL-17A and/or IL-17F, including homodimers and heterodimers. The antagonistic molecules or neutralizing entities described herein can be used to treat autoimmune diseases, such as multiple sclerosis, inflammatory bowel disease, and psoriasis. The antagonistic molecules or neutralizing entities described herein can also be used to treat cancer, including angiogenesis.

The present invention is based on the surprising discovery that antagonizing both IL-23 (via p19) and IL-17A is more effective therapeutically than neutralization of IL-23 alone (either via p19 or p40) or IL-17A alone and thus, necessary for the effective treatment of inflammatory diseases (including cancers). See co-owned U.S. patent application Ser. No. 11/762,738, filed Jun. 13, 2007 and WIPO Publication Number 2007/147019, published Dec. 21, 2007.

The antagonistic molecule or neutralizing entity inhibits the activity of IL-17A or IL-17F and IL-23 (via the p19 subunit), and thus, inhibits the production, maintenance, and activity of new and existing IL-17A and IL-17F and IL-17-producing T cells (Th17). The invention further concerns the use of antagonists or neutralizing entities of IL-17A, IL-17F, and IL-23/p19 in the treatment of inflammatory diseases characterized by the presence of elevated levels of IL-17A, IL-17F, and/or IL-23. The invention also concerns the use of antagonists to IL-17A, IL-17F, and IL-23/p19 in the treatment of cancers characterized by the presence of elevated levels of IL-17A, IL-17F, and/or IL-23.

Accordingly, the present invention is directed to antagonizing IL-17A, IL-17F, and IL-23/p19. Antagonists, including antibodies and antibody fragments of the present invention, which may block, inhibit, reduce, antagonize or neutralize the activity of IL-17A, IL-17F, (including homdimers and heterodimers), and IL-23/p19 will have advantages over therapies that target only one of these three cytokines. The invention further provides uses therefor in inflammatory disease and cancer, as well as related compositions and methods.

One method to treat immune related diseases is to suppress the immune response. Using the antagonists of the present invention (i.e. anti-IL-17A or anti-IL-17F and anti-IL-23/p19 antibodies) that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

IL-17, including IL-17A and IL-17F, has been identified as a potent cytokine that acts to induce proinflammatory responses in a wide variety of peripheral tissues. IL-17 is a disulfide-linked homodimeric cytokine of about 32 kDa which is synthesized and secreted only by CD4+activated memory T cells (reviewed in Fossiez et al., *Int. Rev. Immunol.*, 16: 541-551 [1998]). Specifically, IL-17 is synthesized as a precursor polypeptide of 155 amino acids with an N-terminal signal sequence of 19-23 residues and is secreted as a disulfide-linked homodimeric glycoprotein. IL-17 is disclosed in WO9518826 (1995), WO9715320 (1997) and WO9704097 (1997), as well as U.S. Pat. No. 6,063,372.

Despite its restricted tissue distribution, IL-17 exhibits pleitropic biological activities on various types of cells. IL-17 has been found to stimulate the production of many cytokines. It induces the secretion of IL-6, IL-8, IL-12, leukemia inhibitory factor (LIF), prostaglandin E2, MCP-1 and G-CSF by adherent cells like fibroblasts, keratinocytes, epithelial and endothelial cells. IL-17 also has the ability to induce ICAM-1 surface expression, proliferation of T cells, and growth and differentiation of $CD34^+$ human progenitors into neutrophils. IL-17 is also believed to play a key role in certain other autoimmune disorders such as multiple sclerosis (Matusevicius et al., *Mult. Scler.* 5:101 (1999); Park et al, *Nat. Immunol.* 6:1133 (2005)). IL-17 has further been shown, by intracellular signalling, to stimulate $Ca^{2+}$ influx and a reduction in [cAMP], in human macrophages (Jovanovic et al, *J. Immunol.* 160:3513 (1998)). Fibroblasts treated with IL-17 induce the activation of NF-kappa.B, (Yao et al., Immunity, 3:811 (1995), Jovanovic et al., supra), while macrophages treated with it activate NF-kappa.B and mitogen-activated protein kinases (Shalom-Barek et al, *J. Biol. Chem.* 273: 27467 (1998)).

Despite its restricted tissue distribution, IL-17A exhibits pleitropic biological activities on various types of cells. IL-17A has been found to stimulate the production of many cytokines. It induces the secretion of IL-6, IL-8, IL-12, leukemia inhibitory factor (LIF), prostaglandin E2, MCP-1 and G-CSF by adherent cells like fibroblasts, keratinocytes, epithelial and endothelial cells. IL-17A also has the ability to induce ICAM-1 surface expression, proliferation of T cells, and growth and differentiation of $CD34^+$ human progenitors into neutrophils. IL-17A has also been implicated in bone metabolism, and has been suggested to play an important role in pathological conditions characterized by the presence of activated T cells and TNF-.alpha. production such as rheumatoid arthritis and loosening of bone implants (Van Bezooijen et al., J. Bone Miner. Res. 14: 1513-1521 [1999]). Activated T cells of synovial tissue derived from rheumatoid arthritis patients were found to secrete higher amounts of IL-17A than those derived from normal individuals or osteoarthritis patients (Chabaud et al., Arthritis Rheum. 42: 963-970 [1999]). It was suggested that this proinflammatory cytokine actively contributes to synovial inflammation in rheumatoid arthritis. Apart from its proinflammatory role, IL-17A seems to contribute to the pathology of rheumatoid arthritis by yet another mechanism. For example, IL-17A has been shown to induce the expression of osteoclast differentiation factor (ODF) mRNA in osteoblasts (Kotake et al., J. Clin. Invest., 103: 1345-1352 [1999]). ODF stimulates differentiation of progenitor cells into osteoclasts, the cells involved in bone resorption.

Since the level of IL-17A is significantly increased in synovial fluid of rheumatoid arthritis patients, it appears that IL-17A induced osteoclast formation plays a crucial role in bone resorption in rheumatoid arthritis. IL-17A is also believed to play a key role in certain other autoimmune disorders such as multiple sclerosis (Matusevicius et al., Mult. Scler., 5: 101-104 [1999]). IL-17A has further been shown, by intracellular signalling, to stimulate $Ca.sup.2+$ influx and a reduction in [cAMP], in human macrophages (Jovanovic et al., J. Immunol., 160:3513 [1998]). Fibroblasts treated with IL-17A induce the activation of NF-.kappa.B, [Yao et al., Immunity, 3:811 (1995), Jovanovic et al., supra], while macrophages treated with it activate NF-.kappa.B and mitogen-activated protein kinases (Shalom-Barek et al., J. Biol. Chem., 273:27467 [1998]).

Additionally, IL-17A also shares sequence similarity with mammalian cytokine-like factor 7 that is involved in bone and cartilage growth. Other proteins with which IL-17A polypeptides share sequence similarity are human embryo-derived interleukin-related factor (EDIRF) and interleukin-20.

The expression pattern of IL-17F appears to be similar to that of IL-17A, such that it includes only activated CD4+ T cells and monocytes (Starnes et al. J. Immunol. 167: 4137-4140 [2001]). IL-17F has been demonstrated to induce G-CSF, IL-6, and IL-8 in fibroblasts (Hymowitz et al, EMBO J. 20:5322-5341 [2001]) and TGF-b in endothelial cells (Starnes et al. J. Immunol. 167: 4137-4140 [2001]). It has recently been reported that IL-23, a cytokine produced by dendritic cell, can mediate the production of both IL-17A and IL-17F, primarily in memory T cells (Aggarwal et al. J. Biol. Chem. 278:1910-1914 [2003]).

Moreover, over expression or upregulation of both IL-17A and IL-17F have been shown in arthritic and asthmatic individuals (reviewed in Moseley et al. CytokineGrowth Factor Rev 14:155-174 [2003]). With regards to arthritis, these cytokines act in a manner characteristic to the cartilage and joint destruction that is associated with rheumatoid- and osteo-arthritis. For example, IL-17A and IL-17F have been demonstrated to enhance matrix degradation in articular cartilage explants via release of cartilage proteoglycan glycosaminoglycans and collagen fragments, while inhibiting the synthesis of new proteoglycans and collagens (Cai et al. Cytokine 16:10-21 [2001]; Attur et al Arthritis Rheum 44:2078-2083 [2001]).

Similar to IL-17A, overexpression of IL-17F in mice has also been shown to increase lung neutrophil recruitment and result in increased expression of Th1-associated cytokines in the lung, including IL-6, IFN-gamma, IP-10 and MIG (Starnes et al. J. Immunol. 167: 4137-4140 [2001]). IL-17F was also upregulated in T cells from allergen-challenged asthmatics (Kawaguchi et al J. Immunol 167:4430-4435 [2001]), and found to induce IL-6 and IL-8 production in NHBE. In contrast to IL-17A, IL-17F appears to inhibit angiogenesis in vitro (Starnes et al. J. Immunol. 167: 4137-4140 [2001]).

IL-17F mRNA was not detected by northern blot in various human tissues but was dramatically induced upon activation of CD4+ T cells and monocytes. Id. In mice, Th2 cells and mastr cells were found to express IL-17F upon activation. See Dumont, Expert Opin. Ther. Patents 13(3) (2003). Like IL-17A, the expression of IL-17F was also found to be upregulated by IL-23 in mouse.

The present invention also provides antibodies that bind both IL-17F and IL-23p19 and methods for using such antibodies. The antibodies may act as antagonists or agonists, and find utility for, among other things, in vitro, in situ, or in vivo diagnosis or treatment of mammalian cells or pathological conditions associated with the presence (or absence) of IL-17F and/or IL-23p19. In this embodiment, the antibody would bind IL-17F, but not IL-17A.

Antagonists to IL-17A, IL-17F, and IL-23 activity, such as the antagonists of the present invention (i.e. anti-IL-17A or anti-IL-17F or anti-IL-23/p19 antibodies), are useful in therapeutic treatment of inflammatory diseases, particularly as antagonists to IL-17A, IL-17F, and IL-23/p19, in the treatment of inflammatory diseases, particularly in the treatment of multiple sclerosis, inflammatory bowel disease, and cancer. These antagonists are capable of binding, blocking, inhibiting, reducing, antagonizing or neutralizing IL-17A, IL-17F, their homodimers and heterodimers, and IL-23 (via p19) (either individually or together) in the treatment of atopic and contact dermatitis, multiple sclerosis, colitis, endotoxemia, arthritis, rheumatoid arthritis, psoriatic arthritis, adult respiratory disease (ARD), septic shock, multiple organ failure, inflammatory lung injury such as asthma, chronic obstructive pulmonary disease (COPD), airway hyper-responsiveness, chronic bronchitis, allergic asthma, psoriasis, eczema, IBS and inflammatory bowel disease (IBD) such as ulcerative colitis and Crohn's disease, *Helicobacter pylori* infection, intraabdominal adhesions and/or abscesses as results of peritoneal inflammation (i.e. from infection, injury, etc.), systemic lupus erythematosus (SLE), multiple sclerosis, systemic sclerosis, nephrotic syndrome, organ allograft rejection, graft vs. host disease (GVHD), kidney, lung, heart, etc. transplant rejection, streptococcal cell wall (SCW)-induced arthritis, osteoarthritis, gingivitis/periodontitis, herpetic stromal keratitis, restenosis, Kawasaki disease, and cancers/neoplastic diseases that are characterized by IL-17 and/or IL-23 expression, including but not limited to prostate, renal, colon, ovarian and cervical cancer, and leukemias (Tartour et al, *Cancer Res.* 59:3698 (1999); Kato et al, *Biochem. Biophys. Res. Commun.* 282:735 (2001); Steiner et al, *Prostate.* 56:171 (2003); Langowksi et al, *Nature. May* 10 [Epub ahead of print], (2006)).

The present invention provides novel antagonists of IL-17F and IL-23/p19 and their uses in the treatment of inflammatory diseases and autoimmune diseases. The IL-17F and IL-23/p19 antagonists of the present invention, including the neutralizing anti-IL-17F and IL-23/p19 antibodies of the present invention, can be used to block, inhibit, reduce, antagonize or neutralize the activity of either IL-17F or IL-23 (via p19), or both IL-17F and IL-23 (via p19) in the treatment of inflammation and inflammatory dieases such as multiple sclerosis, cancer (as characterized by the expression of IL-17F and/or IL-23), psoriasis, psoriatic arthritis, rheumatoid arthritis, endotoxemia, IBS, and inflammatory bowel disease (IBD), colitis, asthma, allograft rejection, immune mediated renal diseases, hepatobiliary diseases, atherosclerosis, promotion of tumor growth, or degenerative joint disease and other inflammatory conditions disclosed herein.

The present invention provides isolated polypeptides that bind IL-17F (e.g., human IL-17F polypeptide sequence as shown in SEQ ID NO:6). The present invention also provides isolated polypeptides as disclosed above that bind IL-23 (e.g., human IL-23 polypeptide sequence as shown in SEQ ID NO:4). More specifically, the present invention provides polypeptides that bind to the p19 subunit of IL-23 (e.g. human p19 polypeptide sequence as shown in SEQ ID NO:4).

The present invention also provides isolated polypeptides and epitopes comprising at least 15 contiguous amino acid residues of an amino acid sequence of SEQ ID NO:2 or 4. Illustrative polypeptides include polypeptides that either comprise, or consist of SEQ ID NO:2 or 4, an antigenic epitope thereof. Moreover, the present invention also provides isolated polypeptides as disclosed above that bind to, block, inhibit, reduce, antagonize or neutralize the activity of IL-17F or IL-23.

Preferred embodiments of the invention include binding peptides, antibodies, and any fragments or permutations thereof that bind to IL-17F or IL-23/p19 (herein referred to interchangeably as "IL-17F/IL-23 antagonists", "IL-17F antagonists", "IL-23 antagonists", "p19 antagonists" "IL-17F/IL-23 antibodies", "IL-17F/p19 antibodies", "IL-17F antibodies", "IL-23 antibodies", "p19 antibodies" "IL-17F/IL-23 antibodies", "IL-17F/p19 antibodies", "IL-17F/IL-23/p19 antibodies" etc.). Specifically, such binding peptides or antibodies are capable of specifically binding to both human IL-17F and IL-23 (via p19) and/or are capable of modulating biological activities associated with either or both IL-17F and IL-23, and thus are useful in the treatment of various diseases and pathological conditions such as inflammation and immune-related diseases.

The invention include antibodies, and any fragments or permutations thereof, that cross-reacts with IL-17A and IL-17F (herein refereed to interchangeably as "cross-reactive antibodies", "cross-binding antibodies", "A/F antibodies", "IL-17A/F antibodies" etc.) as well as antibodies, including any fragments or permutations thereof, that bind IL-23p19. Specifically, such antibodies are capable of specifically binding to both human IL-17A and IL-17F and/or are capable of modulating biological activities associated with either or both IL-17A and IL-17F and/or their receptors, IL-17RA and IL-17RC, and thus are useful in the treatment of various diseases and pathological conditions such as immune related diseases. Optionally, the antibody is a monoclonal antibody.

Thus, the present invention provides antibodies and antibody fragments that specifically bind with IL-17 and/or IL-23 (via p19). Exemplary antibodies include neutralizing antibodies, polyclonal antibodies, murine monoclonal antibodies, chimeric antibodies, humanized antibodies derived from murine monoclonal antibodies, and human monoclonal antibodies. Illustrative antibody fragments including F(ab')$_2$, F(ab)$_2$, Fab', Fab, Fv, scFv, bispecific antibodies or antibody fragments, and minimal recognition units. Neutralizing antibodies preferably bind IL-17A, IL-17F, their homodimers or heterodimers, or IL-23/p19 such that the interaction of these ligands with their respective receptors is blocked, inhibited, reduced, antagonized or neutralized. That is, the neutralizing antibodies of the present invention can either bind, block, inhibit, reduce, antagonize or neutralize each of IL-17A, IL-17F, their homodimers or heterodimers, or IL-23 singly, or bind, block, inhibit, reduce, antagonize or neutralize IL-17A, IL-17F, their homodimers and heterodimers and IL-23 together. The present invention further includes compositions comprising a carrier and a peptide, polypeptide, or antibody described herein.

The present invention further includes pharmaceutical compositions, comprising a pharmaceutically acceptable carrier and a polypeptide or antibody described herein.

The present invention also provides fusion proteins, comprising an antagonist of the present invention and an immunoglobulin moiety. In such fusion proteins, the immunoglobulin moiety may be an immunoglobulin heavy chain constant region, such as a human $F_C$ fragment. The present invention further includes isolated nucleic acid molecules that encode such fusion proteins. In another embodiment, the antibodies are linked to one or more non-proteinaceous polymers selected from the group consisting of polyethylene glycol, polypropylene glycol, and polyoxyalkylene, or to a cytotoxic agent or enzyme, or to a radioisotope, fluorescent compound or chemiluminescent compound.

In a particular embodiment, the present invention provides bispecific antibodies or binding proteins that bind both IL-17A, or IL-17F, and IL-23. Bispecific antibodies (BsAbs) are antibodies that have two different antigen binding sites, such that the antibody specifically binds to two different antigens. Antibodies having higher valencies (i.e., the ability to bind to more than two antigens) can also be prepared; they are referred to as multispecific antibodies.

The bispecific antibody can be a monoclonal antibody (MAb). In particular embodiments, the antibody is chimeric, or humanized, or fully human. Fully human antibodies may be generated by procedures that involve immunizing transgenic mice, wherein human immunoglobulin genes have been introduced into the mice, as discussed below.

In yet other particular embodiments, there is provided the hybridoma cell line which produces monoclonal antibodies of the present invention. In another embodiment, the IL-17/IL-23 antibodies are linked to one or more non-proteinaceous polymers selected from the group consisting of polyethylene glycol, polypropylene glycol, and polyoxyalkylene, or to a cytotoxic agent or enzyme, or to a radioisotope, fluorescent compound or chemiluminescent compound.

Compositions of the invention may include pharmaceutically acceptable carriers or diluents. Preferably, the compositions will include one or more antibodies in an amount which is therapeutically effective to treat a pathological condition or disease.

Accordingly, antagonists of the present invention (i.e. antibodies or binding peptides that bind IL-17A or IL-17F, and IL-23 either singly or together) are also useful to prepare medicines and medicaments for the treatment of immune-related and inflammatory diseases, including for example, systemic lupus erythematosis, arthritis, rheumatoid arthritis, osteoarthritis, demyelinating diseases of the central and peripheral nervous systems such as multiple sclerosis, idiopathic demyelinating polyneuropathy or Guillain-Barre syndrome, inflammatory bowel disease, colitis, ulcerative colitis, Crohn's disease, gluten-sensitive enteropathy, cancer, neoplastic diseases, and angiogenesis. In a specific aspect, such medicines and medicaments comprise a therapeutically effective amount of an anti-IL-17A/F cross-binding antibody/IL-23 antibody with a pharmaceutically acceptable carrier. In an embodiment, the admixture is sterile.

For example, the IL-17A/F cross-binding antibodies bind to an epitope on both IL-17A and IL-17F, wherein said epitope comprises residues Ile(23), Lys (25), Gly(27), Thr (29) and Pro(34) of the following sequences of human IL-17F and the equivalent sequence found in human IL-17A shown below. Residues 23, 25, 27, 29, and 34 are predicted to be on the surface of both IL-17A and IL-17F and therefore are accessible to the binding of an antibody of the present invention or an equivalent protein binding antagonist.

```
hIL17F
                (Ile23-Pro34 of SEQ ID NO: 6)
IPKVGHTFFQKP hIL17A
                (Ile20-Pro31 of SEQ ID NO: 2)
IVKAGITIPRNP
```

Optionally, the IL-17A/F antibodies bind to another epitope on both IL-17A and IL-17F, wherein said epitope comprises residues Arg(67), Ser(68), Thr(69), Ser(70), Pro (71), Trp(72), Asn(73) of the following sequences of human IL-17F and the equivalent sequence found in human IL-17A, as shown below. Residues 69, 71 and 73 are predicted to be on the surface of the bioactive cytokine and therefore are accessible to the binding of an antibody of the present invention or equivalent protein binding antagonist.

```
hIL17F
                (Arg67-Asn73 of SEQ ID NO: 6)
RSTSPWN hIL17A
                (Arg69-Asn75 of SEQ ID NO: 2)
RSTSPWN
```

Optionally, the IL-17A/F antibodies bind to another epitope on both IL-17A and IL-17F, wherein said epitope comprises residues Asp(79), Pro(80), Asn(81), Arg(82), Tyr (83), Pro(84) and Ser(85) of the following sequences of human IL-17F and the equivalent sequence found in human IL-17A, as shown below. All residues of this epitope are predicted to be on the surface of the bioactive cytokine and therefore are accessible to the binding of an antibody of the present invention or equivalent protein binding antagonist.

```
hIL-17F
                (Asp79-Ser85 of SEQ ID NO: 6)
DPNRYPS hIL-17A
                (Asp81-Ser87 of SEQ ID NO: 2)
DPERYPS
```

Optionally, the IL-17A/F antibodies bind to another epitope on both IL-17A and IL-17F, wherein said epitope comprises residues Thr(146), Pro(147), Val(148), Ile(149), His(150), His(151), Val(152) of the following sequences of human IL-17F and the corresponding sequence found in human IL-17A, as shown below. These residues are predicted to be on the surface of the bioactive cytokine and therefore to be accessible to the binding of an antibody of the present invention or equivalent protein binding antagonist.

```
hIL-17F
           (Thr146-Val152 of SEQ ID NO: 6)
TPVIHHV hIL-17A
           (Thr148-Val154 of SEQ ID NO: 2)
TPIVHHV
```

Optionally, the IL-17A/F antibodies bind to another epitope on both IL-17A and IL-17F, wherein said epitope is a discontinuous epitope comprising residues from two separate peptide chains of human IL-17F, as shown below; or the equivalent sequence found in human IL-17A, as shown below. Specifically, residues 105-109, 147-152 of hIL-17F and 107-111, 148-154 of hIL-17A are predicted to be on the surface of the bioactive cytokine and therefore are accessible to the binding of an antibody of the present invention or equivalent protein binding antagonist.

hIL-17F Sequences (Asp105-Asn109 [DISMN] and Pro147-Val152 [PVIHHV] of SEQ ID NO:6)

hIL-17A Sequences (Asp 107-Asn111 [DYHMN] and Pro 149-Val154 [PIVHHV] of SEQ ID NO:2)

Optionally, the IL-17A/F antibodies bind to another epitope on both IL-17A and IL-17F, wherein said epitope is a discontinuous epitope comprising residues of two or three separate peptide chains of human IL-17F, as shown below; or the equivalent sequence found in human IL-17A. Specifically, residues 81, 82, 121, 132, 134 of hIL-17F and 83, 84, 123, 134, 136 of hIL-17A are predicted to be on the surface of the bioactive cytokine and therefore to be accessible to the binding of an antibody of the present invention or equivalent protein binding antagonist.

hIL-17F Sequences (Asp79-Ser85 [DPNRYPS] and Val119-Arg122 [VVRR] and Ser130-Glu134 [SFQLE] of SEQ ID NO:6)

hIL-17A Sequences (Asp81-Ser87 [DPERYPS] and Val121-Arg124 [VLRR] and Ser132-Glu136 [SFRLE] of SEQ ID NO:2)

Additionally, an epitope of IL-17A or to IL-17F to which neutralizing cross-reacting antibodies of the present invention may bind may be from residues 34 to residue 41 of SEQ ID NO: 2 (i.e., PNSEDKNF) or from residues 52 to 64 of SEQ ID NO: 2 (i.e., HNRNTNTNPKRSS). The an epitope of IL-17A to which non-neutralizing antibodies of the present invention may bind may be from residues 77 to 85 of SEQ ID NO: 2 (i.e., HRNEDPERY).

Likewise, epitopes of IL-23p19 to which antibodies of the present invention may bind may be from residues 55 to 66 of SEQ ID NO: 4 (i.e., DLREEGDEETTN), from residues 74 to 85 (i.e., GDGCDPQGLRDN); from residues 137 to 146 (i.e., PEGHHWETQQ) and from residues 155 to 164 (i.e, PWQR-LLLRFK).

In a particular embodiment, the present invention provides bispecific antibodies with one binding entity that is cross-reactive for IL-17A and IL-17F and one binding entity that binds IL-23p19. Bispecific antibodies (BsAbs) are antibodies that have two different antigen binding sites, such that the antibody specifically binds to two different antigens. Antibodies having higher valencies (i.e., the ability to bind to more than two antigens) can also be prepared; they are referred to as multispecific antibodies.

In yet other particular embodiments, there is provided the hybridoma cell line which produces monoclonal antibodies of the present invention. In another embodiment, the antibodies that bind to IL-17A or IL-17F are linked to one or more non-proteinaceous polymers selected from the group consisting of polyethylene glycol, polypropylene glycol, and polyoxyalkylene, or to a cytotoxic agent or enzyme, or to a radioisotope, fluorescent compound or chemiluminescent compound.

Typical methods of the invention include methods to treat pathological conditions or diseases in mammals associated with or resulting from increased or enhanced IL-17F expression and/or activity. In the methods of treatment, IL-17F antibodies may be administered which preferably block or reduce the respective receptor binding or activation to their receptor(s).

The invention also provides compositions which comprise IL-17F antibodies. Optionally, the compositions of the invention will include pharmaceutically acceptable carriers or diluents. Preferably, the compositions will include one or more IL-17F antibodies in an amount which is therapeutically effective to treat a pathological condition or disease.

As such, the present invention concerns compositions and methods useful for the diagnosis and treatment of immune related disease in mammals, including humans. The present invention is based on the identification of antibodies that bind to IL-17F (including agonist and antagonist antibodies) which either stimulate or inhibit the immune response in mammals Immune related diseases can be treated by suppressing or enhancing the immune response. Antibodies that enhance the immune response stimulate or potentiate the immune response to an antigen. Antibodies which stimulate the immune response can be used therapeutically where enhancement of the immune response would be beneficial. Alternatively, antibodies that suppress the immune response attenuate or reduce the immune response to an antigen (e.g., neutralizing antibodies) can be used therapeutically where attenuation of the immune response would be beneficial (e.g., inflammation).

Accordingly, antibodies that bind IL-17F of the present invention and are also useful to prepare medicines and medicaments for the treatment of immune-related and inflammatory diseases, including for example, systemic lupus erythematosis, arthritis, psoriatic arthritis, rheumatoid arthritis, osteoarthritis, juvenile chronic arthritis, spondyloarthropathies, systemic sclerosis, idiopathic inflammatory myopathies, Sjogren's syndrome, systemic vasculitis, sarcoidosis, autoimmune hemolytic anemia, autoimmune thrombocytopenia, thyroiditis, diabetes mellitus, immune-mediated renal disease, demyelinating diseases of the central and peripheral nervous systems such as multiple sclerosis, idiopathic demyelinating polyneuropathy or Guillain-Barre syndrome, and chronic inflammatory demyelinating polyneuropathy, hepatobiliary diseases such as infectious, autoimmune chronic active hepatitis, primary biliary cirrhosis, granulomatous hepatitis, and sclerosing cholangitis, inflammatory bowel disease, colitis, Crohn's disease gluten-sensitive enteropathy, and endotoxemia, autoimmune or immune-mediated skin diseases including bullous skin diseases, erythema multiforme and atopic and contact dermatitis, psoriasis, neutrophilic dermatoses, cystic fibrosis, allergic diseases such as asthma, allergic rhinitis, food hypersensitivity and urticaria, cystic fibrosis, immunologic diseases of the lung such as eosinophilic pneumonia, idiopathic pulmonary fibrosis, adult respiratory disease (ARD), acute respiratory distress syndrome (ARDS) and inflammatory lung injury such as asthma, chronic obstructive pulmonary disease (COPD), airway hyper-responsiveness, chronic bronchitis, allergic asthma and hypersensitivity pneumonitis, transplantation associated diseases including graft and organ rejection and graft-versus-host-disease, septic shock, multiple organ failure, cancer and angiogenesis.

Models to test the effects of an antibody that binds IL-17A or IL-17F and binds IL-23p19 on cancer are known in the art. One model is the RENCA model in which tumor growth is measured in groups of mice that are injected s.c with the RENCA tumor on Day 0. Mice are then injected with 50-200 ug control reagent or IL-17/IL-23 antagonist 1×-3×/week for 3 weeks. Tumor volume is monitored 3×/week for 5 weeks. Significantly smaller tumors compared to control reagent injected mice would suggest neutralization or inhibits tumor growth. Ten-week old female BALB/c mice (Charles River Laboratories) are injected s.c. on the right flank with $0.1 \times 10^6$ RENCA cells on Day 0, Starting day 5, groups of mice (n=10/group) are injected i.p. with 50-200 ug of either control reagent or IL-17/IL-23 antagonist 1×-3×/week for 3 weeks. Tumor growth is monitored 3×/week for 5 weeks using caliper measurements. Tumor volume is calculated using the formula $\frac{1}{2}*(B)2*L$ (mm3).

Another model is the B16 Melanoma model. To test if an IL-17/IL-23 antagonist has effects on tumor growth in mice, groups of mice are injected s.c with the B16 tumor on Day 0. Mice are then injected with 50-200 ug control reagent or IL-17/IL-23 antagonist 1×-3×/week for 3 weeks. Tumor volume is monitored 3×/week for 5 weeks. Significantly smaller tumors compared to control reagent injected mice would suggest neutralization or inhibits tumor growth. Ten-week old female C57B1/6 (Charles River Laboratories) are injected s.c. on the right flank with $0.1 \times 10^6$ B16 cells on Day 0, Starting day 5, groups of mice (n=10/group) are injected i.p. with 50-200 ug of either control reagent or IL-17/IL-23 antagonist 1×-3×/week for 3 weeks Tumor growth is monitored 3×/week for 5 weeks using caliper measurements. Tumor volume is calculated using the formula $\frac{1}{2}*(B)2*L$ (mm3).

Another model is the LL/2 Lung Carcinoma model: to test if an IL-17/IL-23 antagonist has effects on tumor growth in mice, groups of mice are injected s.c with the LL/2 tumor on Day 0. Mice are then injected with 50-200 ug control reagent or IL-17/IL-23 antagonist 1×-3×/week for 3 weeks. Tumor volume is monitored 3×/week for 5 weeks. Significantly smaller tumors compared to control reagent injected mice would suggest neutralization or inhibits tumor growth. Ten-week old female C57BL/6 mice (Charles River Laboratories) are injected s.c. on the right flank with $0.1 \times 10^6$ LL/2 cells on Day 0, Starting day 5, groups of mice (n=10/group) are injected i.p. with 50-200 ug of either control reagent or IL-17/IL-23 antagonist 1×-3×/week for 3 weeks Tumor growth is monitored 3×/week for 5 weeks using caliper measurements. Tumor volume is calculated using the formula $\frac{1}{2}*(B)2*L$ (mm3).

Another model measures tumor growth in the Ct-26 Colon Carcinoma model: to test if the IL-17/IL-23 antagonist has effects on tumor growth in mice, groups of mice are injected s.c with the CT-26 tumor on Day 0. Mice are then injected with 50-200 ug control reagent or IL-17/IL-23 antagonist 1×-3×/week for 3 weeks. Tumor volume is monitored 3×/week for 5 weeks. Significantly smaller tumors compared to control reagent injected mice would suggest neutralization or inhibits tumor growth. Ten-week old female BALB/c mice (Charles River Laboratories) are injected s.c. on the right flank with $0.1 \times 10^6$ CT-26 cells on Day 0, Starting day 5, groups of mice (n=10/group) are injected i.p. with 50-200 ug of either control reagent or IL-17/IL-23 antagonist 1×-3×/week for 3 weeks Tumor growth is monitored 3×/week for 5 weeks using caliper measurements. Tumor volume is calculated using the formula $\frac{1}{2}*(B)2*L$ (mm3).

Another model is the 4T1 Breast Carcinoma Model: to test if the IL-17/IL-23 antagonist has effects on tumor growth in mice, groups of mice are injected s.c with the 4T1 tumor on Day 0. Mice are then injected with 50-200 ug control reagent or IL-17/IL-23 antagonist 1×-3×/week for 3 weeks. Tumor volume is monitored 3×/week for 5 weeks. Significantly smaller tumors compared to control reagent injected mice would suggest neutralization or inhibits tumor growth. Ten-week old female BALB/c mice (Charles River Laboratories) are injected s.c. on the right flank with $0.1 \times 10^6$ 4T1 cells on Day 0, Starting day 5, groups of mice (n=10/group) are injected i.p. with 50-200 ug of either control reagent or IL-17/IL-23 antagonist 1×-3×/week for 3 weeks Tumor growth is monitored 3×/week for 5 weeks using caliper measurements. Tumor volume is calculated using the formula $\frac{1}{2}*(B)2*L$ (mm3).

In a specific aspect, such medicines and medicaments comprise a therapeutically effective amount of an IL-17F/IL-23 antibody with a pharmaceutically acceptable carrier. Preferably, the admixture is sterile.

In one aspect, the present invention concerns an isolated antibody which binds to IL-17F. In another aspect, the antibody mimics the activity of IL-17F (an agonist antibody) or conversely the antibody inhibits or neutralizes the activity of IL-17F (an antagonist antibody). In another aspect, the antibody is a monoclonal antibody, which preferably has nonhuman complementarity determining region (CDR) residues and human framework region (FR) residues.

In a further embodiment, the invention concerns a method of identifying antagonist antibodies of IL-17F and IL-23/p19, said method comprising contacting both IL-17F and p19 with a candidate molecule and monitoring a biological activity mediated by IL-17F and/or IL-23. In another embodiment, the invention concerns a composition of matter comprising an IL-17F/IL-23 antagonist antibody which binds both IL-17F and IL-23 in admixture with a carrier or excipient. In one aspect, the composition comprises a therapeutically effective amount of the IL-17F/IL-23 antibody.

In an aspect, antagonistic IL-17A/F antibodies, are useful for: (a) decreasing infiltration of inflammatory cells into a tissue of a mammal in need thereof, (b) inhibiting or reducing an immune response in a mammal in need thereof, (c) decreasing the activity of T-lymphocytes or (d) decreasing the proliferation of T-lymphocytes in a mammal in need thereof in response to an antigen.

In another aspect, the composition comprises a further active ingredient, which may, for example, be a further antibody or a cytotoxic or chemotherapeutic agent. Preferably, the composition is sterile. In another embodiment, the invention concerns a method of treating an immune related disorder in a mammal in need thereof, comprising administering to the mammal a therapeutically effective amount of an IL-17A/F-IL-23 antagonist.

In still another embodiment, the invention concerns an isolated polynucleotide that encodes a polypeptide of the present invention, wherein said polypeptide is capable of binding to IL-17A or IL-17F and IL-23p19. In an embodiment, the polypeptide inhibits the activity of IL-17A or IL-17F and IL-23.

In still another embodiment, the invention concerns an isolated polypeptide of the present invention, wherein said polypeptide is capable of binding to IL-17A or IL-17F and IL-23p19. In an embodiment, the polypeptide inhibits the activity of IL-17A or IL-17F and IL-23.

In yet another embodiment, the invention concerns a method for inhibiting IL-17 production by T cells comprising treating the T cells with an antagonist of IL-23/p19 (IL-23).

Processes for producing the polypeptide of the invention are also herein described, wherein those processes comprise culturing a host cell comprising a vector which comprises the appropriate encoding nucleic acid molecule under conditions suitable for expression of said antibody and recovering said antibody from the cell culture.

In a further embodiment, the invention concerns an article of manufacture, comprising: (a) a composition of matter comprising an antibody described herein; (b) a container containing said composition; and (c) a label affixed to said container, or a package insert included in said container referring to the use of said antibody in the treatment of an immune related disease.

The invention also provides articles of manufacture and kits which include one or more antibodies described herein.

These and other aspects of the invention will become evident upon reference to the following detailed description. In addition, various references are identified below and are incorporated by reference in their entirety.

In the description that follows, a number of terms are used extensively. The following definitions are provided to facilitate understanding of the invention.

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules that lack antigen specificity. Polypeptides of the latter kind are, for example, produced at low levels by the lymph system and at increased levels by myelomas. Thus, as used herein, the term "antibody" or "antibody peptide(s)" refers to an intact antibody, or a binding fragment thereof that competes with the intact antibody for specific binding and includes chimeric, humanized, fully human, and bispecific antibodies. In certain embodiments, binding fragments are produced by recombinant DNA techniques. In additional embodiments, binding fragments are produced by enzymatic or chemical cleavage of intact antibodies. Binding fragments include, but are not limited to, Fab, Fab', $F(ab)^2$, $F(ab')^2$, Fv, and single-chain antibodies.

The term "isolated antibody" as used herein refers to an antibody that has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

A "variant" antibody refers herein to a molecule which differs in amino acid sequence from a "parent" antibody amino acid sequence by virtue of addition, deletion and/or substitution of one or more amino acid residue(s) in the parent antibody sequence. In the preferred embodiment, the variant comprises one or more amino acid substitution(s) in one or more hypervariable region(s) of the parent antibody. For example, the variant may comprise at least one, e.g. from about one to about ten, and preferably from about two to about five, substitutions in one or more hypervariable regions of the parent antibody. Ordinarily, the variant will have an amino acid sequence having at least 75% amino acid sequence identity with the parent antibody heavy or light chain variable domain sequences, more preferably at least 80%, more preferably at least 85%, more preferably at least 90%, and most preferably at least 95%. Identity or homology with respect to this sequence is defined herein as the percentage of amino acid residues in the candidate sequence that are identical with the parent antibody residues, after aligning the sequences and introducing gaps, if necessary, to achieve the maximum percent sequence identity. None of N-terminal, C-terminal, or internal extensions, deletions, or insertions into the antibody sequence shall be construed as affecting sequence identity or homology. The variant retains the ability to bind human IL-17A or IL-1yF and IL-23 (via p19) and preferably has properties which are superior to those of the parent antibody. For example, the variant may have a stronger binding affinity, enhanced ability to inhibit IL-17A or IL-17F and IL-23-induced inflammation. To analyze such properties, one should compare a Fab form of the variant to a Fab form of the parent antibody or a full length form of the variant to a full length form of the parent antibody, for example. The variant antibody of particular interest herein is one which displays at least about 10 fold, preferably at least about 20 fold, and most preferably at least about 50 fold, enhancement in biological activity when compared to the parent antibody.

The term "parent antibody" as used herein refers to an antibody which is encoded by an amino acid sequence used for the preparation of the variant. Preferably, the parent antibody has a human framework region and, if present, has human antibody constant region(s). For example, the parent antibody may be a humanized or human antibody.

The term "agonist" refers to any compound including a protein, polypeptide, peptide, antibody, antibody fragment, large molecule, or small molecule (less than 10 kD), that increases the activity, activation or function of another molecule.

The term "antagonist" refers to any compound including a protein, polypeptide, peptide, antibody, antibody fragment, large molecule, or small molecule (less than 10 kD), that decreases the activity, activation or function of another molecule.

The term "bind(ing) of a polypeptide" includes, but is not limited to, the binding of a ligand polypeptide of the present invention to a receptor; the binding of a receptor polypeptide of the present invention to a ligand; the binding of an antibody of the present invention to an antigen or epitope; the binding of an antigen or epitope of the present invention to an antibody; the binding of an antibody of the present invention to an anti-idiotypic antibody; the binding of an anti-idiotypic antibody of the present invention to a ligand; the biding of an anti-idiotypic antibody of the present invention to a receptor; the binding of an anti-anti-idiotypic antibody of the present invention to a ligand, receptor or antibody, etc.

A "bispecific" or "bifunctional" antibody is a hybrid antibody having two different heavy/light chain pairs and two different binding sites. Bispecific antibodies may be produced by a variety of methods including, but not limited to, fusion of hybridomas or linking of Fab' fragments. See, e.g., Songsivilai & Lachmann (1990), *Clin. Exp. Immunol.* 79:315-321; Kostelny et al. (1992), *J. Immunol.* 148:1547-1553.

The term "chimeric antibody" or "chimeric antibodies" refers to antibodies whose light and heavy chain genes have been constructed, typically by genetic engineering, from immunoglobulin variable and constant region genes belonging to different species. For example, the variable segments of the genes from a mouse monoclonal antibody may be joined to human constant segments, such as gamma 1 and gamma 3. A typical therapeutic chimeric antibody is thus a hybrid protein composed of the variable or antigen-binding domain from a mouse antibody and the constant domain from a human antibody, although other mammalian species may be used. Specifically, a chimeric antibody is produced by recombinant DNA technology in which all or part of the hinge and constant regions of an immunoglobulin light chain, heavy chain, or both, have been substituted for the corresponding regions from another animal's immunoglobulin light chain or heavy chain. In this way, the antigen-binding portion of the parent monoclonal antibody is grafted onto the backbone of another species' antibody. One approach, described in EP 0239400 to Winter et al. describes the substitution of one species' complementarity determining regions (CDRs) for those of another species, such as substituting the CDRs from human heavy and light chain immunoglobulin variable region domains with CDRs from mouse variable region domains. These altered antibodies may subsequently be combined with human immunoglobulin constant regions to form antibodies that are human except for the substituted murine CDRs which are specific for the antigen. Methods for grafting CDR regions of antibodies may be found, for example in Riechmann et al. (1988) *Nature* 332:323-327 and Verhoeyen et al. (1988) *Science* 239:1534-1536.

The term "effective neutralizing titer" as used herein refers to the amount of antibody which corresponds to the amount present in the serum of animals (human or cotton rat) that has been shown to be either clinically efficacious (in humans) or to reduce virus by 99% in, for example, cotton rats. The 99% reduction is defined by a specific challenge of, e.g., $10^3$ pfu, $10^4$ pfu, $10^5$ pfu, $10^6$ pfu, $10^7$ pfu, $10^8$ pfu, or $10^9$ pfu) of RSV.

As used herein, the term "epitope" refers to the portion of an antigen to which an antibody specifically binds. Thus, the term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. More specifically, the term "IL-17 epitope", "IL-23 epitope" and/or "IL-23/p19 epitope" as used herein refers to a portion of the corresponding polypeptide having antigenic or immunogenic activity in an animal, preferably in a mammal, and most preferably in a mouse or a human. An epitope having immunogenic activity is a portion of an IL-17A or IL-17F or IL-23/p19 polypeptide that elicits an antibody response in an animal. An epitope having antigenic activity is a portion of an IL-17A or IL-17F or IL-23/p19 polypeptide to which an antibody immunospecifically binds as determined by any method well known in the art, for example, by immunoassays. Antigenic epitopes need not necessarily be immunogenic. Such epitopes can be linear in nature or can be a discontinuous epitope. Thus, as used herein, the term "conformational epitope" refers to a discontinuous epitope formed by a spatial relationship between amino acids of an antigen other than an unbroken series of amino acids.

The term "epitope tagged" when used herein refers to the anti-IL-17A or anti-Il-17F or anti-IL-23/p19 antibody fused to an "epitope tag". The epitope tag polypeptide has enough residues to provide an epitope against which an antibody can be made, yet is short enough such that it does not interfere with activity of antibodies of the present invention. The epitope tag preferably is sufficiently unique so that the antibody thereagainst does not substantially cross-react with other epitopes. Suitable tag polypeptides generally have at least 6 amino acid residues and usually between about 8-50 amino acid residues (preferably between about 9-30 residues). Examples include the flu HA tag polypeptide and its antibody 12CA5 (Field et al. *Mol. Cell. Biol.* 8:2159-2165 (1988)); the c-myc tag and the 8F9, 3C7, 6E10, G4, B7 and 9E10 antibodies thereto (Evan et al., *Mol. Cell. Biol.* 5(12): 3610-3616 (1985)); and the Herpes Simplex virus glycoprotein D (gD) tag and its antibody (Paborsky et al., *Protein Engineering* 3(6):547-553 (1990)). In certain embodiments, the epitope tag is a "salvage receptor binding epitope". As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

The term "fragment" as used herein refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least contiguous 200 amino acid residues, or at least contiguous 250 amino acid residues of the amino acid sequence of a IL-17 or IL-23/p19 polypeptide or an antibody that immunospecifically binds to a either IL-17 or IL-23 (via p19) or both IL-17 and IL-23/p19 polypeptide.

As used herein, the term "immunoglobulin" refers to a protein consisting of one or more polypeptides substantially encoded by immunoglobulin genes. One form of immunoglobulin constitutes the basic structural unit of an antibody. This form is a tetramer and consists of two identical pairs of immunoglobulin chains, each pair having one light and one heavy chain. In each pair, the light and heavy chain variable regions are together responsible for binding to an antigen, and the constant regions are responsible for the antibody effector functions.

Full-length immunoglobulin "light chains" (about 25 Kd or 214 amino acids) are encoded by a variable region gene at the NH2-terminus (about 110 amino acids) and a kappa or lambda constant region gene at the COOH-terminus. Full-length immunoglobulin "heavy chains" (about 50 Kd or 446 amino acids), are similarly encoded by a variable region gene (about 116 amino acids) and one of the other aforementioned constant region genes (about 330 amino acids). Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 more amino acids. (See generally, Fundamental Immunology (Paul, W., ed., 2nd ed. Raven Press, N.Y., 1989), Ch. 7 (incorporated by reference in its entirety for all purposes).

An immunoglobulin light or heavy chain variable region consists of a "framework" region interrupted by three hypervariable regions. Thus, the term "hypervariable region" refers to the amino acid residues of an antibody which are responsible for antigen binding. The hypervariable region comprises amino acid residues from a "Complementarity Determining Region" or "CDR" (Kabat et al., Sequences of Proteins of Immunological Interest, 5th Ed. Public Health Service, National Institutes of Health, Bethesda, Md. (1991)) and/or those residues from a "hypervariable loop" (Chothia and Lesk, 1987, J. Mol. Biol. 196: 901-917) (both of which are incorporated herein by reference). "Framework Region" or "FR" residues are those variable domain residues other than the hypervariable region residues as herein defined. The sequences of the framework regions of different light or heavy chains are relatively conserved within a species. Thus, a "human framework region" is a framework region that is substantially identical (about 85% or more, usually 90-95% or more) to the framework region of a naturally occurring human immunoglobulin. The framework region of an antibody, that is the combined framework regions of the constituent light and heavy chains, serves to position and align the CDR's. The CDR's are primarily responsible for binding to an epitope of an antigen.

Accordingly, the term "humanized" immunoglobulin refers to an immunoglobulin comprising a human framework region and one or more CDR's from a non-human (usually a mouse or rat) immunoglobulin. The non-human immunoglobulin providing the CDR's is called the "donor" and the human immunoglobulin providing the framework is called the "acceptor". Constant regions need not be present, but if they are, they must be substantially identical to human immunoglobulin constant regions, i.e., at least about 85-90%, preferably about 95% or more identical. Hence, all parts of a humanized immunoglobulin, except possibly the CDR's, are substantially identical to corresponding parts of natural human immunoglobulin sequences. A "humanized antibody" is an antibody comprising a humanized light chain and a humanized heavy chain immunoglobulin. For example, a humanized antibody would not encompass a typical chimeric antibody as defined above, e.g., because the entire variable region of a chimeric antibody is non-human.

As used herein, the term "human antibody" includes and antibody that has an amino acid sequence of a human immunoglobulin and includes antibodies isolated from human immunoglobulin libraries or from animals transgenic for one or more human immunoglobulin and that do not express endogenous immunoglobulins, as described, for example, by Kucherlapati et al. in U.S. Pat. No. 5,939,598.

The term "genetically altered antibodies" means antibodies wherein the amino acid sequence has been varied from that of a native antibody. Because of the relevance of recombinant DNA techniques in the generation of antibodies, one need not be confined to the sequences of amino acids found in natural antibodies; antibodies can be redesigned to obtain desired characteristics. The possible variations are many and range from the changing of just one or a few amino acids to the complete redesign of, for example, the variable or constant region. Changes in the constant region will, in general, be made in order to improve or alter characteristics, such as complement fixation, interaction with membranes and other effector functions. Changes in the variable region will be made in order to improve the antigen binding characteristics.

In addition to antibodies, immunoglobulins may exist in a variety of other forms including, for example, single-chain or Fv, Fab, and (Fab')$_2$, as well as diabodies, linear antibodies, multivalent or multispecific hybrid antibodies (as described above and in detail in: Lanzavecchia et al., *Eur. J. Immunol.* 17, 105 (1987)) and in single chains (e.g., Huston et al., *Proc. Natl. Acad. Sci. U.S.A.*, 85, 5879-5883 (1988) and Bird et al., *Science*, 242, 423-426 (1988), which are incorporated herein by reference). (See, generally, Hood et al., "Immunology", Benjamin, N.Y., 2nd ed. (1984), and Hunkapiller and Hood, *Nature*, 323, 15-16 (1986), which are incorporated herein by reference).

As used herein, the terms "single-chain Fv," "single-chain antibodies," "Fv" or "scFv" refer to antibody fragments that comprises the variable regions from both the heavy and light chains, but lacks the constant regions, but within a single polypeptide chain. Generally, a single-chain antibody further comprises a polypeptide linker between the VH and VL domains which enables it to form the desired structure which would allow for antigen binding. Single chain antibodies are discussed in detail by Pluckthun in The Pharmacology of Monoclonal Antibodies, vol. 113, Rosenburg and Moore eds. Springer-Verlag, New York, pp. 269-315 (1994). Various methods of generating single chain antibodies are known, including those described in U.S. Pat. Nos. 4,694,778 and 5,260,203; International Patent Application Publication No. WO 88/01649; Bird (1988) Science 242:423-442; Huston et al. (1988) *Proc. Natl. Acad. Sci. USA* 85:5879-5883; Ward et al. (1989) *Nature* 334:54454; Skerra et al. (1988) *Science* 242:1038-1041, the disclosures of which are incorporated by reference for any purpose. In specific embodiments, single-chain antibodies can also be bi-specific and/or humanized.

A "Fab fragment" is comprised of one light chain and the $C_{H1}$ and variable regions of one heavy chain. The heavy chain of a Fab molecule cannot form a disulfide bond with another heavy chain molecule.

A "Fab' fragment" contains one light chain and one heavy chain that contains more of the constant region, between the $C_{H1}$ and $C_{H2}$ domains, such that an interchain disulfide bond can be formed between two heavy chains to form a F(ab')$_2$ molecule.

A "F(ab')$_2$ fragment" contains two light chains and two heavy chains containing a portion of the constant region between the $C_{H1}$ and $C_{H2}$ domains, such that an interchain disulfide bond is formed between two heavy chains.

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA* 90:6444-6448 (1993).

The term "linear antibodies" refers to the antibodies described in Zapata et al. *Protein Eng.* 8(10):1057-1062 (1995). Briefly, these antibodies comprise a pair of tandem Fd segments ($V_H$-$C_{H1}$-$V_H$-$C_{H1}$) which form a pair of antigen binding regions. Linear antibodies can be bispecific or monospecific.

The term "immunologically functional immunoglobulin fragment" as used herein refers to a polypeptide fragment that contains at least the variable domains of the immunoglobulin heavy and light chains. An immunologically functional immunoglobulin fragment of the invention is capable of binding to a ligand, preventing binding of the ligand to its receptor, interrupting the biological response resulting from ligand binding to the receptor, or any combination thereof. Preferably, an immunologically functional immunoglobulin fragment of the invention binds specifically to either IL-17A or IL-17F and IL-23/p19.

The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

As used herein, "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., α-enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded.

The term "complement of a nucleic acid molecule" refers to a nucleic acid molecule having a complementary nucleotide sequence and reverse orientation as compared to a reference nucleotide sequence.

The term "degenerate nucleotide sequence" denotes a sequence of nucleotides that includes one or more degenerate codons as compared to a reference nucleic acid molecule that encodes a polypeptide. Degenerate codons contain different triplets of nucleotides, but encode the same amino acid residue (i.e., GAU and GAC triplets each encode Asp).

The term "structural gene" refers to a nucleic acid molecule that is transcribed into messenger RNA (mRNA), which is then translated into a sequence of amino acids characteristic of a specific polypeptide.

An "isolated nucleic acid molecule" is a nucleic acid molecule that is not integrated in the genomic DNA of an organism. For example, a DNA molecule that encodes a growth factor that has been separated from the genomic DNA of a cell is an isolated DNA molecule. Another example of an isolated nucleic acid molecule is a chemically-synthesized nucleic acid molecule that is not integrated in the genome of an organism. A nucleic acid molecule that has been isolated from a particular species is smaller than the complete DNA molecule of a chromosome from that species.

A "nucleic acid molecule construct" is a nucleic acid molecule, either single- or double-stranded, that has been modified through human intervention to contain segments of nucleic acid combined and juxtaposed in an arrangement not existing in nature.

"Linear DNA" denotes non-circular DNA molecules having free 5' and 3' ends. Linear DNA can be prepared from closed circular DNA molecules, such as plasmids, by enzymatic digestion or physical disruption.

"Complementary DNA (cDNA)" is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand. The term "cDNA" also refers to a clone of a cDNA molecule synthesized from an RNA template.

A "promoter" is a nucleotide sequence that directs the transcription of a structural gene. Typically, a promoter is located in the 5' non-coding region of a gene, proximal to the transcriptional start site of a structural gene. Sequence elements within promoters that function in the initiation of transcription are often characterized by consensus nucleotide sequences. These promoter elements include RNA polymerase binding sites, TATA sequences, CAAT sequences, differentiation-specific elements (DSEs; McGehee et al., *Mol. Endocrinol.* 7:551 (1993)), cyclic AMP response elements (CREs), serum response elements (SREs; Treisman, *Seminars in Cancer Biol.* 1:47 (1990)), glucocorticoid response elements (GREs), and binding sites for other transcription factors, such as CRE/ATF (O'Reilly et al., *J. Biol. Chem.* 267:19938 (1992)), AP2 (Ye et al., *J. Biol. Chem.* 269:25728 (1994)), SP1, cAMP response element binding protein (CREB; Loeken, *Gene Expr.* 3:253 (1993)) and octamer factors (see, in general, Watson et al., eds., *Molecular Biology of the Gene,* 4th ed. (The Benjamin/Cummings Publishing Company, Inc. 1987), and Lemaigre and Rousseau, *Biochem. J.* 303:1 (1994)). If a promoter is an inducible promoter, then the rate of transcription increases in response to an inducing agent. In contrast, the rate of transcription is not regulated by an inducing agent if the promoter is a constitutive promoter. Repressible promoters are also known.

A "core promoter" contains essential nucleotide sequences for promoter function, including the TATA box and start of transcription. By this definition, a core promoter may or may not have detectable activity in the absence of specific sequences that may enhance the activity or confer tissue specific activity.

A "regulatory element" is a nucleotide sequence that modulates the activity of a core promoter. For example, a regulatory element may contain a nucleotide sequence that binds with cellular factors enabling transcription exclusively or preferentially in particular cells, tissues, or organelles. These types of regulatory elements are normally associated with genes that are expressed in a "cell-specific," "tissue-specific," or "organelle-specific" manner.

An "enhancer" is a type of regulatory element that can increase the efficiency of transcription, regardless of the distance or orientation of the enhancer relative to the start site of transcription.

"Heterologous DNA" refers to a DNA molecule, or a population of DNA molecules, that does not exist naturally within a given host cell. DNA molecules heterologous to a particular host cell may contain DNA derived from the host cell species (i.e., endogenous DNA) so long as that host DNA is combined with non-host DNA (i.e., exogenous DNA). For example, a DNA molecule containing a non-host DNA segment encoding a polypeptide operably linked to a host DNA segment comprising a transcription promoter is considered to be a heterologous DNA molecule. Conversely, a heterologous DNA molecule can comprise an endogenous gene operably linked with an exogenous promoter. As another illustration, a DNA molecule comprising a gene derived from a wild-type cell is considered to be heterologous DNA if that DNA molecule is introduced into a mutant cell that lacks the wild-type gene.

A "polypeptide" is a polymer of amino acid residues joined by peptide bonds, whether produced naturally or synthetically. Polypeptides of less than about 10 amino acid residues are commonly referred to as "peptides."

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

A peptide or polypeptide encoded by a non-host DNA molecule is a "heterologous" peptide or polypeptide.

A "cloning vector" is a nucleic acid molecule, such as a plasmid, cosmid, or bacteriophage, that has the capability of replicating autonomously in a host cell. Cloning vectors typically contain one or a small number of restriction endonuclease recognition sites that allow insertion of a nucleic acid molecule in a determinable fashion without loss of an essential biological function of the vector, as well as nucleotide sequences encoding a marker gene that is suitable for use in the identification and selection of cells transformed with the cloning vector. Marker genes typically include genes that provide tetracycline resistance or ampicillin resistance.

An "expression vector" is a nucleic acid molecule encoding a gene that is expressed in a host cell. Typically, an expression vector comprises a transcription promoter, a gene, and a transcription terminator. Gene expression is usually placed under the control of a promoter, and such a gene is said to be "operably linked to" the promoter. Similarly, a regulatory element and a core promoter are operably linked if the regulatory element modulates the activity of the core promoter.

A "recombinant host" is a cell that contains a heterologous nucleic acid molecule, such as a cloning vector or expression vector. In the present context, an example of a recombinant host is a cell that produces an antagonist of the present invention from an expression vector. In contrast, such an antagonist can be produced by a cell that is a "natural source" of said antagonist, and that lacks an expression vector.

A "fusion protein" is a hybrid protein expressed by a nucleic acid molecule comprising nucleotide sequences of at least two genes. For example, a fusion protein can comprise at least part of a IL-17RA polypeptide fused with a polypeptide that binds an affinity matrix. Such a fusion protein provides a means to isolate large quantities of IL-17RA using affinity chromatography.

The term "receptor" denotes a cell-associated protein that binds to a bioactive molecule termed a "ligand." This interaction mediates the effect of the ligand on the cell. Receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor). Membrane-bound receptors are characterized by a multi-domain structure comprising an extracellular ligand-binding domain and an intracellular effector domain that is typically involved in signal transduction. In certain membrane-bound receptors, the extracellular ligand-binding domain and the intracellular effector domain are located in separate polypeptides that comprise the complete functional receptor.

In general, the binding of ligand to receptor results in a conformational change in the receptor that causes an interaction between the effector domain and other molecule(s) in the cell, which in turn leads to an alteration in the metabolism of the cell. Metabolic events that are often linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids.

The term "secretory signal sequence" denotes a DNA sequence that encodes a peptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

An "isolated polypeptide" is a polypeptide that is essentially free from contaminating cellular components, such as carbohydrate, lipid, or other proteinaceous impurities associated with the polypeptide in nature. Typically, a preparation of isolated polypeptide contains the polypeptide in a highly purified form, i.e., at least about 80% pure, at least about 90% pure, at least about 95% pure, greater than 95% pure, such as 96%, 97%, or 98% or more pure, or greater than 99% pure. One way to show that a particular protein preparation contains an isolated polypeptide is by the appearance of a single band following sodium dodecyl sulfate (SDS)-polyacrylamide gel electrophoresis of the protein preparation and Coomassie Brilliant Blue staining of the gel. However, the term "isolated" does not exclude the presence of the same polypeptide in alternative physical forms, such as dimers or alternatively glycosylated or derivatized forms.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "expression" refers to the biosynthesis of a gene product. For example, in the case of a structural gene, expression involves transcription of the structural gene into mRNA and the translation of mRNA into one or more polypeptides.

As used herein, the term "immunomodulator" includes cytokines, stem cell growth factors, lymphotoxins, co-stimulatory molecules, hematopoietic factors, and the like, and synthetic analogs of these molecules.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of less than $10^9$ $M^{-1}$.

As used herein, a "therapeutic agent" is a molecule or atom which is conjugated to an antibody moiety to produce a conjugate which is useful for therapy. Examples of therapeutic agents include drugs, toxins, immunomodulators, chelators, boron compounds, photoactive agents or dyes, and radioisotopes.

A "detectable label" is a molecule or atom which can be conjugated to an antibody moiety to produce a molecule useful for diagnosis. Examples of detectable labels include chelators, photoactive agents, radioisotopes, fluorescent agents, paramagnetic ions, or other marker moieties.

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075 (1985); Nilsson et al., *Methods Enzymol.* 198:3 (1991)), glutathione S transferase (Smith and Johnson, *Gene* 67:31 (1988)), Glu-Glu affinity tag (Grussenmeyer et al., *Proc. Natl. Acad. Sci. USA* 82:7952 (1985)), substance P, FLAG peptide (Hopp et al., *Biotechnology* 6:1204 (1988)), streptavidin binding peptide, or other antigenic epitope or binding domain. See, in general, Ford et al., *Protein Expression and Purification* 2:95 (1991). DNA molecules encoding affinity tags are available from commercial suppliers (e.g., Pharmacia Biotech, Piscataway, N.J.).

A "target polypeptide" or a "target peptide" is an amino acid sequence that comprises at least one epitope, and that is expressed on a target cell, such as a tumor cell, or a cell that carries an infectious agent antigen. T cells recognize peptide epitopes presented by a major histocompatibility complex molecule to a target polypeptide or target peptide and typically lyse the target cell or recruit other immune cells to the site of the target cell, thereby killing the target cell.

Due to the imprecision of standard analytical methods, molecular weights and lengths of polymers are understood to be approximate values. When such a value is expressed as "about" X or "approximately" X, the stated value of X will be understood to be accurate to ±10%.

The antibodies of the invention comprise a first antibody portion that binds to IL-17A or IL-17F and second antibody portion that binds to IL-23 (via p19). In some embodiments, the antibodies of the invention specifically bind a monomeric form of both IL-17A or IL-17F. In some embodiments, the antibodies of the invention bind a homodimeric form of either IL-17A or IL-17F. In some embodiments, the antibodies of the invention bind a heterodimeric form of IL-17A/F. In still other embodiments, the antibodies of the invention specifically bind a multimeric form of IL-17 (e.g., a heterodimeric form). For instance, IL-17 can form a heterodimer with any other member of the IL-17 family of ligands, such as IL-17B, IL-17C, or IL-17F. In some embodiments, the antibodies of the invention bind a homodimeric or heterodimeric form of IL-23 (via binding to the p19 subunit) Preferred antibodies of the invention block the biological activities of IL-17A or IL-17F and IL-23, either singly or together.

The antibodies of the invention include portions of intact antibodies that retain antigen-binding specificity, for example, Fab fragments, Fab' fragments, F(ab')$_2$ fragments, F(v) fragments, heavy chain monomers or dimers, light chain monomers or dimers, dimers consisting of one heavy and one light chain, and the like. Thus, antigen binding fragments, as well as full-length dimeric or trimeric polypeptides derived from the above-described antibodies are themselves useful.

The direct use of rodent monoclonal antibodies (MAbs) as human therapeutic agents led to human anti-rodent antibody ("HARA") (for example, human anti-mouse antibody ("HAMA")) responses which occurred in a significant number of patients treated with the rodent-derived antibody (Khazaeli, et al., (1994) *Immunother.* 15:42-52) Chimeric antibodies containing fewer murine amino acid sequences are believed to circumvent the problem of eliciting an immune response in humans.

Refinement of antibodies to avoid the problem of HARA responses led to the development of "humanized antibodies." Humanized antibodies are produced by recombinant DNA technology, in which at least one of the amino acids of a human immunoglobulin light or heavy chain that is not required for antigen binding has been substituted for the corresponding amino acid from a nonhuman mammalian immunoglobulin light or heavy chain. For example, if the immunoglobulin is a mouse monoclonal antibody, at least one amino acid that is not required for antigen binding is substituted using the amino acid that is present on a corresponding human antibody in that position. Without wishing to be bound by any particular theory of operation, it is believed that the "humanization" of the monoclonal antibody inhibits human immunological reactivity against the foreign immunoglobulin molecule.

As a non-limiting example, a method of performing complementarity determining region (CDR) grafting may be performed by sequencing the mouse heavy and light chains of the antibody of interest that binds to the target antigen (e.g., IL-17 and/or IL-23/p19) and genetically engineering the CDR DNA sequences and imposing these amino acid sequences to corresponding human V regions by site directed mutagenesis. Human constant region gene segments of the desired isotype are added, and the "humanized" heavy and light chain genes are co-expressed in mammalian cells to produce soluble humanized antibody. A typical expression cell is a Chinese Hamster Ovary (CHO) cell. Suitable methods for creating the chimeric antibodies may be found, for example, in Jones et al. (1986) *Nature* 321:522-525; Riechmann (1988) *Nature* 332:323-327; Queen et al. (1989) *Proc. Nat. Acad. Sci. USA* 86:10029; and Orlandi et al. (1989) *Proc. Natl. Acad. Sci. USA* 86:3833.

Queen et al. (1989) Proc. *Nat. Acad. Sci. USA* 86:10029-10033 and WO 90/07861 describe the preparation of a humanized antibody. Human and mouse variable framework regions were chosen for optimal protein sequence homology. The tertiary structure of the murine variable region was computer-modeled and superimposed on the homologous human framework to show optimal interaction of amino acid residues with the mouse CDRs. This led to the development of antibodies with improved binding affinity for antigen (which is typically decreased upon making CDR-grafted chimeric antibodies). Alternative approaches to making humanized antibodies are known in the art and are described, for example, in Tempest (1991) *Biotechnology* 9:266-271.

The antibodies of the invention may be used alone or as immunoconjugates with a cytotoxic agent. In some embodiments, the agent is a chemotherapeutic agent. In some embodiments, the agent is a radioisotope, including, but not limited to Lead-212, Bismuth-212, Astatine-211, Iodine-131, Scandium-47, Rhenium-186, Rhenium-188, Yttrium-90, Iodine-123, Iodine-125, Bromine-77, Indium-111, and fissionable nuclides such as Boron-10 or an Actinide. In other embodiments, the agent is a toxin or cytotoxic drug, including but not limited to ricin, modified *Pseudomonas* enterotoxin A, calicheamicin, adriamycin, 5-fluorouracil, and the like. Methods of conjugation of antibodies and antibody fragments to such agents are known in the literature.

The antibodies of the invention include derivatives that are modified, e.g., by the covalent attachment of any type of molecule to the antibody such that covalent attachment does not prevent the antibody from binding to its epitope.

Examples of suitable derivatives include, but are not limited to fucosylated antibodies and fragments, glycosylated antibodies and fragments, acetylated antibodies and fragments, pegylated antibodies and fragments, phosphorylated antibodies and fragments, and amidated antibodies and fragments. The antibodies and derivatives thereof of the invention may themselves by derivatized by known protecting/blocking groups, proteolytic cleavage, linkage to a cellular ligand or other proteins, and the like. In some embodiments of the invention, at least one heavy chain of the antibody is fucosylated. In some embodiments, the fucosylation is N-linked. In some preferred embodiments, at least one heavy chain of the antibody comprises a fucosylated, N-linked oligosaccharide.

The antibodies of the invention include variants having single or multiple amino acid substitutions, deletions, additions, or replacements that retain the biological properties (e.g., block the binding of IL-17A or IL-17F and/or IL-23 to their respective receptors, block the biological activity of IL-17A or IL-17F and IL-23, binding affinity) of the antibodies of the invention. The skilled person can produce variants having single or multiple amino acid substitutions, deletions, additions or replacements. These variants may include, inter alia: (a) variants in which one or more amino acid residues are substituted with conservative or nonconservative amino acids, (b) variants in which one or more amino acids are added to or deleted from the polypeptide, (c) variants in which one or more amino acids include a substituent group, and (d) variants in which the polypeptide is fused with another peptide or polypeptide such as a fusion partner, a protein tag or other chemical moiety, that may confer useful properties to the polypeptide, such as, for example, an epitope for an antibody, a polyhistidine sequence, a biotin moiety and the like. Antibodies of the invention may include variants in which amino acid residues from one species are substituted for the corresponding residue in another species, either at the conserved or nonconserved positions. In another embodiment, amino acid residues at nonconserved positions are substituted with conservative or nonconservative residues. The techniques for obtaining these variants, including genetic (suppressions, deletions, mutations, etc.), chemical, and enzymatic techniques, are known to the person having ordinary skill in the art. Antibodies of the invention also include antibody fragments. A "fragment" refers to polypeptide sequences which are preferably at least about 40, more preferably at least to about 50, more preferably at least about 60, more preferably at least about 70, more preferably at least about 80, more preferably at least about 90, and more preferably at least about 100 amino acids in length, and which retain some biological activity or immunological activity of the full-length sequence, for example, the ability to block the binding of IL-17 and/or IL-23 to their respective receptors, block the biological activity of IL-17 and IL-23, binding affinity.

The invention also encompasses fully human antibodies such as those derived from peripheral blood mononuclear cells of ovarian, breast, renal, colorectal, lung, endometrial, or brain cancer patients. Such cells may be fused with myeloma cells, for example, to form hybridoma cells producing fully human antibodies against both IL-17A or IL-17F and IL-23/p19.

The invention also encompasses bispecific antibodies that bind to both IL-17A or IL-17F and IL-23 (via p19).

The antibodies of the invention are preferably nontoxic as demonstrated, for example, in in vivo toxicology studies.

The antibodies and derivatives thereof of the invention have binding affinities that include a dissociation constant ($K_d$) of less than $1 \times 10^{-2}$. In some embodiments, the $K_d$ is less than $1 \times 10^{-3}$. In other embodiments, the $K_d$ is less than $1 \times 10^{4}$. In some embodiments, the $K_d$ is less than $1 \times 10^{-5}$. In still other embodiments, the $K_d$ is less than $1 \times 10^{-6}$. In other embodiments, the $K_d$ is less than $1 \times 10^{-7}$. In other embodiments, the $K_d$ is less than $1 \times 10^{-8}$. In other embodiments, the v is less than $1 \times 10^{-9}$. In other embodiments, the v is less than $1 \times 10^{-10}$. In still other embodiments, the $K_d$ is less than $1 \times 10^{-11}$. In some embodiments, the $K_d$ is less than $1 \times 10^{-12}$. In other embodiments, the $K_d$ is less than $1 \times 10^{-13}$. In other embodiments, the $K_d$ is less than $1 \times 10^{-14}$. In still other embodiments, the $K_d$ is less than $1 \times 10^{-15}$.

The invention also includes nucleic acids encoding the heavy chain and/or light chain of the antibodies of the invention. Nucleic acids of the invention include nucleic acids having at least 80%, more preferably at least about 90%, more preferably at least about 95%, and most preferably at least about 98% homology to nucleic acids of the invention. The terms "percent similarity", "percent identity" and "percent homology" when referring to a particular sequence are used as set forth in the University of Wisconsin GCG software program. Nucleic acids of the invention also include complementary nucleic acids. In some instances, the sequences will be fully complementary (no mismatches) when aligned. In other instances, there may be up to about a 20% mismatch in the sequences. In some embodiments of the invention are provided nucleic acids encoding both a heavy chain and a light chain of an antibody of the invention.

Nucleic acids of the invention can be cloned into a vector, such as a plasmid, cosmid, bacmid, phage, artificial chromosome (BAC, YAC) or virus, into which another genetic sequence or element (either DNA or RNA) may be inserted so as to bring about the replication of the attached sequence or element. In some embodiments, the expression vector contains a constitutively active promoter segment (such as but not limited to CMV, SV40, Elongation Factor or LTR sequences) or an inducible promoter sequence such as the steroid inducible pIND vector (Invitrogen), where the expression of the nucleic acid can be regulated. Expression vectors of the invention may further comprise regulatory sequences, for example, an internal ribosomal entry site. The expression vector can be introduced into a cell by transfection, for example.

The invention also provides methods of producing antibodies, including monoclonal antibodies that specifically bind to IL-17A or IL-17F and IL-23p19, either singly or together. Antibodies of the invention may be produced in vivo or in vitro. Standard methods are known for creating monoclonal antibodies including, but are not limited to, the hybridoma technique (see Kohler & Milstein, (1975) *Nature* 256:495-497); the trioma technique; the human B-cell hybridoma technique (see Kozbor et al. (1983) *Immunol. Today* 4:72) and the EBV hybridoma technique to produce human monoclonal antibodies (see Cole, et al. in MONOCLONAL ANTIBODIES AND CANCER THERAPY, Alan R. Liss, Inc., 1985, pp. 77-96).

Both IL-17F and IL-23 may be purified from cells or from recombinant systems using a variety of well-known techniques for isolating and purifying proteins. For example, but not by way of limitation, both IL-17F and IL-23 may be isolated based on the apparent molecular weight of the protein by running the protein on an SDS-PAGE gel and blotting the proteins onto a membrane. Thereafter, the appropriate size band corresponding to either protein may be cut from the membrane and used as an immunogen in animals directly, or by first extracting or eluting the protein from the membrane.

As an alternative example, the protein may be isolated by size-exclusion chromatography alone or in combination with other means of isolation and purification.

The invention also provides methods of producing monoclonal antibodies that specifically bind to homodimeric, heterodimeric, and/or multimeric forms of both IL-17F and IL-23/p19. These different forms may be purified from cells or from recombinant systems using a variety of well-known techniques for isolating and purifying proteins. For example, but not by way of limitation, both IL-17F and IL-23/p19 may be isolated based on the apparent molecular weight of the protein by running the protein on an SDS-PAGE gel and blotting the proteins onto a membrane. Thereafter, the appropriate size band corresponding to each may be cut from the membrane and used as an immunogen in animals directly, or by first extracting or eluting the protein from the membrane. As an alternative example, the protein may be isolated by size-exclusion chromatography alone or in combination with other means of isolation and purification.

Other means of purification are available in such standard reference texts as Zola, Monoclonal Antibodies: Preparation And Use Of Monoclonal Antibodies And Engineered Antibody Derivatives (Basics: From Background To Bench) Springer-Verlag Ltd., New York, 2000; Basic Methods In Antibody Production And Characterization, Chapter 11, "Antibody Purification Methods," Howard and Bethell, Eds., CRC Press, 2000; Antibody Engineering (Springer Lab Manual.), Kontermann and Dubel, Eds., Springer-Verlag, 2001.

For in vivo antibody production, animals are generally immunized with either IL-17A, IL-17F, or IL-23 or an immunogenic portion of either. The antigen is generally combined with an adjuvant to promote immunogenicity. Adjuvants vary according to the species used for immunization. Examples of adjuvants include, but are not limited to: Freund's complete adjuvant ("FCA"), Freund's incomplete adjuvant ("FIA"), mineral gels (e.g., aluminum hydroxide), surface active substances (e.g., lysolecithin, pluronic polyols, polyanions), peptides, oil emulsions, keyhole limpet hemocyanin ("KLH"), dinitrophenol ("DNP"), and potentially useful human adjuvants such as Bacille Calmette-Guerin ("BCG") and *corynebacterium parvum*. Such adjuvants are also well known in the art. Immunization may be accomplished using well-known procedures. The dose and immunization regimen will depend on the species of mammal immunized, its immune status, body weight, and/or calculated surface area, etc. Typically, blood serum is sampled from the immunized mammals and assayed for anti-IL-17 and IL-23/p19 antibodies using appropriate screening assays as described below, for example.

A common method for producing humanized antibodies is to graft CDR sequences from a MAb (produced by immunizing a rodent host) onto a human Ig backbone, and transfection of the chimeric genes into Chinese Hamster Ovary (CHO) cells which in turn produce a functional Ab that is secreted by the CHO cells (Shields, R. L., et al. (1995) Anti-IgE monoclonal antibodies that inhibit allergen-specific histamine release. *Int Arch. Allergy Immunol.* 107:412-413). The methods described within this application are also useful for generating genetic alterations within Ig genes or chimeric Igs transfected within host cells such as rodent cell lines, plants, yeast and prokaryotes (Frigerio L, et al. (2000) Assembly, secretion, and vacuolar delivery of a hybrid immunoglobulin in plants. *Plant Physiol.* 123:1483-1494).

Splenocytes from immunized animals may be immortalized by fusing the splenocytes (containing the antibody-producing B cells) with an immortal cell line such as a myeloma line. Typically, myeloma cell line is from the same species as the splenocyte donor. In one embodiment, the immortal cell line is sensitive to culture medium containing hypoxanthine, aminopterin and thymidine ("HAT medium"). In some embodiments, the myeloma cells are negative for Epstein-Barr virus (EBV) infection. In preferred embodiments, the myeloma cells are HAT-sensitive, EBV negative and Ig expression negative. Any suitable myeloma may be used. Murine hybridomas may be generated using mouse myeloma cell lines (e.g., the P3-NS1/1-Ag4-1, P3-x63-Ag8.653 or Sp2/O-Ag14 myeloma lines). These murine myeloma lines are available from the ATCC. These myeloma cells are fused to the donor splenocytes polyethylene glycol ("PEG"), preferably 1500 molecular weight polyethylene glycol ("PEG 1500"). Hybridoma cells resulting from the fusion are selected in HAT medium which kills unfused and unproductively fused myeloma cells. Unfused splenocytes die over a short period of time in culture. In some embodiments, the myeloma cells do not express immunoglobulin genes.

Hybridomas producing a desired antibody which are detected by screening assays such as those described below may be used to produce antibodies in culture or in animals. For example, the hybridoma cells may be cultured in a nutrient medium under conditions and for a time sufficient to allow the hybridoma cells to secrete the monoclonal antibodies into the culture medium. These techniques and culture media are well known by those skilled in the art. Alternatively, the hybridoma cells may be injected into the peritoneum of an unimmunized animal. The cells proliferate in the peritoneal cavity and secrete the antibody, which accumulates as ascites fluid. The ascites fluid may be withdrawn from the peritoneal cavity with a syringe as a rich source of the monoclonal antibody.

Hybridomas expressing mouse monoclonal antibodies that cross bind to human IL-17A and human IL-17F were produced using methods similar to those described above were deposited with the American Type Tissue Culture Collection (ATCC; Manassas Va.) patent depository as original deposits under the Budapest Treaty and were given the following ATCC Accession No.s: clone 339.15.5.3 (ATCC Patent Deposit Designation PTA-7987, deposited on Nov. 7, 2006); clone 339.15.3.6 (ATCC Patent Deposit Designation PTA-7988, deposited on Nov. 7, 2006); and clone 339.15.6.16 (ATCC Patent Deposit Designation PTA-7989, deposited on Nov. 7, 2006. These monoclonal antibodies and hybridomas are further described in co-owned US Patent Publication No. 2007-0218065, published Sep. 20, 2007 and in U.S. patent application Ser. No. 11/741,189, filed Apr. 27, 2007, herein incorporated by reference.

Another non-limiting method for producing human antibodies is described in U.S. Pat. No. 5,789,650 which describes transgenic mammals that produce antibodies of another species (e.g., humans) with their own endogenous immunoglobulin genes being inactivated. The genes for the heterologous antibodies are encoded by human immunoglobulin genes. The transgenes containing the unrearranged immunoglobulin encoding regions are introduced into a non-human animal. The resulting transgenic animals are capable of functionally rearranging the transgenic immunoglobulin sequences and producing a repertoire of antibodies of various isotypes encoded by human immunoglobulin genes. The B-cells from the transgenic animals are subsequently immortalized by any of a variety of methods, including fusion with an immortalizing cell line (e.g., a myeloma cell).

The antibodies of the present invention may also be prepared in vitro using a variety of techniques known in the art. For example, but not by way of limitation, fully human monoclonal antibodies against IL-17A or IL-17F and IL-23/p19 may be prepared by using in vitro-primed human splenocytes (Boerner et al. (1991) *J. Immunol.* 147:86-95).

Alternatively, for example, the antibodies of the invention may be prepared by "repertoire cloning" (Persson et al. (1991) *Proc. Nat. Acad. Sci. USA* 88:2432-2436; and Huang and Stollar (1991) *J. Immunol. Methods* 141:227-236). Further, U.S. Pat. No. 5,798,230 describes preparation of human monoclonal antibodies from human B antibody-producing B cells that are immortalized by infection with an Epstein-Barr virus that expresses Epstein-Barr virus nuclear antigen 2 (EBNA2). EBNA2, required for immortalization, is then inactivated resulting in increased antibody titers.

In another embodiment, antibodies of the invention are formed by in vitro immunization of peripheral blood mononuclear cells ("PBMCs"). This may be accomplished by any means known in the art, such as, for example, using methods described in the literature (Zafiropoulos et al. (1997) *J. Immunological Methods* 200:181-190).

Within an aspect the invention provides a method for inhibiting inflammation in a mammal comprising administering an antagonist of IL-23 and an antagonist of IL-17A or IL-17F to the mammal, wherein the antagonist of IL-17A or IL-17F can bind IL-17A or IL-17F. Within an embodiment, the antagonist of IL-17A or IL-17F is an antibody or antibody fragment. Within another embodiment, the antibody or antibody fragment is a cross-reactive antibody to IL-17A and IL-17F. Within another embodiment the antagonist of IL-23 binds the p19 subunit. Within an embodiment the antagonist of IL-23 is an antibody or antibody fragment.

The invention provides a method for inhibiting inflammation in a mammal comprising administering an antagonist of IL2-3 and an antagonist of IL-17A or IL-17F, wherein the antagonist of IL-17A or IL-17F comprises an antibody or antibody fragment comprising a HCDR1 amino acid sequence, a HCDR2 amino acid sequence, and a HCDR3 amino acid sequence of the variable heavy region selected from the group consisting of: the variable heavy region of the hybridoma of ATCC Patent Deposit Designation PTA-7987; the variable heavy region of the hybridoma of ATCC Patent Deposit Designation PTA-7988; and the variable heavy region of the hybridoma of ATCC Patent Deposit Designation PTA-7989 and wherein the variable light region comprises a LCDR1 amino acid sequence, a LCDR2 amino acid sequence, and a LCDR3 amino acid sequence of the variable light region selected from the group consisting of: the variable light region of the hybridoma of ATCC Patent Deposit Designation PTA-7987; the variable light region of the hybridoma of ATCC Patent Deposit Designation PTA-7988; and the variable light region of the hybridoma of ATCC Patent Deposit Designation PTA-7989. Within an embodiment the antibody or antibody fragment that binds IL-17A or IL-17F comprises an amino acid sequence of the variable heavy region selected from the group consisting of: a) the variable heavy region of the hybridoma of ATCC Patent Deposit Designation PTA-7987; the variable heavy region of the hybridoma of ATCC Patent Deposit Designation PTA-7988; and the variable heavy region of the hybridoma of ATCC Patent Deposit Designation PTA-7989. Within a different embodiment, the antibody or antibody fragment that binds IL-17A or IL-17F comprises an amino acid sequence of the variable light region selected from the group consisting of: the variable light region of the hybridoma of ATCC Patent Deposit Designation PTA-7987; the variable light region of the hybridoma of ATCC Patent Deposit Designation PTA-7988; and the variable light region of the hybridoma of ATCC Patent Deposit Designation PTA-7989. Within an embodiment the antagonist of IL2-3 and the antagonist of IL-17A or IL-17F are contained on one molecule.

The invention provides a method for inhibiting inflammation in a mammal comprising administering an antagonist of IL2-3 and an antagonist of IL-17A or IL-17F, wherein the antagonist of IL-17A or IL-17F comprises an antibody or antibody fragment comprising an amino acid sequence of the variable heavy region and an amino acid sequence of the variable light region and wherein the amino acid sequence of the variable heavy region is selected from the group consisting of: the amino acid sequence of the variable heavy region of the hybridoma of ATCC Patent Deposit Designation PTA-7987; the amino acid sequence of the variable heavy region of the hybridoma of ATCC Patent Deposit Designation PTA-7988; and the amino acid sequence of the variable heavy region of the hybridoma of ATCC Patent Deposit Designation PTA-7989 and wherein the variable light region comprises the amino acid sequence of the variable light region selected from the group consisting of: the amino acid sequence of the variable light region of the hybridoma of ATCC Patent Deposit Designation PTA-7987; the amino acid sequence of the variable light region of the hybridoma of ATCC Patent Deposit Designation PTA-7988; and the amino acid sequence of the variable light region of the hybridoma of ATCC Patent Deposit Designation PTA-7989. Within an embodiment the antagonist of IL2-3 and the antagonist of IL-17A or IL-17F are contained on one molecule.

Within aspects, the antibody or antibody fragment is humanized. Within other aspects the antibody is chimeric. Within other aspects the antibody fragment is selected from the group consisting of Fv, Fab, Fab', F(ab)$_2$, and F(ab')2.

The invention provides a method for inhibiting inflammation in a mammal comprising administering an antagonist of IL2-3 and an antagonist of IL-17A or IL-17F, wherein the antagonist of IL-23 comprises an antibody or antibody fragment that binds the p19 subunit of IL-23 and wherein the antibody or antibody fragment comprises a HCDR1 amino acid sequence, a HCDR2 amino acid sequence, and a HCDR3 amino acid sequence of the amino acid sequence of variable heavy region as shown in SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 116, SEQ ID NO: 118, SEQ ID NO: 120, SEQ ID NO: 122, SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142, SEQ ID NO: 144, SEQ ID NO: 146, SEQ ID NO: 148, SEQ ID NO: 150, SEQ ID NO: 152, SEQ ID NO: 154, SEQ ID NO: 156, SEQ ID NO: 158, SEQ ID NO: 160, SEQ ID NO: 162, SEQ ID NO: 164, SEQ ID NO: 166, SEQ ID NO: 168, SEQ ID NO: 170, SEQ ID NO: 172, SEQ ID NO: 174, SEQ ID NO: 176, SEQ ID NO: 178, SEQ ID NO: 180, SEQ ID NO: 182, SEQ ID NO: 184, SEQ ID NO: 186, SEQ ID NO: 187, SEQ ID NO: 189, SEQ ID NO: 191, SEQ ID NO: 193, SEQ ID NO: 195, SEQ ID NO: 197, SEQ ID NO: 199, SEQ ID NO: 201, SEQ ID NO: 203, SEQ ID NO: 205, SEQ ID NO: 207, SEQ ID NO: 209, SEQ ID NO: 211, SEQ ID NO: 213, SEQ ID NO: 215, SEQ ID NO: 217, SEQ ID NO: 219, SEQ ID NO: 221, SEQ ID NO: 223, SEQ ID NO: 225, SEQ ID NO: 227, SEQ ID NO: 229, SEQ ID NO: 231, SEQ ID NO: 233, SEQ ID NO: 235, SEQ ID NO: 237, SEQ ID NO: 239, SEQ ID NO: 241, SEQ ID NO: 243, SEQ ID NO: 245, SEQ ID NO: 247, SEQ ID NO: 249, SEQ ID NO: 251, SEQ ID NO: 253, SEQ ID NO: 255, SEQ ID NO: 257, SEQ ID NO: 259, SEQ ID NO: 261, SEQ ID NO: 265, SEQ ID NO: 267, and SEQ ID NO: 268 and wherein the variable light region comprises a LCDR1 amino acid sequence, a LCDR2 amino acid sequence, and a LCDR3 amino acid sequence of the amino acid sequence of variable light region as shown in SEQ ID NO:7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO:85, SEQ ID NO: 87, SEQ ID NO: 89, SEQ ID NO: 91, SEQ ID NO: 93, SEQ ID NO:95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 115, SEQ ID NO: 117, SEQ ID NO: 119, SEQ ID NO: 121, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 155, SEQ ID NO: 157, SEQ ID NO: 159, SEQ ID NO: 161, SEQ ID NO: 163, SEQ ID NO: 165, SEQ ID NO: 167, SEQ ID NO: 169, SEQ ID NO: 171, SEQ ID NO: 173, SEQ ID NO: 175, SEQ ID NO: 177, SEQ ID NO: 179, SEQ ID NO: 181, SEQ ID NO: 183, SEQ ID NO: 185, SEQ ID NO: 188, SEQ ID NO: 190, SEQ ID NO: 192, SEQ ID NO: 194, SEQ ID NO: 196, SEQ ID NO: 198, SEQ ID NO: 200, SEQ ID NO: 202, SEQ ID NO: 204, SEQ ID NO: 206, SEQ ID NO: 208, SEQ ID NO: 210, SEQ ID NO: 212, SEQ ID NO: 214, SEQ ID NO: 216, SEQ ID NO: 218, SEQ ID NO: 220, SEQ ID NO: 222, SEQ ID NO: 224, SEQ ID NO: 226, SEQ ID NO: 228, SEQ ID NO: 230, SEQ ID NO: 232, SEQ ID NO: 234, SEQ ID NO: 236, SEQ ID NO: 238, SEQ ID NO: 240, SEQ ID NO: 242, SEQ ID NO: 244, SEQ ID NO: 246, SEQ ID NO: 248, SEQ ID NO: 250, SEQ ID NO: 252, SEQ ID NO: 254, SEQ ID NO: 256, SEQ ID NO: 258, SEQ ID NO: 260, SEQ ID NO: 262, SEQ ID NO: 263, SEQ ID NO: 264, or SEQ ID NO: 266. Within an embodiment the antagonist of IL2-3 and the antagonist of IL-17A or IL-17F are contained on one molecule. Within an embodiment the variable heavy region of the antibody or antibody fragment that binds the p19 subunit of IL-23 comprises an amino acid sequence as shown in SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106v 108, SEQ ID NO: 110, SEQ ID NO: 112, SEQ ID NO: 114, SEQ ID NO: 116, SEQ ID NO: 118, SEQ ID NO: 120, SEQ ID NO: 122, SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142, SEQ ID NO: 144, SEQ ID NO: 146, SEQ ID NO: 148, SEQ ID NO: 150, SEQ ID NO: 152, SEQ ID NO: 154, SEQ ID NO: 156, SEQ ID NO: 158, SEQ ID NO: 160, SEQ ID NO: 162, SEQ ID NO: 164, SEQ ID NO: 166, SEQ ID NO: 168, SEQ ID NO: 170, SEQ ID NO: 172, SEQ ID NO: 174, SEQ ID NO: 176, SEQ ID NO: 178, SEQ ID NO: 180, SEQ ID NO: 182, SEQ ID NO: 184, SEQ ID NO: 186, SEQ ID NO: 187, SEQ ID NO: 189, SEQ ID NO: 191, SEQ ID NO: 193, SEQ ID NO: 195, SEQ ID NO: 197, SEQ ID NO: 199, SEQ ID NO: 201, SEQ ID NO: 203, SEQ ID NO: 205, SEQ ID NO: 207, SEQ ID NO: 209, SEQ ID NO: 211, SEQ ID NO: 213, SEQ ID NO: 215, SEQ ID NO: 217, SEQ ID NO: 219, SEQ ID NO: 221, SEQ ID NO: 223, SEQ ID NO: 225, SEQ ID NO: 227, SEQ ID NO: 229, SEQ ID NO: 231, SEQ ID NO: 233, SEQ ID NO: 235, SEQ ID NO: 237, SEQ ID NO: 239, SEQ ID NO: 241, SEQ ID NO: 243, SEQ ID NO: 245, SEQ ID NO: 247, SEQ ID NO: 249, SEQ ID NO: 251, SEQ ID NO: 253, SEQ ID NO: 255, SEQ ID NO: 257, SEQ ID NO: 259, SEQ ID NO: 261, SEQ ID NO: 265, SEQ ID NO: 267, and SEQ ID NO: 268. Within an embodiment the variable light region of the antibody or antibody fragment that binds the p19 subunit of IL-23 comprises an amino acid sequence as shown in SEQ ID NO:7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO:85, SEQ ID NO: 87, SEQ ID NO: 89, SEQ ID NO: 91, SEQ ID NO: 93, SEQ ID NO:95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 115, SEQ ID NO: 117, SEQ ID NO: 119, SEQ ID NO: 121, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 155, SEQ ID NO: 157, SEQ ID NO: 159, SEQ ID NO: 161, SEQ ID NO: 163, SEQ ID NO: 165, SEQ ID NO: 167, SEQ ID NO: 169, SEQ ID NO: 171, SEQ ID NO: 173, SEQ ID NO: 175, SEQ ID NO: 177, SEQ ID NO: 179, SEQ ID NO: 181, SEQ ID NO: 183, SEQ ID NO: 185, SEQ ID NO: 188, SEQ ID NO: 190, SEQ ID NO: 192, SEQ ID NO: 194, SEQ ID NO: 196, SEQ ID NO: 198, SEQ ID NO: 200, SEQ ID NO: 202, SEQ ID NO: 204, SEQ ID NO: 206, SEQ ID NO: 208, SEQ ID NO: 210, SEQ ID NO: 212, SEQ ID NO: 214, SEQ ID NO: 216, SEQ ID NO: 218, SEQ ID NO: 220, SEQ ID NO: 222, SEQ ID NO: 224, SEQ ID NO: 226, SEQ ID NO: 228, SEQ ID NO: 230, SEQ ID NO: 232, SEQ ID NO: 234, SEQ ID NO: 236, SEQ ID NO: 238, SEQ ID NO: 240, SEQ ID NO: 242, SEQ ID NO: 244, SEQ ID NO: 246, SEQ ID NO: 248, SEQ ID NO: 250, SEQ ID NO: 252, SEQ ID NO: 254, SEQ ID NO: 256, SEQ ID NO: 258, SEQ ID NO: 260, SEQ ID NO: 262, SEQ ID NO: 263, SEQ ID NO: 264, or SEQ ID NO: 266. Within an embodiment the antagonist of IL2-3 and the antagonist of IL-17A or IL-17F are contained on one molecule.

The invention provides a method of inhibiting inflammation comprising administering an antagonist to a mammal wherein the antagonist is an antibody or antibody fragment that binds the p19 subunit of IL-23 comprises a variable heavy region and a variable light region and wherein the amino acid sequence of the variable heavy region is shown in SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78 SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 10214, SEQ ID NO: 10416, SEQ ID NO: 106v 108, SEQ ID NO: 110, SEQ ID NO: 112, SEQ ID NO: 114, SEQ ID NO: 116, SEQ ID NO: 118, SEQ ID NO: 120, SEQ ID NO: 122, SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142, SEQ ID NO: 144, SEQ ID NO: 146, SEQ ID NO: 148, SEQ ID NO: 150, SEQ ID NO: 152, SEQ ID NO: 154, SEQ ID NO: 156, SEQ ID NO: 158, SEQ ID NO: 160, SEQ ID NO: 162, SEQ ID NO: 164, SEQ ID NO: 166, SEQ ID NO: 168, SEQ ID NO: 170, SEQ ID NO: 172, SEQ ID NO: 174, SEQ ID NO: 176, SEQ ID NO: 178, SEQ ID NO: 180, SEQ ID NO: 182, SEQ ID NO: 184, SEQ ID NO: 186, SEQ ID NO: 187, SEQ ID NO: 189, SEQ ID NO: 191, SEQ ID NO: 193, SEQ ID NO: 195, SEQ ID NO: 197, SEQ ID NO: 199, SEQ ID NO: 201, SEQ ID NO: 203, SEQ ID NO: 205, SEQ ID NO: 207, SEQ ID NO: 209, SEQ ID NO: 211, SEQ ID NO: 213, SEQ ID NO: 215, SEQ ID NO: 217, SEQ ID NO: 219, SEQ ID NO: 221, SEQ ID NO: 223, SEQ ID NO: 225, SEQ ID NO: 227, SEQ ID NO: 229, SEQ ID NO: 231, SEQ ID NO: 233, SEQ ID NO: 235, SEQ ID NO: 237, SEQ ID NO: 239, SEQ ID NO: 241, SEQ ID NO: 243, SEQ ID NO: 245, SEQ ID NO: 247, SEQ ID NO: 249, SEQ ID NO: 251, SEQ ID NO: 253, SEQ ID NO: 255, SEQ ID NO: 257, SEQ ID NO: 259, SEQ ID NO: 261, SEQ ID NO: 265, SEQ ID NO: 267, and SEQ ID NO: 268 and wherein the amino acid sequence of the variable light region is shown in SEQ ID NO:7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO:85, SEQ ID NO: 87, SEQ ID NO: 89, SEQ ID NO: 91, SEQ ID NO: 93, SEQ ID NO:95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 115, SEQ ID NO: 117, SEQ ID NO: 119, SEQ ID NO: 121, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 155, SEQ ID NO: 157, SEQ ID NO: 159, SEQ ID NO: 161, SEQ ID NO: 163, SEQ ID NO: 165, SEQ ID NO: 167, SEQ ID NO: 169, SEQ ID NO: 171, SEQ ID NO: 173, SEQ ID NO: 175, SEQ ID NO: 177, SEQ ID NO: 179, SEQ ID NO: 181, SEQ ID NO: 183, SEQ ID NO: 185, SEQ ID NO: 188, SEQ ID NO: 190, SEQ ID NO: 192, SEQ ID NO: 194, SEQ ID NO: 196, SEQ ID NO: 198, SEQ ID NO: 200, SEQ ID NO: 202, SEQ ID NO: 204, SEQ ID NO: 206, SEQ ID NO: 208, SEQ ID NO: 210, SEQ ID NO: 212, SEQ ID NO: 214, SEQ ID NO: 216, SEQ ID NO: 218, SEQ ID NO: 220, SEQ ID NO: 222, SEQ ID NO: 224, SEQ ID NO: 226, SEQ ID NO: 228, SEQ ID NO: 230, SEQ ID NO: 232, SEQ ID NO: 234, SEQ ID NO: 236, SEQ ID NO: 238, SEQ ID NO: 240, SEQ ID NO: 242, SEQ ID NO: 244, SEQ ID NO: 246, SEQ ID NO: 248, SEQ ID NO: 250, SEQ ID NO: 252, SEQ ID NO: 254, SEQ ID NO: 256, SEQ ID NO: 258, SEQ ID NO: 260, SEQ ID NO: 262, SEQ ID NO: 263, SEQ ID NO: 264, or SEQ ID NO: 266. Within an embodiment the antagonist of IL2-3 and the antagonist of IL-17A or IL-17F are contained on one molecule.

The invention provides a method for inhibiting inflammation in a mammal comprising administering an antagonist of IL-23 and an antagonist of IL-17A or IL-17F to the mammal, wherein the antagonist of IL-17A or IL-17F can bind IL-17A or IL-17F, and wherein the inflammation is associated with a disease selected from the group consisting of multiple sclerosis (MS), chronic inflammation, autoimmune diabetes, rheumatoid arthritis (RA) and other arthritic conditions, asthma, systhemic lupus erythrematosus, psoriasis, Crohn's Disease, ulcerative colitis, irritable bowel syndrome (IBS) and inflammatory bowel disease (IBD).

The invention provides an antibody or antibody fragment that is a single chain antibody. The invention provides an antibody or antibody fragment that is a bispecific antibody. The invention provides an antibody that is a tascFv, a biscFv, or a BiAb antibody.

The invention provides a method for inhibiting inflammation in a mammal comprising administering an antagonist of IL-23 and an antagonist of IL-17A or IL-17F to the mammal, wherein the antagonist of IL-17A or IL-17F can bind IL-17A or IL-17F, and wherein the antibody or antibody fragment binds an IL-17F epitope, wherein said epitope is selected from the group consisting of: a) an epitope comprising amino acid residues 23, 25, 27, 29 and 34 of SEQ ID NO:6; b) an epitope comprising amino acid residues 23-34 of SEQ ID NO:6; c) an epitope comprising amino acid residues 67-73 of SEQ ID NO:6; d) an epitope comprising amino acid residues 79-85 of SEQ ID NO:6; e) an epitope comprising amino acid residues 146-152 of SEQ ID NO:4; f) an epitope comprising at least one amino acid residue from residues 105-109 and at least one amino acid residue from residues 147-152 of SEQ ID NO:6; g) an epitope comprising at least one amino acid residue from residues 79-85, and at least one amino acid residue from residues 119-122 and at least one amino acid residue from residues 130-134 of SEQ ID NO:6; h) an epitope comprising amino acid residues 34 to 41 of SEQ ID NO: 6; i)

an epitope comprising amino acid residues 52 to 64 of SEQ ID NO: 6; and j) an epitope comprising amino acid residues 77 to 85 of SEQ ID NO: 6.

The invention provides a method for inhibiting inflammation in a mammal comprising administering an antagonist of IL-23 and an antagonist of IL-17A or IL-17F to the mammal, wherein the antagonist of IL-17A or IL-17F can bind IL-17A or IL-17F, and wherein the antibody or antibody fragment binds an IL-17A epitope, wherein said epitope is selected from the group consisting of: a) an epitope comprising amino acid residues 23, 25, 27, 29 and 34 of SEQ ID NO:2; b) an epitope comprising amino acid residues 20-31 of SEQ ID NO:2; c) an epitope comprising amino acid residues 69-75 of SEQ ID NO:2; d) an epitope comprising amino acid residues 81-87 of SEQ ID NO:2; e) an epitope comprising amino acid residues 148-154 of SEQ ID NO:2; f) an epitope comprising at least one amino acid residue from residues 107-111 and at least one amino acid residue from residues 149-154 of SEQ ID NO:2; g) an epitope comprising at least one amino acid residue from residues 81-87 and at least one amino acid residue from residues 121-124 and at least one amino acid residue from residues 132-136 of SEQ ID NO:2; h) an epitope comprising amino acid residues 34 to 41 of SEQ ID NO: 2; i) an epitope comprising amino acid residues 52 to 64 of SEQ ID NO: 2; and j) an epitope comprising amino acid residues 77 to 85 of SEQ ID NO: 2.

The invention provides a method for inhibiting inflammation in a mammal comprising administering an antagonist of IL-23 and an antagonist of IL-17A or IL-17F to the mammal, wherein the antagonist of IL-17A or IL-17F can bind IL-17A or IL-17F, and wherein the antibody or antibody fragment binds an IL-1723 epitope, wherein said epitope is selected from the group consisting of: a) an epitope comprising amino acid residues 55 to 66 of SEQ ID NO: 4; b) an epitope comprising amino acid residues 74 to 85 of SEQ ID NO: 4; and c) an epitope comprising amino acid residues 155 to 164 of SEQ ID NO: 4.

Within an aspect the antibody or antibody fragment also comprises a PEG moiety. Within an aspect the antibody or antibody fragment also comprises an Fc moiety. Within an aspect the antibody or antibody fragment is bivalent, trivalent, or tetravalent.

The invention provides a method for treating disease characterized by elevated expression of IL-17A, IL-17F or IL-23 in a mammalian subject, comprising administering to said subject an effective amount of an antagonist of IL-17A, IL-17F and IL-23.

The invention provides an antagonist of IL-23 and of IL-17A or IL-17F comprising a an antibody or antibody fragment that binds the p19 subunit of IL-23 as shown in SEQ ID NO: 4 and that comprises an antibody or antibody fragment that binds IL-17A as shown in SEQ ID NO: 2 or that binds IL-17F as shown in SEQ ID NO: 6. Within an embodiment the antibody or antibody fragment that binds IL-17A is a cross-reactive antibody that binds IL-17F.

The invention provides an antagonist of IL-23 and of IL-17A or IL-17F comprising an antibody or antibody fragment that binds IL-17A or IL-17F wherein the antibody or antibody fragment comprises a HCDR1 amino acid sequence, a HCDR2 amino acid sequence, and a HCDR3 amino acid sequence of the variable heavy region selected from the group consisting of: a) the variable heavy region of the hybridoma of ATCC Patent Deposit Designation PTA-7987; b) the variable heavy region of the hybridoma of ATCC Patent Deposit Designation PTA-7988; and c) the variable heavy region of the hybridoma of ATCC Patent Deposit Designation PTA-7989 and wherein the variable light region comprises a LCDR1 amino acid sequence, a LCDR2 amino acid sequence, and a LCDR3 amino acid sequence of the variable light region selected from the group consisting of: d) the variable light region of the hybridoma of ATCC Patent Deposit Designation PTA-7987; e) the variable light region of the hybridoma of ATCC Patent Deposit Designation PTA-7988; and f) the variable light region of the hybridoma of ATCC Patent Deposit Designation PTA-7989. Within an embodiment the antibody or antibody fragment that binds IL-17A or IL-17F comprises an amino acid sequence of the variable heavy region selected from the group consisting of: a. the variable heavy region of the hybridoma of ATCC Patent Deposit Designation PTA-7987; b. the variable heavy region of the hybridoma of ATCC Patent Deposit Designation PTA-7988; and c. the variable heavy region of the hybridoma of ATCC Patent Deposit Designation PTA-7989. Within another embodiment, the antibody or antibody fragment that binds IL-17A or IL-17F comprises an amino acid sequence of the variable light region selected from the group consisting of: a. the variable light region of the hybridoma of ATCC Patent Deposit Designation PTA-7987; b. the variable light region of the hybridoma of ATCC Patent Deposit Designation PTA-7988; and c. the variable light region of the hybridoma of ATCC Patent Deposit Designation PTA-7989. Within an embodiment the antagonist of IL2-3 and the antagonist of IL-17A or IL-17F are contained on one molecule.

The invention provides an antagonist of IL-23 and of IL-17A or IL-17F, wherein the antibody or antibody fragment that binds IL-17A or IL-17F comprises an amino acid sequence of the variable heavy region and an amino acid sequence of the variable light region and wherein the amino acid sequence of the variable heavy region is selected from the group consisting of: the amino acid sequence of the variable heavy region of the hybridoma of ATCC Patent Deposit Designation PTA-7987; the amino acid sequence of the variable heavy region of the hybridoma of ATCC Patent Deposit Designation PTA-7988; and the amino acid sequence of the variable heavy region of the hybridoma of ATCC Patent Deposit Designation PTA-7989 and wherein the variable light region comprises the amino acid sequence of the variable light region selected from the group consisting of: the amino acid sequence of the variable light region of the hybridoma of ATCC Patent Deposit Designation PTA-7987; the amino acid sequence of the variable light region of the hybridoma of ATCC Patent Deposit Designation PTA-7988; and the amino acid sequence of the variable light region of the hybridoma of ATCC Patent Deposit Designation PTA-7989. Within an embodiment the antagonist of IL2-3 and the antagonist of IL-17A or IL-17F are contained on one molecule.

Within an aspect the antibody or antibody fragment is humanized Within an aspect the antibody or antibody fragment is chimeric. Within an aspect the antibody fragment is selected from the group consisting of Fv, Fab, Fab', F(ab)$_2$, and F(ab')2.

The invention provides an antagonist of IL-23 and of IL-17A or IL-17F, wherein the antagonist comprises an antibody or antibody fragment that binds the p19 subunit of IL-23 and wherein the antibody or antibody fragment comprises a HCDR1 amino acid sequence, a HCDR2 amino acid sequence, and a HCDR3 amino acid sequence of the amino acid sequence of variable heavy region as shown in SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 116, SEQ ID NO: 118, SEQ ID NO: 120, SEQ ID NO: 122, SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142, SEQ ID NO: 144, SEQ ID NO: 146, SEQ ID NO: 148, SEQ ID NO: 150, SEQ ID NO: 152, SEQ ID NO: 154, SEQ ID NO: 156, SEQ ID NO: 158, SEQ ID NO: 160, SEQ ID NO: 162, SEQ ID NO: 164, SEQ ID NO: 166, SEQ ID NO: 168, SEQ ID NO: 170, SEQ ID NO: 172, SEQ ID NO: 174, SEQ ID NO: 176, SEQ ID NO: 178, SEQ ID NO: 180, SEQ ID NO: 182, SEQ ID NO: 184, SEQ ID NO: 186, SEQ ID NO: 187, SEQ ID NO: 189, SEQ ID NO: 191, SEQ ID NO: 193, SEQ ID NO: 195, SEQ ID NO: 197, SEQ ID NO: 199, SEQ ID NO: 201, SEQ ID NO: 203, SEQ ID NO: 205, SEQ ID NO: 207, SEQ ID NO: 209, SEQ ID NO: 211, SEQ ID NO: 213, SEQ ID NO: 215, SEQ ID NO: 217, SEQ ID NO: 219, SEQ ID NO: 221, SEQ ID NO: 223, SEQ ID NO: 225, SEQ ID NO: 227, SEQ ID NO: 229, SEQ ID NO: 231, SEQ ID NO: 233, SEQ ID NO: 235, SEQ ID NO: 237, SEQ ID NO: 239, SEQ ID NO: 241, SEQ ID NO: 243, SEQ ID NO: 245, SEQ ID NO: 247, SEQ ID NO: 249, SEQ ID NO: 251, SEQ ID NO: 253, SEQ ID NO: 255, SEQ ID NO: 257, SEQ ID NO: 259, SEQ ID NO: 261, SEQ ID NO: 265, SEQ ID NO: 267, and SEQ ID NO: 268 and wherein the variable light region comprises a LCDR1 amino acid sequence, a LCDR2 amino acid sequence, and a LCDR3 amino acid sequence of the amino acid sequence of variable light region as shown in SEQ ID NO:7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO:85, SEQ ID NO: 87, SEQ ID NO: 89, SEQ ID NO: 91, SEQ ID NO: 93, SEQ ID NO:95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 115, SEQ ID NO: 117, SEQ ID NO: 119, SEQ ID NO: 121, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 155, SEQ ID NO: 157, SEQ ID NO: 159, SEQ ID NO: 161, SEQ ID NO: 163, SEQ ID NO: 165, SEQ ID NO: 167, SEQ ID NO: 169, SEQ ID NO: 171, SEQ ID NO: 173, SEQ ID NO: 175, SEQ ID NO: 177, SEQ ID NO: 179, SEQ ID NO: 181, SEQ ID NO: 183, SEQ ID NO: 185, SEQ ID NO: 188, SEQ ID NO: 190, SEQ ID NO: 192, SEQ ID NO: 194, SEQ ID NO: 196, SEQ ID NO: 198, SEQ ID NO: 200, SEQ ID NO: 202, SEQ ID NO: 204, SEQ ID NO: 206, SEQ ID NO: 208, SEQ ID NO: 210, SEQ ID NO: 212, SEQ ID NO: 214, SEQ ID NO: 216, SEQ ID NO: 218, SEQ ID NO: 220, SEQ ID NO: 222, SEQ ID NO: 224, SEQ ID NO: 226, SEQ ID NO: 228, SEQ ID NO: 230, SEQ ID NO: 232, SEQ ID NO: 234, SEQ ID NO: 236, SEQ ID NO: 238, SEQ ID NO: 240, SEQ ID NO: 242, SEQ ID NO: 244, SEQ ID NO: 246, SEQ ID NO: 248, SEQ ID NO: 250, SEQ ID NO: 252, SEQ ID NO: 254, SEQ ID NO: 256, SEQ ID NO: 258, SEQ ID NO: 260, SEQ ID NO: 262, SEQ ID NO: 263, SEQ ID NO: 264, or SEQ ID NO: 266. Within an embodiment the antagonist of IL2-3 and the antagonist of IL-17A or IL-17F are contained on one molecule.

The invention provides an antagonist of IL-23 and of IL-17A or IL-17F, wherein the antagonist comprises an antibody or antibody fragment that binds the p19 subunit of IL-23 and wherein the antibody or antibody fragment comprises an amino acid sequence of a variable heavy region as shown in SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106v 108, SEQ ID NO: 110, SEQ ID NO: 112, SEQ ID NO: 114, SEQ ID NO: 116, SEQ ID NO: 118, SEQ ID NO: 120, SEQ ID NO: 122, SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142, SEQ ID NO: 144, SEQ ID NO: 146, SEQ ID NO: 148, SEQ ID NO: 150, SEQ ID NO: 152, SEQ ID NO: 154, SEQ ID NO: 156, SEQ ID NO: 158, SEQ ID NO: 160, SEQ ID NO: 162, SEQ ID NO: 164, SEQ ID NO: 166, SEQ ID NO: 168, SEQ ID NO: 170, SEQ ID NO: 172, SEQ ID NO: 174, SEQ ID NO: 176, SEQ ID NO: 178, SEQ ID NO: 180, SEQ ID NO: 182, SEQ ID NO: 184, SEQ ID NO: 186, SEQ ID NO: 187, SEQ ID NO: 189, SEQ ID NO: 191, SEQ ID NO: 193, SEQ ID NO: 195, SEQ ID NO: 197, SEQ ID NO: 199, SEQ ID NO: 201, SEQ ID NO: 203, SEQ ID NO: 205, SEQ ID NO: 207, SEQ ID NO: 209, SEQ ID NO: 211, SEQ ID NO: 213, SEQ ID NO: 215, SEQ ID NO: 217, SEQ ID NO: 219, SEQ ID NO: 221, SEQ ID NO: 223, SEQ ID NO: 225, SEQ ID NO: 227, SEQ ID NO: 229, SEQ ID NO: 231, SEQ ID NO: 233, SEQ ID NO: 235, SEQ ID NO: 237, SEQ ID NO: 239, SEQ ID NO: 241, SEQ ID NO: 243, SEQ ID NO: 245, SEQ ID NO: 247, SEQ ID NO: 249, SEQ ID NO: 251, SEQ ID NO: 253, SEQ ID NO: 255, SEQ ID NO: 257, SEQ ID NO: 259, SEQ ID NO: 261, SEQ ID NO: 265, SEQ ID NO: 267, and SEQ ID NO: 268. Within an embodiment the antagonist of IL2-3 and the antagonist of IL-17A or IL-17F are contained on one molecule.

The invention provides an antagonist of IL-23 and of IL-17A or IL-17F, wherein the antagonist comprises an antibody or antibody fragment that binds the p19 subunit of IL-23 wherein the antibody or antibody fragment comprises an amino acid sequence of the variable light region as shown in SEQ ID NO:7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO:85, SEQ ID NO: 87, SEQ ID NO: 89, SEQ ID NO: 91, SEQ ID NO: 93, SEQ ID NO:95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 115, SEQ ID NO: 117, SEQ ID NO: 119, SEQ ID NO: 121, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 155, SEQ ID NO: 157, SEQ ID NO: 159, SEQ ID NO: 161, SEQ ID NO: 163, SEQ ID NO: 165, SEQ ID NO: 167, SEQ ID NO: 169, SEQ ID NO: 171, SEQ ID NO: 173, SEQ ID NO: 175, SEQ ID NO: 177, SEQ ID NO: 179, SEQ ID NO: 181, SEQ ID NO: 183, SEQ ID NO: 185, SEQ ID NO: 188, SEQ ID NO: 190, SEQ ID NO: 192, SEQ ID NO: 194, SEQ ID NO: 196, SEQ ID NO: 198, SEQ ID NO: 200, SEQ ID NO: 202, SEQ ID NO: 204, SEQ ID NO: 206, SEQ ID NO: 208, SEQ ID NO: 210, SEQ ID NO: 212, SEQ ID NO: 214, SEQ ID NO: 216, SEQ ID NO: 218, SEQ ID NO: 220, SEQ ID NO: 222, SEQ ID NO: 224, SEQ ID NO: 226, SEQ ID NO: 228, SEQ ID NO: 230, SEQ ID NO: 232, SEQ ID NO: 234, SEQ ID NO: 236, SEQ ID NO: 238, SEQ ID NO: 240, SEQ ID NO: 242, SEQ ID NO: 244, SEQ ID NO: 246, SEQ ID NO: 248, SEQ ID NO: 250, SEQ ID NO: 252, SEQ ID NO: 254, SEQ ID NO: 256, SEQ ID NO: 258, SEQ ID NO: 260, SEQ ID NO: 262, SEQ ID NO: 263, SEQ ID NO: 264, or SEQ ID NO: 266. Within an embodiment the antagonist of IL2-3 and the antagonist of IL-17A or IL-17F are contained on one molecule.

The invention provides an antagonist of IL-23 and of IL-17A or IL-17F, wherein the antagonist comprises an antibody or antibody fragment that binds the p19 subunit of IL-23 and comprises an amino acid sequence of a variable heavy region and an amino acid sequence of a variable light region and wherein the amino acid sequence of the variable heavy region is shown in SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106v 108, SEQ ID NO: 110, SEQ ID NO: 112, SEQ ID NO: 114, SEQ ID NO: 116, SEQ ID NO: 118, SEQ ID NO: 120, SEQ ID NO: 122, SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142, SEQ ID NO: 144, SEQ ID NO: 146, SEQ ID NO: 148, SEQ ID NO: 150, SEQ ID NO: 152, SEQ ID NO: 154, SEQ ID NO: 156, SEQ ID NO: 158, SEQ ID NO: 160, SEQ ID NO: 162, SEQ ID NO: 164, SEQ ID NO: 166, SEQ ID NO: 168, SEQ ID NO: 170, SEQ ID NO: 172, SEQ ID NO: 174, SEQ ID NO: 176, SEQ ID NO: 178, SEQ ID NO: 180, SEQ ID NO: 182, SEQ ID NO: 184, SEQ ID NO: 186, SEQ ID NO: 187, SEQ ID NO: 189, SEQ ID NO: 191, SEQ ID NO: 193, SEQ ID NO: 195, SEQ ID NO: 197, SEQ ID NO: 199, SEQ ID NO: 201, SEQ ID NO: 203, SEQ ID NO: 205, SEQ ID NO: 207, SEQ ID NO: 209, SEQ ID NO: 211, SEQ ID NO: 213, SEQ ID NO: 215, SEQ ID NO: 217, SEQ ID NO: 219, SEQ ID NO: 221, SEQ ID NO: 223, SEQ ID NO: 225, SEQ ID NO: 227, SEQ ID NO: 229, SEQ ID NO: 231, SEQ ID NO: 233, SEQ ID NO: 235, SEQ ID NO: 237, SEQ ID NO: 239, SEQ ID NO: 241, SEQ ID NO: 243, SEQ ID NO: 245, SEQ ID NO: 247, SEQ ID NO: 249, SEQ ID NO: 251, SEQ ID NO: 253, SEQ ID NO: 255, SEQ ID NO: 257, SEQ ID NO: 259, SEQ ID NO: 261, SEQ ID NO: 265, and SEQ ID NO: SEQ ID NO: 267, and SEQ ID NO: 268 and wherein the amino acid sequence of the variable light region is shown in SEQ ID NO:7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO:85, SEQ ID NO: 87, SEQ ID NO: 89, SEQ ID NO: 91, SEQ ID NO: 93, SEQ ID NO:95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 115, SEQ ID NO: 117, SEQ ID NO: 119, SEQ ID NO: 121, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 155, SEQ ID NO: 157, SEQ ID NO: 159, SEQ ID NO: 161, SEQ ID NO: 163, SEQ ID NO: 165, SEQ ID NO: 167, SEQ ID NO: 169, SEQ ID NO: 171, SEQ ID NO: 173, SEQ ID NO: 175, SEQ ID NO: 177, SEQ ID NO: 179, SEQ ID NO: 181, SEQ ID NO: 183, SEQ ID NO: 185, SEQ ID NO: 188, SEQ ID NO: 190, SEQ ID NO: 192, SEQ ID NO: 194, SEQ ID NO: 196, SEQ ID NO: 198, SEQ ID NO: 200, SEQ ID NO: 202, SEQ ID NO: 204, SEQ ID NO: 206, SEQ ID NO: 208, SEQ ID NO: 210, SEQ ID NO: 212, SEQ ID NO: 214, SEQ ID NO: 216, SEQ ID NO: 218, SEQ ID NO: 220, SEQ ID NO: 222, SEQ ID NO: 224, SEQ ID NO: 226, SEQ ID NO: 228, SEQ ID NO: 230, SEQ ID NO: 232, SEQ ID NO: 234, SEQ ID NO: 236, SEQ ID NO: 238, SEQ ID NO: 240, SEQ ID NO: 242, SEQ ID NO: 244, SEQ ID NO: 246, SEQ ID NO: 248, SEQ ID NO: 250, SEQ ID NO: 252, SEQ ID NO: 254, SEQ ID NO: 256, SEQ ID NO: 258, SEQ ID NO: 260, SEQ ID NO: 262, SEQ ID NO: 263, SEQ ID NO: 264, or SEQ ID NO: 266. Within an embodiment the antagonist of IL2-3 and the antagonist of IL-17A or IL-17F are contained on one molecule.

The invention provides an antagonist of IL-23 and of IL-17A or IL-17F, wherein antagonist can be used to treat inflammation is associated with a disease selected from the group consisting of multiple sclerosis (MS), chronic inflammation, autoimmune diabetes, rheumatoid arthritis (RA) and other arthritic conditions, asthma, systhemic lupus erythrematosus, psoriasis, Crohn's Disease, ulcerative colitis, irritable bowel syndrome (IBS) and inflammatory bowel disease (IBD).

The invention provides an antagonist of IL-23 and of IL-17A or IL-17F, wherein the antagonist comprises an antibody or antibody fragment that binds an IL-17F epitope, wherein said epitope is selected from the group consisting of: a) an epitope comprising amino acid residues 23, 25, 27, 29 and 34 of SEQ ID NO:6; b) an epitope comprising g amino acid residues 23-34 of SEQ ID NO:6; c) an epitope comprising amino acid residues 67-73 of SEQ ID NO:6; d) an epitope comprising amino acid residues 79-85 of SEQ ID NO:6; e) an epitope comprising amino acid residues 146-152 of SEQ ID NO:6; f) an epitope comprising at least one amino acid residue from residues 105-109 and at least one amino acid residue from residues 147-152 of SEQ ID NO:6; g) an epitope comprising at least one amino acid residue from residues 79-85, and at least one amino acid residue from residues 119-122 and at least one amino acid residue from residues 130-134 of SEQ ID NO:6; h) an epitope comprising amino acid residues 34 to 41 of SEQ ID NO: 6; i) an epitope comprising amino acid residues 52 to 64 of SEQ ID NO: 6; and j) an epitope comprising amino acid residues 77 to 85 of SEQ ID NO: 6.

The invention provides an antagonist of IL-23 and of IL-17A or IL-17F, wherein the antagonist comprises an antibody or antibody fragment that binds an IL-17A epitope, wherein said epitope is selected from the group consisting of: a) an epitope comprising amino acid residues 23, 25, 27, 29 and 34 of SEQ ID NO:2; b) an epitope comprising amino acid residues 20-31 of SEQ ID NO:2; c) an epitope comprising amino acid residues 69-75 of SEQ ID NO:2; d) an epitope comprising amino acid residues 81-87 of SEQ ID NO:2; e) an epitope comprising amino acid residues 148-154 of SEQ ID NO:2; f) an epitope comprising at least one amino acid residue from residues 107-111 and at least one amino acid residue from residues 149-154 of SEQ ID NO:2; g) an epitope comprising at least one amino acid residue from residues 81-87 and at least one amino acid residue from residues 121-124 and at least one amino acid residue from residues 132-136 of SEQ ID NO:2; h) an epitope comprising amino acid residues 34 to 41 of SEQ ID NO: 2; i) an epitope comprising amino acid residues 52 to 64 of SEQ ID NO: 2; and j) an epitope comprising amino acid residues 77 to 85 of SEQ ID NO: 2.

The invention provides an antagonist of IL-23 and of IL-17A or IL-17F, wherein the antagonist comprises an antibody or antibody fragment that binds an IL-23p19 epitope selected from the group consisting of: a) an epitope comprising amino acid residues 55 to 66 of SEQ ID NO: 4; b) an epitope comprising amino acid residues 74 to 85 of SEQ ID NO: 4; and c) an epitope comprising amino acid residues 155 to 164 of SEQ ID NO: 4.

The invention provides an antagonist of IL-23 and of IL-17A or IL-17F, wherein the antagonist comprises an antibody or antibody fragment comprises a PEG moiety. The invention provides an antagonist of IL-23 and of IL-17A or IL-17F, wherein the antagonist comprises an Fc moiety. The invention provides an antagonist of IL-23 and of IL-17A or IL-17F, wherein the antagonist is bivalent, trivalent, or tetravalent.

In a specific embodiment, bispecific and single chain antibodies that bind both IL-17A or IL-17F and IL-23 are made. One method comprises fusing hybridoma cells that secrete a monoclonal antibody that cross binds with IL-17A and IL-17F, with hybridoma cells that secrete a monoclonal antibody that binds IL-23/p19, thereby preparing a hybrid hybridoma that secretes a bispecific monoclonal antibody that cross binds with IL-17A or IL-17F and also binds IL-23p19 monoclonal antibody. In one embodiment, the method comprises fusing hybridoma cells that secrete an antagonistic (or agonistic) IL-17A or IL-17F MAb, with hybridoma cells that secrete an antagonistic (or agonistic) IL-23/p19 MAb. Conventional techniques for conducting such a fusion, and for isolating the desired hybrid hybridoma, include those described elsewhere herein, and those illustrated in the examples below.

U.S. Pat. No. 6,060,285 discloses a process for the production of bispecific antibodies, in which at least the genes for the light chain and the variable portion of the heavy chain of an antibody having a first specificity are transfected into a hybridoma cell secreting an antibody having a second specificity. When the transfected hybridoma cells are cultured, bispecific antibodies are produced, and may be isolated by various means known in the art.

Other investigators have used chemical coupling of antibody fragments to prepare antigen-binding molecules having specificity for two different antigens (Brennan et al., Science 229:81 1985; Glennie et al., J. Immunol. 139:2367, 1987). U.S. Pat. No. 6,010,902 also discusses techniques known in the art by which bispecific antibodies can be prepared, for example by the use of heterobifunctional cross-linking reagents such as GMBS (maleimidobutryloxy succinimide) or SPDP (N-succinimidyl 3-(2-pyridyldithio)propionate). (See, e.g., Hardy, "Purification And Coupling Of Fluorescent Proteins For Use In Flow Cytometry", Handbook Of Experimental Immunology, 4.sup.th Ed., Volume 1, Immunochemistry, Weir et al. (eds.), pp. 31.4-31.12, 1986).

The ability to produce antibodies via recombinant DNA technology has facilitated production of bispecific antibodies. Kostelny et al. utilized the leucine zipper moieties from the fos and jun proteins (which preferentially form heterodimers) to produce bispecific antibodies able to bind both the cell surface molecule CD3 and the receptor for IL-2 (J. Immunol. 148:1547; 1992).

Single chain antibodies may be formed by linking heavy and light chain variable region (Fv region) fragments via an amino acid bridge (short peptide linker), resulting in a single polypeptide chain. Such single-chain Fvs (scFvs) have been prepared by fusing DNA encoding a peptide linker between DNAs encoding the two variable region polypeptides ($V_L$ and $V_H$). The resulting antibody fragments can form dimers or higher oligomers, depending on such factors as the length of a flexible linker between the two variable domains (Kortt et al., Protein Engineering 10:423, 1997). In particular embodiments, two or more scFvs are joined by use of a chemical cross-linking agent.

Techniques developed for the production of single chain antibodies can be adapted to produce single chain antibodies of the present invention that bind both IL-17A or IL-17F and IL-23. Such techniques include those described in U.S. Pat. No. 4,946,778; Bird (Science 242:423, 1988); Huston et al. (Proc. Natl. Acad. Sci. USA 85:5879, 1988); and Ward et al. (Nature 334:544, 1989). Once desired single chain antibodies are identified (for example, from a phage-display library), those of skill in the art can further manipulate the DNA encoding the single chain antibody(ies) to yield bispecific antibodies, including bispecific antibodies having Fc regions.

Single chain antibodies against IL-17A or IL-17F and IL-23 may be concatamerized in either order (i.e., anti-IL-17A-anti-IL-23 or anti-IL-23-anti-IL-17A). In particular embodiments, starting materials for preparing a bispecific antibody include an antagonistic (or agonistic) single chain antibody directed against IL-17A or against IL-17F and an antagonistic (or agonistic) single chain antibody directed against IL-23/p19.

The scFv entities that bind IL-17A or IL-17F and IL-23p19 can be oriented with the variable light region either amino terminal to the variable heavy region or carboxylterminal to it. Additionally, tandem scFvs can be prepared in a number of configurations, such that each target, i.e, IL-17A or IL-17F and IL-23p19 can be bound by its respective variable regions. Thus, the construct for a tandem scFV molecule can be prepared such that the variable light region and variable heavy region of one antibody can be interspersed with the variable light and variable heavy regions of the other antibody as long as the variable regions are able to bind the targets. Tandem scFv molecules that bind both targets can be prepared with a linker between the scFv entites, including a Gly-Ser linker comprising a series of glycine and serine residues and can also include additional amino acids.

U.S. Pat. No. 5,582,996 discloses the use of complementary interactive domains (such as leucine zipper moieties or other lock and key interactive domain structures) to facilitate heterodimer formation in the production of bispecific antibodies. The complementary interactive domain(s) may be inserted between an Fab fragment and another portion of a heavy chain (i.e., C.sub.H1 or C.sub.H2 regions of the heavy chain). The use of two different Fab fragments and complementary interactive domains that preferentially heterodimerize will result in bispecific antibody molecules. Cysteine residues may be introduced into the complementary interactive domains to allow disulphide bonding between the complementary interactive domains and stabilize the resulting bispecific antibodies.

Tetravalent, bispecific molecules can be prepared by fusion of DNA encoding the heavy chain of an F(ab')$_2$ fragment of an antibody with either DNA encoding the heavy chain of a second F(ab)$_2$ molecule (in which the CH1 domain is replaced by a CH3 domain), or with DNA encoding a single chain Fv fragment of an antibody, as described in U.S. Pat. No. 5,959,083. Expression of the resultant fusion genes in mammalian cells, together with the genes for the corresponding light chains, yields tetravalent bispecific molecules having specificity for selected antigens.

Bispecific antibodies can also be produced as described in U.S. Pat. No. 5,807,706, which is incorporated by reference herein. Generally, the method involves introducing a protuberance in a first polypeptide and a corresponding cavity in a second polypeptide, polypeptides interface. The protuberance and cavity are positioned so as to promote heteromultimer formation and hinder homomultimer formation. The protuberance is created by replacing amino acids having small side chains with amino acids having larger side chains. The cavity is created by the opposite approach, i.e., replacing amino acids having relatively large side chains with amino acids having smaller side chains.

The protuberance and cavity can be generated by conventional methods for making amino acid substitutions in polypeptides. For example, a nucleic acid encoding a polypeptide may be altered by conventional in vitro mutagenesis techniques. Alternatively, a polypeptide incorporating a desired amino acid substitution may be prepared by peptide synthesis. Amino acids chosen for substitution are located at the interface between the first and second polypeptides.

Screening for antibodies that specifically bind to IL-17A or IL-17F and IL-23/p19 may be accomplished using an enzyme-linked immunosorbent assay (ELISA) in which microtiter plates are coated with IL-17A or IL-17F and IL-23 (or p19 alone). In some embodiments, antibodies that bind both IL-17A or IL-17F and IL-23/p19 from positively reacting clones can be further screened for reactivity in an ELISA-based assay using microtiter plates coated with the other forms IL-17 and IL-23/p19, or other IL-17 family members. Clones that produce antibodies that are reactive to another forms or family members are eliminated, and clones that produce antibodies that are reactive to both IL-17A or IL-17F and IL-23/p19 may be selected for further expansion. Confirmation of reactivity of the antibodies to both IL-17A or IL-17F and IL-23/p19 may be accomplished, for example, using a Western Blot assay in which protein from ovarian, breast, renal, colorectal, lung, endometrial, or brain cancer cells and purified FR-.alpha. and other folate receptor isoforms are run on an SDS-PAGE gel, and subsequently are blotted onto a membrane. The membrane may then be probed with the putative anti-FR-.alpha. antibodies. Reactivity with both IL-17A or IL-17F and IL-23/p19 and not another family member confirms specificity of reactivity for IL-17A/F cross-binding antibodies and IL-23/p19.

Antibody-producing cells of the invention include any insect expression cell line known, such as for example, *Spodoptera frugiperda* cells. The expression cell lines may also be yeast cell lines, such as, for example, *Saccharomyces cerevisiae* and *Schizosaccharomyces pombe* cells. The expression cells may also be mammalian cells such as, for example, hybridoma cells (e.g., NS0 cells), Chinese hamster ovary cells, baby hamster kidney cells, human embryonic kidney line 293, normal dog kidney cell lines, normal cat kidney cell lines, monkey kidney cells, African green monkey kidney cells, COS cells, and non-tumorigenic mouse myoblast G8 cells, fibroblast cell lines, myeloma cell lines, mouse NIH/3T3 cells, LMTK31 cells, mouse sertoli cells, human cervical carcinoma cells, buffalo rat liver cells, human lung cells, human liver cells, mouse mammary tumor cells, TR1 cells, MRC 5 cells, and FS4 cells.

In some preferred embodiments, the antibody-producing cells of the invention produce antibodies that specifically bind to IL-17A or IL-17F and IL-23/p19 (either singly or together as with a bispecific antibody or scFV). The cells preferably are substantially free of IL-17A, IL-17F and IL-23 binding competitors. In preferred embodiments, the antibody-producing cells comprise less than about 10%, preferably less than about 5%, more preferably less than about 1%, more preferably less than about 0.5%, more preferably less than about 0.1%, and most preferably 0% by weight IL-17A, IL-17F, or IL-23 binding competitors. In some embodiments, the antibodies produced by the antibody-producing cells are substantially free of IL-17A, IL-17F, and IL-23 competitors. In preferred embodiments, antibodies produced by the antibody-producing cells comprise less than about 10%, preferably less than about 5%, more preferably less than about 1%, more preferably less than about 0.5%, more preferably less than about 0.1%, and most preferably 0% by weight both IL-17 and IL-23 binding competitors. P Methods of antibody purification are known in the art. In some embodiments of the invention, methods for antibody purification include filtration, affinity column chromatography, cation exchange chromatography, anion exchange chromatography, and concentration. The filtration step preferably comprises ultrafiltration, and more preferably ultrafiltration and diafiltration. Filtration is preferably performed at least about 5-50 times, more preferably 10 to 30 times, and most preferably 14 to 27 times. Affinity column chromatography, may be performed using, for example, PROSEP Affinity Chromatography (Millipore, Billerica, Mass.). In a preferred embodiment, the affinity chromatography step comprises PROSEP-VA column chromatography. Eluate may be washed in a solvent detergent. Cation exchange chromatography may include, for example, SP-Sepharose Cation Exchange Chromatography. Anion exchange chromatography may include, for example but not limited to, Q-Sepharose Fast Flow Anion Exchange. The anion exchange step is preferably non-binding, thereby allowing removal of contaminants including DNA and BSA. The antibody product is preferably nanofiltered, for example, using a Pall DV 20 Nanofilter. The antibody product may be concentrated, for example, using ultrafiltration and diafiltration. The method may further comprise a step of size exclusion chromatography to remove aggregates.

Antibodies that bind to both IL-17A or IL-17F and IL-23 can be used to modulate the immune system by binding IL-17A or IL-17F and IL-23/p19 (either singly or together as with a bispecific antibody or scFV), and thus, preventing the binding of IL-17A or IL-17F with either IL-17RA or IL-17RC and IL-23 with its receptor or any other receptor that they may bind. The antibodies of the invention can also be used to modulate the immune system by inhibiting the binding of both IL-17A or IL-17F with the endogenous IL-17RA and/or IL-17RC receptor and IL-23 with its endogenous receptor. The antibodies of the invention can be also used to treat a subject which produces an excess of either IL-17A or IL-17F and/or IL-23. Suitable subjects include mammals, such as humans. For example, the antibodies of the invention are useful in binding, blocking, inhibiting, reducing, antagonizing or neutralizing of both IL-17A or IL-17F and IL-23 (either singly or together as with a bispecific antibody or scFV), in the treatment of inflammation and inflammatory dieases such as multiple sclerosis, cancer (characterized by IL-17A or IL-17F and IL-23 expression), psoriasis, psoriatic arthritis, atopic dermatitis, inflammatory skin conditions, rheumatoid arthritis, inflammatory bowel disease (IBD), Crohn's Disease, diverticulosis, asthma, pancreatitis, type I diabetes (IDDM), pancreatic cancer, pancreatitis, Graves Disease, colon and intestinal cancer, autoimmune disease, sepsis, organ or bone marrow transplant; inflammation due to endotoxemia, trauma, surgery or infection; amyloidosis; splenomegaly; graft versus host disease; and where inhibition of inflammation, immune suppression, reduction of proliferation of hematopoietic, immune, inflammatory or lymphoid cells, macrophages, T-cells (including Th1 and Th2 cells), suppression of immune response to a pathogen or antigen, or other instances where inhibition of IL-17F and IL-17A cytokines is desired.

Within preferred embodiments, the antibodies of the invention bind to, blocks, inhibits, reduces, antagonizes or neutralizes IL-23 (via p19) and IL-17A IL-17F either singly or together as with a bispecific antibody or scFV), in vivo.

Moreover, the antibodies of the invention are useful to:

(1) Block, inhibit, reduce, antagonize or neutralize signaling via IL-17A or IL-17F and IL-23 in the treatment of cancer, acute inflammation, and chronic inflammatory diseases such as inflammatory bowel disease (IBD), IBS, chronic colitis, splenomegaly, rheumatoid arthritis, and other diseases associated with the induction of acute-phase response.

(2) Block, inhibit, reduce, antagonize or neutralize signaling via IL-17A or IL-17F or IL-23 in the treatment of autoimmune diseases such as insulin-dependent diabetes mellitus (IDDM), multiple sclerosis (MS), systemic Lupus erythematosus (SLE), myasthenia gravis, rheumatoid arthritis, IBS and IBD to prevent or inhibit signaling in immune cells (e.g. lymphocytes, monocytes, leukocytes) via their receptors (e.g. IL-17RA and IL-17RC). Blocking, inhibiting, reducing, or antagonizing signaling via IL-17RA and IL-17RC, using the antibodies of the present invention, may also benefit diseases of the pancreas, kidney, pituitary and neuronal cells. IDDM, non-insulin dependent diabetes mellitus (NIDDM), pancreatitis, and pancreatic carcinoma may benefit.

(3) Agonize, enhance, increase or initiate signaling via IL-17A or IL-17F receptors in the treatment of autoimmune diseases such as IDDM, MS, SLE, myasthenia gravis, rheumatoid arthritis, IBS, and IBD. Anti-IL-17A and IL-17F neutralizing and monoclonal antibodies may signal lymphocytes or other immune cells to differentiate, alter proliferation, or change production of cytokines or cell surface proteins that ameliorate autoimmunity. Specifically, modulation of a T-helper cell response to an alternate pattern of cytokine secretion may deviate an autoimmune response to ameliorate disease (Smith J A et al., *J. Immunol.* 160:4841-4849, 1998). Similarly, agonistic antibodies may be used to signal, deplete and deviate immune cells involved in asthma, allergy and atopoic disease. Signaling via IL-17RA and IL-17RC may also benefit diseases of the pancreas, kidney, pituitary and neuronal cells. IDDM, NIDDM, pancreatitis, and pancreatic carcinoma may benefit.

The antibodies described herein can be used to bind, block, inhibit, reduce, antagonize or neutralize IL-23 and IL-17A or IL-17F activity, either singly or together as with a bispecific antibody or scFV, in the treatment of multiple sclerosis, cancer, autoimmune disease, atopic disease, NIDDM, pancreatitis and kidney dysfunction as described above. The antibodies of the present invention are useful as antagonists of IL-17A or IL-17F or IL-23. Such antagonistic effects can be achieved by direct neutralization or binding of IL-17A or IL-17F and IL-23 (via p19).

Antibodies herein can also be directly or indirectly conjugated to drugs, toxins, radionuclides and the like, and these conjugates used for in vivo diagnostic or therapeutic applications. For instance, antibodies or binding polypeptides which recognize IL-17A or IL-17F or IL-23 can be used to identify or treat tissues or organs that express a corresponding anti-complementary molecule. More specifically, antibodies to IL-17 or IL-23 or bioactive fragments or portions thereof, can be coupled to detectable or cytotoxic molecules and delivered to a mammal having cells, tissues or organs that express these cytokines IL-17 or IL-23-expressing cancers.

Suitable detectable molecules may be directly or indirectly attached to the antagonists of the present invention, such as "binding polypeptides," (including binding peptides disclosed above), antibodies, or bioactive fragments or portions thereof. Suitable detectable molecules include radionuclides, enzymes, substrates, cofactors, inhibitors, fluorescent markers, chemiluminescent markers, magnetic particles and the like. Suitable cytotoxic molecules may be directly or indirectly attached to the polypeptide or antibody, and include bacterial or plant toxins (for instance, diphtheria toxin, *Pseudomonas* exotoxin, ricin, abrin and the like), as well as therapeutic radionuclides, such as iodine-131, rhenium-188 or yttrium-90 (either directly attached to the polypeptide or antibody, or indirectly attached through means of a chelating moiety, for instance). Binding polypeptides or antibodies may also be conjugated to cytotoxic drugs, such as adriamycin. For indirect attachment of a detectable or cytotoxic molecule, the detectable or cytotoxic molecule can be conjugated with a member of a complementary/anticomplementary pair, where the other member is bound to the binding polypeptide or antibody portion. For these purposes, biotin/streptavidin is an exemplary complementary/anticomplementary pair.

In another embodiment, binding polypeptide-toxin fusion proteins or antibody-toxin fusion proteins can be used for targeted cell or tissue inhibition or ablation (for instance, to treat cancer cells or tissues). Alternatively, if the binding polypeptide has multiple functional domains (i.e., an activation domain or a ligand binding domain, plus a targeting domain), a fusion protein including only the targeting domain may be suitable for directing a detectable molecule, a cytotoxic molecule or a complementary molecule to a cell or tissue type of interest. In instances where the fusion protein including only a single domain includes a complementary molecule, the anti-complementary molecule can be conjugated to a detectable or cytotoxic molecule. Such domain-complementary molecule fusion proteins thus represent a generic targeting vehicle for cell/tissue-specific delivery of generic anti-complementary-detectable/cytotoxic molecule conjugates.

Inflammation is a protective response by an organism to fend off an invading agent. Inflammation is a cascading event that involves many cellular and humoral mediators. On one hand, suppression of inflammatory responses can leave a host immunocompromised; however, if left unchecked, inflammation can lead to serious complications including chronic inflammatory diseases (e.g., psoriasis, arthritis, rheumatoid arthritis, multiple sclerosis, inflammatory bowel disease and the like), septic shock and multiple organ failure. Importantly, these diverse disease states share common inflammatory mediators. The collective diseases that are characterized by inflammation have a large impact on human morbidity and mortality. Therefore it is clear that anti-inflammatory proteins, such as antagonists to IL-17A or IL-17F and IL-23/p19, such as IL-17A or IL-17F and IL-23/p19 antibodies, could have crucial therapeutic potential for a vast number of human and animal diseases, from asthma and allergy to autoimmunity, cancers, and septic shock.

Arthritis

Arthritis, including osteoarthritis, rheumatoid arthritis, arthritic joints as a result of injury, and the like, are common inflammatory conditions which would benefit from the therapeutic use of anti-inflammatory proteins, such as the antagonists of the present invention. For example, rheumatoid arthritis (RA) is a systemic disease that affects the entire body and is one of the most common forms of arthritis. It is characterized by the inflammation of the membrane lining the joint, which causes pain, stiffness, warmth, redness and swelling. Inflammatory cells release enzymes that may digest bone and cartilage. As a result of rheumatoid arthritis, the inflamed joint lining, the synovium, can invade and damage bone and cartilage leading to joint deterioration and severe pain amongst other physiologic effects. The involved joint can lose its shape and alignment, resulting in pain and loss of movement.

Rheumatoid arthritis (RA) is an immune-mediated disease particularly characterized by inflammation and subsequent tissue damage leading to severe disability and increased mortality. A variety of cytokines are produced locally in the rheumatoid joints. Numerous studies have demonstrated that IL-1 and TNF-alpha, two prototypic pro-inflammatory cytokines, play an important role in the mechanisms involved in synovial inflammation and in progressive joint destruction. Indeed, the administration of TNF-alpha and IL-1 inhibitors in patients with RA has led to a dramatic improvement of clinical and biological signs of inflammation and a reduction of radiological signs of bone erosion and cartilage destruction. However, despite these encouraging results, a significant percentage of patients do not respond to these agents, suggesting that other mediators are also involved in the pathophysiology of arthritis (Gabay, *Expert. Opin. Biol. Ther.* 2(2): 135-149 (2002). One of those mediators could be IL-17 or IL-23, as demonstrated in several reports to play a role in rheumatoid arthritis. For example, IL-17 and IL-23/p19 are overexpressed in the synovium and synovial fibroblasts of patients with rheumatoid arthritis compared to individuals without rheumatoid arthritis. Furthermore, IL-17 and IL-23/p19 have been demonstrated to promote matrix degradation and enhance the expression of inflammatory, matrix-destructive cytokines when added to synovium/synoviocyte cultures. (Murphy et al, J. Exp. Med. 198:1951 (2003); reviewed in Lubberts et al, *Arthritis Res Ther.* 7:29 (2005) and Kim et al, Rheumatology, Jun. 12, 2006 (online publication ahead of print)). Therefore, such a molecule that binds or inhibits IL-17 or IL-23 activity, such as the antagonists of the present invention, could serve as a valuable therapeutic to reduce inflammation in rheumatoid arthritis, and other arthritic diseases.

There are several animal models for rheumatoid arthritis known in the art. For example, in the collagen-induced arthritis (CIA) model, mice develop chronic inflammatory arthritis that closely resembles human rheumatoid arthritis. Since CIA shares similar immunological and pathological features with RA, this makes it an ideal model for screening potential human anti-inflammatory compounds. The CIA model is a well-known model in mice that depends on both an immune response, and an inflammatory response, in order to occur. The immune response comprises the interaction of B-cells and CD4+ T-cells in response to collagen, which is given as antigen, and leads to the production of anti-collagen antibodies. The inflammatory phase is the result of tissue responses from mediators of inflammation, as a consequence of some of these antibodies cross-reacting to the mouse's native collagen and activating the complement cascade. An advantage in using the CIA model is that the basic mechanisms of pathogenesis are known. The relevant T-cell and B-cell epitopes on type II collagen have been identified, and various immunological (e.g., delayed-type hypersensitivity and anti-collagen antibody) and inflammatory (e.g., cytokines, chemokines, and matrix-degrading enzymes) parameters relating to immune-mediated arthritis have been determined, and can thus be used to assess test compound efficacy in the CIA model (Wooley, *Curr. Opin. Rheum.* 3:407-20 (1999); Williams et al., *Immunol.* 89:9784-788 (1992); Myers et al., *Life Sci.* 61:1861-78 (1997); and Wang et al., *Immunol.* 92:8955-959 (1995)).

One group has shown that an anti-mouse IL-17 antibody reduces symptoms in a mouse CIA-model relative to control mice, and another group has shown that deficiency of IL-23/p19 is protective in CIA (Murphy et al, *J. Exp. Med* 198:1951 (2003)), thus showing conceptually that antagonists of the present invention may be beneficial in treating human disease. The administration of a single mouse-IL-17-specific rat antisera reduced the symptoms of arthritis in the animals when introduced prophylactically or after symptoms of arthritis were already present in the model (Lubberts et al, *Arthritis Rheum.* 50:650-9 (2004)).

As described in the Examples below, both IL-17 and IL-23/p19 are overexpressed in CIA. Therefore, antagonists of the present invention can be used to neutralize IL-17 and/or IL-23 (via p19) in the treatment of specific human diseases such as arthritis, psoriasis, psoriatic arthritis, endotoxemia, inflammatory bowel disease (IBD), IBS, colitis, and other inflammatory conditions disclosed herein.

The administration of antagonists of the present invention to these CIA model mice is used to evaluate the use of these antagonists to ameliorate symptoms and alter the course of disease. Moreover, results showing inhibition of IL-17 and/or IL-23 signalling by these antagonists would provide proof of concept that IL-17 and IL-23/p19 antagonists, such as those disclosed herein, can also be used to ameliorate symptoms and alter the course of disease. By way of example and without limitation, the injection of 10-200 ug of an anti-IL-17 and anti-IL-23/p19 per mouse (one to seven times a week for up to but not limited to 4 weeks via s.c., i.p., or i.m route of administration) can significantly reduce the disease score (paw score, incident of inflammation, or disease). Depending on the initiation of administration (e.g. prior to or at the time of collagen immunization, or at any time point following the second collagen immunization, including those time points at which the disease has already progressed), antagonists of the present invention can be efficacious in preventing rheumatoid arthritis, as well as preventing its progression.

Endotoxemia

Endotoxemia is a severe condition commonly resulting from infectious agents such as bacteria and other infectious disease agents, sepsis, toxic shock syndrome, or in immunocompromised patients subjected to opportunistic infections, and the like. Therapeutically useful of anti-inflammatory proteins, such as antibodies of the invention, could aid in preventing and treating endotoxemia in humans and animals. Such antibodies could serve as a valuable therapeutic to reduce inflammation and pathological effects in endotoxemia.

Inflammatory Bowel Disease IBD

In the United States approximately 500,000 people suffer from Inflammatory Bowel Disease (IBD) which can affect either colon and rectum (Ulcerative colitis) or both, small and large intestine (Crohn's Disease). In both Crohn's disease and ulcerative colitis, the tissue damage results from an inappropriate or exaggerated immune response to antigens of the gut microflora. This review summarizes current knowledge regarding the role of immune-inflammatory mediators in the pathogenesis of inflammatory bowel disease. Despite having a common basis in overresponsiveness to luminal antigens, Crohn's disease and ulcerative colitis are immunologically distinct entities. Crohn's disease is associated with a Th1 T cell-mediated response, characterized by enhanced production of interferon-[gamma] and tumor necrosis factor-[alpha]. Interleukin (IL)-12 and, possibly, IL-23 govern the Th1 cell differentiation, but optimal induction and stabilization of polarized Th1 cells would require additional cytokines, such as IL-15, IL-18 and IL-21. In ulcerative colitis, the local immune response is less polarized, but it is characterized by CD1-reactive natural killer T cell production of IL-13. Beyond these differences, Crohn's disease and ulcerative colitis share important end-stage effector pathways of intestinal injury, which are mediated by an active cross-talk between immune and non-immune mucosal cells. As shown in the Examples below, IL-17 and IL-23 are both overexpressed in intestines and/or serum from humans with IBD and in mouse models of IBD. Moreover, neutralization of IL-17 and/or IL-23/p19 can reduced disease symptoms and pathology in animals models of IBD (Nielson et al, *Scand J Gastroenterol.* 38:180 (2003); Schmidt et al, *Inflamm. Bowel Dis.* 11:16 (2005); Fuss et al, *Inflamm Bowel Dis.* 12:9 (2006)). Moreover, neutralization of IL-17 and/or IL-23/p19 can reduce disease symptoms and pathology in animals models of IBD (Yen et al, *J. Clin. Invest.* 116:1310 (2006); Zhang et al, *Inflamm Bowel Dis.* 12:382 (2006)).

As shown in the Examples below, both IL-17 and IL-23/p19 expression is increased in DSS colitis. Thus, antagonists of the present invention could serve as a valuable therapeutic to reduce inflammation and pathological effects in IBD and related diseases.

Ulcerative colitis (UC) is an inflammatory disease of the large intestine, commonly called the colon, characterized by inflammation and ulceration of the mucosa or innermost lining of the colon. This inflammation causes the colon to empty frequently, resulting in diarrhea. Symptoms include loosening of the stool and associated abdominal cramping, fever and weight loss.

Although the exact cause of UC is unknown, recent research suggests that the body's natural defenses are operating against proteins in the body which the body thinks are foreign (an "autoimmune reaction"). Perhaps because they resemble bacterial proteins in the gut, these proteins may either instigate or stimulate the inflammatory process that begins to destroy the lining of the colon. As the lining of the colon is destroyed, ulcers form releasing mucus, pus and blood. The disease usually begins in the rectal area and may eventually extend through the entire large bowel. Repeated episodes of inflammation lead to thickening of the wall of the intestine and rectum with scar tissue. Death of colon tissue or sepsis may occur with severe disease. The symptoms of ulcerative colitis vary in severity and their onset may be gradual or sudden. Attacks may be provoked by many factors, including respiratory infections or stress.

Although there is currently no cure for UC available, treatments are focused on suppressing the abnormal inflammatory process in the colon lining. Treatments including corticosteroids immunosuppressives (eg. azathioprine, mercaptopurine, and methotrexate) and aminosalicytates are available to treat the disease. However, the long-term use of immunosuppressives such as corticosteroids and azathioprine can result in serious side effects including thinning of bones, cataracts, infection, and liver and bone marrow effects. In the patients in whom current therapies are not successful, surgery is an option. The surgery involves the removal of the entire colon and the rectum.

There are several animal models that can partially mimic chronic ulcerative colitis. One of the most widely used models is the 2,4,6-trinitrobenesulfonic acid/ethanol (TNBS) induced colitis model, which induces chronic inflammation and ulceration in the colon. When TNBS is introduced into the colon of susceptible mice via intra-rectal instillation, it induces T-cell mediated immune response in the colonic mucosa, in this case leading to a massive mucosal inflammation characterized by the dense infiltration of T-cells and macrophages throughout the entire wall of the large bowel. Moreover, this histopathologic picture is accompanies by the clinical picture of progressive weight loss (wasting), bloody diarrhea, rectal prolapse, and large bowel wall thickening (Neurath et al., *Intern. Rev. Immunol.* 19:51-62, 2000).

Another colitis model uses dextran sulfate sodium (DSS), which induces an acute colitis manifested by bloody diarrhea, weight loss, shortening of the colon and mucosal ulceration with neutrophil infiltration. DSS-induced colitis is characterized histologically by infiltration of inflammatory cells into the lamina propria, with lymphoid hyperplasia, focal crypt damage, and epithelial ulceration. These changes are thought to develop due to a toxic effect of DSS on the epithelium and by phagocytosis of lamina propria cells and production of TNF-alpha and IFN-gamma. Despite its common use, several issues regarding the mechanisms of DSS about the relevance to the human disease remain unresolved. DSS is regarded as a T cell-independent model because it is observed in T cell-deficient animals such as SCID mice.

The administration of antagonists of the present invention to these TNBS or DSS models can be used to evaluate the use of those antagonists to ameliorate symptoms and alter the course of gastrointestinal disease. Moreover, the results showing inhibition of IL-17 or IL-23 signalling provide proof of concept that other IL-17/IL-23 antagonists can also be used to ameliorate symptoms in the colitis/IBD models and alter the course of disease.

Psoriasis

Psoriasis is a chronic skin condition that affects more than seven million Americans. Psoriasis occurs when new skin cells grow abnormally, resulting in inflamed, swollen, and scaly patches of skin where the old skin has not shed quickly enough. Plaque psoriasis, the most common form, is characterized by inflamed patches of skin ("lesions") topped with silvery white scales. Psoriasis may be limited to a few plaques or involve moderate to extensive areas of skin, appearing most commonly on the scalp, knees, elbows and trunk. Although it is highly visible, psoriasis is not a contagious disease. The pathogenesis of the diseases involves chronic inflammation of the affected tissues. IL-17 and IL-23 are both overexpressed in psoriatic skin compared to non-psoriatic skin (Li et al, *J Huazhong Univ Sci Technolog Med Sci.* 24:294 (2004); Piskin et al, *J Immunol.* 176:1908 (2006)). Therefore, antagonists of the present invention could serve as a valuable therapeutic to reduce inflammation and pathological effects in psoriasis, other inflammatory skin diseases, skin and mucosal allergies, and related diseases.

Psoriasis is a T-cell mediated inflammatory disorder of the skin that can cause considerable discomfort. It is a disease for which there is no cure and affects people of all ages. Psoriasis affects approximately two percent of the populations of European and North America. Although individuals with mild psoriasis can often control their disease with topical agents, more than one million patients worldwide require ultraviolet or systemic immunosuppressive therapy. Unfortunately, the inconvenience and risks of ultraviolet radiation and the toxicities of many therapies limit their long-term use. Moreover, patients usually have recurrence of psoriasis, and in some cases rebound, shortly after stopping immunosuppressive therapy.

Antibodies that bind IL-17A and IL-17F may also be used within diagnostic systems for the detection of circulating levels of IL-17F or IL-17A, and in the detection of IL-17A and/or IL-17F associated with acute phase inflammatory response. Elevated or depressed levels of ligand or receptor polypeptides may be indicative of pathological conditions, including inflammation or cancer. IL-17A and IL-17F are known to induce associated acute phase inflammatory response. Moreover, detection of acute phase proteins or molecules such as IL-17A or IL-17F can be indicative of a chronic inflammatory condition in certain disease states (e.g., asthma, psoriasis, rheumatoid arthritis, colitis, IBD). Detection of such conditions serves to aid in disease diagnosis as well as help a physician in choosing proper therapy.

In addition to other disease models described herein, the activity of antagonists of the present invention on inflammatory tissue derived from human psoriatic lesions can be measured in vivo using a severe combined immune deficient (SCID) mouse model. Several mouse models have been developed in which human cells are implanted into immunodeficient mice (collectively referred to as xenograft models); see, for example, Cattan A R, Douglas E, *Leuk. Res.* 18:513-22 (1994) and Flavell, D J, *Hematological Oncology* 14:67-82 (1996). As an in vivo xenograft model for psoriasis, human psoriatic skin tissue is implanted into the SCID mouse model, and challenged with an appropriate antagonist. Moreover, other psoriasis animal models in the art may be used to evaluate the present antagonists, such as human psoriatic skin grafts implanted into AGR129 mouse model, and challenged with an appropriate antagonist (e.g., see, Boyman, O. et al., *J. Exp. Med.* Online publication #20031482, 2004, incorporated hereing by reference). IL-17/IL-23 antibodies or binding peptides that bind, block, inhibit, reduce, antagonize or neutralize the activity of IL-17, IL-23 or both IL-17 and IL-23 are preferred antagonists. Similarly, tissues or cells derived from human colitis, IBD, arthritis, or other inflammatory lestions can be used in the SCID model to assess the anti-inflammatory properties of the IL-17 and IL-23 antagonists described herein.

Therapies designed to abolish, retard, or reduce inflammation using antibodies of the invention can be tested by administration of such antibodies to SCID mice bearing human inflammatory tissue (e.g., psoriatic lesions and the like), or other models described herein. Efficacy of treatment is measured and statistically evaluated as increased anti-inflammatory effect within the treated population over time using methods well known in the art. Some exemplary methods include, but are not limited to measuring for example, in a psoriasis model, epidermal thickness, the number of inflammatory cells in the upper dermis, and the grades of parakeratosis. Such methods are known in the art and described herein. For example, see Zeigler, M. et al. *Lab Invest* 81:1253 (2001); Zollner, T. M. et al. *J. Clin. Invest.* 109:671 (2002); Yamanaka, N. et al. *Microbio.l Immunol.* 45:507 (2001); Raychaudhuri, S. P. et al. *Br. J. Dermatol.* 144:931 (2001); Boehncke, W. H et al. *Arch. Dermatol. Res.* 291:104, (1999); Boehncke, W. H et al. *J. Invest. Dermatol.* 116:596 (2001); Nickoloff, B. J. et al. *Am. J. Pathol.* 146:580 (1995); Boehncke, W. H et al. *J. Cutan. Pathol.* 24:1, (1997); Sugai, J., M. et al. *J. Dermatol. Sci.* 17:85 (1998); and Villadsen L. S. et al. *J. Clin. Invest.* 112:1571 (2003). Inflammation may also be monitored over time using well-known methods such as flow cytometry (or PCR) to quantitate the number of inflammatory or lesional cells present in a sample, score (weight loss, diarrhea, rectal bleeding, colon length) for IBD. For example, therapeutic strategies appropriate for testing in such a model include direct treatment using IL-17 and IL-23 antagonists (singly or together), or related conjugates or antagonists based on the disrupting interaction of IL-17 and IL-23 with their receptors.

Moreover, Psoriasis is a chronic inflammatory skin disease that is associated with hyperplastic epidermal keratinocytes and infiltrating mononuclear cells, including CD4+ memory T cells, neutrophils and macrophages (Christophers, Int. Arch. Allergy Immunol., 110:199, 1996). It is currently believed that environmental antigens play a significant role in initiating and contributing to the pathology of the disease. However, it is the loss of tolerance to self-antigens that is thought to mediate the pathology of psoriasis. Dendritic cells and CD4+ T cells are thought to play an important role in antigen presentation and recognition that mediate the immune response leading to the pathology. We have recently developed a model of psoriasis based on the CD4+ CD45RB transfer model (Davenport et al., Internat. Immunopharmacol., 2:653-672). Antibodies of the present invention are administered to the mice. Inhibition of disease scores (skin lesions, inflammatory cytokines) indicates the effectiveness of such antibodies in psoriasis.

Atopic Dermatitis

AD is a common chronic inflammatory disease that is characterized by hyperactivated cytokines of the helper T cell subset 2 (Th2). Although the exact etiology of AD is unknown, multiple factors have been implicated, including hyperactive Th2 immune responses, autoimmunity, infection, allergens, and genetic predisposition. Key features of the disease include xerosis (dryness of the skin), pruritus (itchiness of the skin), conjunctivitis, inflammatory skin lesions, *Staphylococcus aureus* infection, elevated blood eosinophilia, elevation of serum IgE and IgG1, and chronic dermatitis with T cell, mast cell, macrophage and eosinophil infiltration. Colonization or infection with *S. aureus* has been recognized to exacerbate AD and perpetuate chronicity of this skin disease.

AD is often found in patients with asthma and allergic rhinitis, and is frequently the initial manifestation of allergic disease. About 20% of the population in Western countries suffer from these allergic diseases, and the incidence of AD in developed countries is rising for unknown reasons. AD typically begins in childhood and can often persist through adolescence into adulthood. Current treatments for AD include topical corticosteroids, oral cyclosporin A, non-corticosteroid immunosuppressants such as tacrolimus (FK506 in ointment form), and interferon-gamma. Despite the variety of treatments for AD, many patients' symptoms do not improve, or they have adverse reactions to medications, requiring the search for other, more effective therapeutic agents. The antagonists of the present invention can be used to neutralize IL-17 and IL-23 (via p19) in the treatment of specific human diseases such as atoptic dermatitis, inflammatory skin conditions, and other inflammatory conditions disclosed herein.

Asthma

IL-17 plays an important role in allergen-induced T cell activation and neutrophilic influx in the airways. The receptor for IL-17 is expressed in the airways (Yao, et al. *Immunity* 3:811 (1995)) and IL-17 mediated neutrophil recruitment in allergic asthma is largely induced by the chemoattractant IL-8, GRO- and macrophage inflammatory protein-2 (MIP-2) produced by IL-17 stimulated human bronchial epithelial cells (HBECs) and human bronichial fibroblasts (Yao, et al. *J Immunol* 155:5483 (1995)); Molet, et al. *J Allergy Clin Immunol* 108:430 (2001)). IL-17 also stimulates HBECs to release IL-6, a neutrophil-activating factor (Fossiez, et al, *J Exp Med* 183:2593 (1996), and Linden, et al. *Int Arch Allergy Immunol* 126:179 (2001)) and has been shown to synergize with TNF-alpha to prolong the survival of human neutrophils in vitro (Laan, et al. *Eur Respir J* 21:387 (2003)). Moreover, IL-17 is capable of amplifying the inflammatory responses in asthma by its ability to enhance the secretion of cytokines implicated in airway remodeling such as the profibrotic cytokines, IL-6 and IL-11 and inflammatory mediators granulocyte colony-stimulating factor (G-CSF) and granulocyte macrophage colony-stimulating factor (GM-CSF) (Molet, et al. *J Allergy Clin Immunol* 108:430 (2001)).

Clinical evidence shows that acute, severe exacerbations of asthma are associated with recruitment and activation of neutrophils in the airways, thus IL-17 is likely to play a significant role in asthma. Furthermore, since IL-23 is important in the maintenance and differentiation of IL-17 producing cells (e.g. Th17 cells), IL-23 is also likely to play a role in asthma. Patients with mild asthma display a detectable increase in the local concentration of free, soluble IL-17 protein (Molet, et al. *J Allergy Clin Immunol* 108:430 (2001)) while healthy human volunteers with induced, severe airway inflammation due to the exposure to a swine confinement, display a pronounced increase in the concentration of free, soluble IL-17 protein in the bronchoalveolar space (Fossiez et al, *J Exp Med* 183:2593 (1996), and Linden, et al. *Int Arch Allergy Immunol* 126:179 (2001)). Furthermore, IL-17 levels in sputum have correlated with individuals who have increased airway hyper-reactivity Barczyk, et al. *Respir Med* 97:726 (2003).

In animal models of airway hyper-responsiveness, chronic inhalation of ovalbumin by sensitized mice resulted in bronchial eosinophilic inflammation and early induction of IL-17 mRNA expression in inflamed lung tissue, together with a bronchial neutrophilia Hellings, et al. *Am J Respir Cell Mol Biol* 28:42 (2003). Anti-IL-17 monoclonal antibodies strongly reduced bronchial neutrophilic influx but significantly enhanced IL-5 levels in both bronchoalveolar lavage fluid and serum, and aggravated allergen-induced bronchial eosinophilic influx, suggesting that IL-17 may be involved in determining the balance between neutrophil and eosinophil accumulation following antigen insult Id.

Among the IL-17 family members, IL-17F is most closely related to IL-17A. The biological activities mediated by IL-17F are similar to those of IL-17A, where IL-17F stimulates production of IL-6, IL-8 and G-CSF Hurst, et al. *J Immunol* 169:443 (2002). IL-17F also induces production of IL-2, transforming growth factor (TGF)-α, and monocyte chemoattractant protein (MCP) in endothelial cells Starnes, et al. *J Immunol* 167:4137 (2001). Similarly, allergen challenge can increase local IL-17F in patients with allergic asthma Kawaguchi, et al. *J Immunol* 167:4430 (2001). Gene delivery of IL-17F in murine lung increases neutrophils in the bronchoalveolar space, while mucosal transfer of the IL-17F gene enhances the levels of Ag-induced pulmonary neutrophilia and airway responsiveness to methacholine Oda, et al. *Am J Respir Crit Care Med* 171:12 (2005).

Apart from asthma, several chronic inflammatory airway diseases are characterized by neutrophil recruitment in the airways and IL-17 has been reported to play an important role in the pathogenesis of respiratory conditions such as chronic obstructive pulmonary disease (COPD), bacterial pneumonia and cystic fibrosis (Linden, et al. *Eur Respir J* 15:973 (2000), Ye, et al. *Am J Respir Cell Mol Biol* 25:335 (2001), Rahman, et al. *Clin Immunol* 115:268 (2005)). An anti-IL-17 and/or anti-IL-23 therapeutic molecule could be demonstrated to be efficacious for chronic inflammatory airway disease in an in vitro model of inflammation. The ability of antagonists to IL-17 and/or IL-23 activity to inhibit IL-17 or and/or IL-23 signalling to induce cytokine and chemokine production from cultured HBECs or bronchial fibroblasts could be used as a measure of efficacy for such antagonists in the prevention of the production of inflammatory mediators directly resulting from IL-17 and/or IL-23 stimulation. If the addition of antagonists to IL-17 and/or IL-23 activity markedly reduces the production and expression of inflammatory mediators, it would be expected to be efficacious in inflammatory aspects associated with chronic airway inflammation.

Multiple Sclerosis

Multiple sclerosis is a relatively commonly occurring autoimmune disease characterized by demyelination and chronic inflammation of the central nervous system (CNS). Although the mechanisms underlying disease initiation are not clearly understood, the disease processes that contribute to clinical progression of multiple sclerosis are inflammation, demyelination, and axonal loss, or neurodegeneration. Macrophages and microglia are the main immune cells of the CNS. These cells, as well as T cells, neutrophils, astrocytes, and microglia, can contribute to the immune-related pathology of, e.g., multiple sclerosis. Furthermore, T cell reactivity/autoimmunity to several myelin proteins, including myelin basic protein (MBP), proteolipid protein (PLP), myelin oligodendrocyte protein (MOG), and perhaps other myeline proteins, have been implicated in the induction and perpetuation of disease state and pathology of multiple sclerosis. This interaction of autoreactive T cells and myelin proteins can result in the release of proinflammatory cytokines, including TNF-a, IFN-g, and IL-17, among others. Additional consequences are the proliferation of T cells, activation of B cells and macrophages, upregulation of chemokines and adhesion molecules, and the disruption of the blood-brain barrier. The ensuing pathology is a loss of oligodendrocytes and axons, and the formation of a demyelinated "plaque". The plaque consists of a lesion in which the myelin sheath is now absent and the demyelinated axons are embedded within glial scar tissue. Demyelination can also occur as the result of specific recognition and opsinization of myelin antigens by autoantibodies, followed by complement- and/or activated macrophage-mediated destruction. It is this axonal loss and neurodegeneration that is thought to be primarily responsible for the irreversible neurological impairment that is observed in progressive multiple sclerosis.

There is a large amount of clinical and pathological heterogeneity in the course of human multiple sclerosis. Symptoms most often begin between the ages of 18 and 50 years old, but can begin at any age. The clinical symptoms of multiple sclerosis can vary from mild vision disturbances and headaches, to blindness, severe ataxia and paralysis. The majority of the patients (70-75%) have relapsing-remitting multiple sclerosis, in which disease symptoms can recur within a matter of hours to days, followed by a much slower recovery; the absence of symptoms during stages of remission is not uncommon. The incidence and frequency of relapses and remissions can vary greatly, but as time progresses, the recovery phases can be incomplete and slow to occur. This worsening of disease in these cases is classified as secondary-progressive multiple sclerosis, and occurs in approximately 10-15% of multiple sclerosis patients. Another 10-15% of patients are diagnosed with primary-progressive multiple sclerosis, in which disease symptoms and physical impairment progress at a steady rate throughout the disease process.

Both IL-23 and IL-17 are overexpressed in the central nervous system of humans with multiple sclerosis and in mice undergoing an animal model of multiple sclerosis, experimental autoimmune encephalomyelitis (EAE). The overexpression is observed in mice when the EAE is induced by either myelin oligodendrocyte glycoprotein (MOG) 35-55 peptide- or proteolipid peptide (PLP). Furthermore, neutralization of either IL-23/p19 or IL-17 results in amelioration of EAE symptoms in mice (Park et al, *Nat Immunol.* 6:1133 (2005);); Chen et al, *J Clin Invest.* 116:1317 (2006)).

The ability of antagonists to IL-17 and/or IL-23 activity to inhibit IL-17 or and/or IL-23 signalling-induced cytokine and chemokine production could be used as a measure of efficacy for such antagonists in the treatment of multiple sclerosis. If the addition of antagonists to IL-17 and/or IL-23 activity markedly reduces the production and expression of inflammatory mediators (i.e. CNS-infiltrating immune cells; CNS expression of inflammatory cytokines/chemokines, etc.) and symptoms of multiple sclerosis (e.g. paralysis; ataxia; weight loss, etc), it would be expected to be efficacious in the treatment of humans.

Cancer

Chronic inflammation has long been associated with increased incidence of malignancy and similarities in the regulatory mechanisms have been suggested for more than a century. Infiltration of innate immune cells, elevated activities of matrix metalloproteases (MMP) and increased angiogenesis and vasculature density are a few examples of the similarities between chronic and tumour-associated inflammation. Conversely, the elimination of early malignant lesions by immune surveillance, which relies on the cytotoxic activity of tumour-infiltrating T cells or intra-epithelial lymphocytes, is thought to be rate-limiting for the risk to develop cancer.

There are numerous publications describing important roles for IL-23 and IL-17 in tumor biology and/or angiogenesis. Both IL-23 and IL-17 have been published to be upregulated in several human tumors and cancers, including but not limited to those of the colon, breast, ovarian, cervical, prostate, lung, and stomach, as well as melanoma and T cell lymphoma (Tartour et al, *Cancer Res.* 59:3698 (1999); Kato et al, *Biochem. Biophys. Re.s Commun.* 282:735 (2001); Steiner et al, *Prostate.* 56:171 (2003); Langowksi et al, *Nature. May* 10 [Epub ahead of print], (2006)). Thus, neutralization of both IL-17 and a key upstream regulator of IL-17, IL-23 (via p19), is a potent and effective means of treating cancer and other neoplastic diseases. Therefore, neutralizing both IL-17 and IL-23 with antagonists of the present invention (i.e. a single neutralizing entity or antibody to IL-17 and IL-23 or an antagonistic molecule that will neutralize both together, such as a bispecific antibody or bispecific scFV) will have better efficacy in these diseases than antagonists directed toward either of IL-17 or IL-23 alone.

Angiogenesis refers to the formation of new capillaries from preexisting vessels. There are several reports that angiogenesis plays important roles in hematological malignancies and solid tumors. The initiation of angiogenesis and the switch to the angiogenic phenotype requires a change between proangiogenic factors and angiogenic inhibitors (Folkman, *Nat. Med.* 1:27 (1995)). IL-17 acts as a stimulatory hematopoietic cytokine by initiating proliferation of mature neutrophils and by expanding myeloid progenitors. It has been well documented that IL-17 has pro-angiogenic activities and stimulates the migration of vascular endothelial cells, which are associated with tumor promotion (Numasaki et al, *Blood,* 101:2620 (2003); Yang et al, *J. Biol. Chem.,* 278: 33232 (2003); Fujino et al, *Gut,* 52:65 (2003)). In vitro angiogenic activity can be suppressed by neutralizing IL-17 with a neutralizing anti-IL-17 monoclonal antibody, further supporting the role of IL-17 in this action. It is also able to selectively enhance mitogenic activity of basic fibroblast growth factor (bFGF), hepatocyte growth factor (HGF), and vascular endothelial growth factor (VEGF), and IL-17 may also promote bFGF-, HGF- and VEGF-mediated angiogenesis via bFGF-, HGF- and VEGF-induced growth of vascular endothelial cells (Takahashi et al, *Immunol Lett.* 98:189 (2005)). IL-17 has been reported to augment the secretion of several angiogenic CXC chemokines (e.g. CXCL1, CXCL5, CXCL6, and CXCL8) in non-small cell lung cancer (NSCLC) lines. Endothelial cell chemotactic activity (a measure of net angiogenic potential) is increased in response to conditioned medium from NSCLC stimulated with recombinant IL-17. NSCLC lines transfected with IL-17 grew more rapidly versus controls when transplanted in SCID mice (Numasaki et al, *J Immunol.* 175:6177 (2005)). Furthermore, IL-17 has been reported to be associated with increased IL-6 at the site of tumors and is well reported to increase MMP-9 expression. MMP-9 is an important modulator in diseases of inflammation, autoimmunity, and cancer. These reports, therefore, clearly implicate a pro-angiogenic and tumor promoting action for IL-17. Therefore, neutralizing both IL-17 and IL23 with antagonists of the present invention (i.e. a single neutralizing entity or antibody to IL-17 and IL-23 or an antagonistic molecule that will neutralize both together, such as a bispecific antibody or bispecific scFV) will have better efficacy than antagonists directed toward either of IL-17 or IL-23 alone.

Similar to IL-17, IL-23 promotes inflammatory responses including upregulation of MMP9, and is also reported to increase angiogenesis and reduce CD8+ T-cell infiltration. Taken together, these actions can lead to enhanced initiation, progression, and/or maintenance of tumors, cancers, and other transformed growths. That IL-23 plays an important role in cancerous diseases is supported by the observation that neutralization of IL-23 with a monoclonal antibody or with genetic deletion in mice reduces tumor growth in several murine tumor models (Langowksi et al. Nature. May 10 (2006) [Epub ahead of print]). Efficacy is associated with reduced IL-17 expression and reductions in IL-17-related tumorogenic biomarkers, such as granulocyte infiltration, G-CSF and MMP-9. Therefore, neutralizing both IL-17 and IL23 with antagonists of the present invention (i.e. a single neutralizing entity or antibody to IL-17 and IL-23 or an antagonistic molecule that will neutralize both together, such as a bispecific antibody or bispecific scFV) will have better efficacy in these diseases than antagonists directed toward either of IL-17 or IL-23 alone.

Irritable Bowel Syndrome ("IBS")

Irritable bowel syndrome represents a disease characterized by abdominal pain or discomfort and an erratic bowel habit. IBS patients can be characterized into three main groups based on bowel habits: those with predominantly loose or frequent stools, those with predominantly hard or infrequent stools, and those with variable or normal stools (Talley et al., 2002). Altered intestinal motility, abnormalities in epithelial function, abnormal transit of stool and gas, and stress, may contribute to symptoms, while visceral hypersensitivity is a key feature in most patients. Genetic factors affecting pain-signaling and disturbances in central processing of afferent signals are postulated to predispose individuals to IBS following specific environmental exposures. Studies have also demonstrated that inflammatory responses in the colon may contribute to increased sensitivity of smooth muscle and enteric nerves and therefore perturb sensory-motor functions in the intestine (Collins et al., 2001). There is clinical overlap between IBS and IBD, with IBS-like symptoms frequently reported in patients before the diagnosis of IBD, and a higher than expected IBS symptoms in patients in remission from established IBD. Thus, these conditions may coexist with a higher than expected frequency, or may exist on a continuum, with IBS and IBD at different ends of the same spectrum. However, it should be noted that in most IBS patients, colonic biopsy specimens appear normal. Nevertheless, IBS significantly affects a very large number of individuals (U.S. prevalence in 2000, approximately 16 million individuals), resulting in a total cost burden of 1.7 billion dollars (year 2000). Thus, among the most prevalent and costly gastrointestinal diseases and disorders, IBS is second only to gastroesophageal reflux disease (GERD). Yet unlike GERD, treatment for IBS remains unsatisfactory (Talley et al., 2002; Farhadi et al., 21001; Collins et al., 2001), demonstrating that IBS clearly represents an unmet medical need.

Converging disease models have been proposed that postulate an enhanced responsiveness of neural, immune or neuroimmune circuits in the central nervous system (CNS) or in the gut to central (psychosocial) or peripheral (tissue irritation, inflammation, infection) perturbations of normal homeostasis (Talley et al., 2002). This enhanced responsiveness results in dysregulation of gut motility, epithelial function (immune, permeability), and visceral hypersensitivity, which in turn results in IBS symptoms.

There may be a role for a number of different molecules in the pathogenesis of IBS including a role for molecules that stimulate neurons and those that are involved in initiation of inflammatory process. A number of our in-house molecules are known to be linked to possible activity on neurons due to their direct expression by neurons or expression of their receptors on neurons, including IL-17D, IL-17B and IL-31. Moreover, a number of IL-17 family members and related molecules have been associated with inflammation in the gut, including IL-17A, IL-17F, IL-23 and IL-31.

Efficacy of inhibitors of these molecules could be tested in vivo in animal models of disease. Several animal models have been proposed that mimic key features of IBS and involve centrally targeted stimuli (stress) or peripherally targeted stimuli (infection, inflammation). Two examples of in vivo animal models that can be used to determine the effectiveness of inhibitors in the treatment of IBS are (i) models focusing on primary CNS-directed pathogeneisis of IBS (stress models), and (ii) models focusing on gut-directed inducers of stress (i.e. gut inflammation, infection or physical stress). It should be noted however, that events within the CNS or in the gastrointestinal (GI) tract do not occur in isolation and that symptoms of IBS most likely result from a complex interaction between signals from the CNS on the GI and vice versa.

Thus, in summary, there are several molecules and pathogenic pathways that are shared by IL-17 and IL-23 which play important roles in the development, progression, and maintenance of both autoimmune diseases and cancerous diseases. These include the pro-angiogenic roles of IL-17 and IL-23; enhanced MMP-9 levels and activity by IL-17 and IL-23; IL-23, TGF-b and IL-6-mediated production and/or maintenance of Th17 cells; roles of TGF-b and IL-6 in the generation of Foxp3+ regulatory T cells; and additional pathways and molecules. Therefore, the IL-17/IL-23 axis represents an important link to the inappropriate and pathogenic T cell responses associated with autoimmune diseases, tumour-promoting pro-inflammatory processes, and the failure of the adaptive immune surveillance to infiltrate tumours. Therefore, neutralizing both IL-17 and IL23 with antagonists of the present invention (i.e. a single neutralizing entity or antibody to IL-17 and IL-23 or an antagonistic molecule that will neutralize both together, such as a bispecific antibody or bispecific scFV) will have better efficacy in these diseases than antagonists directed toward either of IL-17 or IL-23 alone.

For pharmaceutical use, the antibodies of the present invention are formulated for parenteral, particularly intravenous or subcutaneous, delivery according to conventional methods. Intravenous administration will be by bolus injection, controlled release, e.g, using mini-pumps or other appropriate technology, or by infusion over a typical period of one to several hours. In general, pharmaceutical formulations will include a hematopoietic protein in combination with a pharmaceutically acceptable vehicle, such as saline, buffered saline, 5% dextrose in water or the like. Formulations may further include one or more excipients, preservatives, solubilizers, buffering agents, albumin to provent protein loss on vial surfaces, etc. When utilizing such a combination therapy, the cytokines may be combined in a single formulation or may be administered in separate formulations. Methods of formulation are well known in the art and are disclosed, for example, in *Remington's Pharmaceutical Sciences*, Gennaro, ed., Mack Publishing Co., Easton Pa., 1990, which is incorporated herein by reference. Therapeutic doses will generally be in the range of 0.1 to 100 mg/kg of patient weight per day, preferably 0.5-20 mg/kg per day, with the exact dose determined by the clinician according to accepted standards, taking into account the nature and severity of the condition to be treated, patient traits, etc. Determination of dose is within the level of ordinary skill in the art. More commonly, the proteins will be administered over one week or less, often over a period of one to three days. In general, a therapeutically effective amount of antibodies of the present invention is an amount sufficient to produce a clinically significant increase in the proliferation and/or differentiation of lymphoid or myeloid progenitor cells, which will be manifested as an increase in circulating levels of mature cells (e.g. platelets or neutrophils). The antibodies of the present invention can also be administered in combination with other cytokines such as IL-3, -6 and -11; stem cell factor; erythropoietin; G-CSF and GM-CSF. Within regimens of combination therapy, daily doses of other cytokines are commonly known by one skilled in the art, or can be determined without undue experimentation. Combination therapy with EPO, for example, is indicated in anemic patients with low EPO levels.

Generally, the dosage of administered antibodies will vary depending upon such factors as the patient's age, weight, height, sex, general medical condition and previous medical history. Typically, it is desirable to provide the recipient with a dosage of antibodies which is in the range of from about 1 pg/kg to 10 mg/kg (amount of agent/body weight of patient), although a lower or higher dosage also may be administered as circumstances dictate.

Administration of antibodies of the invention to a subject can be intravenous, intraarterial, intraperitoneal, intramuscular, subcutaneous, intrapleural, intrathecal, by perfusion through a regional catheter, or by direct intralesional injection. When administering therapeutic proteins by injection, the administration may be by continuous infusion or by single or multiple boluses.

Additional routes of administration include oral, mucosalmembrane, pulmonary, and transcutaneous. Oral delivery is suitable for polyester microspheres, zein microspheres, proteinoid microspheres, polycyanoacrylate microspheres, and lipid-based systems (see, for example, DiBase and Morrel, "Oral Delivery of Microencapsulated Proteins," in *Protein Delivery: Physical Systems*, Sanders and Hendren (eds.), pages 255-288 (Plenum Press 1997)). The feasibility of an intranasal delivery is exemplified by such a mode of insulin administration (see, for example, Hinchcliffe and Illum, *Adv. Drug Deliv. Rev.* 35:199 (1999)). Dry or liquid particles comprising antibodies of the invention can be prepared and inhaled with the aid of dry-powder dispersers, liquid aerosol generators, or nebulizers (e.g., Pettit and Gombotz, *TIBTECH* 16:343 (1998); Patton et al., *Adv. Drug Deliv. Rev.* 35:235 (1999)). This approach is illustrated by the AERX diabetes management system, which is a hand-held electronic inhaler that delivers aerosolized insulin into the lungs. Studies have shown that proteins as large as 48,000 kDa have been delivered across skin at therapeutic concentrations with the aid of low-frequency ultrasound, which illustrates the feasibility of trascutaneous administration (Mitragotri et al., *Science* 269: 850 (1995)). Transdermal delivery using electroporation provides another means to administer a molecule having IL-17 and IL-23/p19 binding activity (Potts et al., *Pharm. Biotechnol.* 10:213 (1997)).

A pharmaceutical composition comprising an antibodies of the invention can be formulated according to known methods to prepare pharmaceutically useful compositions, whereby the therapeutic proteins are combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. See, for example, Gennaro (ed.), *Remington's Pharmaceutical Sciences,* 19th Edition (Mack Publishing Company 1995).

For purposes of therapy, antibodies of the invention and a pharmaceutically acceptable carrier are administered to a patient in a therapeutically effective amount. A combination of a therapeutic molecule of the present invention and a pharmaceutically acceptable carrier is said to be administered in a "therapeutically effective amount" if the amount administered is physiologically significant. An agent is physiologically significant if its presence results in a detectable change in the physiology of a recipient patient. For example, an agent used to treat inflammation is physiologically significant if its presence alleviates the inflammatory response. Effective treatment may be assessed in a variety of ways. In one embodiment, effective treatment is determined by reduced inflammation. In other embodiments, effective treatment is marked by inhibition of inflammation. In still other embodiments, effective therapy is measured by increased well-being of the patient including such signs as weight gain, regained strength, decreased pain, thriving, and subjective indications from the patient of better health.

A pharmaceutical composition comprising antibodies of the invention can be furnished in liquid form, in an aerosol, or in solid form. Liquid forms, are illustrated by injectable solutions and oral suspensions. Exemplary solid forms include capsules, tablets, and controlled-release forms. The latter form is illustrated by miniosmotic pumps and implants (Bremer et al., *Pharm. Biotechnol.* 10:239 (1997); Ranade, "Implants in Drug Delivery," in *Drug Delivery Systems*, Ranade and Hollinger (eds.), pages 95-123 (CRC Press 1995); Bremer et al., "Protein Delivery with Infusion Pumps," in *Protein Delivery: Physical Systems*, Sanders and Hendren (eds.), pages 239-254 (Plenum Press 1997); Yewey et al., "Delivery of Proteins from a Controlled Release Injectable Implant," in *Protein Delivery: Physical Systems*, Sanders and Hendren (eds.), pages 93-117 (Plenum Press 1997)).

Liposomes provide one means to deliver therapeutic polypeptides to a subject intravenously, intraperitoneally, intrathecally, intramuscularly, subcutaneously, or via oral administration, inhalation, or intranasal administration. Liposomes are microscopic vesicles that consist of one or more lipid bilayers surrounding aqueous compartments (see, generally, Bakker-Woudenberg et al., *Eur. J. Clin. Microbiol. Infect. Dis.* 12 (*Suppl.* 1):561 (1993), Kim, *Drugs* 46:618 (1993), and Ranade, "Site-Specific Drug Delivery Using Liposomes as Carriers," in Drug Delivery Systems, Ranade and Hollinger (eds.), pages 3-24 (CRC Press 1995)). Liposomes are similar in composition to cellular membranes and as a result, liposomes can be administered safely and are biodegradable. Depending on the method of preparation, liposomes may be unilamellar or multilamellar, and liposomes can vary in size with diameters ranging from 0.02 μm to greater than 10 μm. A variety of agents can be encapsulated in liposomes: hydrophobic agents partition in the bilayers and hydrophilic agents partition within the inner aqueous space(s) (see, for example, Machy et al., *Liposomes In Cell Biology And Pharmacology* (John Libbey 1987), and Ostro et al., *American J. Hosp. Pharm.* 46:1576 (1989)). Moreover, it is possible to control the therapeutic availability of the encapsulated agent by varying liposome size, the number of bilayers, lipid composition, as well as the charge and surface characteristics of the liposomes.

Liposomes can adsorb to virtually any type of cell and then slowly release the encapsulated agent. Alternatively, an absorbed liposome may be endocytosed by cells that are phagocytic. Endocytosis is followed by intralysosomal degradation of liposomal lipids and release of the encapsulated agents (Scherphof et al., *Ann. N.Y. Acad. Sci.* 446:368 (1985)). After intravenous administration, small liposomes (0.1 to 1.0 μm) are typically taken up by cells of the reticuloendothelial system, located principally in the liver and spleen, whereas liposomes larger than 3.0 μm are deposited in the lung. This preferential uptake of smaller liposomes by the cells of the reticuloendothelial system has been used to deliver chemotherapeutic agents to macrophages and to tumors of the liver.

The reticuloendothelial system can be circumvented by several methods including saturation with large doses of liposome particles, or selective macrophage inactivation by pharmacological means (Claassen et al., *Biochim. Biophys. Acta* 802:428 (1984)). In addition, incorporation of glycolipid- or polyethelene glycol-derivatized phospholipids into liposome membranes has been shown to result in a significantly reduced uptake by the reticuloendothelial system (Allen et al., *Biochim. Biophys. Acta* 1068:133 (1991); Allen et al., Biochim. Biophys. Acta 1150:9 (1993)).

Liposomes can also be prepared to target particular cells or organs by varying phospholipid composition or by inserting receptors or ligands into the liposomes. For example, liposomes, prepared with a high content of a nonionic surfactant, have been used to target the liver (Hayakawa et al., Japanese Patent 04-244,018; Kato et al., *Biol. Pharm. Bull.* 16:960 (1993)). These formulations were prepared by mixing soybean phospatidylcholine, α-tocopherol, and ethoxylated hydrogenated castor oil (HCO-60) in methanol, concentrating the mixture under vacuum, and then reconstituting the mixture with water. A liposomal formulation of dipalmitoylphosphatidylcholine (DPPC) with a soybean-derived sterylglucoside mixture (SG) and cholesterol (Ch) has also been shown to target the liver (Shimizu et al., *Biol. Pharm. Bull.* 20:881 (1997)).

Alternatively, various targeting ligands can be bound to the surface of the liposome, such as antibodies, antibody fragments, carbohydrates, vitamins, and transport proteins. For example, liposomes can be modified with branched type galactosyllipid derivatives to target asialoglycoprotein (galactose) receptors, which are exclusively expressed on the surface of liver cells (Kato and Sugiyama, *Crit. Rev. Ther. Drug Carrier Syst.* 14:287 (1997); Murahashi et al., *Biol. Pharm. Bull.* 20:259 (1997)). Similarly, Wu et al., *Hepatology* 27:772 (1998), have shown that labeling liposomes with asialofetuin led to a shortened liposome plasma half-life and greatly enhanced uptake of asialofetuin-labeled liposome by hepatocytes. On the other hand, hepatic accumulation of liposomes comprising branched type galactosyllipid derivatives can be inhibited by preinjection of asialofetuin (Murahashi et al., *Biol. Pharm. Bull.* 20:259 (1997)). Polyaconitylated human serum albumin liposomes provide another approach for targeting liposomes to liver cells (Kamps et al., *Proc. Nat'l Acad. Sci. USA* 94:11681 (1997)). Moreover, Geho, et al. U.S. Pat. No. 4,603,044, describe a hepatocyte-directed liposome vesicle delivery system, which has specificity for hepatobiliary receptors associated with the specialized metabolic cells of the liver.

In a more general approach to tissue targeting, target cells are prelabeled with biotinylated antibodies specific for a ligand expressed by the target cell (Harasym et al., *Adv. Drug Deliv. Rev.* 32:99 (1998)). After plasma elimination of free antibody, streptavidin-conjugated liposomes are administered. In another approach, targeting antibodies are directly attached to liposomes (Harasym et al., *Adv. Drug Deliv. Rev.* 32:99 (1998)).

Antibodies can be encapsulated within liposomes using standard techniques of protein microencapsulation (see, for example, Anderson et al., *Infect. Immun.* 31:1099 (1981), Anderson et al., *Cancer Res.* 50:1853 (1990), and Cohen et al., *Biochim. Biophys. Acta* 1063:95 (1991), Alving et al. "Preparation and Use of Liposomes in Immunological Studies," in *Liposome Technology*, 2nd Edition, Vol. III, Gregoriadis (ed.), page 317 (CRC Press 1993), Wassef et al., *Meth. Enzymol.* 149:124 (1987)). As noted above, therapeutically useful liposomes may contain a variety of components. For example, liposomes may comprise lipid derivatives of poly (ethylene glycol) (Allen et al., *Biochim. Biophys. Acta* 1150:9 (1993)).

Degradable polymer microspheres have been designed to maintain high systemic levels of therapeutic proteins. Microspheres are prepared from degradable polymers such as poly (lactide-co-glycolide) (PLG), polyanhydrides, poly (ortho esters), nonbiodegradable ethylvinyl acetate polymers, in which proteins are entrapped in the polymer (Gombotz and Pettit, *Bioconjugate Chem.* 6:332 (1995); Ranade, "Role of Polymers in Drug Delivery," in *Drug Delivery Systems*, Ranade and Hollinger (eds.), pages 51-93 (CRC Press 1995); Roskos and Maskiewicz, "Degradable Controlled Release Systems Useful for Protein Delivery," in *Protein Delivery: Physical Systems*, Sanders and Hendren (eds.), pages 45-92 (Plenum Press 1997); Bartus et al., Science 281:1161 (1998); Putney and Burke, *Nature Biotechnology* 16:153 (1998); Putney, *Curr. Opin. Chem. Biol.* 2:548 (1998)). Polyethylene glycol (PEG)-coated nanospheres can also provide carriers for intravenous administration of therapeutic proteins (see, for example, Gref et al., *Pharm. Biotechnol.* 10:167 (1997)).

The present invention also contemplates chemically modified polypeptides having binding IL-17 and IL-23 activity such as anti-IL-17A and IL-23/p19 antibodies, which a polypeptide is linked with a polymer, as discussed above.

Other dosage forms can be devised by those skilled in the art, as shown, for example, by Ansel and Popovich, *Pharmaceutical Dosage Forms and Drug Delivery Systems*, 5$^{th}$ Edition (Lea & Febiger 1990), Gennaro (ed.), *Remington Pharmaceutical Sciences*, 19$^{th}$ Edition (Mack Publishing Company 1995), and by Ranade and Hollinger, *Drug Delivery Systems* (CRC Press 1996).

As an illustration, pharmaceutical compositions may be supplied as a kit comprising a container that comprises an antibody of the invention. Antibodies of the invention can be provided in the form of an injectable solution for single or multiple doses, or as a sterile powder that will be reconstituted before injection. Alternatively, such a kit can include a dry-powder disperser, liquid aerosol generator, or nebulizer for administration of a therapeutic polypeptide. Such a kit may further comprise written information on indications and usage of the pharmaceutical composition. Moreover, such information may include a statement that the antibody composition is contraindicated in patients with known hypersensitivity to IL-17 and IL-23.

A pharmaceutical composition comprising antibodies of the invention can be furnished in liquid form, in an aerosol, or in solid form. Liquid forms, are illustrated by injectable solutions, aerosols, droplets, topological solutions and oral suspensions. Exemplary solid forms include capsules, tablets, and controlled-release forms. The latter form is illustrated by miniosmotic pumps and implants (Bremer et al., *Pharm. Biotechnol.* 10:239 (1997); Ranade, "Implants in Drug Delivery," in *Drug Delivery Systems*, Ranade and Hollinger (eds.), pages 95-123 (CRC Press 1995); Bremer et al., "Protein Delivery with Infusion Pumps," in *Protein Delivery: Physical Systems*, Sanders and Hendren (eds.), pages 239-254 (Plenum Press 1997); Yewey et al., "Delivery of Proteins from a Controlled Release Injectable Implant," in *Protein Delivery: Physical Systems*, Sanders and Hendren (eds.), pages 93-117 (Plenum Press 1997)). Other solid forms include creams, pastes, other topological applications, and the like.

Liposomes provide one means to deliver therapeutic polypeptides to a subject intravenously, intraperitoneally, intrathecally, intramuscularly, subcutaneously, or via oral administration, inhalation, or intranasal administration. Liposomes are microscopic vesicles that consist of one or more lipid bilayers surrounding aqueous compartments (see, generally, Bakker-Woudenberg et al., *Eur. J. Clin. Microbiol. Infect. Dis.* 12 (*Suppl.* 1):561 (1993), Kim, *Drugs* 46:618 (1993), and Ranade, "Site-Specific Drug Delivery Using Liposomes as Carriers," in *Drug Delivery Systems*, Ranade and Hollinger (eds.), pages 3-24 (CRC Press 1995)). Liposomes are similar in composition to cellular membranes and as a result, liposomes can be administered safely and are biodegradable. Depending on the method of preparation, liposomes may be unilamellar or multilamellar, and liposomes can vary in size with diameters ranging from 0.02 µm to greater than 10 µm. A variety of agents can be encapsulated in liposomes: hydrophobic agents partition in the bilayers and hydrophilic agents partition within the inner aqueous space(s) (see, for example, Machy et al., *Liposomes In Cell Biology And Pharmacology* (John Libbey 1987), and Ostro et al., *American J. Hosp. Pharm.* 46:1576 (1989)). Moreover, it is possible to control the therapeutic availability of the encapsulated agent by varying liposome size, the number of bilayers, lipid composition, as well as the charge and surface characteristics of the liposomes.

Other dosage forms can be devised by those skilled in the art, as shown, for example, by Ansel and Popovich, *Pharmaceutical Dosage Forms and Drug Delivery Systems*, 5$^{th}$ Edition (Lea & Febiger 1990), Gennaro (ed.), *Remington Pharmaceutical Sciences*, 19$^{th}$ Edition (Mack Publishing Company 1995), and by Ranade and Hollinger, *Drug Delivery Systems* (CRC Press 1996).

The present invention contemplates antagonists of IL-17 and IL-23 and methods and therapeutic uses comprising an such antagonists as described herein. Such compositions can further comprise a carrier. The carrier can be a conventional organic or inorganic carrier. Examples of carriers include water, buffer solution, alcohol, propylene glycol, macrogol, sesame oil, corn oil, and the like.

The invention is further illustrated by the following non-limiting examples.

EXAMPLES

Example 1

Antibodies that Bind IL-17A and IL-17F

Hybridomas expressing monoclonal antibodies to IL-17A and IL-17F were described in co-pending and co-owned US Patent Publication No. 2007-0218065, published Sep. 20, 2007 and in U.S. patent application Ser. No. 11/741,189, filed Apr. 27, 2007, herein incorporated by reference. These hybridomas were deposited with the American Type Tissue Culture Collection (ATCC; Manassas Va.) patent depository as original deposits under the Budapest Treaty and were given the following ATCC Accession No.s: clone 339.15.5.3 (ATCC Patent Deposit Designation PTA-7987, deposited on Nov. 7, 2006); clone 339.15.3.6 (ATCC Patent Deposit Designation PTA-7988, deposited on Nov. 7, 2006); and clone 339.15.6.16 (ATCC Patent Deposit Designation PTA-7989, deposited on Nov. 7, 2006. The variable heavy regions and variable light regions of the antibodies expressed by these hybridomas can be determined by amino acid sequencing. The polypeptides comprising the variable heavy regions or variable light regions can also be separated by conventional protein isolation techniques. The complementarity determining regions (CDRs) of the heavy and light variable regions can be determined by one of ordinary skill in the art. Thus, heavy chain and light chain complementarity determining regions and variable heavy and light regions can be expressed in cell culture and purified or produced synthetically.

Example 2

Antibodies that Bind the p-19 Subunit of IL-23

Antibodies and antibody fragments that bind to IL-23p19 were identified by screening a phage display library designed so that the antibody light-chain variable region and a portion of the heavy-chain variable region are combined with synthetic DNA encoding human antibody sequences, which are then displayed on phage and phagemid libraries as Fab antibody fragments (Dyax® Human Antibody Libraries, Dyax Corp., Cambridge, Mass.). These antibodies and antibody fragments and are described in co-pending and co-owned U.S. patent application Ser. No. 11/762,738, filed Jun. 13, 2007 and WIPO Publication Number 2007/147019, published Dec. 21, 2007, herein incorporated by reference. The amino acid sequences of the variable heavy and variable light regions of these sequences are shown in Table 1, below.

The variable light and heavy chain fragments of antibodies can be isolated in a Fab format. These variable regions can then be manipulated to generate antibodies, including antigen-binding fragments, such as scFvs, to IL-23p19. Using this technology the variable regions of Fabs have been identified for their characteristics of binding and or neutralizing IL-23p19 in plate-based assays described in WIPO Publication Number 2007/147019.

Table 1 below shows a list of the Fabs or scFvs that bind IL-23p19

TABLE 1

| Cluster # | VL polypeptide SEQ ID NO: | VH polypeptide SEQ ID NO: | Light FR1 range | Light CDR1 range | Light FR2 range | Light CDR2 range | Light FR3 range | Light CDR3 range | Light FR4 range | Heavy FR1 range | Heavy CDR1 range | Heavy FR2 range | Heavy CDR2 range | Heavy FR3 range | Heavy CDR3 range | Heavy FR4 range |
|---|---|---|---|---|---|---|---|---|---|---|---|---|---|---|---|---|
| 26 | 7 | 8 | 1-23 | 24-35 | 36-50 | 51-57 | 58-89 | 90-98 | 99-108 | 1-30 | 31-35 | 36-49 | 50-66 | 67-98 | 99-105 | 106-116 |
| 27 | 9 | 10 | 1-23 | 24-34 | 35-49 | 50-56 | 57-88 | 89-97 | 98-107 | 1-30 | 31-35 | 36-49 | 50-66 | 67-98 | 99-106 | 107-117 |
| 28 | 11 | 12 | 1-23 | 24-35 | 36-50 | 51-57 | 58-89 | 90-98 | 99-108 | 1-30 | 31-35 | 36-49 | 50-66 | 67-98 | 99-108 | 109-119 |
| 29 | 13 | 14 | 1-22 | 23-36 | 37-51 | 52-58 | 59-90 | 91-102 | 103-112 | 1-30 | 31-35 | 36-49 | 50-66 | 67-98 | 99-112 | 113-123 |
| 33 | 15 | 16 | 1-23 | 24-34 | 35-49 | 50-56 | 57-88 | 89-97 | 98-107 | 1-30 | 31-35 | 36-49 | 50-66 | 67-98 | 99-113 | 114-124 |
| 36 | 17 | 18 | 1-23 | 24-34 | 35-49 | 50-56 | 57-88 | 89-97 | 98-107 | 1-30 | 31-35 | 36-49 | 50-66 | 67-98 | 99-105 | 106-116 |
| 40 | 19 | 20 | 1-22 | 23-33 | 34-48 | 49-55 | 56-87 | 88-96 | 97-106 | 1-30 | 31-35 | 36-49 | 50-66 | 67-98 | 99-116 | 117-127 |
| 41 | 21 | 22 | 1-23 | 24-39 | 40-54 | 55-61 | 62-93 | 94-102 | 103-112 | 1-30 | 31-35 | 36-49 | 50-66 | 67-98 | 99-112 | 113-123 |
| 43 | 23 | 24 | 1-23 | 24-39 | 40-54 | 55-61 | 62-93 | 94-102 | 103-112 | 1-30 | 31-35 | 36-49 | 50-66 | 67-98 | 99-107 | 108-118 |
| 101 | 25 | 26 | 1-22 | 23-36 | 37-51 | 52-58 | 59-90 | 91-102 | 103-112 | 1-30 | 31-35 | 36-49 | 50-66 | 67-98 | 99-112 | 113-123 |
| 102 | 27 | 28 | 1-23 | 24-34 | 35-49 | 50-56 | 57-88 | 89-97 | 98-107 | 1-30 | 31-35 | 36-49 | 50-66 | 67-98 | 99-110 | 111-121 |
| 103 | 29 | 30 | 1-23 | 24-39 | 40-54 | 55-61 | 62-93 | 94-102 | 103-112 | 1-30 | 31-35 | 36-49 | 50-66 | 67-98 | 99-113 | 114-124 |
| 110 | 31 | 32 | 1-22 | 23-35 | 36-50 | 51-57 | 58-89 | 90-98 | 99-108 | 1-30 | 31-35 | 36-49 | 50-66 | 67-98 | 99-119 | 120-130 |
| 114 | 33 | 34 | 1-23 | 24-34 | 35-49 | 50-56 | 57-88 | 89-97 | 98-107 | 1-30 | 31-35 | 36-49 | 50-66 | 67-98 | 99-108 | 109-119 |
| 115 | 35 | 36 | 1-23 | 24-39 | 40-54 | 55-61 | 62-93 | 94-102 | 103-112 | 1-30 | 31-35 | 36-49 | 50-66 | 67-98 | 99-108 | 109-119 |

TABLE 1-continued

| Cluster # | VL polypeptide SEQ ID NO: | VH polypeptide SEQ ID NO: | Light FR1 range | Light CDR1 range | Light FR2 range | Light CDR2 range | Light FR3 range | Light CDR3 range | Light FR4 range | Heavy FR1 range | Heavy CDR1 range | Heavy FR2 range | Heavy CDR2 range | Heavy FR3 range | Heavy CDR3 range | Heavy FR4 range |
|---|---|---|---|---|---|---|---|---|---|---|---|---|---|---|---|---|
| 119 | 37 | 38 | 1-23 | 24-34 | 35-49 | 50-56 | 57-88 | 89-97 | 98-107 | 1-30 | 31-35 | 36-49 | 50-66 | 67-98 | 99-106 | 107-117 |
| 120 | 39 | 40 | 1-23 | 24-39 | 40-54 | 55-61 | 62-93 | 94-102 | 103-112 | 1-30 | 31-35 | 36-49 | 50-66 | 67-98 | 99-108 | 109-119 |
| 121 | 41 | 42 | 1-23 | 24-34 | 35-49 | 50-56 | 57-88 | 89-97 | 98-107 | 1-30 | 31-35 | 36-49 | 50-66 | 67-98 | 99-109 | 110-120 |
| 122 | 43 | 44 | 1-23 | 24-34 | 35-49 | 50-56 | 57-88 | 89-96 | 97-106 | 1-30 | 31-35 | 36-49 | 50-66 | 67-98 | 99-108 | 109-119 |
| 123 | 45 | 46 | 1-22 | 23-33 | 34-48 | 49-55 | 56-87 | 88-97 | 98-107 | 1-30 | 31-35 | 36-49 | 50-66 | 67-98 | 99-111 | 112-122 |
| 124 | 47 | 48 | 1-23 | 24-34 | 35-49 | 50-56 | 57-88 | 89-97 | 98-107 | 1-30 | 31-35 | 36-49 | 50-66 | 67-98 | 99-110 | 111-121 |
| 125 | 49 | 50 | 1-23 | 24-34 | 35-49 | 50-56 | 57-88 | 89-97 | 98-107 | 1-30 | 31-35 | 36-49 | 50-66 | 67-98 | 99-106 | 107-117 |
| 126 | 51 | 52 | 1-22 | 23-35 | 36-50 | 51-57 | 58-89 | 90-100 | 101-110 | 1-30 | 31-35 | 36-49 | 50-66 | 67-98 | 99-106 | 107-117 |
| 127 | 53 | 54 | 1-22 | 23-35 | 36-50 | 51-57 | 58-89 | 90-100 | 101-110 | 1-30 | 31-35 | 36-49 | 50-66 | 67-98 | 99-111 | 112-122 |
| 128 | 55 | 56 | 1-22 | 23-35 | 36-50 | 51-57 | 58-89 | 90-100 | 101-110 | 1-30 | 31-35 | 36-49 | 50-66 | 67-98 | 99-111 | 112-122 |
| 129 | 57 | 58 | 1-23 | 24-34 | 35-49 | 50-56 | 57-88 | 89-98 | 99-108 | 1-30 | 31-35 | 36-49 | 50-66 | 67-98 | 99-107 | 108-118 |
| 130 | 59 | 60 | 1-23 | 24-34 | 35-49 | 50-56 | 57-88 | 89-97 | 98-107 | 1-30 | 31-35 | 36-49 | 50-66 | 67-98 | 99-109 | 110-120 |
| 131 | 61 | 62 | 1-23 | 24-34 | 35-49 | 50-56 | 57-88 | 89-97 | 98-107 | 1-30 | 31-35 | 36-49 | 50-66 | 67-98 | 99-109 | 110-120 |
| 132 | 63 | 64 | 1-23 | 24-34 | 35-49 | 50-56 | 57-88 | 89-97 | 98-107 | 1-30 | 31-35 | 36-49 | 50-66 | 67-98 | 99-115 | 116-126 |
| 134 | 65 | 66 | 1-22 | 23-33 | 34-48 | 49-55 | 56-87 | 88-96 | 97-106 | 1-30 | 31-35 | 36-49 | 50-66 | 67-98 | 99-111 | 112-122 |
| 135 | 67 | 68 | 1-23 | 24-34 | 35-49 | 50-56 | 57-88 | 89-98 | 99-108 | 1-30 | 31-35 | 36-49 | 50-66 | 67-98 | 99-116 | 117-127 |
| 136 | 69 | 70 | 1-23 | 24-34 | 35-49 | 50-56 | 57-88 | 89-98 | 99-108 | 1-30 | 31-35 | 36-49 | 50-66 | 67-98 | 99-109 | 110-120 |
| 137 | 71 | 72 | 1-22 | 23-36 | 37-51 | 52-58 | 59-90 | 91-100 | 101-110 | 1-30 | 31-35 | 36-49 | 50-66 | 67-98 | 99-105 | 106-116 |
| 138 | 73 | 74 | 1-23 | 24-39 | 40-54 | 55-61 | 62-93 | 94-102 | 103-112 | 1-30 | 31-35 | 36-49 | 50-66 | 67-98 | 99-107 | 108-118 |
| 139 | 75 | 76 | 1-23 | 24-34 | 35-49 | 50-56 | 57-88 | 89-97 | 98-107 | 1-30 | 31-35 | 36-49 | 50-66 | 67-98 | 99-111 | 112-122 |
| 140 | 77 | 78 | 1-23 | 24-39 | 40-54 | 55-61 | 62-93 | 94-102 | 103-112 | 1-30 | 31-35 | 36-49 | 50-66 | 67-98 | 99-111 | 112-122 |
| 141 | 79 | 80 | 1-23 | 24-39 | 40-54 | 55-61 | 62-93 | 94-102 | 103-112 | 1-30 | 31-35 | 36-49 | 50-66 | 67-98 | 99-107 | 108-118 |
| 142 | 81 | 82 | 1-23 | 24-34 | 35-49 | 50-56 | 57-88 | 89-97 | 98-107 | 1-30 | 31-35 | 36-49 | 50-66 | 67-98 | 99-113 | 114-124 |
| 143 | 83 | 84 | 1-23 | 24-34 | 35-49 | 50-56 | 57-88 | 89-97 | 98-107 | 1-30 | 31-35 | 36-49 | 50-66 | 67-98 | 99-107 | 108-118 |
| 144 | 85 | 86 | 1-23 | 24-39 | 40-54 | 55-61 | 62-93 | 94-102 | 103-112 | 1-30 | 31-35 | 36-49 | 50-66 | 67-98 | 99-111 | 112-122 |
| 145 | 87 | 88 | 1-23 | 24-34 | 35-49 | 50-56 | 57-88 | 89-96 | 97-106 | 1-30 | 31-35 | 36-49 | 50-66 | 67-98 | 99-107 | 108-118 |
| 146 | 89 | 90 | 1-22 | 23-36 | 37-51 | 52-58 | 59-90 | 91-100 | 101-110 | 1-30 | 31-35 | 36-49 | 50-66 | 67-98 | 99-111 | 112-122 |
| 148 | 91 | 92 | 1-23 | 24-34 | 35-49 | 50-56 | 57-88 | 89-97 | 98-107 | 1-30 | 31-35 | 36-49 | 50-66 | 67-98 | 99-105 | 106-116 |
| 149 | 93 | 94 | 1-23 | 24-34 | 35-49 | 50-56 | 57-88 | 89-98 | 99-108 | 1-30 | 31-35 | 36-49 | 50-66 | 67-98 | 99-105 | 106-116 |
| 150 | 95 | 96 | 1-23 | 24-39 | 40-54 | 55-61 | 62-93 | 94-101 | 102-111 | 1-30 | 31-35 | 36-49 | 50-66 | 67-98 | 99-108 | 109-119 |
| 151 | 97 | 98 | 1-23 | 24-34 | 35-49 | 50-56 | 57-88 | 89-97 | 98-107 | 1-30 | 31-35 | 36-49 | 50-66 | 67-98 | 99-108 | 109-119 |
| 152 | 99 | 100 | 1-23 | 24-34 | 35-49 | 50-56 | 57-88 | 89-98 | 99-108 | 1-30 | 31-35 | 36-49 | 50-65 | 66-97 | 98-110 | 111-121 |
| 153 | 101 | 102 | 1-23 | 24-34 | 35-49 | 50-56 | 57-88 | 89-97 | 98-107 | 1-30 | 31-35 | 36-49 | 50-66 | 67-98 | 99-110 | 111-121 |
| 154 | 103 | 104 | 1-23 | 24-39 | 40-54 | 55-61 | 62-93 | 94-102 | 103-112 | 1-30 | 31-35 | 36-49 | 50-66 | 67-98 | 99-107 | 108-118 |
| 155 | 105 | 106 | 1-23 | 24-35 | 36-50 | 51-57 | 58-89 | 90-100 | 101-110 | 1-30 | 31-35 | 36-49 | 50-66 | 67-98 | 99-109 | 110-120 |
| 156 | 107 | 108 | 1-22 | 23-35 | 36-50 | 51-57 | 58-89 | 90-100 | 101-110 | 1-30 | 31-35 | 36-49 | 50-66 | 67-98 | 99-109 | 110-120 |
| 157 | 109 | 110 | 1-22 | 23-35 | 36-50 | 51-57 | 58-89 | 90-100 | 101-110 | 1-30 | 31-35 | 36-49 | 50-66 | 67-98 | 99-113 | 114-124 |
| 158 | 111 | 112 | 1-23 | 24-39 | 40-54 | 55-61 | 62-93 | 94-102 | 103-112 | 1-30 | 31-35 | 36-49 | 50-66 | 67-98 | 99-113 | 114-124 |
| 159 | 113 | 114 | 1-23 | 24-39 | 40-54 | 55-61 | 62-93 | 94-102 | 103-112 | 1-30 | 31-35 | 36-49 | 50-66 | 67-98 | 99-112 | 113-123 |
| 160 | 115 | 116 | 1-23 | 24-34 | 35-49 | 50-56 | 57-88 | 89-96 | 97-106 | 1-30 | 31-35 | 36-49 | 50-66 | 67-98 | 99-105 | 106-116 |
| 161 | 117 | 118 | 1-23 | 24-39 | 40-54 | 55-61 | 62-93 | 94-102 | 103-112 | 1-30 | 31-35 | 36-49 | 50-66 | 67-98 | 99-107 | 108-118 |
| 162 | 119 | 120 | 1-23 | 24-35 | 36-50 | 51-57 | 58-89 | 90-98 | 99-108 | 1-30 | 31-35 | 36-49 | 50-66 | 67-98 | 99-105 | 106-116 |
| 163 | 121 | 122 | 1-23 | 24-35 | 36-50 | 51-57 | 58-89 | 90-98 | 99-108 | 1-30 | 31-35 | 36-49 | 50-66 | 67-98 | 99-108 | 109-119 |
| 164 | 123 | 124 | 1-23 | 24-35 | 36-50 | 51-57 | 58-89 | 90-98 | 99-108 | 1-30 | 31-35 | 36-49 | 50-66 | 67-98 | 99-107 | 108-118 |
| 165 | 125 | 126 | 1-23 | 24-39 | 40-54 | 55-61 | 62-93 | 94-102 | 103-112 | 1-30 | 31-35 | 36-49 | 50-66 | 67-98 | 99-109 | 110-120 |
| 166 | 127 | 128 | 1-23 | 24-35 | 36-50 | 51-57 | 58-89 | 90-98 | 99-108 | 1-30 | 31-35 | 36-49 | 50-66 | 67-98 | 99-105 | 106-116 |
| 167 | 129 | 130 | 1-23 | 24-34 | 35-49 | 50-56 | 57-88 | 89-97 | 98-107 | 1-30 | 31-35 | 36-49 | 50-66 | 67-98 | 99-103 | 104-114 |
| 168 | 131 | 132 | 1-23 | 24-34 | 35-49 | 50-56 | 57-88 | 89-97 | 98-107 | 1-30 | 31-35 | 36-49 | 50-66 | 67-98 | 99-108 | 109-119 |
| 169 | 133 | 134 | 1-23 | 24-35 | 36-50 | 51-57 | 58-89 | 90-99 | 100-109 | 1-30 | 31-35 | 36-49 | 50-66 | 67-98 | 99-112 | 113-123 |
| 170 | 135 | 136 | 1-23 | 24-39 | 40-54 | 55-61 | 62-93 | 94-101 | 102-111 | 1-30 | 31-35 | 36-49 | 50-66 | 67-98 | 99-112 | 113-123 |
| 171 | 137 | 138 | 1-23 | 24-35 | 36-50 | 51-57 | 58-89 | 90-101 | 102-111 | 1-30 | 31-35 | 36-49 | 50-66 | 67-98 | 99-112 | 113-123 |
| 172 | 139 | 140 | 1-23 | 24-34 | 35-49 | 50-56 | 57-88 | 89-96 | 97-106 | 1-30 | 31-35 | 36-49 | 50-66 | 67-98 | 99-107 | 108-118 |
| 173 | 141 | 142 | 1-23 | 24-34 | 35-49 | 50-56 | 57-88 | 89-97 | 98-107 | 1-30 | 31-35 | 36-49 | 50-66 | 67-98 | 99-109 | 110-120 |
| 174 | 143 | 144 | 1-23 | 24-34 | 35-49 | 50-56 | 57-88 | 89-97 | 98-107 | 1-30 | 31-35 | 36-49 | 50-66 | 67-98 | 99-106 | 107-117 |
| 175 | 145 | 146 | 1-23 | 24-34 | 35-49 | 50-56 | 57-88 | 89-99 | 100-109 | 1-30 | 31-35 | 36-49 | 50-66 | 67-98 | 99-112 | 113-123 |
| 176 | 147 | 148 | 1-23 | 24-34 | 35-49 | 50-56 | 57-88 | 89-98 | 99-108 | 1-30 | 31-35 | 36-49 | 50-66 | 67-98 | 99-109 | 110-120 |
| 178 | 149 | 150 | 1-23 | 24-39 | 40-54 | 55-61 | 62-93 | 94-101 | 102-111 | 1-30 | 31-35 | 36-49 | 50-66 | 67-98 | 99-113 | 114-124 |
| 179 | 151 | 152 | 1-23 | 24-39 | 40-54 | 55-61 | 62-93 | 94-102 | 103-112 | 1-30 | 31-35 | 36-49 | 50-66 | 67-98 | 99-110 | 111-121 |
| 180 | 153 | 154 | 1-23 | 24-34 | 35-49 | 50-56 | 57-88 | 89-98 | 99-108 | 1-30 | 31-35 | 36-49 | 50-66 | 67-98 | 99-109 | 110-120 |
| 181 | 155 | 156 | 1-23 | 24-34 | 35-49 | 50-56 | 57-88 | 89-97 | 98-107 | 1-30 | 31-35 | 36-49 | 50-66 | 67-98 | 99-114 | 115-125 |
| 182 | 157 | 158 | 1-23 | 24-39 | 40-54 | 55-61 | 62-93 | 94-102 | 103-112 | 1-30 | 31-35 | 36-49 | 50-66 | 67-98 | 99-108 | 109-119 |
| 183 | 159 | 160 | 1-23 | 24-35 | 36-50 | 51-57 | 58-89 | 90-98 | 99-108 | 1-30 | 31-35 | 36-49 | 50-66 | 67-98 | 99-107 | 108-118 |
| 184 | 161 | 162 | 1-23 | 24-34 | 35-49 | 50-56 | 57-88 | 89-97 | 98-107 | 1-30 | 31-35 | 36-49 | 50-66 | 67-98 | 99-117 | 118-128 |
| 185 | 163 | 164 | 1-23 | 24-39 | 40-54 | 55-61 | 62-93 | 94-101 | 102-111 | 1-30 | 31-35 | 36-49 | 50-66 | 67-98 | 99-110 | 111-121 |
| 186 | 165 | 166 | 1-23 | 24-35 | 36-50 | 51-57 | 58-89 | 90-99 | 100-109 | 1-30 | 31-35 | 36-49 | 50-66 | 67-98 | 99-107 | 108-118 |
| 187 | 167 | 168 | 1-23 | 24-34 | 35-49 | 50-56 | 57-88 | 89-97 | 98-107 | 1-30 | 31-35 | 36-49 | 50-66 | 67-98 | 99-107 | 108-118 |
| 188 | 169 | 170 | 1-23 | 24-39 | 40-54 | 55-61 | 62-93 | 94-103 | 104-113 | 1-30 | 31-35 | 36-49 | 50-66 | 67-98 | 99-111 | 112-122 |
| 189 | 171 | 172 | 1-23 | 24-39 | 40-54 | 55-61 | 62-93 | 94-102 | 103-112 | 1-30 | 31-35 | 36-49 | 50-66 | 67-98 | 99-110 | 111-120 |
| 190 | 173 | 174 | 1-23 | 24-39 | 40-54 | 55-61 | 62-93 | 94-102 | 103-112 | 1-30 | 31-35 | 36-49 | 50-66 | 67-98 | 99-105 | 106-116 |
| 194 | 175 | 176 | 1-23 | 24-39 | 40-54 | 55-61 | 62-93 | 94-102 | 103-112 | 1-30 | 31-35 | 36-49 | 50-66 | 67-98 | 99-113 | 114-124 |
| 197 | 177 | 178 | 1-23 | 24-39 | 40-54 | 55-61 | 62-93 | 94-102 | 103-112 | 1-30 | 31-35 | 36-49 | 50-66 | 67-98 | 99-113 | 114-124 |
| 198 | 179 | 180 | 1-23 | 24-39 | 40-54 | 55-61 | 62-93 | 94-102 | 103-112 | 1-30 | 31-35 | 36-49 | 50-66 | 67-98 | 99-106 | 107-117 |

TABLE 1-continued

| Cluster # | VL polypeptide SEQ ID NO: | VH polypeptide SEQ ID NO: | Light FR1 range | Light CDR1 range | Light FR2 range | Light CDR2 range | Light FR3 range | Light CDR3 range | Light FR4 range | Heavy FR1 range | Heavy CDR1 range | Heavy FR2 range | Heavy CDR2 range | Heavy FR3 range | Heavy CDR3 range | Heavy FR4 range |
|---|---|---|---|---|---|---|---|---|---|---|---|---|---|---|---|---|
| 201 | 181 | 182 | 1-23 | 24-39 | 40-54 | 55-61 | 62-93 | 94-102 | 103-112 | 1-30 | 31-35 | 36-49 | 50-66 | 67-98 | 99-110 | 111-121 |
| 205 | 183 | 184 | 1-23 | 24-39 | 40-54 | 55-61 | 62-93 | 94-102 | 103-112 | 1-30 | 31-35 | 36-49 | 50-66 | 67-98 | 99-113 | 114-124 |
| 206 | 185 | 186 | 1-23 | 24-39 | 40-54 | 55-61 | 62-93 | 94-102 | 103-112 | 1-30 | 31-35 | 36-49 | 50-66 | 67-98 | 99-112 | 113-123 |
| 208 |  | 187 | — | — | — | — | — | — | — | 1-30 | 31-35 | 36-49 | 50-66 | 67-98 | 99-112 | 113-123 |
| 211 | 188 | 189 | 1-23 | 24-39 | 40-54 | 55-61 | 62-93 | 94-102 | 103-112 | 1-30 | 31-35 | 36-49 | 50-66 | 67-98 | 99-110 | 111-121 |
| 251 | 190 | 191 | 1-22 | 23-33 | 34-48 | 49-55 | 56-87 | 88-97 | 98-107 | 1-30 | 31-35 | 36-49 | 50-66 | 67-98 | 99-115 | 116-126 |
| 252 | 192 | 193 | 1-22 | 23-33 | 34-48 | 49-55 | 56-87 | 88-96 | 97-106 | 1-30 | 31-35 | 36-49 | 50-66 | 67-98 | 99-120 | 121-131 |
| 253 | 194 | 195 | 1-22 | 23-33 | 34-48 | 49-55 | 56-87 | 88-96 | 97-106 | 1-30 | 31-35 | 36-49 | 50-66 | 67-98 | 99-115 | 116-126 |
| 254 | 196 | 197 | 1-22 | 23-33 | 34-48 | 49-55 | 56-87 | 88-96 | 97-106 | 1-30 | 31-35 | 36-49 | 50-66 | 67-98 | 99-115 | 116-126 |
| 255 | 198 | 199 | 1-23 | 24-35 | 36-50 | 51-57 | 58-89 | 90-98 | 99-108 | 1-30 | 31-35 | 36-49 | 50-66 | 67-98 | 99-114 | 115-125 |
| 256 | 200 | 201 | 1-22 | 23-33 | 34-48 | 49-55 | 56-87 | 88-96 | 97-106 | 1-30 | 31-35 | 36-49 | 50-66 | 67-98 | 99-105 | 106-116 |
| 257 | 202 | 203 | 1-22 | 23-33 | 34-48 | 49-55 | 56-87 | 88-96 | 97-106 | 1-30 | 31-35 | 36-49 | 50-66 | 67-98 | 99-118 | 119-129 |
| 259 | 204 | 205 | 1-22 | 23-33 | 34-48 | 49-55 | 56-87 | 88-96 | 97-106 | 1-30 | 31-35 | 36-49 | 50-66 | 67-98 | 99-114 | 115-125 |
| 260 | 206 | 207 | 1-23 | 24-34 | 35-49 | 50-56 | 57-88 | 89-98 | 99-108 | 1-30 | 31-35 | 36-49 | 50-66 | 67-98 | 99-114 | 115-125 |
| 261 | 208 | 209 | 1-23 | 24-35 | 36-50 | 51-57 | 58-89 | 90-98 | 99-108 | 1-30 | 31-35 | 36-49 | 50-66 | 67-98 | 99-113 | 114-124 |
| 262 | 210 | 211 | 1-23 | 24-34 | 35-49 | 50-56 | 57-88 | 89-98 | 99-108 | 1-30 | 31-35 | 36-49 | 50-66 | 67-98 | 99-108 | 109-119 |
| 263 | 212 | 213 | 1-23 | 24-34 | 35-49 | 50-56 | 57-88 | 89-98 | 99-108 | 1-30 | 31-35 | 36-49 | 50-66 | 67-98 | 99-112 | 113-123 |
| 264 | 214 | 215 | 1-23 | 24-34 | 35-49 | 50-56 | 57-88 | 89-98 | 99-108 | 1-30 | 31-35 | 36-49 | 50-66 | 67-98 | 99-109 | 110-120 |
| 265 | 216 | 217 | 1-23 | 24-34 | 35-49 | 50-56 | 57-88 | 89-97 | 98-107 | 1-30 | 31-35 | 36-49 | 50-66 | 67-98 | 99-113 | 114-124 |
| 266 | 218 | 219 | 1-23 | 24-34 | 35-49 | 50-56 | 57-88 | 89-99 | 100-109 | 1-30 | 31-35 | 36-49 | 50-66 | 67-98 | 99-108 | 109-119 |
| 267 | 220 | 221 | 1-23 | 24-34 | 35-49 | 50-56 | 57-88 | 89-97 | 98-107 | 1-30 | 31-35 | 36-49 | 50-66 | 67-98 | 99-106 | 107-117 |
| 270 | 222 | 223 | 1-23 | 24-39 | 40-54 | 55-61 | 62-93 | 94-102 | 103-112 | 1-30 | 31-35 | 36-49 | 50-66 | 67-98 | 99-112 | 113-123 |
| 271 | 224 | 225 | 1-23 | 24-39 | 40-54 | 55-61 | 62-93 | 94-102 | 103-112 | 1-30 | 31-35 | 36-49 | 50-66 | 67-98 | 99-112 | 113-123 |
| 272 | 226 | 227 | 1-23 | 24-39 | 40-54 | 55-61 | 62-93 | 94-102 | 103-112 | 1-30 | 31-35 | 36-49 | 50-66 | 67-98 | 99-113 | 114-124 |
| 273 | 228 | 229 | 1-23 | 24-34 | 35-49 | 50-56 | 57-88 | 89-97 | 98-107 | 1-30 | 31-35 | 36-49 | 50-66 | 67-98 | 99-105 | 106-116 |
| 274 | 230 | 231 | 1-23 | 24-39 | 40-54 | 55-61 | 62-93 | 94-102 | 103-112 | 1-30 | 31-35 | 36-49 | 50-66 | 67-98 | 99-112 | 113-123 |
| 275 | 232 | 233 | 1-23 | 24-39 | 40-54 | 55-61 | 62-93 | 94-102 | 103-112 | 1-30 | 31-35 | 36-49 | 50-66 | 67-98 | 99-105 | 106-138 |
| 276 | 234 | 235 | 1-23 | 24-34 | 35-49 | 50-56 | 57-88 | 89-97 | 98-107 | 1-30 | 31-35 | 36-49 | 50-66 | 67-98 | 99-105 | 106-116 |
| 277 | 236 | 237 | 1-23 | 24-34 | 35-49 | 50-56 | 57-88 | 89-97 | 98-107 | 1-30 | 31-35 | 36-49 | 50-66 | 67-98 | 99-105 | 106-116 |
| 278 | 238 | 239 | 1-23 | 24-39 | 40-54 | 55-61 | 62-93 | 94-102 | 103-112 | 1-30 | 31-35 | 36-49 | 50-66 | 67-98 | 99-112 | 113-123 |
| 279 | 240 | 241 | 1-22 | 23-36 | 37-51 | 52-58 | 59-90 | 91-102 | 103-112 | 1-30 | 31-35 | 36-49 | 50-66 | 67-98 | 99-112 | 113-123 |
| 280 | 242 | 243 | 1-23 | 24-39 | 40-54 | 55-61 | 62-93 | 94-102 | 103-112 | 1-30 | 31-35 | 36-49 | 50-66 | 67-98 | 99-112 | 113-123 |
| 281 | 244 | 245 | 1-23 | 24-39 | 40-54 | 55-61 | 62-93 | 94-102 | 103-112 | 1-30 | 31-35 | 36-49 | 50-66 | 67-98 | 99-112 | 113-123 |
| 282 | 246 | 247 | 1-23 | 24-39 | 40-54 | 55-61 | 62-93 | 94-102 | 103-112 | 1-30 | 31-35 | 36-49 | 50-66 | 67-98 | 99-112 | 113-123 |
| 283 | 248 | 249 | 1-22 | 23-36 | 37-51 | 52-58 | 59-90 | 91-102 | 103-112 | 1-30 | 31-35 | 36-49 | 50-66 | 67-98 | 99-112 | 113-123 |
| 284 | 250 | 251 | 1-22 | 23-36 | 37-51 | 52-58 | 59-90 | 91-102 | 103-112 | 1-30 | 31-35 | 36-49 | 50-66 | 67-98 | 99-112 | 113-123 |
| 285 | 252 | 253 | 1-23 | 24-39 | 40-54 | 55-61 | 62-93 | 94-102 | 103-112 | 1-30 | 31-35 | 36-49 | 50-66 | 67-98 | 99-112 | 113-123 |
| 287 | 254 | 255 | 1-23 | 24-39 | 40-54 | 55-61 | 62-93 | 94-102 | 103-112 | 1-30 | 31-35 | 36-49 | 50-66 | 67-98 | 99-113 | 114-124 |
| 288 | 256 | 257 | 1-22 | 23-36 | 37-51 | 52-58 | 59-90 | 91-102 | 103-112 | 1-30 | 31-35 | 36-49 | 50-66 | 67-98 | 99-112 | 113-123 |
| 289 | 258 | 259 | 1-23 | 24-39 | 40-54 | 55-61 | 62-93 | 94-102 | 103-112 | 1-30 | 31-35 | 36-49 | 50-66 | 67-98 | 99-112 | 113-123 |
| 290 | 260 | none | 1-23 | 24-34 | 35-49 | 50-56 | 57-88 | 89-97 | 98-107 | — | — | — | — | — | — | — |
| 298 | none | 261 | — | — | — | — | — | — | — | 1-30 | 31-35 | 36-49 | 50-66 | 67-98 | 99-115 | 116-126 |
| 299 | 262 | none | 1-23 | 24-34 | 35-49 | 50-56 | 57-88 | 89-97 | 98-107 | — | — | — | — | — | — | — |
| 301 | 263 | none | 1-23 | 24-34 | 35-49 | 50-56 | 57-88 | 89-97 | 98-107 | — | — | — | — | — | — | — |
| 304 | 264 | 265 | 1-22 | 23-36 | 37-51 | 52-58 | 59-90 | 91-102 | 103-112 | 1-30 | 31-35 | 36-49 | 50-66 | 67-98 | 99-112 | 113-123 |
| 305 | 266 | 267 or 268 | 1-22 | 23-36 | 37-51 | 52-58 | 59-90 | 91-102 | 103-112 | 1-30 | 31-35 | 36-49 | 50-66 | 67-98 | 99-112 | 113-123 |

Example 3

Bispecific Antibodies that Bind IL-17A or IL-17F and the p19 Subunit of IL-23

Bispecific antibodies can be constructed from the variable heavy and variable light regions of antibodies that cross-bind to IL-17A and IL-17F with variable heavy and variable light regions of antibodies that bind the p19 subunit of IL-23.

As an example, the antibodies that bind to IL-17A or to IL-17F, which are produced by the ATCC deposited hybridomas described in Example 1 can be joined with the variable heavy and variable light regions of the anti-IL-23p19 antibodies described in Example 2. Such bispecific antibodies can be joined in a variety of different configurations and can comprise tandem scFv molecules (herein referred to as "tascFv"), and scFv molecules that are not tandem (herein referred to as "biscFv" and "BiAb").

For the tascFv molecule, two scFv molecules are constructed such that one scFv is amino terminal to the other one in a tandem configuration. This can be done in each orientation, and use a tether (e.g., a lambda stump tether or a CH1 stump tether, both of which are derived from the native sequence just after the V region in the Fab, or a Gly-Ser tether). The tascFv can be further constructed as fusion protein to contain a Fc component ("tascFv Fc"). Thus the anti-IL-17A or anti-IL-17F binding entity can be the scFv entity that is either proximal or distal to a Fc component. Likewise, an anti-IL-23 binding entity can be the scFv entity that is either proximal or distal to a Fc component.

The biscFv molecule is not a tandem configuration. Rather, it has a scFv at the N terminus and another at the C terminus of an Fc ("biscFv Fc"). These molecules can be made with the N terminal scFv directly fused to the Fc hinge and with either a short or a long linker at the C terminus connecting to the second scFv. These linkers are Gly-Ser. Thus, an anti-IL-17A or anti-IL-17F binding entity can be the scFv entity that is either at the N terminus or at the C terminus to a Fc component. Likewise, an anti-IL-23 binding entity can be the scFv entity that is either at the N terminus or at the C terminus to a Fc component.

The Biab molecule is also not a tandem format. It comprises of a monoclonal antibody with a scFv fused to the C terminus of the heavy chain. These molecules can be made by converting one scFv back to a light chain (kappa or lambda) and a gamma1 heavy chain with the second scFv connected by either a short or long Gly-Ser linker. Thus an anti-IL-17A or anti-IL-17F binding entity can be either scFv that is converted back to a light chain (kappa or lambda) and a gamma1 heavy chain or the second scFv fused to the C terminus. Likewise, an anti-IL-23 binding entity can be either scFv that is converted back to a light chain (kappa or lambda) and a gamma1 heavy chain or the second scFv fused to the C terminus. Also, a Fab (either anti-IL-17A Fab, anti-IL-17F Fab or anti-IL-23 binding Fab) can be fused to the Fc portion rather than converting a scFv back to a light chain (kappa or lambda) and a gamma1 heavy chain.

Additional bispecific molecules are known in the art and include single variable domain antibodies, camelid antibodies, variable domains fused to human serum albumin (See Muller, D, et al., J. Biol. Chem. 282 (Issue 17):12650-12660, 2007), and dual variable domain immunoglobin molecules (See WIPO patent publication number WO/2007/024715, published Mar. 1, 2007, by Wu, Chengbin, et al.), "Knob-into-hole" configurations described by Carter, et al. (1996); "IgG-C-terminal scFv" configuration described by Morrison, et al. (1997); "Tandem scFv-Fc" configuration described by Kanner, et al. (1998); "Diabody-Fc" configuration described by Kontermann, et al. (1999); "scFv-Fc-scFv" configuration described by Barbas, et al. (2003).

Example 4

IL-17A/F mAb Competitive Binding Assay Protocol

To assess the ability of the anti-IL-17A/anti-IL-17F cross-binding antibodies of the present invention to bind the ligands IL-17A and IL-17F, a Flow Cytometry-based competitive binding assay is utilized. Incubation of a BHK cell line stably transfected with full length IL-17RC in the presence of the ligands IL-17A or IL-17F, and an IL-17A/F antibody of the present invention targeted to bind the ligands allows for detection and relative quantification of ligand bound to the cell surface (and therefore unbound by the antibody). The biotinylation of the ligand allows for FACS detection using a secondary Streptavidin conjugated fluorophore. A reduction in cell bound ligand over a titration of the antibody is recorded as a reduction in the mean fluorescence of the cells.

Biotinylated ligands are individually pre-mixed at 1 ug/ml with titrating amounts of antibody in staining media (HBSS+1% BSA+0.1% NaAzide+10 mM HEPES) in 100 ul volumes and incubated at RT for 15 minutes. A BHK cell line stably transfected with full length IL17RC is prepared for ligand staining by resuspension with Versene (Invitrogen cat. 15040-066), equilibrating to 2×10e5 cells/100 ul, pelleting, and resuspension in the ligand/antibody pre-mix. Stained cells are incubated at 4° for 30 minutes, washed 1× in staining media, and stained with Streptavidin-PE (BD Pharmingen cat. 554061) at a 1:100 ratio. Cells are incubated at 4° in the dark for 30 minutes, washed 2× in staining media, and re-suspended in a 1:1 ratio of staining media and Cytofix (BD Bioscience 554655). The BD LSRII Flow Cytometer or similar instrument is used for data collection and analysis. The software calculates the IC50 for each curve. Antibodies having an IC50 value similar to those of the ATCC Patent Deposit Designation PTA-7987 (clone 339.15.5.3), ATCC Patent Deposit Designation PTA-7988 (clone 339.15.3.6), and ATCC Patent Deposit Designation PTA-7989 (clone 339.15.6.16), will be effective at inhibiting, reducing, or neutralizing the effects of IL-17A or IL-17F and thus be useful in methods for inhibiting inflammation in a mammal comprising administering an antagonist of IL-23 and an antagonist of IL-17A or IL-17F to the mammal, wherein the antagonist of IL-17A or IL-17F can bind IL-17A or IL-17F. In this assay, the IC50 (ug/ml) against IL-17A was between 28 and 38 (i.e., 28 ug/ml, 35 ug/ml, and 38 ug/ml). In this assay the IC50 against IL-17F was between 3.5 and 3.6 ug/ml. IC50 values against IL-17A and IL-17F between 2 ug/ml and 380 ug/ml are contemplated by this invention.

Example 5

Inhibition of Activation by Human IL-17A and Human IL-17AF in Murine Nih3t3 Cells Using an Antagonist to Human IL-17A or IL-17F A murine nih3t3 cell line was stably transfected with the kz170 (nfkb) reporter construct, containing a neomycin-selectable marker. See U.S. patent application Ser. No. 11/762,738, filed Jun. 13, 2007. This cell line, or a similar one, can be used to determine the EC50 levels of the antibodies that bind to IL-17A or IL-17F.

Antibodies to human IL-17A are used as antagonists of human IL-17A or human IL-17AF activation of nfkb elements in a luciferase assay. In this assay, EC50 levels of human IL-17A- or IL-17AF-mediated nfkb activation in the murine nih3t3/kz170 assay cell line is measured. For highly effective antibodies, when used at approx. 10 m/mL concentration, the antibody can completely neutralize activity induced by human IL-17A or IL-17AF, with the inhibition of activity decreasing in a dose dependent fashion at the lower concentrations. An isotype-matched negative control mAb, tests at the concentrations described above, provided no inhibition of activity. These results demonstrate that antibodies against IL-17A or IL-17F are able to antagonize the activity of the pro-inflammatory cytokines, IL-17A and IL-17AF.

Example 6

Bioassay for Neutralization of huIL-17-Induced Cytokine Production in Human Small Airway Epithelial Cells (SAEC IL-12 PHA Bioassay)

Treatment of human small airway epithelial cells (SAEC) with rhIL-17 induces the production of cytokines G-CSF, IL-6, and IL-8, which in turn, play a role in the pathology associated with the diseases for which a bispecific neutralizing antibody comprising an antibody or antibody fragment that cross-binds IL-17A and IL-17F and an antibody or antibody fragment that binds IL-23p19 would be efficacious. The ability of any of the neutralizing entities described herein to inhibit IL-17-mediated production of these cytokines is measured in this bioassay, thus being predictive of in vivo efficacy against these cytokines as well.

Method: SAEC (cells and growth media purchased from Cambrex, Inc.) are plated at 8,000 cells/well in 96-well flat bottom tissue culture multi-well plates, and placed in a 370 C, 5% CO2 incubator. The following day, cells are treated with a dose range of the neutralizing entity in combination with 10-20 ng/mL rhIL-17. The ligand and neutralizing entity are incubated together for 30 minutes at 37° C before adding to the cells. Duplicate or triplicate wells are set up for each dose. After 24-48 hours, supernatants are collected, and stored at −80° C if not used directly. Before taking supernatants, wells are scanned by inverted microscope to make note of which wells had considerable cell death. Those wells are not included in the final calculations. Supernatants are then assayed for cytokines huG-CSF, huIL-6, and huIL-8 in a multiplex bead-based assay system (Bio-Rad Laboratories), and IC50 determined.

In the presence of rhIL-17, antibodies that cross-bind to IL-17A or IL-17F are efficacious at reducing cytokine production with IC50 values ranging from 0.1-100 nM.

Example 7

Bioassay for Neutralization of huIL17A-Induced G-CSF and IL-6 Cytokine Production in U373MG and U87MG Human Glioblastoma Cells rhIL-17A treatment induces the production of cytokine IL-6 in human glioblastoma cells U373MG, and of cytokines G-CSF and IL-6 in human glioblastoma cells U87MG. The cell lines are available from commercial vendors such as ATCC (Manassas, Va.). These cytokines, in turn, play a role in the pathology associated with the diseases for which antagonists of IL-17A and IL23p19 would be efficacious. The ability of any of the antagonists described herein to inhibit rhIL-17A-mediated production of G-CSF and IL-6 is measured in this bioassay, thus being predictive of in vivo efficacy against this cytokine as well.

Method: Cells are plated in media (MEM w/Earle's salts, 10% FCS, 2 mM L-glutamine, 1 mM sodium pyruvate, 100 uM NEAA) at 3,000-7,000 cells/well in 96-well flat bottom tissue culture multi-well plates and placed in a 37° C., 5% CO2 incubator from 1 hr to overnight. Doses of the neutralizing entities are prepared in culture media with FCS concentration reduced to 2%. The cells are treated with a dose range of the neutralizing entity in combination with 0.20-0.5 nM rhIL-17A. The ligand and neutralizing entity are incubated together for 30 minutes at 37° C. before adding to the cells. Supernatants are collected after 24 hours and assayed for huG-CSF and huIL-6 using a bead-based assay system (Bio-Rad Laboratories), and IC50 determined.

In the presence of rhIL-17A, the anti-IL-17A antagonists are efficacious at reducing huIL-6 cytokine production by U373MG cells, with IC50 values ranging from 2.3-45 nM. For U87MG cells, neutralization of huG-CSF cytokine production with IC50 values ranging from 0.17-0.52 nM is efficacious.

Example 8

IL-12 Bioassy

Leukopheresis PBMC: To obtain a consistent pool of PBMC's, normal human donors are voluntarily apheresed. The leukopheresis PBMC are poured into a sterile 500 ml plastic bottle, diluted to 400 ml with room temperature PBS+1 mM EDTA and transferred to 250 ml conical tubes. The 250 ml tubes are centrifuged at 1500 rpm for 10 minutes to pellet the cells. The cell supernatant is then removed and discarded. The cell pellets are then combined and suspended in 400 ml PBS+1 mM EDTA. The cell suspension (25 ml/tube) is overlaid onto Ficoll (20 ml/tube) in 50 ml conical tubes. The tubes are centrifuged at 2000 rpm for 20 minutes at room temperature. The interface layer ("buffy coat") containing the white blood cells and residual platelets is collected, pooled and washed repeatedly with PBS+1 mM EDTA until the majority of the platelets are removed. The white blood cells are suspended in 100 ml of ice-cold Cryopreservation medium (70% RPMI+20% FCS+10% DMSO) and distributed into sterile cryovials (1 ml cells/vial). The cryovials are placed in a −80° C. freezer for 24 hours before transfer to a liquid-nitrogen freezer. The white blood-cell yield from a typical apheresis is $0.5$-$1.0 \times 10^{10}$ cells. Apheresis cells processed in this manner contain T cells, B cells, NK cells, monocytes and dendritic cells.

Preparation of PHA blasts: T cells must be activated in order to express the IL-12 receptor and be able to respond to IL-12 and IL-23. Cryopreserved leukopheresis PBMC are thawed, transferred to a sterile 50 ml conical tube, washed once with 50 ml of warm RPMI+10% heat-inactivated FBS+1 ug/ml DNAse I (Calbiochem), resuspended in 50 ml of fresh RPMI/FBS/DNAse medium and incubated in a 37° C. water bath for at least 1 hour to allow the cells to recover from being thawed. The cells are then centrifuged and the cell-supernatant discarded. The cell pellet is resuspended in RPMI+10% FBS and distributed into sterile 75 cm2 tissue culture flasks ($1 \times 10^7$ cells/flask in 40 ml/flask). PHA-L (5 mg/ml stock in PBS) is added to the cells at a final concentration of 5 ug/ml. The cells are then cultured at 37° C. in a humidified incubator for a total of 5 days. The cells are "rested" for some experiments by harvesting the cells on the afternoon of day 4, replacing the culture medium with fresh RPMI+10% FBS without PHA-L (40 ml/flask) and returning the cells to their flasks and incubating at 37° C. the cells in a humidified incubator for the remainder of the 5 day culture period.

IL-12 and IL1-23 bioassays: Three in vitro assays for detection of human IL-12 and Il-23 bioactivity on normal human T cells have been established: 1) IFN-gamma and MIP-1 alpha production, 2) proliferation ([3H]-incorporation) and 3) STAT3 activation. Human PHA blasts (activated T cells) are harvested on day 5 of culture, suspended in fresh RPMI+10% FBS and plated at the desired cell number per well in 96 well plates.

The inclusion of an IL-12 assay is used to determine specificity of the neutralizing entities described herein for IL-23p19 and not IL-12.

For the IFN-gamma production assay, the cells are plated at $1 \times 10^6$/well in flat-bottom 96-well plates. The cells are cultured at 37° C. in a final volume of 200 ul/well with either medium alone, human IL-2 alone (10 ng/ml; R & D Systems), human IL-12 alone (graded doses; Invitrogen), human IL-23 alone (graded doses; made in-house; CHO-derived), anti-human CD28 mAb alone (graded doses; clone 28.2, e-Biosciences), or each cytokine in combination with anti-human CD28 mAb. Triplicate wells are set up for each culture condition. For the IFN-gamma production assay, cell supernatants (120 ul/well) are harvested after 24-48 hours of culturing the cells at 37° C. in a humidified incubator. Human IFN-gamma and MIP-1alpha concentrations in these supernatants (pooled for each triplicate) are measured using a commercial Luminex bead-based ELISA kit (Invitrogen) following the manufacturer's instructions.

Effects of IL-23 on IFN-gamma and MIP-1 alpha production are enhanced by culturing the cells with plate-immobilized anti-human CD3 mAb (5 ug/ml) and soluble anti-human CD28 mAb (1 ug/ml) as well as harvesting the supernatants (120 ul/well) after 48 hrs of culture at 37° C. the cells in a humidified incubator. Human IFN-gamma concentrations in these supernatants (pooled for each triplicate) are measured using a commercial Luminex bead-based ELISA kit (Invitrogen) following the manufacturer's instructions.

For the [3H]-incorporation assay the cells are plated at $2 \times 10^5$ cells/well in U-bottom 96-well plates. The cells are cultured at 37 degrees C. for 72 hours. The cells are pulsed with 1 uCi/well of [3H]-Thymidine (Amersham) for the last 8 hours of this culture period. The cells are then harvested onto glass-fiber filters and the CPMs of [3H] incorporated are quantitated using a beta counter (Topcount NXT, Packard).

For each of these above endpoint parameters, effective neutralization of activity mediated by IL-23 is observed in the presence of anti-IL23p19 neutralizing entities described herein at IC50 values that range from 0.1 to ~100 nM. No effect of the anti-IL-23p19 antagonists on neutralizing the effects mediated by IL-12, indicates specificity of the antagonists to IL-23p19.

STAT3 Bioassay: For the STAT3 Bioassay the cells are plated at $2 \times 10^5$ cells/well in U-bottom 96-well plates. Serial dilutions of human IL-12 (R&D) or recombinant human IL-23 (in-house CHO-derived material or eBioscience's Insect heterodimer material) are prepared in assay media (RPMI 1640 with L-Glutamine plus 10% fetal bovine serum), added to the plates containing the cells and incubated together at 37° C. for 15 minutes. Additionally, the assay is also used to measure neutralization of IL-12 and IL-23 activity using either commercially-available neutralizing reagents (as "controls") or the anti-IL-23p19-containing neutralizing entities described herein. A half-maximal concentration (EC50, effective concentration at 50 percent) of IL-12 or IL-23 are combined with serial dilutions of anti-human IL-12 p40 monoclonal antibody (Pharmingen), anti-human IL-23 p19 polyclonal antibody (R&D, AF1716), human IL-23R-Fc Soluble Receptor, or any of the neutralizing entities described herein, and incubated together at 37° C. for 30 minutes in assay media prior to addition to cells. Following pre-incubation, treatments are added to the plates containing the cells and incubated together at 37° C. for 15 minutes.

Following incubation, cells are washed with ice-cold wash buffer and put on ice to stop the reaction, according to manufacturer's instructions (BIO-PLEX Cell Lysis Kit, BIO-RAD Laboratories, Hercules, Calif.). Cells are then spun down at 2000 rpm at 4° C. for 5 minutes prior to removing the media. 50 ul/well lysis buffer is added to each well; lysates are pipetted up and down five times while on ice, then agitated on a microplate platform shaker for 20 minutes at 300 rpm and 4° C. Plates are centrifuged at 4500 rpm at 4° C. for 20 minutes. Supernatants are collected and transferred to a new micro titer plate for storage at −20° C.

Capture beads (BIO-PLEX Phospho-STAT3 Assay, BIO-RAD Laboratories) are combined with 50 ul of 1:1 diluted lysates and added to a 96-well filter plate according to manufacture's instructions (BIO-PLEX Phosphoprotein Detection Kit, BIO-RAD Laboratories). The aluminum foil-covered plate is incubated overnight at room temperature, with shaking at 300 rpm. The plate is transferred to a microtiter vacuum apparatus and washed three times with wash buffer. After addition of 25 μL/well detection antibody, the foil-covered plate is incubated at room temperature for 30 minutes with shaking at 300 rpm. The plate is filtered and washed three times with wash buffer. Streptavidin-PE (50 ul/well) was added, and the foil-covered plate is incubated at room temperature for 15 minutes with shaking at 300 rpm. The plate is filtered and washed two times with bead resuspension buffer. After the final wash, beads are resuspended in 125 ul/well of bead suspension buffer, shaken for 30 seconds, and read on an array reader (BIO-PLEX, BIO-RAD Laboratories) according to the manufacture's instructions. Data are analyzed using analytical software (BIO-PLEX MANAGER 3.0, BIO-RAD Laboratories).

Increases in the level of the phosphorylated STAT3 transcription factor present in the lysates are indicative of an IL-12 or IL-23 receptor-ligand interaction. For the neutralization assay, decreases in the level of the phosphorylated STAT3 transcription factor present in the lysates are indicative of neutralization of the IL-12 or IL-23 receptor-ligand interaction. IC50 (inhibitory concentration at 50 percent) values are calculated using GraphPad Prism®4 software (GraphPad Software, Inc., San Diego Calif.) and expressed as molar ratios for each reagent and/or neutralizing entity in the neutralization assay.

Efficacious anti-IL-23p19 neutralizing entities are equally or better than the commercially available reagents at neutralizing the effects of rhIL-23 and they specifically inhibit rhIL-23 and not IL-12.

Example 9

IL-12 Bioassy

Bioassay for Neutralization of Human IL-23 Mediated IL-17A and IL-17F Production in Murine Splenocytes Recombinant human IL-23 (rhIL-23) induces the production of IL-17A and IL-17F in murine splenocytes. To evaluate antagonists to IL-23, neutralization of IL-17A and IL-17F production in rhIL-23 treated murine splenocytes is examined. Antagonists to rhIL-23 are compared to the commercial neutralizing antibody anti-IL-12p40 (Pharmingen, Franklin Lakes, N.J.).

Experimental protocol: A single cell suspension of splenocytes are prepared from whole spleens harvested from either C57BL/6 or BALB/c mice. After red blood cell lysis with ACK buffer (0.010 M KHCO3, 0.0001 M EDTA, 0.150 M NH4Cl), splenocytes are washed and resuspended in RPMI buffer (containing 1% non-essential amino acids, 1% Sodium Pyruvate, 2.5 mM HEPES, 1% L-glutamine, 0.00035% 2-mercaptoethanol, 1% Pen/Strep, 10% FCS and 50 ng/ml human IL-2 (R&D Systems, Minneapolis, Minn.)). Cells are seeded at 500,000 cells per well in a 96-well round bottom plate. In a separate plate, rhIL-23 at a concentration of 10 pM is pre-incubated for 30-90 minutes at 37° C. with 3-fold serial dilutions of the antagonists. Concentrations of the antagonists range from 0-343 nM. The IL-23 ligand plus antagonists are then added to the splenocytes and incubated at 37° C., 5% CO2 for 24-72 hours. The supernatants are collected and frozen at −80° C. until ready to process. The levels of IL-17A and IL-17F protein in the supernatants are measured using bead-based sandwich ELISAs. A commercial kit (Upstate, Charlottesville, Va.) is used to measure IL-17A protein. A bead-based ELISA developed in-house using an antibody to IL-17F (R&D) conjugated to a bead is used to measure IL-17F. IC50 values for each antagonist are calculated as the amount of antagonist needed to neutralize 50% of the activity of rhIL-23.

In the presence of rhIL-23, the anti-IL-23p19 antibodies are efficacious at reducing IL-17A and IL-17F production with IC50 values in the range of 0.27-100.0 nM.

Example 10

Disease Incidence and Progression in Mouse Experimental Allergic Encephalomyelitis (EAE) as a Model of Multiple Sclerosis Recombinant Human IL-23 (rhIL-23

A) Mouse Allergic Encephalomyelitis (EAE) Model

To study mechanism and evaluate the effects of potential therapies for multiple sclerosis, the animal model of experimental autoimmune encephalomyelitis (EAE) is commonly used. For the relapsing-remitting EAE model, 9 to 10 week old female SJL mice (Jackson or Charles River Labs) are immunized subcutaneously with proteolipid peptide (PLP) emulsified in complete Freund's adjuvant, and with intravenous pertussis toxin. Within approximately 6 to 23 days, animals begin to show symptoms of weight loss and paralysis that are characteristic of this model. The extent of disease is evaluated daily in the mice by taking their body weights and assigning a clinical score (0-8) to each mouse, as detailed below. The typical pattern of disease symptoms in immunized, but otherwise untreated mice, is one of weight loss and paralysis, followed by a period of disease symptom remission, and a subsequent relapse of disease symptoms. A pattern of relapses and remissions of disease symptoms ensues, which is also found in humans with this type of multiple sclerosis, known as relapsing-remitting disease. Chronic progressive and secondary progressive multiple sclerosis are also targeted indications for this therapeutic combination of an antibody that binds IL-17A or IL-17F and IL-23/p19 such as a bispecific antibody or scFV as described in this invention. These latter types of multiple sclerosis are tested in a similar manner using MOG35-55 peptide in C57BL/6 mice, instead of PLP in SJL mice.

Neutralizing monoclonal antibodies to mouse IL-17A and IL-23p19 are administered separately or as a therapeutic combination, during remission from the first peak of EAE disease symptoms. The antibodies are delivered as intraperitoneal injections every other day, or as a similar dosing regimen. Groups receive either 25, 50 or 100 ug of each antibody, alone or as a therapeutic combination, per animal per dose, and control groups receive the vehicle control, PBS (Life Technologies, Rockville, Md.) or antibody isotype control.

B) Monitoring Disease

Animals can begin to show signs of paralysis and weight loss between approximately 6 and 23 days following PLP or MOG35-55 immunizations. Most animals develop symptoms within 11-17 days of the immunizations, but some may show symptoms sooner or later than this.

All animals are observed, weighed, and assigned a clinical score daily to assess the status of disease.

C) Clinical Score

Clinical Score is measured as follows: 0=Normal; healthy; 1=slight tail weakness (tip of tail does not curl and); 2=tail paralysis (unable to hold tail upright); 3=tail paralysis and mild waddle; 4=tail paralysis and severe waddle; 5=tail paralysis and paralysis of one limb; 6=tail paralysis and paralysis of any 2 limbs; 7=tetraparesis (all 4 limbs paralysed); and 8=moribund or dead.

Blood is collected throughout the experiment to monitor serum levels of cytokine and levels of other mediators of disease. At the time of euthanasia, blood is collected for serum, and brain and spinal cord collected in 10% NBF for histology. In separate animals, tissues (including lymph nodes, brain, spinal cord, spleen, and others) are harvested for the quantification of mRNA by TaqMan quantitative real-time PCR.

D) Results

Groups of mice (n=13-15 each) receiving the therapeutic combination of neutralizing monoclonal antibodies to IL-17 and IL-23/p19 are characterized by a significant ($p<0.05$) reduction in disease severity as evidenced by significant ($p<0.05$) reductions in clinical score and body weight loss compared to mice treated with PBS, either of the antibodies alone at similar doses as those used in the combination, or isotype control antibodies. Furthermore, the mice treated with the therapeutic antibody combination, i.e., an antibody that binds IL-17A or IL-17F and IL-23p19 may show a complete absence of disease relapse.

Significant reductions in serum IL-6, IL-13, IL-17A, IL-23, G-CSF, and TNF-a concentrations compared to PBS-treated mice will also be efficacious. Samples are collected at the same time point following peak of first disease onset and after the same number of antibody doses. Draining lymph nodes are harvested from the mice at this same time point and cultured for 24 h with PLP139-151.

Thus the therapeutic combination of an antibody that binds IL-17A or IL-17F and IL23/p19 may be more efficacious in the treatment of EAE as a model of human multiple sclerosis. The therapeutic combination can reduce clinical disease symptoms and works at the molecular level to reduce inflammation, inflammatory infiltrates, inflammatory cytokines/chemokines, and other mechanisms known to be affected in this manner.

Example 11

Disease Incidence and Progression in Mouse Murine Colitis

IL-23 and IL-17 are important players in murine colitis and human IBD, via the actions of Th17 cells. IL-23 and IL-17 are upregulated in colitis and IBD, and neutralization of either cytokine alone is efficacious in several animal models of colitis (Fujino et al, Gut, 2003, 52:65-70; Schmidt et al, Inflamm Bowel Dis. 2005, 11:16-23; Yen et al, J Clin Invest. 2006, 116:1310-1316; Zhang et al, Inflamm Bowel Dis. 2006, 12:382-388; Kullberg et al, J Exp Med. 2006, 203:2485-94.). Since IL-23 is important for the maintenance, differentiation, and/or induction of Th17 cells, neutralization of both cytokines would be more efficacious at reducing disease than either cytokine alone.

Methods: For this experiment, 40 C57BL/10 female mice (obtained from Harlan) are used. On day −5, mice are treated topically with 200 ul of 3.0% (w/v) oxazalone in 100% ethanol ("sensitization") on the abdomen. On day 0, all mice receive intrarectal injections (120 uL each) of 2.0% (w/v) oxazalone in 50% ethanol while under light isoflurane gas anesthesia ("challenge"). Mice are monitored for disease using a Disease Activity Index (DAI) score, which includes stool consistency, body weight, and blood in stool. For mAb treatments, mice are administered one of the following, via i.p. injection on days −5, −3, and −1: PBS, 50 ug neutralizing anti-mouse IL-17, 50 ug neutralizing anti-mouse IL-23p19 mAb, or a combination of the anti-IL17+IL-23p19 mAb's.

Mice are euthanized on day 2. Serum is collected and stored for later analysis; colons are removed and observed for any gross signs of colitis (lesion, colon shortening, and colon wall thickening). Colons are then cut longitudinally and processed for histology and for 24 h colon cultures.

A significant reduction in DAI score and significant improvement in histological morphology (e.g. reduced colonic damage and reduced inflammation, shortened colon) in mice treated with the combination of anti-IL-17+anti-IL- 23p19 antibodies, compared to PBS and either mAb alone would show efficacious treatment.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method of treating inflammation in a patient in need thereof, comprising administering an effective amount of an antagonist of IL-23 and IL-17A or IL-17F to the patient, wherein the antagonist comprises an anti-IL-23 antibody or fragment thereof, which binds the p19 subunit of IL-23, and comprises a heavy chain variable region polypeptide as shown in SEQ ID NO:268 and a light chain variable region polypeptide as shown in SEQ ID NO:266; and a cross-reactive antibody or fragment thereof, which binds IL-17A or IL-17F, and comprises the CDRs of an antibody selected from the group consisting of:
   a) the antibody produced by the hybridoma of ATCC Patent Deposit Designation PTA-7987;
   b) the antibody produced by the hybridoma of ATCC Patent Deposit Designation PTA-7988; and
   c) the antibody produced by the hybridoma of ATCC Patent Deposit Designation PTA-7989.

2. The method of claim 1, wherein the cross-reactive antibody or fragment thereof comprises heavy chain variable region polypeptide selected from the group consisting of:
   a. the heavy chain variable region of the antibody produced by the hybridoma of ATCC Patent Deposit Designation PTA-7987;
   b. the heavy chain variable region of the antibody produced by the hybridoma of ATCC Patent Deposit Designation PTA-7988; and
   c. the heavy chain variable region of the antibody produced by the hybridoma of ATCC Patent Deposit Designation PTA-7989.

3. The method of claim 1, wherein the cross-reactive antibody or fragment thereof comprises a light chain variable region polypeptide selected from the group consisting of:
   a. the light chain variable region of the antibody produced by the hybridoma of ATCC Patent Deposit Designation PTA-7987;
   b. the light chain variable region of the antibody produced by the hybridoma of ATCC Patent Deposit Designation PTA-7988; and
   c. the light chain variable region of the antibody produced by the hybridoma of ATCC Patent Deposit Designation PTA-7989.

4. The method of claim 1, wherein the cross-reactive antibody or fragment thereof comprises a heavy chain variable region polypeptide and a light chain variable region polypeptide of the antibody selected from the group consisting of:
   a) the antibody produced by the hybridoma of ATCC Patent Deposit Designation PTA-7987;

b) the antibody produced by the hybridoma of ATCC Patent Deposit Designation PTA-7988; and
c) the antibody produced by the hybridoma of ATCC Patent Deposit Designation PTA-7989.

5. The method of claim 1, wherein said cross-reactive antibody or fragment thereof is humanized.

6. The method of claim 1, wherein said cross-reactive antibody or fragment thereof is chimeric.

7. The method of claim 1, wherein the cross-reactive antibody or fragment thereof is a single chain antibody.

8. The method of claim 1, wherein the anti-IL-23 antibody or fragment thereof is a single chain antibody.

9. The method of claim 1, wherein the anti-IL-23 antibody fragment is selected from the group consisting of Fv, Fab, Fab', F(ab)$_2$, and F(ab')$_2$, and wherein the cross-reactive antibody fragment is selected from the group consisting of Fv, Fab, Fab', F(ab)$_2$, and F(ab')$_2$.

10. The method of claim 1, wherein the antagonist is a bispecific antibody.

11. The method of antagonist of claim 10, wherein the antibody is a tascFv, a biscFv, or a BiAb antibody.

12. The method of claim 1, wherein the antagonist comprises a PEG moiety.

13. The method of claim 1, wherein the antagonist comprises an Fc moiety.

14. The method of claim 1, wherein the antagonist is a bivalent, trivalent, or tetravalent antibody.

* * * * *

UNITED STATES PATENT AND TRADEMARK OFFICE
CERTIFICATE OF CORRECTION

PATENT NO. : 8,333,968 B2  
APPLICATION NO. : 13/032501  
DATED : December 18, 2012  
INVENTOR(S) : Katherine E. Lewis et al.

Page 1 of 1

It is certified that error appears in the above-identified patent and that said Letters Patent is hereby corrected as shown below:

On the Title Page:

Item (57), ABSTRACT:

Column 2, line 6 (Abstract), change "Il-17F" to --IL-17F--.

Signed and Sealed this
Seventeenth Day of March, 2015

Michelle K. Lee
*Director of the United States Patent and Trademark Office*

SEQUENCE LISTING

```
<160> NUMBER OF SEQ ID NOS: 268

<210> SEQ ID NO 1
<211> LENGTH: 1874
<212> TYPE: DNA
<213> ORGANISM: Homo sapiens

<400> SEQUENCE: 1
gaattccggc aggcacaaac tcatccatcc ccagttgatt ggaagaaaca acgatgactc      60
ctgggaagac ctcattggtg tcactgctac tgctgctgag cctggaggcc atagtgaagg     120
caggaatcac aatcccacga aatccaggat gcccaaattc tgaggacaag aacttccccc     180
ggactgtgat ggtcaacctg aacatccata accggaatac caataccaat cccaaaaggt     240
cctcagatta ctacaaccga tccacctcac cttggaatct ccaccgcaat gaggaccctg     300
agagatatcc ctctgtgatc tgggaggcaa agtgccgcca cttgggctgc atcaacgctg     360
atgggaacgt ggactaccac atgaactctg tccccatcca gcaagagatc ctggtcctgc     420
gcagggagcc tccacactgc cccaactcct tccggctgga aagatactg gtgtccgtgg      480 gctgcacctg tgtcaccccg attgtccacc atgtggccta agagctctgg ggagcccaca     540
ctccccaaag cagttagact atggagagcc gacccagccc tcaggaacc ctcatccttc      600 aaagacagcc tcatttcgga ctaaactcat tagagttctt aaggcagttt gtccaattaa     660
agcttcagag gtaacacttg gccaagatat gagatctgaa ttacctttcc ctctttccaa     720
gaaggaaggt ttgactgagt accaatttgc ttcttgttta cttttttaag ggctttaagt     780
tatttatgta tttaatatgc cctgagataa ctttggggta taagattcca ttttaatgaa     840
ttacctactt tattttgttt gtcttttttaa agaagataag attctgggct tgggaatttt     900
attatttaaa aggtaaaacc tgtatttatt tgagctattt aaggatctat ttatgtttaa     960
gtatttagaa aaaggtgaaa aagcactatt atcagttctg cctaggtaaa tgtaagatag    1020
aattaaatgg cagtgcaaaa tttctgagtc tttacaacat acggatatag tatttcctcc    1080
tctttgtttt taaaagttat aacatggctg aaaagaaaga ttaaacctac tttcatatgt    1140
attaatttaa atttttgcaat ttgttgaggt tttacaagag atacagcaag tctaactctc    1200
tgttccatta aaccttata ataaaatcct tctgtaataa taaagtttca aaagaaaatg     1260
tttatttgtt ctcattaaat gtattttagc aaactcagct cttccctatt gggaagagtt    1320
atgcaaattc tcctataagc aaaacaaagc atgtctttga gtaacaatga cctggaaata    1380
cccaaaattc caagttctcg atttcacatg ccttcaagac tgaacaccga ctaaggtttt    1440
catactatta gccaatgctg tagacagaag cattttgata ggaatagagc aaataagata    1500
atggccctga ggaatggcat gtcattatta aagatcatat ggggaaaatg aaaccctccc    1560
caaaatacaa gaagttctgg gaggagacat tgtcttcaga ctacaatgtc cagtttctcc    1620
cctagactca ggcttccttt ggagattaag gcccctcaga gatcaacaga ccaacatttt    1680
tctcttcctc aagcaacact cctagggcct ggcttctgtc tgatcaaggc accacacaac    1740
ccagaaagga gctgatgggg cagaatgaac tttaagtatg agaaaagttc agcccaagta    1800
aaataaaaac tcaatcacat tcaattccag agtagtttca agtttcacat cgtaaccatt    1860
```

-continued ttcgcccgga attc 1874

<210> SEQ ID NO 2
<211> LENGTH: 155
<212> TYPE: PRT
<213> ORGANISM: Homo sapiens

<400> SEQUENCE: 2

```
Met Thr Pro Gly Lys Thr Ser Leu Val Ser Leu Leu Leu Leu Ser
 1               5                  10                  15

Leu Glu Ala Ile Val Lys Ala Gly Ile Thr Ile Pro Arg Asn Pro Gly
                20                  25                  30

Cys Pro Asn Ser Glu Asp Lys Asn Phe Pro Arg Thr Val Met Val Asn
            35                  40                  45

Leu Asn Ile His Asn Arg Asn Thr Asn Thr Asn Pro Lys Arg Ser Ser
        50                  55                  60

Asp Tyr Tyr Asn Arg Ser Thr Ser Pro Trp Asn Leu His Arg Asn Glu
65                  70                  75                  80

Asp Pro Glu Arg Tyr Pro Ser Val Ile Trp Glu Ala Lys Cys Arg His
                85                  90                  95

Leu Gly Cys Ile Asn Ala Asp Gly Asn Val Asp Tyr His Met Asn Ser
            100                 105                 110

Val Pro Ile Gln Gln Glu Ile Leu Val Leu Arg Arg Glu Pro Pro His
        115                 120                 125

Cys Pro Asn Ser Phe Arg Leu Glu Lys Ile Leu Val Ser Val Gly Cys
    130                 135                 140

Thr Cys Val Thr Pro Ile Val His His Val Ala
145                 150                 155
```

<210> SEQ ID NO 3
<211> LENGTH: 1025
<212> TYPE: DNA
<213> ORGANISM: Homo sapiens

<400> SEQUENCE: 3

| ccgaattcgg cacgagaaca actgagggaa ccaaaccaga gacgcgctga acagagagaa | 60 |
| tcaggctcaa agcaagtgga agtgggcaga gattccacca ggactggtgc aaggcgcaga | 120 |
| gccagccaga tttgagaaga aggcaaaaag atgctgggga gcagagctgt aatgctgctg | 180 |
| ttgctgctgc cctggacagc tcagggcaga gctgtgcctg ggggcagcag ccctgcctgg | 240 |
| actcagtgcc agcagctttc acagaagctc tgcacactgg cctggagtgc acatccacta | 300 |
| gtgggacaca tggatctaag agaagaggga gatgaagaga ctacaaatga tgttccccat | 360 |
| atccagtgtg gagatggctg tgaccccaa ggactcaggg acaacagtca gttctgcttg | 420 |
| caaaggatcc accagggtct gatttttat gagaagctgc taggatcgga tattttcaca | 480 |
| ggggagcctt tctgctcccc tgatagccct gtggcgcagc ttcatgcctc cctactgggc | 540 |
| ctcagccaac tcctgcagcc tgagggtcac cactgggaga ctcagcagat ccaagcctc | 600 |
| agtcccagcc agcctatggca gcgtctcctt ctccgcttca aaatccttcg cagcctccag | 660 |
| gcctttgtgg ctgtagccgc ccgggtcttt gcccatggag cagcaaccct gagtccctaa | 720 |
| aggcagcagc tcaaggatgg cactcagatc tccatggccc agcaaggcca agataaatct | 780 |
| accacccag gcacctgtga gccaacaggt taattagtcc attaatttta gtgggacctg | 840 |
| catatgttga aaattaccaa tactgactga catgtgatgc tgacctatga taaggttgag | 900 |
| tatttattag atgggaaggg aaatttgggg attatttatc ctcctgggga cagtttgggg | 960 |

```
aggattattt attgtattta tattgaatta tgtacttttt tcaataaagt cttatttttg    1020
tggct                                                                1025

<210> SEQ ID NO 4
<211> LENGTH: 189
<212> TYPE: PRT
<213> ORGANISM: Homo sapiens

<400> SEQUENCE: 4

Met Leu Gly Ser Arg Ala Val Met Leu Leu Leu Leu Pro Trp Thr
 1               5                  10                  15

Ala Gln Gly Arg Ala Val Pro Gly Gly Ser Ser Pro Ala Trp Thr Gln
             20                  25                  30

Cys Gln Gln Leu Ser Gln Lys Leu Cys Thr Leu Ala Trp Ser Ala His
         35                  40                  45

Pro Leu Val Gly His Met Asp Leu Arg Glu Glu Gly Asp Glu Glu Thr
     50                  55                  60

Thr Asn Asp Val Pro His Ile Gln Cys Gly Asp Gly Cys Asp Pro Gln
 65                  70                  75                  80

Gly Leu Arg Asp Asn Ser Gln Phe Cys Leu Gln Arg Ile His Gln Gly
                 85                  90                  95

Leu Ile Phe Tyr Glu Lys Leu Leu Gly Ser Asp Ile Phe Thr Gly Glu
            100                 105                 110

Pro Ser Leu Leu Pro Asp Ser Pro Val Gly Gln Leu His Ala Ser Leu
        115                 120                 125

Leu Gly Leu Ser Gln Leu Gln Pro Glu Gly His His Trp Glu Thr
    130                 135                 140

Gln Gln Ile Pro Ser Leu Ser Pro Ser Gln Pro Trp Gln Arg Leu Leu
145                 150                 155                 160

Leu Arg Phe Lys Ile Leu Arg Ser Leu Gln Ala Phe Val Ala Val Ala
                165                 170                 175

Ala Arg Val Phe Ala His Gly Ala Ala Thr Leu Ser Pro
            180                 185

<210> SEQ ID NO 5
<211> LENGTH: 923
<212> TYPE: DNA
<213> ORGANISM: Homo sapiens

<400> SEQUENCE: 5
ggcttcagtt actagctagg ctactgagtt tagttctcag tttggcacct tgatacctt      60 aggtgtgagt gttcccattt ccaggtgagg aactgaggtg caaagagaag ccctgatccc    120
ataaaaggac aggaatgctg agttccgcca gaccatgcat ctcttgctag taggtgaggc    180
gagtctctaa ctgattgcag cgtcttctat tttccaggtc aagtacttgc tgctgtcgat    240 attgggctt gcctttctga gtgaggcggc agctcggaaa atccccaaag taggacatac    300 tttttttccaa aagcctgaga gttgcccgcc tgtgccagga ggtagtatga agcttgacat    360
tggcatcatc aatgaaaacc agcgcgtttc catgtcacgt aacatcgaga gccgctccac    420 ctcccccctgg aattacactg tcacttggga ccccaaccgg taccccctcgg aagttgtaca    480 ggcccagtgt aggaacttgg gctgcatcaa tgctcaagga aaggaagaca tctccatgaa    540
ttccgttccc atccagcaag agaccctggt cgtccggagg aagcaccaag gctgctctgt    600
ttctttccag ttggagaagg tgctggtgac tgttggctgc acctgcgtca cccctgtcat    660
ccaccatgtg cagtaagagg tgcatatcca ctcagctgaa gaagctgtag aaatgccact    720
```

```
ccttacccag tgctctgcaa caagtcctgt ctgaccccca attccctcca cttcacagga      780
ctcttaataa gacctgcacg gatggaaaca taaatattc acaatgtatg tgtgtatgta       840 ctcacacttta tatttgatat ctaaaatgtt aggagaaaaa ttaatatatt cagtgctaat    900
ataataaagt attaataatg tta                                              923
```

<210> SEQ ID NO 6
<211> LENGTH: 153
<212> TYPE: PRT
<213> ORGANISM: Homo sapiens

<400> SEQUENCE: 6

```
Met Val Lys Tyr Leu Leu Ser Ile Leu Gly Leu Ala Phe Leu Ser
1               5                   10                  15

Glu Ala Ala Arg Lys Ile Pro Lys Val Gly His Thr Phe Gln
            20                  25                  30

Lys Pro Glu Ser Cys Pro Pro Val Gly Gly Ser Met Lys Leu Asp
            35                  40                  45

Ile Gly Ile Ile Asn Glu Asn Gln Arg Val Ser Met Ser Arg Asn Ile
        50                  55                  60

Glu Ser Arg Ser Thr Ser Pro Trp Asn Tyr Thr Val Thr Trp Asp Pro
65                  70                  75                  80

Asn Arg Tyr Pro Ser Glu Val Val Gln Ala Gln Cys Arg Asn Leu Gly
                85                  90                  95

Cys Ile Asn Ala Gln Gly Lys Glu Asp Ile Ser Met Asn Ser Val Pro
            100                 105                 110

Ile Gln Gln Glu Thr Leu Val Val Arg Arg Lys His Gln Gly Cys Ser
        115                 120                 125

Val Ser Phe Gln Leu Glu Lys Val Leu Val Thr Val Gly Cys Thr Cys
    130                 135                 140

Val Thr Pro Val Ile His His Val Gln
145                 150
```

<210> SEQ ID NO 7
<211> LENGTH: 108
<212> TYPE: PRT
<213> ORGANISM: Homo sapiens

<400> SEQUENCE: 7

```
Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Arg
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Ala Glu Asp Phe Ala Val Tyr Tyr Cys Gln Gln Tyr Ser Thr Ser Pro
                85                  90                  95

Tyr Thr Phe Gly Gln Gly Thr Lys Leu Glu Ile Lys
            100                 105
```

<210> SEQ ID NO 8
<211> LENGTH: 116
<212> TYPE: PRT
<213> ORGANISM: Homo sapiens

```
<400> SEQUENCE: 8

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Arg Tyr
             20                  25                  30

Gly Met His Trp Val Arg Gln Ala Pro Gly Lys Gly Leu Glu Trp Val
         35                  40                  45

Ser Tyr Ile Val Ser Ser Gly Tyr Thr Glu Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Thr Thr Gly Ile Ala Val Ala Arg Tyr Trp Gly Gln Gly Thr Leu Val
            100                 105                 110

Thr Val Ser Ser
            115

<210> SEQ ID NO 9
<211> LENGTH: 107
<212> TYPE: PRT
<213> ORGANISM: Homo sapiens

<400> SEQUENCE: 9

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Gly Tyr
             20                  25                  30

Leu His Trp Tyr Gln Gln Lys Pro Gly Lys Ala Pro Asn Leu Leu Ile
         35                  40                  45

Phe Ala Thr Ser Asn Leu His Ser Gly Val Pro Ser Arg Phe Ser Gly
     50                  55                  60

Ser Arg Ser Gly Thr Asp Phe Thr Leu Thr Ile Ser Ser Leu Gln Pro
 65                  70                  75                  80

Glu Asp Phe Ala Thr Tyr Phe Cys Gln Gln Ser Phe Ser Thr Pro Pro
                 85                  90                  95

Thr Phe Gly His Gly Thr Arg Leu Glu Ile Lys
            100                 105

<210> SEQ ID NO 10
<211> LENGTH: 117
<212> TYPE: PRT
<213> ORGANISM: Homo sapiens

<400> SEQUENCE: 10

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ala Tyr
             20                  25                  30

Ser Met Thr Trp Val Arg Gln Ala Pro Gly Lys Gly Leu Glu Trp Val
         35                  40                  45

Ser Gly Ile Tyr Ser Ser Gly Phe Thr Trp Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
```

```
                85                  90                  95

Ala Arg Val Gly Leu Trp Ala Phe Asp Ile Trp Gly Gln Gly Thr Met
                100                 105                 110

Val Thr Val Ser Ser
        115

<210> SEQ ID NO 11
<211> LENGTH: 108
<212> TYPE: PRT
<213> ORGANISM: Homo sapiens

<400> SEQUENCE: 11

Asp Ile Gln Met Thr Gln Ser Pro Ser Ser Leu Pro Ala Ser Val Gly
1               5                   10                  15

Asp Arg Val Ala Ile Thr Cys Arg Ala Ser Gln Ser Ile Ser Ser Ser
            20                  25                  30

Tyr Leu Asn Trp Tyr Gln His Lys Pro Gly Lys Ala Pro Lys Leu Leu
        35                  40                  45

Ile Tyr Ala Ala Ser Asn Leu Asn Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Asp Asp Phe Ala Thr Tyr Tyr Cys Gln Glu Ser His Ser Ala Ser
                85                  90                  95

Leu Thr Phe Gly Gly Gly Thr Lys Val Glu Val Lys
                100                 105

<210> SEQ ID NO 12
<211> LENGTH: 119
<212> TYPE: PRT
<213> ORGANISM: Homo sapiens

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Tyr
            20                  25                  30

Lys Met Gly Trp Val Arg Gln Ala Pro Gly Lys Gly Leu Glu Trp Val
        35                  40                  45

Ser Tyr Ile Trp Ser Ser Gly Gly Trp Thr Arg Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Gly Gly Tyr Asn Ser Pro Leu Ser Tyr Trp Gly Gln Gly
                100                 105                 110

Thr Leu Val Thr Val Ser Ser
        115

<210> SEQ ID NO 13
<211> LENGTH: 112
<212> TYPE: PRT
<213> ORGANISM: Homo sapiens

<400> SEQUENCE: 13

Gln Tyr Glu Leu Thr Gln Pro Ala Ser Val Ser Gly Ser Pro Gly Gln
1               5                   10                  15
```

```
Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Phe Tyr Val Phe Gly Thr Gly Thr Lys Val Thr Val Leu
            100                 105                 110
```

<210> SEQ ID NO 14
<211> LENGTH: 123
<212> TYPE: PRT
<213> ORGANISM: Homo sapiens

<400> SEQUENCE: 14

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Gly Met Asp Trp Val Arg Gln Ala Pro Gly Lys Gly Leu Glu Trp Val
        35                  40                  45

Ser Ser Ile Ser Pro Ser Gly Gly Gln Thr Lys Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Gly Gly Gly Tyr Tyr Tyr Tyr Gly Met Asp Val
            100                 105                 110

Trp Gly Gln Gly Thr Leu Val Thr Val Ser Ser
        115                 120
```

<210> SEQ ID NO 15
<211> LENGTH: 107
<212> TYPE: PRT
<213> ORGANISM: Homo sapiens

<400> SEQUENCE: 15

```
Asp Ile Gln Met Thr Gln Ser Pro Gly Thr Leu Ser Val Ser Pro Gly
1               5                   10                  15

Glu Arg Ala Thr Leu Ser Cys Arg Ala Ser Gln Ser Val Ser Asn Lys
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Thr Ser Leu Gln Ser
65                  70                  75                  80

Glu Asp Phe Ala Val Tyr Tyr Cys Gln Gln Arg Ile Asn Trp Pro Leu
                85                  90                  95

Thr Phe Gly Gly Gly Thr Lys Val Glu Ile Lys
            100                 105
```

```
<210> SEQ ID NO 16
<211> LENGTH: 124
<212> TYPE: PRT
<213> ORGANISM: Homo sapiens

<400> SEQUENCE: 16

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Thr Tyr
             20                  25                  30

Trp Met Glu Trp Val Arg Gln Ala Pro Gly Lys Gly Leu Glu Trp Val
         35                  40                  45

Ser Ser Ile Val Ser Ser Gly Gly Pro Thr Met Tyr Ala Asp Ser Val
 50                  55                  60

Lys Gly Arg Phe Thr Ile Ser Arg Asp Asn Ser Lys Asn Thr Phe Tyr
 65                  70                  75                  80

Leu Gln Met Asn Ser Leu Arg Ala Glu Asp Thr Ala Val Tyr Tyr Cys
             85                  90                  95

Ala Arg Ala Arg Glu Ile Ser Ile Phe Gly Val Val Lys Asp Leu Asp
            100                 105                 110

Ile Trp Gly Gln Gly Thr Met Val Thr Val Ser Ser
            115                 120

<210> SEQ ID NO 17
<211> LENGTH: 107
<212> TYPE: PRT
<213> ORGANISM: Homo sapiens

<400> SEQUENCE: 17

Asp Ile Gln Met Thr Gln Ser Pro Ser Ser Val Ser Ala Ser Val Gly
  1               5                  10                  15

Asp Arg Val Thr Ile Thr Cys Arg Ala Ser Gln Gly Val Ser Thr Trp
             20                  25                  30

Leu Ala Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln His Tyr Asn Phe Pro Leu
             85                  90                  95

Thr Phe Gly Gly Gly Thr Glu Val Glu Ile Lys
            100                 105

<210> SEQ ID NO 18
<211> LENGTH: 116
<212> TYPE: PRT
<213> ORGANISM: Homo sapiens

<400> SEQUENCE: 18

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser His Tyr
             20                  25                  30

Val Met Gly Trp Val Arg Gln Ala Pro Gly Lys Gly Leu Glu Trp Val
         35                  40                  45

Ser Tyr Ile Ser Pro Ser Gly Gly Trp Thr Trp Tyr Ala Asp Phe Val
 50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Val His Asp Ala Phe Asp Ile Trp Gly Gln Gly Thr Met Val
            100                 105                 110

Thr Val Ser Ser
        115

<210> SEQ ID NO 19
<211> LENGTH: 106
<212> TYPE: PRT
<213> ORGANISM: Homo sapiens

<400> SEQUENCE: 19

Gln Ser Ala Leu Thr Gln Pro Pro Ser Val Ser Val Ser Pro Gly Gln
 1               5                  10                  15

Thr Ala Ser Ile Thr Cys Ser Gly Asp Arg Leu Gly Asp Lys Tyr Ala
                20                  25                  30

Ser Trp Tyr Gln Gln Lys Pro Gly Gln Ser Pro Val Leu Val Ile Tyr
             35                  40                  45

Gln Asp Thr Lys Arg Pro Ser Gly Ile Pro Glu Arg Phe Ser Gly Ser
 50                  55                  60

Asn Ser Gly Ser Thr Ala Thr Leu Thr Ile Ser Gly Thr Gln Ala Met
 65                  70                  75                  80

Asp Glu Ala Asp Tyr Tyr Cys Gln Ala Trp Asp Ser Ser Thr Val Val
                 85                  90                  95

Phe Gly Gly Gly Thr Lys Leu Thr Val Leu
            100                 105

<210> SEQ ID NO 20
<211> LENGTH: 127
<212> TYPE: PRT
<213> ORGANISM: Homo sapiens

<400> SEQUENCE: 20

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
                20                  25                  30

Phe Met Ala Trp Val Arg Gln Ala Pro Gly Lys Gly Leu Glu Trp Val
             35                  40                  45

Ser Ser Ile Val Pro Ser Gly Gly Trp Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Leu Asn Gly Trp Ser Ser Gly Trp Leu Gly Tyr Tyr Tyr Tyr
            100                 105                 110

Gly Met Asp Val Trp Gly Gln Gly Thr Thr Val Thr Val Ser Ser
            115                 120                 125

<210> SEQ ID NO 21
<211> LENGTH: 112
<212> TYPE: PRT
<213> ORGANISM: Homo sapiens

<400> SEQUENCE: 21
```

```
Asp Ile Gln Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu His Ser
             20                  25                  30

Asn Gly Tyr Asn Tyr Leu Asp Trp Tyr Leu Gln Lys Pro Gly Gln Ser
         35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Asn Ser Ile Thr Phe Gly Gln Gly Thr Arg Leu Glu Ile Lys
            100                 105                 110
```

<210> SEQ ID NO 22
<211> LENGTH: 123
<212> TYPE: PRT
<213> ORGANISM: Homo sapiens

<400> SEQUENCE: 22

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Val Tyr
             20                  25                  30

Ala Met His Trp Val Arg Gln Ala Pro Gly Lys Gly Leu Glu Trp Val
         35                  40                  45

Ser Val Ile Ser Pro Ser Gly Gly Phe Thr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Gly Tyr Ser Trp Gly Tyr Tyr Tyr Tyr Met Asp Val
            100                 105                 110

Trp Gly Lys Gly Thr Thr Val Thr Val Ser Ser
        115                 120
```

<210> SEQ ID NO 23
<211> LENGTH: 112
<212> TYPE: PRT
<213> ORGANISM: Homo sapiens

<400> SEQUENCE: 23

```
Asp Ile Gln Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu His Ser
             20                  25                  30

Asn Gly Tyr Asn Tyr Leu Asp Trp Phe Leu Gln Lys Pro Gly Gln Ser
         35                  40                  45

Pro Gln Leu Leu Ile Tyr Leu Gly Ser His Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95
```

```
Leu Gln Ser Arg Tyr Thr Phe Gly Gln Gly Thr Lys Leu Glu Ile Lys
            100                 105                 110
```

<210> SEQ ID NO 24
<211> LENGTH: 118
<212> TYPE: PRT
<213> ORGANISM: Homo sapiens

<400> SEQUENCE: 24

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Trp Tyr
             20                  25                  30

Gly Met Val Trp Val Arg Gln Ala Pro Gly Lys Gly Leu Glu Trp Val
         35                  40                  45

Ser Ser Ile Ser Pro Ser Gly Gly Ser Thr Asp Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Val Gly Ser Ser Trp Tyr Leu Asp Val Trp Gly Gln Gly Thr
            100                 105                 110

Thr Val Thr Val Ser Ser
            115
```

<210> SEQ ID NO 25
<211> LENGTH: 112
<212> TYPE: PRT
<213> ORGANISM: Homo sapiens

<400> SEQUENCE: 25

```
Gln Ser Glu Leu Thr Gln Pro Arg Ser Val Ser Gly Ser Pro Gly Gln
  1               5                  10                  15

Ser Val Thr Ile Ser Cys Thr Gly Thr Ser Ser Asp Val Gly Gly Tyr
             20                  25                  30

Asn Tyr Val Ser Trp Tyr Arg Gln Asp Pro Gly Lys Ala Pro Lys Leu
         35                  40                  45

Ile Ile Tyr Glu Val Ser Lys Arg Pro Ser Gly Val Ser Asn Arg Phe
     50                  55                  60

Ser Gly Ser Lys Ser Gly Asn Thr Ala Ser Leu Thr Ile Ser Gly Leu
 65                  70                  75                  80

His Ile Glu Asp Glu Gly Leu Tyr Tyr Cys Ser Ser Phe Arg Tyr Ser
                 85                  90                  95

Arg Ser Leu Asp Tyr Val Phe Gly Thr Gly Thr Gln Val Thr Val Leu
            100                 105                 110
```

<210> SEQ ID NO 26
<211> LENGTH: 123
<212> TYPE: PRT
<213> ORGANISM: Homo sapiens

<400> SEQUENCE: 26

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Asp Tyr
             20                  25                  30

Leu Met Thr Trp Val Arg Gln Ala Pro Gly Lys Gly Leu Glu Trp Val
         35                  40                  45
```

Ser Gly Ile Trp Pro Ser Gly Gly Phe Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Lys Gly Gly Asp Tyr Gly Asp Pro Ser Pro Phe Asp Tyr
            100                 105                 110

Trp Gly Gln Gly Thr Leu Val Thr Val Ser Ser
            115                 120

<210> SEQ ID NO 27
<211> LENGTH: 107
<212> TYPE: PRT
<213> ORGANISM: Homo sapiens

<400> SEQUENCE: 27

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Gly Tyr Trp
            20                  25                  30

Leu Ala Trp Tyr Gln Gln Lys Pro Gly Asn Ser Pro Lys Leu Leu Ile
        35                  40                  45

Tyr Val Ser Ser Thr Leu Gln Arg Gly Val Pro Ser Arg Phe Ser Gly
    50                  55                  60

Arg Gly Ser Gly Thr Asp Phe Thr Leu Thr Ile Asn Asn Leu Gln Pro
65                  70                  75                  80

Glu Asp Phe Ala Thr Tyr Tyr Cys Gln Gln Ala Lys Ala Phe Pro Leu
                85                  90                  95

Thr Phe Gly Gly Gly Thr Lys Val Glu Ile Asn
            100                 105

<210> SEQ ID NO 28
<211> LENGTH: 121
<212> TYPE: PRT
<213> ORGANISM: Homo sapiens

<400> SEQUENCE: 28

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Val Tyr
            20                  25                  30

Phe Met Ser Trp Val Arg Gln Ala Pro Gly Lys Gly Leu Glu Trp Val
        35                  40                  45

Ser Tyr Ile Gly Pro Ser Gly Gly Phe Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Val Arg Gly Tyr Tyr Tyr Tyr Gly Met Asp Val Trp Gly
            100                 105                 110

Gln Gly Thr Thr Val Thr Val Ser Ser
            115                 120

<210> SEQ ID NO 29
<211> LENGTH: 112

<212> TYPE: PRT
<213> ORGANISM: Homo sapiens

<400> SEQUENCE: 29

```
Asp Ile Gln Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Ile Thr Phe Gly Gln Gly Thr Arg Leu Glu Ile Lys
            100                 105                 110
```

<210> SEQ ID NO 30
<211> LENGTH: 124
<212> TYPE: PRT
<213> ORGANISM: Homo sapiens

<400> SEQUENCE: 30

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ala Met Trp Trp Val Arg Gln Ala Pro Gly Lys Gly Leu Glu Trp Val
        35                  40                  45

Ser Gly Ile Val Pro Ser Gly Gly Leu Thr Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Glu Val Ser Glu Gln Trp Leu Phe Pro Gly Asn Phe Asp
            100                 105                 110

Tyr Trp Gly Gln Gly Thr Leu Val Thr Val Ser Ser
        115                 120
```

<210> SEQ ID NO 31
<211> LENGTH: 108
<212> TYPE: PRT
<213> ORGANISM: Homo sapiens

<400> SEQUENCE: 31

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ile Asn
            20                  25                  30

Pro Val Asn Trp Tyr Gln Gln Phe Pro Gly Thr Ala Pro Lys Leu Leu
        35                  40                  45

Ile Tyr Asn Gln Arg Pro Ser Gly Val Pro Asp Arg Phe Ser Gly Ser
    50                  55                  60

Lys Ser Gly Thr Ser Ala Ser Leu Ala Ile Ser Gly Leu Gln Ser Glu
65                  70                  75                  80
```

```
Asp Glu Ala Asp Tyr Tyr Cys Ala Ala Trp Asp Asp Ser Leu Asn Gly
                85                  90                  95
Val Val Phe Gly Gly Gly Thr Lys Leu Thr Val Leu
            100                 105
```

<210> SEQ ID NO 32
<211> LENGTH: 130
<212> TYPE: PRT
<213> ORGANISM: Homo sapiens

<400> SEQUENCE: 32

```
Glu Val Gln Leu Leu Glu Ser Gly Gly Gly Leu Val Gln Pro Gly Gly
 1               5                  10                  15
Ser Leu Arg Leu Ser Cys Ala Ala Ser Gly Phe Thr Phe Ser Tyr Tyr
            20                  25                  30
Pro Met Val Trp Val Arg Gln Ala Pro Gly Lys Gly Leu Glu Trp Val
        35                  40                  45
Ser Arg Ile Ser Ser Gly Gly Ser Thr Leu Tyr Ala Asp Ser Val
    50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                85                  90                  95
Ala Arg Gly Ala Val Val Pro Ala Ala Ile Glu Trp Phe Trp Ser Gly
            100                 105                 110
Tyr Ser Asn Tyr Phe Asp Tyr Trp Gly Gln Gly Thr Leu Val Thr Val
        115                 120                 125
Ser Ser
    130
```

<210> SEQ ID NO 33
<211> LENGTH: 107
<212> TYPE: PRT
<213> ORGANISM: Homo sapiens

<400> SEQUENCE: 33

```
Asp Ile Gln Met Thr Gln Ser Pro Ser Ser Leu Ser Ala Ser Val Gly
 1               5                  10                  15
Asp Arg Val Thr Ile Thr Cys Arg Ala Ser Gln Asn Ile Asn Phe Tyr
            20                  25                  30
Leu Ser Trp Phe Gln Gln Lys Pro Gly Lys Ala Pro Lys Leu Leu Ile
        35                  40                  45
His Ser Val Asn Asn Leu Leu Gly Pro Val Pro Ser Arg Phe Ser Gly
    50                  55                  60
Ser Gly Ser Gly Thr Asp Phe Thr Leu Thr Ile Val Ser Leu Gln Pro
 65                  70                  75                  80
Glu Asp Phe Ala Thr Tyr Tyr Cys Gln Gln Gly Tyr Arg Pro Pro Tyr
                85                  90                  95
Thr Phe Gly Gln Gly Thr Lys Leu Glu Ile Lys
            100                 105
```

<210> SEQ ID NO 34
<211> LENGTH: 119
<212> TYPE: PRT
<213> ORGANISM: Homo sapiens

<400> SEQUENCE: 34

```
Glu Val Gln Leu Leu Glu Ser Gly Gly Gly Leu Val Gln Pro Gly Gly
```

```
                1               5                  10                 15
Ser Leu Arg Leu Ser Cys Ala Ala Ser Gly Phe Thr Phe Ser Trp Tyr
                    20                 25                 30

Val Met Met Trp Val Arg Gln Ala Pro Gly Lys Gly Leu Glu Trp Val
                    35                 40                 45

Ser Gly Ile Ser Ser Ser Gly Gly Thr Gln Tyr Ala Asp Ser Val
                    50                 55                 60

Lys Gly Arg Phe Thr Ile Ser Arg Asp Asn Ser Lys Asn Thr Leu Tyr
65                         70                 75                 80

Leu Gln Met Asn Ser Leu Arg Ala Glu Asp Thr Ala Val Tyr Tyr Cys
                    85                 90                 95

Ala Arg Gly Gly Tyr Tyr Tyr Asp Val Pro Tyr Tyr Trp Gly Gln Gly
                    100                105                110

Thr Leu Val Thr Val Ser Ser
                    115
```

<210> SEQ ID NO 35
<211> LENGTH: 112
<212> TYPE: PRT
<213> ORGANISM: Homo sapiens

<400> SEQUENCE: 35

```
Asp Ile Gln Met Thr Gln Ser Pro Leu Ser Leu Pro Val Thr Pro Gly
1               5                  10                 15

Glu Pro Ala Ser Ile Ser Cys Arg Ser Ser Gln Ser Leu Leu His Ser
                    20                 25                 30

Asn Gly Tyr Asn Tyr Leu Asp Trp Tyr Leu Gln Lys Pro Gly Gln Ser
                    35                 40                 45

Pro Gln Leu Leu Ile Tyr Leu Gly Ser Asn Arg Ala Ser Gly Val Pro
                    50                 55                 60

Asp Arg Phe Ser Gly Ser Gly Ser Gly Thr Asp Phe Thr Leu Lys Ile
65                         70                 75                 80

Ser Arg Val Glu Ala Glu Asp Val Gly Val Tyr Tyr Cys Met Gln Ala
                    85                 90                 95

Leu Gln Thr Pro Ile Thr Phe Gly Gln Gly Thr Arg Leu Glu Ile Lys
                    100                105                110
```

<210> SEQ ID NO 36
<211> LENGTH: 119
<212> TYPE: PRT
<213> ORGANISM: Homo sapiens

<400> SEQUENCE: 36

```
Glu Val Gln Leu Leu Glu Ser Gly Gly Gly Leu Val Gln Pro Gly Gly
1               5                  10                 15

Ser Leu Arg Leu Ser Cys Ala Ala Ser Gly Phe Thr Phe Ser Trp Tyr
                    20                 25                 30

Val Met Met Trp Val Arg Gln Ala Pro Gly Lys Gly Leu Glu Trp Val
                    35                 40                 45

Ser Gly Ile Ser Ser Ser Gly Gly Thr Gln Tyr Ala Asp Ser Val
                    50                 55                 60

Lys Gly Arg Phe Thr Ile Ser Arg Asp Asn Ser Lys Asn Thr Leu Tyr
65                         70                 75                 80

Leu Gln Met Asn Ser Leu Arg Ala Glu Asp Thr Ala Val Tyr Tyr Cys
                    85                 90                 95

Ala Arg Gly Gly Tyr Tyr Tyr Asp Val Pro Tyr Tyr Trp Gly Gln Gly
                    100                105                110
```

Thr Leu Val Thr Val Ser Ser
                115

<210> SEQ ID NO 37
<211> LENGTH: 107
<212> TYPE: PRT
<213> ORGANISM: Homo sapiens

<400> SEQUENCE: 37

Arg His Pro Met Thr Gln Ser Pro Leu Ser Leu Ser Ala Ser Val Gly
1               5                   10                  15

Asp Arg Val Thr Val Thr Cys Arg Ala Ser Gln Ser Ile Ser Thr Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Arg Ser Leu Gln Pro
65                  70                  75                  80

Asp Asp Phe Ala Thr Tyr Tyr Cys Gln Gln Ser Tyr Ser Ser Pro Phe
                85                  90                  95

Thr Phe Gly Pro Gly Thr Lys Val Asp Phe Lys
                100                 105

<210> SEQ ID NO 38
<211> LENGTH: 117
<212> TYPE: PRT
<213> ORGANISM: Homo sapiens

<400> SEQUENCE: 38

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Thr Met Glu Trp Val Arg Gln Ala Pro Gly Lys Gly Leu Glu Trp Val
        35                  40                  45

Ser Ser Ile Tyr Pro Ser Gly Gly Trp Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Arg Ala Arg Ser Ala Cys Tyr Asp Asp Trp Gly Gln Gly Thr Leu
            100                 105                 110

Val Thr Val Ser Ser
        115

<210> SEQ ID NO 39
<211> LENGTH: 112
<212> TYPE: PRT
<213> ORGANISM: Homo sapiens

<400> SEQUENCE: 39

Asp Ile Gln Met Thr Gln Ser Pro Ser Ser Leu Pro Val Thr Pro Gly
1               5                   10                  15

Glu Pro Ala Ser Ile Ser Cys Arg Ser Ser Gln Ser Leu Leu His Thr
            20                  25                  30

Asn Gly His Asn Tyr Leu Asp Trp Tyr Leu Gln Lys Pro Gly Gln Ser

```
                35                  40                  45
Pro Lys Leu Leu Ile Tyr Leu Gly Ser Asn Arg Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Leu Tyr Tyr Cys Met Gln Gly
                 85                  90                  95

Leu Gln Ile Pro Leu Thr Phe Gly Gly Gly Thr Lys Val Glu Ile Lys
                100                 105                 110
```

<210> SEQ ID NO 40
<211> LENGTH: 119
<212> TYPE: PRT
<213> ORGANISM: Homo sapiens

<400> SEQUENCE: 40

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ala Tyr
                 20                  25                  30

Val Met Leu Trp Val Arg Gln Ala Pro Gly Lys Gly Leu Glu Trp Val
                 35                  40                  45

Ser Tyr Ile Trp Pro Ser Gly Gly Glu Thr Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ser Met Gly Tyr Gly Asp Ala Phe Asp Ile Trp Gly Gln Gly
                100                 105                 110

Thr Met Val Thr Val Ser Ser
        115
```

<210> SEQ ID NO 41
<211> LENGTH: 107
<212> TYPE: PRT
<213> ORGANISM: Homo sapiens

<400> SEQUENCE: 41

```
Asp Ile Gln Met Thr Gln Ser Pro Ser Ser Leu Ser Ala Ser Val Gly
  1               5                  10                  15

Asp Arg Val Thr Ile Thr Cys Arg Ser Ser Gln Gly Val Arg Tyr Asp
                 20                  25                  30

Leu Gly Trp Tyr Gln Gln Lys Pro Gly Lys Ala Pro Lys Leu Leu Ile
                 35                  40                  45

Tyr Gly Ala Phe Asn Leu Gln Gly Gly Val Pro Ser Arg Phe Ser Gly
 50                  55                  60

Ser Gly Ser Gly Thr Asp Phe Thr Leu Thr Ile Ser Gly Leu Gln Pro
 65                  70                  75                  80

Glu Asp Phe Ala Thr Tyr Tyr Cys Leu Gln Asp Phe Gln Tyr Pro Phe
                 85                  90                  95

Thr Phe Gly Pro Gly Thr Lys Val Asp Val Lys
                100                 105
```

<210> SEQ ID NO 42
<211> LENGTH: 120
<212> TYPE: PRT
<213> ORGANISM: Homo sapiens

<400> SEQUENCE: 42

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Asp Met Ser Trp Val Arg Gln Ala Pro Gly Lys Gly Leu Glu Trp Val
        35                  40                  45

Ser Ser Ile Trp Ser Ser Gly Gly Tyr Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Gly Val Gly Gly Ser Gly Ser Leu Leu Tyr Trp Gly Gln
            100                 105                 110

Gly Thr Leu Val Thr Val Ser Ser
            115                 120

<210> SEQ ID NO 43
<211> LENGTH: 106
<212> TYPE: PRT
<213> ORGANISM: Homo sapiens

<400> SEQUENCE: 43

Asp Ile Gln Met Thr Gln Ser Pro Ser Ser Leu Ser Ala Ser Val Gly
1               5                   10                  15

Asp Arg Val Thr Val Thr Cys Arg Ala Ser Gln Ser Ile Ser Ser Tyr
            20                  25                  30

Leu Asn Trp Tyr Gln Gln Lys Pro Gly Lys Ala Pro Asp Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Val Thr Tyr Tyr Cys Gln Glu Thr Tyr Ser Ala Leu Thr
                85                  90                  95

Phe Gly Gly Gly Thr Lys Val Glu Ile Lys
            100                 105

<210> SEQ ID NO 44
<211> LENGTH: 119
<212> TYPE: PRT
<213> ORGANISM: Homo sapiens

<400> SEQUENCE: 44

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ser Met Leu Trp Val Arg Gln Ala Pro Gly Lys Gly Leu Glu Trp Val
        35                  40                  45

Ser Tyr Ile Ser Ser Ser Gly Pro Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Tyr Cys

```
                85                  90                  95
Ala Arg Arg His Tyr Asn Lys Arg Tyr Phe Asp Tyr Trp Gly Gln Gly
            100                 105                 110

Thr Leu Val Thr Val Ser Ser
            115

<210> SEQ ID NO 45
<211> LENGTH: 107
<212> TYPE: PRT
<213> ORGANISM: Homo sapiens

<400> SEQUENCE: 45

Gln Ser Ala Leu Thr Gln Pro Pro Ser Val Ser Val Ser Pro Gly Gln
  1               5                  10                  15

Thr Ala Ser Ile Thr Cys Ser Gly Asp Asn Leu Gly Asp Lys Tyr Ala
             20                  25                  30

Ser Trp Tyr Gln Gln Lys Pro Gly Gln Ser Pro Val Leu Val Ile Tyr
         35                  40                  45

Gln Asp Asn Lys Arg Pro Ser Gly Ile Pro Glu Arg Phe Ser Gly Ser
     50                  55                  60

Asn Ser Gly Asn Thr Ala Thr Leu Thr Leu Ser Arg Val Glu Ala Gly
 65                  70                  75                  80

Asp Glu Ala Asp Tyr Tyr Cys Gln Val Trp Asp Ser Ser Tyr Asn Trp
                 85                  90                  95

Val Phe Gly Gly Gly Thr Lys Leu Thr Val Leu
            100                 105

<210> SEQ ID NO 46
<211> LENGTH: 122
<212> TYPE: PRT
<213> ORGANISM: Homo sapiens

<400> SEQUENCE: 46

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Arg Tyr
             20                  25                  30

Asn Met Val Trp Val Arg Gln Ala Pro Gly Lys Gly Leu Glu Trp Val
         35                  40                  45

Ser Ser Ile Ser Ser Ser Gly Gly Phe Thr Tyr Arg Tyr Ala Asp Ser Val
     50                  55                  60

Lys Gly Arg Phe Thr Ile Ser Arg Asp Asn Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Trp Tyr Ser Ser Ser Trp Tyr Gly Asn Trp Phe Asp Pro Trp
            100                 105                 110

Gly Gln Gly Thr Leu Val Thr Val Ser Ser
            115                 120

<210> SEQ ID NO 47
<211> LENGTH: 107
<212> TYPE: PRT
<213> ORGANISM: Homo sapiens

<400> SEQUENCE: 47

Asp Ile Gln Met Thr Gln Ser Pro Gly Thr Leu Ser Leu Ser Pro Gly
  1               5                  10                  15
```

```
Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Phe Asp Ala Ser Asn Arg Ala Thr Gly Ile Pro Ala Arg Phe Ser Gly
 50                  55                  60

Ala Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Trp
                 85                  90                  95

Thr Phe Gly Gln Gly Thr Lys Val Glu Ile Lys
                100                 105

<210> SEQ ID NO 48
<211> LENGTH: 121
<212> TYPE: PRT
<213> ORGANISM: Homo sapiens

<400> SEQUENCE: 48

Glu Val Gln Leu Leu Glu Ser Gly Gly Leu Val Gln Pro Gly Gly
 1               5                  10                  15

Ser Leu Arg Leu Ser Cys Ala Ala Ser Gly Phe Thr Phe Ser Lys Tyr
            20                  25                  30

Trp Met Ala Trp Val Arg Gln Ala Pro Gly Lys Gly Leu Glu Trp Val
        35                  40                  45

Ser Tyr Ile Ser Pro Ser Gly Gly Trp Thr Arg Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Val Gly Gly Ser Tyr Ser Leu Gly Ala Leu Asp Ile Trp Gly
                100                 105                 110

Gln Gly Thr Met Val Thr Val Ser Ser
        115                 120

<210> SEQ ID NO 49
<211> LENGTH: 107
<212> TYPE: PRT
<213> ORGANISM: Homo sapiens

<400> SEQUENCE: 49

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Leu
                 85                  90                  95

Thr Phe Gly Gly Gly Thr Lys Val Glu Ile Lys
                100                 105
```

```
<210> SEQ ID NO 50
<211> LENGTH: 117
<212> TYPE: PRT
<213> ORGANISM: Homo sapiens

<400> SEQUENCE: 50

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Tyr Tyr
             20                  25                  30

Thr Met Gly Trp Val Arg Gln Ala Pro Gly Lys Gly Leu Glu Trp Val
         35                  40                  45

Ser Ser Ile Trp Pro Ser Gly Gly Ala Thr Trp Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                 85                  90                  95

Ala Arg Asp Arg Asp Thr Ala Met Ala Asp Trp Gly Gln Gly Thr Leu
            100                 105                 110

Val Thr Val Ser Ser
            115

<210> SEQ ID NO 51
<211> LENGTH: 110
<212> TYPE: PRT
<213> ORGANISM: Homo sapiens

<400> SEQUENCE: 51

Gln Ser Glu Leu Thr Gln Pro Pro Ser Ala Ser Gly Ile Pro Gly Gln
 1               5                  10                  15

Arg Val Thr Ile Ser Cys Ser Gly Ser His Ser Asn Ile Gly Arg Asn
             20                  25                  30

Tyr Val Tyr Trp Tyr Gln Gln Leu Pro Gly Thr Ala Pro Lys Leu Leu
         35                  40                  45

Ile Tyr Ser Asn Asn Glu Arg Pro Ala Gly Val Pro Asp Arg Phe Ser
     50                  55                  60

Gly Ser Lys Ser Gly Thr Ser Ala Ser Leu Ala Ile Ser Gly Leu Arg
 65                  70                  75                  80

Ser Glu Asp Glu Val Asp Tyr Tyr Cys Ala Thr Trp Asp Asp Ser Leu
                 85                  90                  95

Ser Gly Pro Val Phe Gly Gly Gly Thr Lys Leu Thr Val Leu
            100                 105                 110

<210> SEQ ID NO 52
<211> LENGTH: 117
<212> TYPE: PRT
<213> ORGANISM: Homo sapiens

<400> SEQUENCE: 52

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ala Tyr
             20                  25                  30

Pro Met Arg Trp Val Arg Gln Ala Pro Gly Lys Gly Leu Glu Trp Val
         35                  40                  45

Ser Tyr Ile Tyr Pro Ser Gly Gly Pro Thr Tyr Tyr Ala Asp Ser Val
     50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Gln Gly Val Gly Ala Pro Val Asp Ser Trp Gly Gln Gly Thr Leu
            100                 105                 110

Val Thr Val Ser Ser
            115
```

<210> SEQ ID NO 53
<211> LENGTH: 110
<212> TYPE: PRT
<213> ORGANISM: Homo sapiens

<400> SEQUENCE: 53

```
Gln Ser Glu Leu Thr Gln Pro Pro Ser Ala Ser Gly Ile Pro Gly Gln
  1               5                  10                  15

Arg Val Thr Ile Ser Cys Ser Gly Ser His Ser Asn Ile Gly Arg Asn
             20                  25                  30

Tyr Val Tyr Trp Tyr Gln Gln Leu Pro Gly Thr Ala Pro Lys Leu Leu
             35                  40                  45

Ile Tyr Ser Asn Asn Glu Arg Pro Ala Gly Val Pro Asp Arg Phe Ser
 50                  55                  60

Gly Ser Lys Ser Gly Thr Ser Ala Ser Leu Asp Val Ser Gly Leu Gln
 65                  70                  75                  80

Ser Glu Asp Glu Ala Asp Tyr Tyr Cys Ala Ser Trp Asp Asp Ser Leu
             85                  90                  95

Ile Ala Trp Val Phe Gly Gly Gly Thr Met Leu Thr Val Leu
            100                 105                 110
```

<210> SEQ ID NO 54
<211> LENGTH: 122
<212> TYPE: PRT
<213> ORGANISM: Homo sapiens

<400> SEQUENCE: 54

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Trp Tyr
             20                  25                  30

Gly Thr Ala Trp Val Arg Gln Ala Pro Gly Lys Gly Leu Glu Trp Val
             35                  40                  45

Ser Val Ile Ser Pro Ser Gly Gly Pro Thr Phe Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Met Ala Val Tyr Tyr Cys
             85                  90                  95

Ala Arg Asp Ser Ser Gly Trp Arg Thr Ala Tyr Tyr Phe Asp Tyr Trp
            100                 105                 110

Gly Gln Gly Thr Leu Val Thr Val Ser Ser
            115                 120
```

<210> SEQ ID NO 55
<211> LENGTH: 110
<212> TYPE: PRT
<213> ORGANISM: Homo sapiens

<400> SEQUENCE: 55

Gln Ser Ala Leu Thr Gln Pro Pro Ser Ala Ser Gly Thr Pro Gly Gln
1               5                   10                  15

Arg Val Thr Ile Ser Cys Ser Gly Gly Tyr Ser Asn Met Gly Ser Asn
            20                  25                  30

Tyr Ala His Trp Tyr Gln Gln Leu Pro Gly Thr Ala Pro Lys Leu Leu
        35                  40                  45

Ile Tyr Asn Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Pro Val Phe Gly Gly Gly Thr Lys Leu Thr Val Leu
            100                 105                 110

<210> SEQ ID NO 56
<211> LENGTH: 122
<212> TYPE: PRT
<213> ORGANISM: Homo sapiens

<400> SEQUENCE: 56

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Met Glu Trp Val Arg Gln Ala Pro Gly Lys Gly Leu Glu Trp Val
        35                  40                  45

Ser Ser Ile Ser Pro Ser Gly Gly Tyr Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Leu Tyr Ser Ser Ser Leu Asp Ala Phe Asp Ile Trp
            100                 105                 110

Gly Gln Gly Thr Met Val Thr Val Ser Ser
        115                 120

<210> SEQ ID NO 57
<211> LENGTH: 108
<212> TYPE: PRT
<213> ORGANISM: Homo sapiens

<400> SEQUENCE: 57

Asp Ile Gln Met Thr Gln Ser Pro Ser Ser Leu Ser Ala Ser Val Gly
1               5                   10                  15

Asp Arg Val Ala Ile Thr Cys Arg Ala Ser Gln Ser Ile Asp Thr Tyr
            20                  25                  30

Leu Asn Trp Tyr Gln Gln Lys Pro Gly Lys Ala Pro Lys Leu Leu Ile
        35                  40                  45

Tyr Ala Ala Ser Lys Leu Glu Asp Gly Val Pro Ser Arg Phe Ser Gly
    50                  55                  60

Ser Gly Thr Gly Thr Asp Phe Thr Leu Thr Ile Arg Ser Leu Gln Pro
65                  70                  75                  80

Glu Asp Phe Ala Ser Tyr Phe Cys Gln Gln Ser Tyr Ser Ser Pro Gly
                85                  90                  95

```
Ile Thr Phe Gly Pro Gly Thr Lys Val Glu Ile Lys
            100                 105
```

<210> SEQ ID NO 58
<211> LENGTH: 118
<212> TYPE: PRT
<213> ORGANISM: Homo sapiens

<400> SEQUENCE: 58

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ile Trp Val Arg Gln Ala Pro Gly Lys Gly Leu Glu Trp Val
        35                  40                  45

Ser Arg Ile Val Pro Ser Gly Gly Leu Thr Gly Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Ser Leu Trp Leu Gly Ala Asp Tyr Trp Gly Gln Gly Thr
            100                 105                 110

Leu Val Thr Val Ser Ser
            115
```

<210> SEQ ID NO 59
<211> LENGTH: 107
<212> TYPE: PRT
<213> ORGANISM: Homo sapiens

<400> SEQUENCE: 59

```
Asp Ile Gln Met Thr Gln Ser Pro Ser Thr Leu Ser Ala Ser Val Gly
1               5                   10                  15

Asp Arg Val Thr Leu Thr Cys Arg Ala Ser Gln Ser Ile Ser Arg Tyr
            20                  25                  30

Leu Ala Trp Tyr Gln Gln Lys Pro Gly Lys Ala Pro Lys Leu Leu Ile
        35                  40                  45

Tyr Lys Ala Ser Ser Leu Val Ser Gly Phe Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Ser Ala Thr Tyr Tyr Cys Gln Gln Tyr Asn Asp Tyr Pro Gly
                85                  90                  95

Thr Phe Gly Gln Gly Thr Lys Leu Glu Ile Lys
            100                 105
```

<210> SEQ ID NO 60
<211> LENGTH: 120
<212> TYPE: PRT
<213> ORGANISM: Homo sapiens

<400> SEQUENCE: 60

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Gly Met Gly Trp Val Arg Gln Ala Pro Gly Lys Gly Leu Glu Trp Val
        35                  40                  45
```

Ser Gly Ile Trp Pro Ser Gly Gly Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Lys Tyr Thr Gly Ser Arg Thr Arg Val Phe Asp Tyr Trp Gly Gln
            100                 105                 110

Gly Thr Leu Val Thr Val Ser Ser
            115                 120

<210> SEQ ID NO 61
<211> LENGTH: 107
<212> TYPE: PRT
<213> ORGANISM: Homo sapiens

<400> SEQUENCE: 61

Asp Ile Gln Met Thr Gln Ser Pro Ser Phe Leu Ser Ala Ser Val Gly
1               5                   10                  15

Asp Arg Val Thr Ile Thr Cys Arg Ala Ser Gln Gly Phe Gly Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln His Leu Asn Ser Phe Arg Phe
                85                  90                  95

Thr Phe Gly Pro Gly Thr Lys Val Asp Ile Lys
            100                 105

<210> SEQ ID NO 62
<211> LENGTH: 120
<212> TYPE: PRT
<213> ORGANISM: Homo sapiens

<400> SEQUENCE: 62

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Glu Met Val Trp Val Arg Gln Ala Pro Gly Lys Gly Leu Glu Trp Val
        35                  40                  45

Ser Arg Ile Trp Pro Ser Gly Gly Tyr Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Val Leu Thr Asp Pro Gly Ala Phe Asp Ile Trp Gly Gln
            100                 105                 110

Gly Thr Met Val Thr Val Ser Ser
            115                 120

<210> SEQ ID NO 63
<211> LENGTH: 107

```
<212> TYPE: PRT
<213> ORGANISM: Homo sapiens

<400> SEQUENCE: 63

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asn Ile Asn Phe Tyr
             20                  25                  30

Leu Ser Trp Phe Gln Gln Lys Pro Gly Lys Ala Pro Lys Leu Leu Ile
         35                  40                  45

His Ser Val Asn Asn Leu Leu Gly Pro Val Pro Ser Arg Phe Ser Gly
     50                  55                  60

Ser Gly Ser Gly Thr Asp Phe Thr Leu Thr Ile Val Ser Leu Gln Pro
 65                  70                  75                  80

Glu Asp Phe Ala Thr Tyr Tyr Cys Gln Gln Gly Tyr Arg Pro Pro Tyr
                 85                  90                  95

Thr Phe Gly Gln Gly Thr Lys Leu Glu Ile Lys
            100                 105

<210> SEQ ID NO 64
<211> LENGTH: 126
<212> TYPE: PRT
<213> ORGANISM: Homo sapiens

<400> SEQUENCE: 64

Glu Val Gln Leu Leu Glu Ser Gly Gly Leu Val Gln Pro Gly Gly
 1               5                  10                  15

Ser Leu Arg Leu Ser Cys Ala Ala Ser Gly Phe Thr Phe Ser Tyr Tyr
             20                  25                  30

Glu Met Val Trp Val Arg Gln Ala Pro Gly Lys Gly Leu Glu Trp Val
         35                  40                  45

Ser Arg Ile Trp Pro Ser Gly Gly Tyr Thr Arg Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Gly Tyr Asp Tyr Val Trp Gly Ser Tyr Arg Pro Tyr Tyr
            100                 105                 110

Phe Asp Tyr Trp Gly Gln Gly Thr Leu Val Thr Val Ser Ser
        115                 120                 125

<210> SEQ ID NO 65
<211> LENGTH: 106
<212> TYPE: PRT
<213> ORGANISM: Homo sapiens

<400> SEQUENCE: 65

Gln Ser Val Leu Thr Gln Pro Pro Ser Val Ser Val Thr Pro Gly Gln
 1               5                  10                  15

Thr Ala Ile Leu Ser Cys Ser Gly Asp Lys Leu Gly Asp Thr Tyr Ala
             20                  25                  30

Ser Trp Phe Gln Gln Lys Pro Gly Gln Ser Pro Val Met Val Met Tyr
         35                  40                  45

Arg Gly Asn Lys Arg Pro Ser Gly Ile Pro Glu Arg Phe Ser Gly Ser
     50                  55                  60

Ser Ser Gly Asn Thr Ala Thr Leu Thr Ile Ser Gly Thr Gln Ala Val
 65                  70                  75                  80
```

Asp Glu Ala Asp Tyr Tyr Cys Gln Ala Trp Asp Arg Thr Thr Gly Val
            85                  90                  95

Phe Gly Thr Gly Thr Arg Leu Thr Val Leu
            100                 105

<210> SEQ ID NO 66
<211> LENGTH: 122
<212> TYPE: PRT
<213> ORGANISM: Homo sapiens

<400> SEQUENCE: 66

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Arg Met Val Trp Val Arg Gln Ala Pro Gly Lys Gly Leu Glu Trp Val
            35                  40                  45

Ser Ser Ile Tyr Pro Ser Gly Gly His Thr Gly Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Asp Glu Gly Ser Asn Trp Tyr Ser Asn Trp Phe Asp Pro Trp
            100                 105                 110

Gly Gln Gly Thr Leu Val Thr Val Ser Ser
            115                 120

<210> SEQ ID NO 67
<211> LENGTH: 108
<212> TYPE: PRT
<213> ORGANISM: Homo sapiens

<400> SEQUENCE: 67

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
            85                  90                  95

Tyr Thr Phe Gly Gln Gly Thr Lys Leu Glu Ile Lys
            100                 105

<210> SEQ ID NO 68
<211> LENGTH: 127
<212> TYPE: PRT
<213> ORGANISM: Homo sapiens

<400> SEQUENCE: 68

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr

```
                        20                  25                  30
Thr Met Gln Trp Val Arg Gln Ala Pro Gly Lys Gly Leu Glu Trp Val
            35                  40                  45
Ser Arg Ile Ser Ser Ser Gly Gly Ala Thr Arg Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                85                  90                  95
Ala Arg Asp Leu Gly Gln Thr Ile Phe Gly Val Val Ile Gly Phe Gly
            100                 105                 110
Gly Met Asp Val Trp Gly Gln Gly Thr Thr Val Thr Val Ser Ser
            115                 120                 125

<210> SEQ ID NO 69
<211> LENGTH: 108
<212> TYPE: PRT
<213> ORGANISM: Homo sapiens

<400> SEQUENCE: 69

Asp Ile Gln Met Thr Gln Ser Pro Ser Ser Leu Ser Ala Ser Val Gly
  1               5                  10                  15
Asp Arg Val Ala Ile Thr Cys Arg Ala Ser Gln Ser Ile Asp Thr Tyr
             20                  25                  30
Leu Asn Trp Tyr Gln Gln Lys Pro Gly Lys Ala Pro Lys Leu Leu Ile
             35                  40                  45
Tyr Ala Ala Ser Lys Leu Glu Asp Gly Val Pro Ser Arg Phe Ser Gly
  50                  55                  60
Ser Gly Thr Gly Thr Asp Phe Thr Leu Thr Ile Arg Ser Leu Gln Pro
 65                  70                  75                  80
Glu Asp Phe Ala Ser Tyr Phe Cys Gln Gln Ser Tyr Ser Ser Pro Gly
                85                  90                  95
Ile Thr Phe Gly Pro Gly Thr Lys Val Glu Ile Lys
            100                 105

<210> SEQ ID NO 70
<211> LENGTH: 120
<212> TYPE: PRT
<213> ORGANISM: Homo sapiens

<400> SEQUENCE: 70

Glu Val Gln Leu Leu Glu Ser Gly Gly Gly Leu Val Gln Pro Gly Gly
  1               5                  10                  15
Ser Leu Arg Leu Ser Cys Ala Ala Ser Gly Phe Thr Phe Ser Ser Tyr
             20                  25                  30
Gly Met Gly Trp Val Arg Gln Ala Pro Gly Lys Gly Leu Glu Trp Val
            35                  40                  45
Ser Trp Ile Tyr Pro Ser Gly Gly His Thr Ile Tyr Ala Asp Ser Val
  50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Thr Tyr Tyr Cys
                85                  90                  95
Ala Lys Asp Arg Arg Asn Tyr Gly Ser Tyr Phe Asp Tyr Trp Gly Gln
            100                 105                 110
Gly Thr Leu Val Thr Val Ser Ser
            115                 120
```

<210> SEQ ID NO 71
<211> LENGTH: 110
<212> TYPE: PRT
<213> ORGANISM: Homo sapiens

<400> SEQUENCE: 71

Gln Ser Ala Leu Thr Gln Pro Ala Ser Val Ser Gly Ser Pro Gly Gln
 1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Ala Ser Ser
                85                  90                  95

Gly Ala Arg Val Phe Gly Thr Gly Thr Lys Val Thr Val Leu
            100                 105                 110

<210> SEQ ID NO 72
<211> LENGTH: 116
<212> TYPE: PRT
<213> ORGANISM: Homo sapiens

<400> SEQUENCE: 72

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Ser Phe Tyr
            20                  25                  30

Trp Met Gly Trp Val Arg Gln Ala Pro Gly Lys Gly Leu Glu Trp Val
        35                  40                  45

Ser Ser Ile Ser Ser Ser Gly Gly Lys Thr Gln Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Gly Ile Ala Val Ala Arg Tyr Trp Gly Gln Gly Thr Leu Val
            100                 105                 110

Thr Val Ser Ser
        115

<210> SEQ ID NO 73
<211> LENGTH: 112
<212> TYPE: PRT
<213> ORGANISM: Homo sapiens

<400> SEQUENCE: 73

Asp Ile Val Met Thr Gln Thr Pro Ser Leu Pro Val Asn Pro Gly
 1               5                   10                  15

Glu Pro Ala Ser Ile Ser Cys Arg Ser Ser Gln Ser Leu Gln His Ser
            20                  25                  30

Asn Gly Tyr Asn Tyr Val Ala Trp Tyr Leu Gln Lys Pro Gly Gln Ser
        35                  40                  45

Pro Gln Leu Leu Ile Tyr Leu Gly Ser Asn Arg Ala Ser Gly Val Pro

```
                50                  55                  60
Asp Arg Phe Ser Gly Ser Gly Ser Gly Thr Asp Phe Lys Leu Lys Ile
 65                  70                  75                  80

Ser Arg Val Glu Ala Glu Asp Val Gly Asp Tyr Phe Cys Met Gln Leu
                 85                  90                  95

Leu Glu Thr Pro Leu Thr Phe Gly Gly Gly Thr Lys Val Glu Ile Lys
            100                 105                 110

<210> SEQ ID NO 74
<211> LENGTH: 118
<212> TYPE: PRT
<213> ORGANISM: Homo sapiens

<400> SEQUENCE: 74

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Gln Tyr
             20                  25                  30

Gly Met Arg Trp Val Arg Gln Ala Pro Gly Lys Gly Leu Glu Trp Val
         35                  40                  45

Ser Ser Ile Gly Pro Ser Gly Gly Phe Thr Arg Tyr Ala Asp Ser Val
 50                  55                  60

Lys Gly Arg Phe Thr Ile Ser Arg Asp Asn Ser Lys Asn Thr Phe Tyr
 65                  70                  75                  80

Leu Gln Met Asn Ser Leu Arg Ala Glu Asp Thr Ala Val Tyr Tyr Cys
                 85                  90                  95

Ala Arg Ser Gly Ser Thr Trp Tyr Phe Asp Leu Trp Gly Arg Gly Thr
            100                 105                 110

Leu Val Thr Val Ser Ser
        115

<210> SEQ ID NO 75
<211> LENGTH: 107
<212> TYPE: PRT
<213> ORGANISM: Homo sapiens

<400> SEQUENCE: 75

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Asn Tyr
             20                  25                  30

Leu Ala Trp Tyr Gln Gln Lys Pro Gly Lys Val Pro Lys Leu Leu Ile
         35                  40                  45

Tyr Gly Ala Ser Thr Val Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Lys Tyr Asn Arg Val Pro Trp
                 85                  90                  95

Thr Phe Gly Gln Gly Thr Lys Val Glu Ile Lys
            100                 105

<210> SEQ ID NO 76
<211> LENGTH: 122
<212> TYPE: PRT
<213> ORGANISM: Homo sapiens

<400> SEQUENCE: 76
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Asp Met Asp Trp Val Arg Gln Ala Pro Gly Lys Gly Leu Glu Trp Val
            35                  40                  45

Ser Ser Ile Ser Ser Gly Gly Leu Thr Phe Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Asp Tyr Asp Phe Trp Ser Gly His Ala Phe Asp Ile Trp
            100                 105                 110

Gly Gln Gly Thr Met Val Thr Val Ser Ser
            115                 120
```

<210> SEQ ID NO 77
<211> LENGTH: 112
<212> TYPE: PRT
<213> ORGANISM: Homo sapiens

<400> SEQUENCE: 77

```
Asp Ile Gln Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Arg
            20                  25                  30

Asn Gly Tyr Asn Tyr Leu Asp Trp Tyr Val Gln Arg Pro Gly Gln Ser
            35                  40                  45

Pro Gln Leu Leu Ile Tyr Leu Gly Ser Asn Arg Ala Ser Gly Val Pro
50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Val Tyr Tyr Cys Met Glu Ala
                85                  90                  95

Leu Gln Thr Pro Pro Thr Phe Gly Gly Gly Thr Lys Val Glu Ile Lys
            100                 105                 110
```

<210> SEQ ID NO 78
<211> LENGTH: 122
<212> TYPE: PRT
<213> ORGANISM: Homo sapiens

<400> SEQUENCE: 78

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Gly Met Asn Trp Val Arg Gln Ala Pro Gly Lys Gly Leu Glu Trp Val
            35                  40                  45

Ser Gly Ile Val Ser Ser Gly Gly Gln Thr Pro Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Val Arg Gly Tyr Gly Asp Tyr Trp Tyr Phe Asp Leu Trp
```

```
                   100                 105                 110
Gly Arg Gly Thr Leu Val Thr Val Ser Ser
        115                 120

<210> SEQ ID NO 79
<211> LENGTH: 112
<212> TYPE: PRT
<213> ORGANISM: Homo sapiens

<400> SEQUENCE: 79

Asp Ile Gln Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Glu Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Arg Gln Thr Pro Leu Thr Phe Gly Gly Gly Thr Lys Val Glu Ile Lys
            100                 105                 110

<210> SEQ ID NO 80
<211> LENGTH: 118
<212> TYPE: PRT
<213> ORGANISM: Homo sapiens

<400> SEQUENCE: 80

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Met Tyr
            20                  25                  30

Gly Met Leu Trp Val Arg Gln Ala Pro Gly Lys Gly Leu Glu Trp Val
        35                  40                  45

Ser Tyr Ile Gly Pro Ser Gly Gly Ala Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Pro Gly Trp Tyr Phe Asp Leu Trp Gly Arg Gly Thr
            100                 105                 110

Leu Val Thr Val Ser Ser
        115

<210> SEQ ID NO 81
<211> LENGTH: 107
<212> TYPE: PRT
<213> ORGANISM: Homo sapiens

<400> SEQUENCE: 81

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30
```

Leu Asn Trp Tyr Gln Gln Lys Pro Gly Lys Ala Pro Lys Leu Leu Met
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Lys Val Glu Ile Lys
                100                 105

<210> SEQ ID NO 82
<211> LENGTH: 124
<212> TYPE: PRT
<213> ORGANISM: Homo sapiens

<400> SEQUENCE: 82

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Pro Met Ala Trp Val Arg Gln Ala Pro Gly Lys Gly Leu Glu Trp Val
        35                  40                  45

Ser Ser Ile Ser Pro Ser Gly Gly Asn Thr Gln Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Pro Tyr Ser Ser Gly Trp Ser His Tyr Val Pro Phe Asp
            100                 105                 110

Tyr Trp Gly Gln Gly Thr Leu Val Thr Val Ser Ser
        115                 120

<210> SEQ ID NO 83
<211> LENGTH: 107
<212> TYPE: PRT
<213> ORGANISM: Homo sapiens

<400> SEQUENCE: 83

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Arg Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Gly Asp Phe Ala Thr Tyr Tyr Cys Gln Gln Ser Tyr Ser Ile Pro Tyr
                85                  90                  95

Thr Phe Gly Gln Gly Thr Lys Leu Glu Ile Lys
                100                 105

<210> SEQ ID NO 84
<211> LENGTH: 118
<212> TYPE: PRT

<213> ORGANISM: Homo sapiens

<400> SEQUENCE: 84

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Ala Met Gly Trp Val Arg Gln Ala Pro Gly Lys Gly Leu Glu Trp Val
        35                  40                  45

Ser Tyr Ile Gly Pro Ser Gly Gly Trp Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Trp Val Ser Asp Pro Phe Asp Tyr Trp Gly Gln Gly Thr
            100                 105                 110

Leu Val Thr Val Ser Ser
        115

<210> SEQ ID NO 85
<211> LENGTH: 112
<212> TYPE: PRT
<213> ORGANISM: Homo sapiens

<400> SEQUENCE: 85

Asp Ile Gln Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Asn Gly Tyr Asn His Leu Asp Trp Tyr Val Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr His Phe Thr Leu Lys Ile
65                  70                  75                  80

Ser Thr Val Glu Ala Glu Asp Val Gly Val Tyr Tyr Cys Met Gln Ser
                85                  90                  95

Leu His Thr Pro Gln Ala Phe Gly Gln Gly Thr Lys Val Glu Ile Lys
            100                 105                 110

<210> SEQ ID NO 86
<211> LENGTH: 122
<212> TYPE: PRT
<213> ORGANISM: Homo sapiens

<400> SEQUENCE: 86

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Tyr
            20                  25                  30

Asn Met Thr Trp Val Arg Gln Ala Pro Gly Lys Gly Leu Glu Trp Val
        35                  40                  45

Ser Ser Ile Gly Pro Ser Gly Gly Asp Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                85                  90                  95

Ala Arg Val Met Gly Tyr Tyr Tyr Tyr Tyr Gly Met Asp Val Trp
            100                 105                 110

Gly Gln Gly Thr Thr Val Thr Val Ser Ser
        115                 120

<210> SEQ ID NO 87
<211> LENGTH: 106
<212> TYPE: PRT
<213> ORGANISM: Homo sapiens

<400> SEQUENCE: 87

Asp Ile Gln Met Thr Gln Ser Pro Val Thr Leu Ser Val Ser Pro Gly
1               5                   10                  15

Glu Arg Ala Thr Leu Ser Cys Arg Ser Ser Gln Pro Ile Leu Asn Asn
            20                  25                  30

Leu Ala Trp Tyr Gln His Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asn Asn Trp Ile Thr
                85                  90                  95

Phe Gly Gln Gly Thr Arg Leu Asp Ile Lys
            100                 105

<210> SEQ ID NO 88
<211> LENGTH: 118
<212> TYPE: PRT
<213> ORGANISM: Homo sapiens

<400> SEQUENCE: 88

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Trp Met Asp Trp Val Arg Gln Ala Pro Gly Lys Gly Leu Glu Trp Val
        35                  40                  45

Ser Arg Ile Tyr Pro Ser Gly Gly Met Thr Trp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Leu Asn Gly Tyr Phe Asp Leu Trp Gly Arg Gly Thr
            100                 105                 110

Leu Val Thr Val Ser Ser
        115

<210> SEQ ID NO 89
<211> LENGTH: 110
<212> TYPE: PRT
<213> ORGANISM: Homo sapiens

<400> SEQUENCE: 89

Gln Ser Glu Leu Thr Gln Pro Ala Ser Val Ser Gly Ser Pro Gly Gln
1               5                   10                  15
```

Ser Ile Thr Ile Ser Cys Ser Gly Thr Ser Ser Asp Val Gly Gly His
            20                  25                  30

Asn Phe Val Ser Trp Tyr Gln Glu Arg Pro Gly Lys Val Pro Lys Leu
            35                  40                  45

Ile Ile Tyr Asp Val Asn Asn Arg Pro Ser Gly Ile Ser Ser Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Phe Cys Asn Ser Tyr Thr Ile Thr
            85                  90                  95

Gly Thr Tyr Val Phe Gly Thr Gly Thr Lys Val Thr Val Leu
            100                 105                 110

<210> SEQ ID NO 90
<211> LENGTH: 122
<212> TYPE: PRT
<213> ORGANISM: Homo sapiens

<400> SEQUENCE: 90

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Ser Met Tyr
            20                  25                  30

Arg Met Met Trp Val Arg Gln Ala Pro Gly Lys Gly Leu Glu Trp Val
            35                  40                  45

Ser Ser Ile Arg Pro Ser Gly Gly Met Thr Met Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
            85                  90                  95

Thr Arg Gly Trp Ala Leu Phe Gly Val Val Arg Met Gly Asp Tyr Trp
            100                 105                 110

Gly Gln Gly Thr Leu Val Thr Val Ser Ser
            115                 120

<210> SEQ ID NO 91
<211> LENGTH: 107
<212> TYPE: PRT
<213> ORGANISM: Homo sapiens

<400> SEQUENCE: 91

Asp Ile Gln Met Thr Gln Ser Pro Gly Thr Leu Ser Leu Ser Pro Gly
 1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
            35                  40                  45

Tyr Gly Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Phe Cys Gln Gln Tyr Ala Ser Pro Pro Arg
            85                  90                  95

Thr Phe Gly Gln Gly Thr Lys Leu Glu Met Lys
            100                 105

```
<210> SEQ ID NO 92
<211> LENGTH: 116
<212> TYPE: PRT
<213> ORGANISM: Homo sapiens

<400> SEQUENCE: 92

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
            20                  25                  30

Ser Met Ser Trp Val Arg Gln Ala Pro Gly Lys Gly Leu Glu Trp Val
        35                  40                  45

Ser Ser Ile Arg Ser Ser Gly Gly Arg Thr Asp Tyr Ala Asp Ser Val
    50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
                85                  90                  95

Ala Thr Gly Ile Ala Val Ala Arg Tyr Trp Gly Gln Gly Thr Leu Val
            100                 105                 110

Thr Val Ser Ser
        115

<210> SEQ ID NO 93
<211> LENGTH: 108
<212> TYPE: PRT
<213> ORGANISM: Homo sapiens

<400> SEQUENCE: 93

Asp Ile Gln Met Thr Gln Ser Pro Gly Thr Leu Ser Val Phe Pro Gly
 1               5                  10                  15

Glu Arg Ala Thr Leu Ser Cys Arg Ala Ser Gln Asn Ile Gly Ile Asn
            20                  25                  30

Leu Ala Trp Tyr Gln Gln Lys Pro Gly Gln Thr Pro Arg Leu Leu Ile
        35                  40                  45

Tyr Gly Ala Ser Ser Arg Ala Thr Gly Ile Pro Ala Arg Phe Ser Gly
    50                  55                  60

Ser Gly Ser Gly Thr Glu Phe Ala Leu Thr Ile Ser Ser Met Gln Ser
 65                 70                  75                  80

Glu Asp Phe Ala Val Tyr Phe Cys Gln Gln Tyr His Arg Trp Pro Pro
                85                  90                  95

Leu Thr Phe Gly Gly Gly Thr Lys Val Glu Ile Lys
            100                 105

<210> SEQ ID NO 94
<211> LENGTH: 116
<212> TYPE: PRT
<213> ORGANISM: Homo sapiens

<400> SEQUENCE: 94

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
            20                  25                  30

Ser Met Ser Trp Val Arg Gln Ala Pro Gly Lys Gly Leu Glu Trp Val
        35                  40                  45

Ser Ser Ile Arg Ser Ser Gly Gly Arg Thr Asp Tyr Ala Asp Ser Val
    50                  55                  60
```

-continued

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Thr Gly Ile Ala Val Ala Arg Tyr Trp Gly Gln Gly Thr Leu Val
            100                 105                 110

Thr Val Ser Ser
        115

<210> SEQ ID NO 95
<211> LENGTH: 111
<212> TYPE: PRT
<213> ORGANISM: Homo sapiens

<400> SEQUENCE: 95

Asp Ile Gln Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu Gln Asn
             20                  25                  30

Asn Gly Tyr Asn Tyr Leu Asp Trp Tyr Leu Gln Lys Pro Gly Gln Ser
         35                  40                  45

Pro Gln Leu Leu Ile Phe Leu Gly Ser Asn Arg Ala Ser Gly Val Pro
     50                  55                  60

Asp Arg Phe Ser Gly Ser Gly Ser Gly Thr Asp Phe Thr Leu Arg Ile
 65                  70                  75                  80

Ser Lys Val Glu Ala Glu Asp Val Gly Val Tyr Tyr Cys Met Gln Ala
                 85                  90                  95

Leu His Ala Pro Thr Phe Gly Gln Gly Thr Arg Leu Glu Ile Arg
            100                 105                 110

<210> SEQ ID NO 96
<211> LENGTH: 119
<212> TYPE: PRT
<213> ORGANISM: Homo sapiens

<400> SEQUENCE: 96

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Trp Tyr
             20                  25                  30

Gly Met Arg Trp Val Arg Gln Ala Pro Gly Lys Gly Leu Glu Trp Val
         35                  40                  45

Ser Ser Ile Ser Ser Ser Gly Gly Lys Thr Arg Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Val Asp Gln Trp Leu Arg Ser Asn Asp Tyr Trp Gly Gln Gly
            100                 105                 110

Thr Leu Val Thr Val Ser Ser
        115

<210> SEQ ID NO 97
<211> LENGTH: 107
<212> TYPE: PRT
<213> ORGANISM: Homo sapiens
```

<400> SEQUENCE: 97

Asp Ile Gln Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Asn Tyr
            20                  25                  30

Leu Ala Trp Tyr Gln Gln Lys Pro Gly Gln Ser Pro Arg Leu Leu Ile
        35                  40                  45

Tyr Tyr Ala Ser Thr Arg Ala Thr Gly Ile Pro Asp Arg Phe Ser Gly
50                  55                  60

Ser Gly Ser Gly Thr Asp Phe Thr Leu Thr Ile Arg Arg Leu Glu Pro
65                  70                  75                  80

Glu Asp Phe Ala Val Tyr Tyr Cys Gln Gln Tyr Ala Thr Ser Pro Trp
                85                  90                  95

Thr Phe Gly Gln Gly Thr Lys Val Glu Ile Lys
            100                 105

<210> SEQ ID NO 98
<211> LENGTH: 119
<212> TYPE: PRT
<213> ORGANISM: Homo sapiens

<400> SEQUENCE: 98

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Phe Met Asn Trp Val Arg Gln Ala Pro Gly Lys Gly Leu Glu Trp Val
        35                  40                  45

Ser Ser Ile Ser Ser Ser Gly Ala Thr Thr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Gly Tyr Thr Asn Trp Ser Ile Asp Asn Trp Gly Gln Gly
            100                 105                 110

Thr Leu Val Thr Val Ser Ser
        115

<210> SEQ ID NO 99
<211> LENGTH: 108
<212> TYPE: PRT
<213> ORGANISM: Homo sapiens

<400> SEQUENCE: 99

Asp Ile Gln Met Thr Gln Ser Pro Ser Ser Leu Ser Ala Ser Val Gly
1               5                   10                  15

Asp Arg Val Ala Ile Thr Cys Arg Ala Ser Gln Ser Ile Asp Thr Tyr
            20                  25                  30

Leu Asn Trp Tyr Gln Gln Lys Pro Gly Lys Ala Pro Lys Leu Leu Ile
        35                  40                  45

Tyr Ala Ala Ser Lys Leu Glu Asp Gly Val Pro Ser Arg Phe Ser Gly
50                  55                  60

Ser Gly Thr Gly Thr Asp Phe Thr Leu Thr Ile Arg Ser Leu Gln Pro
65                  70                  75                  80

Glu Asp Phe Ala Ser Tyr Phe Cys Gln Gln Ser Tyr Ser Ser Pro Gly
                85                  90                  95

Ile Thr Phe Gly Pro Gly Thr Lys Val Glu Ile Lys
            100                 105

<210> SEQ ID NO 100
<211> LENGTH: 121
<212> TYPE: PRT
<213> ORGANISM: Homo sapiens

<400> SEQUENCE: 100

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Trp Met Ser Trp Val Arg Gln Ala Pro Gly Lys Gly Leu Glu Trp Val
        35                  40                  45

Ser Gly Ile Gly Pro Ser Gly Tyr Thr Ser Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Leu Gln Val Asp Phe Trp Ser Gly Tyr Tyr Phe Asp Gln Trp Gly
            100                 105                 110

Gln Gly Thr Leu Val Thr Val Ser Ser
        115                 120

<210> SEQ ID NO 101
<211> LENGTH: 107
<212> TYPE: PRT
<213> ORGANISM: Homo sapiens

<400> SEQUENCE: 101

Asp Ile Gln Met Thr Gln Ser Pro Ser Thr Leu Ser Ala Ser Val Gly
1               5                   10                  15

Asp Thr Val Thr Ile Thr Cys Arg Ala Ser Gln Ser Ile Ser Asn Trp
            20                  25                  30

Val Ala Trp Tyr Gln Gln Lys Pro Gly Lys Ala Pro Lys Val Leu Ile
        35                  40                  45

Tyr Lys Ala Ser Leu Leu Glu Ser Gly Val Pro Ser Arg Phe Ser Gly
    50                  55                  60

Ser Gln Ser Gly Ala Asp Phe Thr Leu Thr Ile Ser Ser Leu Gln Pro
65                  70                  75                  80

Glu Asp Phe Ala Val Tyr Tyr Cys Gln Gln Ser Gly Thr Ser Pro Phe
                85                  90                  95

Thr Phe Gly Pro Gly Thr Lys Val Asp Leu Lys
            100                 105

<210> SEQ ID NO 102
<211> LENGTH: 121
<212> TYPE: PRT
<213> ORGANISM: Homo sapiens

<400> SEQUENCE: 102

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Arg Met Tyr Trp Val Arg Gln Ala Pro Gly Lys Gly Leu Glu Trp Val

```
                35                  40                  45
Ser Gly Ile Ser Pro Ser Gly Gly Lys Thr Thr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Gly Arg Gly Asp Ile Leu Thr Ala Tyr Phe Asp Tyr Trp Gly
                100                 105                 110
Gln Gly Thr Leu Val Thr Val Ser Ser
            115                 120

<210> SEQ ID NO 103
<211> LENGTH: 112
<212> TYPE: PRT
<213> ORGANISM: Homo sapiens

<400> SEQUENCE: 103

Asp Ile Gln Met Thr Gln Ser Pro Leu Ser Leu Pro Val Thr Pro Gly
  1               5                  10                  15
Glu Pro Ala Ser Ile Ser Cys Arg Ser Ser Gln Ser Leu Leu His Ser
                 20                  25                  30
Asn Gly Tyr Asn Tyr Leu Asp Trp Tyr Leu Gln Lys Pro Gly Gln Ser
             35                  40                  45
Pro Gln Leu Leu Ile Tyr Leu Gly Ser Asn Arg Ala Ser Gly Val Pro
 50                  55                  60
Asp Arg Phe Ser Gly Ser Gly Ser Gly Thr Asp Phe Thr Leu Lys Ile
 65                  70                  75                  80
Ser Arg Val Glu Ala Glu Asp Val Gly Val Tyr Tyr Cys Met Gln Ala
                 85                  90                  95
Leu Gln Thr Pro Gln Thr Phe Gly Gln Gly Thr Lys Leu Glu Ile Lys
                100                 105                 110

<210> SEQ ID NO 104
<211> LENGTH: 118
<212> TYPE: PRT
<213> ORGANISM: Homo sapiens

<400> SEQUENCE: 104

Glu Val Gln Leu Leu Glu Ser Gly Gly Gly Leu Val Gln Pro Gly Gly
  1               5                  10                  15
Ser Leu Arg Leu Ser Cys Ala Ala Ser Gly Phe Thr Phe Ser Trp Tyr
                 20                  25                  30
Trp Met Gly Trp Val Arg Gln Ala Pro Gly Lys Gly Leu Glu Trp Val
             35                  40                  45
Ser Ser Ile Tyr Pro Ser Gly Gly Phe Thr Asp Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Gly Gly Asp Tyr Tyr Tyr Met Asp Val Trp Gly Lys Gly Thr
                100                 105                 110
Thr Val Thr Val Ser Ser
            115

<210> SEQ ID NO 105
```

```
<211> LENGTH: 110
<212> TYPE: PRT
<213> ORGANISM: Homo sapiens

<400> SEQUENCE: 105

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
50                  55                  60

Gly Ser Gly Ser Glu Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Arg Lys Tyr Thr Phe Gly Gln Gly Thr Lys Leu Glu Ile Lys
            100                 105                 110

<210> SEQ ID NO 106
<211> LENGTH: 120
<212> TYPE: PRT
<213> ORGANISM: Homo sapiens

<400> SEQUENCE: 106

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Thr Met His Trp Val Arg Gln Ala Pro Gly Lys Gly Leu Glu Trp Val
            35                  40                  45

Ser Tyr Ile Ser Pro Ser Gly Gly Trp Thr Ser Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gln Gln Trp Pro Gly Val Ala Phe Glu Ile Trp Gly Gln
            100                 105                 110

Gly Thr Met Val Thr Val Ser Ser
            115                 120

<210> SEQ ID NO 107
<211> LENGTH: 110
<212> TYPE: PRT
<213> ORGANISM: Homo sapiens

<400> SEQUENCE: 107

Gln Tyr Glu Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Phe Val Thr Trp Tyr Gln Gln Leu Pro Gly Thr Ala Pro Lys Leu Leu
            35                  40                  45

Ser Tyr Thr Asn Asn Gln Arg Pro Ser Gly Val Pro Asp Arg Phe Ser
50                  55                  60

Ala Ser Lys Ser Gly Thr Ser Ala Ser Leu Ala Ile Ser Gly Leu Gln
```

-continued

```
                 65                  70                  75                  80
Ser Glu Asp Glu Ala Asp Tyr Tyr Cys Ala Ala Trp Asp Asp Asn Leu
                         85                  90                  95

Asn Cys Pro Val Phe Gly Gly Gly Thr Lys Leu Thr Val Leu
                100                 105                 110

<210> SEQ ID NO 108
<211> LENGTH: 120
<212> TYPE: PRT
<213> ORGANISM: Homo sapiens

<400> SEQUENCE: 108

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ser Arg Ile Trp Pro Ser Gly Gly Tyr Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Lys Gly Ser Gly Ser Phe Pro Leu Asp Tyr Trp Gly Gln
            100                 105                 110

Gly Thr Leu Val Thr Val Ser Ser
        115                 120

<210> SEQ ID NO 109
<211> LENGTH: 110
<212> TYPE: PRT
<213> ORGANISM: Homo sapiens

<400> SEQUENCE: 109

Gln Ser Glu Leu Thr Gln Pro Pro Ser Ala Ser Gly Thr Pro Gly Gln
1               5                   10                  15

Arg Val Thr Ile Ser Cys Ser Gly Thr Leu Ser Asn Ile Gly Thr Asn
            20                  25                  30

Ile Val Ser Trp Phe Gln Gln Leu Pro Gly Thr Ala Pro Lys Leu Leu
        35                  40                  45

Ile Tyr Asn Asp His Arg Arg Pro Ser Gly Val Pro Asp Arg Phe Ser
    50                  55                  60

Gly Ser Lys Ser Ala Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Val Val Phe Gly Gly Gly Thr Lys Leu Thr Val Leu
            100                 105                 110

<210> SEQ ID NO 110
<211> LENGTH: 124
<212> TYPE: PRT
<213> ORGANISM: Homo sapiens

<400> SEQUENCE: 110

Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Pro Tyr
            20                  25                  30

Ala Met Tyr Trp Val Arg Gln Ala Pro Gly Lys Gly Leu Glu Trp Val
        35                  40                  45

Ser Tyr Ile Ser Pro Ser Gly Gly Ile Thr Gln Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Gly Asp Phe Asp Trp Leu Leu His His Pro Asn Ala Phe Asp
            100                 105                 110

Ile Trp Gly Gln Gly Thr Met Val Thr Val Ser Ser
            115                 120

<210> SEQ ID NO 111
<211> LENGTH: 112
<212> TYPE: PRT
<213> ORGANISM: Homo sapiens

<400> SEQUENCE: 111

Asp Ile Gln Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Thr
            20                  25                  30

His Gly Tyr Asn Tyr Leu Asp Trp Phe Leu Gln Lys Pro Gly Gln Ser
        35                  40                  45

Pro Gln Leu Leu Ile Tyr Met Gly Ser Asn Arg Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                85                  90                  95

Arg Gln Thr Pro Tyr Thr Phe Gly Gln Gly Thr Lys Leu Glu Ile Lys
            100                 105                 110

<210> SEQ ID NO 112
<211> LENGTH: 124
<212> TYPE: PRT
<213> ORGANISM: Homo sapiens

<400> SEQUENCE: 112

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
            20                  25                  30

Pro Met Gln Trp Val Arg Gln Ala Pro Gly Lys Gly Leu Glu Trp Val
        35                  40                  45

Ser Ser Ile Trp Ser Ser Gly Gly Ile Thr Leu Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Gly Thr His Gly Gly Pro Pro Trp Tyr Tyr Met Asp
            100                 105                 110

Val Trp Gly Lys Gly Thr Thr Val Thr Val Ser Ser
```

<210> SEQ ID NO 113
<211> LENGTH: 112
<212> TYPE: PRT
<213> ORGANISM: Homo sapiens

<400> SEQUENCE: 113

Asp Ile Gln Met Thr Gln Ser Pro Leu Ser Leu Ser Val Thr Pro Gly
1               5                   10                  15

Glu Pro Ala Ser Ile Ser Cys Met Ser Ser Gln Ser Leu Leu Tyr Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ala Asn Arg Ala Ser Gly Val Pro
    50                  55                  60

Asp Arg Phe Ser Gly Gly Gly Ser Gly Thr Asp Phe Arg Leu Lys Ile
65                  70                  75                  80

Ser Arg Val Glu Ala Glu Asp Val Gly Val Tyr Tyr Cys Val Gln Thr
                85                  90                  95

Leu Gln Thr Pro Tyr Thr Phe Gly Gln Gly Thr Lys Leu Glu Ile Lys
            100                 105                 110

<210> SEQ ID NO 114
<211> LENGTH: 123
<212> TYPE: PRT
<213> ORGANISM: Homo sapiens

<400> SEQUENCE: 114

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ser Met Ser Trp Val Arg Gln Ala Pro Gly Lys Gly Leu Glu Trp Val
        35                  40                  45

Ser Tyr Ile Tyr Ser Ser Gly Pro Thr Gln Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Met Ala Val Tyr Tyr Cys
                85                  90                  95

Ala Arg Gly Gly Gly Tyr Ser Tyr Gly Phe Pro Leu Pro Phe Asp Tyr
            100                 105                 110

Trp Gly Gln Gly Thr Leu Val Thr Val Ser Ser
        115                 120

<210> SEQ ID NO 115
<211> LENGTH: 106
<212> TYPE: PRT
<213> ORGANISM: Homo sapiens

<400> SEQUENCE: 115

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Asn Ile Gly Thr Trp
            20                  25                  30

Val Val Trp Tyr Gln Gln Arg Pro Gly Lys Ala Pro Ser Leu Leu Ile
        35                  40                  45

-continued

Tyr Lys Ala Ser Thr Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
 65              70                  75                  80

Asp Asp Phe Ala Thr Tyr Tyr Cys Gln Gln Phe Tyr Thr Ser Lys Thr
                 85                  90                  95

Phe Gly Gln Gly Thr Lys Val Glu Ile Lys
                100                 105

<210> SEQ ID NO 116
<211> LENGTH: 116
<212> TYPE: PRT
<213> ORGANISM: Homo sapiens

<400> SEQUENCE: 116

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Ser Asn Tyr
             20                  25                  30

Ser Met Ser Trp Val Arg Gln Ala Pro Gly Lys Gly Leu Glu Trp Val
         35                  40                  45

Ser Ser Ile Arg Ser Ser Gly Gly Arg Thr Asp Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Thr Gly Ile Ala Val Ala Arg Tyr Trp Gly Gln Gly Thr Leu Val
                100                 105                 110

Thr Val Ser Ser
        115

<210> SEQ ID NO 117
<211> LENGTH: 112
<212> TYPE: PRT
<213> ORGANISM: Homo sapiens

<400> SEQUENCE: 117

Asp Ile Gln Met Thr Gln Ser Pro Leu Ser Leu Pro Val Thr Pro Gly
 1               5                   10                  15

Glu Pro Ala Ser Ile Ser Cys Arg Ser Ser Gln Ser Leu Leu Gln Ser
             20                  25                  30

Asn Gly Tyr Asn Tyr Leu Asp Trp Tyr Leu Gln Lys Pro Gly Gln Ser
         35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Ile Ile
 65                  70                  75                  80

Ser Arg Val Glu Ala Asp Asp Val Gly Val Tyr Tyr Cys Met Gln Gly
                 85                  90                  95

Leu Gln Thr Pro His Thr Phe Gly Gln Gly Thr Lys Leu Glu Ile Lys
                100                 105                 110

<210> SEQ ID NO 118
<211> LENGTH: 118
<212> TYPE: PRT
<213> ORGANISM: Homo sapiens

<400> SEQUENCE: 118

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Met Met His Trp Val Arg Gln Ala Pro Gly Lys Gly Leu Glu Trp Val
        35                  40                  45

Ser Ser Ile Gly Ser Ser Gly Gly Phe Thr Thr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Gly Ala Met Gly Ser Ala Phe Asp Ile Trp Gly Gln Gly Thr
            100                 105                 110

Met Val Thr Val Ser Ser
        115

<210> SEQ ID NO 119
<211> LENGTH: 108
<212> TYPE: PRT
<213> ORGANISM: Homo sapiens

<400> SEQUENCE: 119

Asp Ile Gln Met Thr Gln Ser Pro Gly Thr Leu Ser Leu Ser Pro Gly
1               5                   10                  15

Glu Arg Ala Thr Val Ser Cys Arg Ala Ser Gln Ser Val Ser Ser Ser
            20                  25                  30

Tyr Leu Ala Trp Tyr Gln Gln Lys Pro Gly Leu Ala Pro Arg Leu Leu
        35                  40                  45

Ile Tyr Asp Ala Ser Asn Arg Ala Thr Gly Ile Pro Asp Arg Phe Ser
        50                  55                  60

Gly Ser Gly Ser Gly Thr Asp Phe Thr Leu Thr Ile Thr Arg Leu Glu
65                  70                  75                  80

Pro Glu Asp Phe Ala Val Tyr Tyr Cys Gln Gln Tyr Ser Thr Ser Pro
                85                  90                  95

Phe Thr Phe Gly Pro Gly Thr Lys Val Asp Ile Lys
            100                 105

<210> SEQ ID NO 120
<211> LENGTH: 116
<212> TYPE: PRT
<213> ORGANISM: Homo sapiens

<400> SEQUENCE: 120

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ser Met Ser Trp Val Arg Gln Ala Pro Gly Lys Gly Leu Glu Trp Val
        35                  40                  45

Ser Ser Ile Arg Ser Ser Gly Gly Arg Thr Asp Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

```
Ala Thr Gly Ile Ala Val Ala Arg Tyr Trp Gly Gln Gly Thr Leu Val
            100                 105                 110
Thr Val Ser Ser
        115

<210> SEQ ID NO 121
<211> LENGTH: 108
<212> TYPE: PRT
<213> ORGANISM: Homo sapiens

<400> SEQUENCE: 121

Asp Ile Gln Met Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Asn
             20                  25                  30

Tyr Leu Ala Trp Tyr Gln Gln Lys Pro Gly Gln Ala Pro Arg Leu Leu
             35                  40                  45

Met Tyr Gly Ala Ser Thr Arg Ala Thr Gly Val Pro Asp Arg Phe Ser
 50                  55                  60

Gly Ser Gly Ser Gly Thr Glu Phe Thr Leu Thr Ile Asn Ser Leu Gln
 65                  70                  75                  80

Ser Glu Asp Phe Ala Val Tyr Tyr Cys Gln Gln Tyr Asn Tyr Trp Pro
             85                  90                  95

Arg Thr Phe Gly Thr Gly Thr Lys Val Glu Ile Lys
            100                 105

<210> SEQ ID NO 122
<211> LENGTH: 119
<212> TYPE: PRT
<213> ORGANISM: Homo sapiens

<400> SEQUENCE: 122

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Lys Tyr
             20                  25                  30

Asn Met Phe Trp Val Arg Gln Ala Pro Gly Lys Gly Leu Glu Trp Val
             35                  40                  45

Ser Val Ile Gly Ser Ser Gly Gly Thr Thr Gly Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
             85                  90                  95

Ala Arg Glu Lys Gly Ile Ala Ala Ala Tyr Asp Tyr Trp Gly Gln Gly
            100                 105                 110

Thr Leu Val Thr Val Ser Ser
        115

<210> SEQ ID NO 123
<211> LENGTH: 108
<212> TYPE: PRT
<213> ORGANISM: Homo sapiens

<400> SEQUENCE: 123

Asp Ile Gln Met Thr Gln Ser Pro Gly Thr Leu Ser Leu Ser Pro Gly
  1               5                  10                  15

Glu Arg Ala Thr Leu Ser Cys Trp Ala Ser Gln Ser Val Lys Ser Asn
             20                  25                  30
```

Tyr Leu Ala Trp Tyr Gln Gln Lys Pro Gly Gln Ala Pro Arg Leu Leu
                35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Arg Thr Phe Gly Gln Gly Thr Lys Val Glu Ile Lys
                100                 105

<210> SEQ ID NO 124
<211> LENGTH: 118
<212> TYPE: PRT
<213> ORGANISM: Homo sapiens

<400> SEQUENCE: 124

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Leu Tyr
                20                  25                  30

Lys Met Met Trp Val Arg Gln Ala Pro Gly Lys Gly Leu Glu Trp Val
                35                  40                  45

Ser Ser Ile Tyr Ser Ser Gly Arg Thr Asn Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Thr Asp Val Thr Trp Trp Pro Arg Ser Tyr Trp Gly Gln Gly Thr
                100                 105                 110

Leu Val Thr Val Ser Ser
           115

<210> SEQ ID NO 125
<211> LENGTH: 112
<212> TYPE: PRT
<213> ORGANISM: Homo sapiens

<400> SEQUENCE: 125

Asp Ile Gln Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
                35                  40                  45

Pro Gln Leu Leu Ile Tyr Leu Gly Ser Asn Arg Ala Ser Gly Val Pro
            50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Leu Thr Phe Gly Gly Gly Thr Lys Val Glu Ile Lys
                100                 105                 110

<210> SEQ ID NO 126
<211> LENGTH: 120

```
<212> TYPE: PRT
<213> ORGANISM: Homo sapiens

<400> SEQUENCE: 126

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Met Tyr
            20                  25                  30

Ser Met His Trp Val Arg Gln Ala Pro Gly Lys Gly Leu Glu Trp Val
        35                  40                  45

Ser Gly Ile Ser Ser Ser Gly Gly Ala Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Ala Pro Ile Tyr Asn Tyr Tyr Met Asp Val Trp Gly Lys
            100                 105                 110

Gly Thr Thr Val Thr Val Ser Ser
        115                 120

<210> SEQ ID NO 127
<211> LENGTH: 108
<212> TYPE: PRT
<213> ORGANISM: Homo sapiens

<400> SEQUENCE: 127

Asp Ile Gln Met Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

<210> SEQ ID NO 128
<211> LENGTH: 116
<212> TYPE: PRT
<213> ORGANISM: Homo sapiens

<400> SEQUENCE: 128

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Tyr
            20                  25                  30

Ser Met Gly Trp Val Arg Gln Ala Pro Gly Lys Gly Leu Glu Trp Val
        35                  40                  45

Ser Tyr Ile Ser Ser Ser Gly Gly Val Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Thr Gly Ile Ala Val Ala Arg Tyr Trp Gly Gln Gly Thr Leu Val
            100                 105                 110

Thr Val Ser Ser
        115

<210> SEQ ID NO 129
<211> LENGTH: 107
<212> TYPE: PRT
<213> ORGANISM: Homo sapiens

<400> SEQUENCE: 129

Asp Ile Gln Met Thr Gln Ser Pro Ala Thr Leu Ser Val Ser Pro Gly
1               5                   10                  15

Glu Thr Ala Thr Leu Ser Cys Trp Ala Ser Gln Ser Val Lys Ser Asn
            20                  25                  30

Leu Ala Trp Tyr Gln Gln Lys Pro Gly Gln Ala Pro Arg Leu Leu Ile
        35                  40                  45

Tyr Gly Ala Thr Arg Ala Thr Gly Val Pro Ala Arg Phe Ser Gly
    50                  55                  60

Ser Gly Ser Arg Thr Glu Phe Thr Leu Thr Ile Ser Gly Leu Gln Ser
65                  70                  75                  80

Glu Asp Phe Ala Val Tyr Tyr Cys Gln Gln Tyr Asp Val Trp Pro Phe
                85                  90                  95

Thr Phe Gly Pro Gly Thr Val Asp Ile Lys
            100                 105

<210> SEQ ID NO 130
<211> LENGTH: 114
<212> TYPE: PRT
<213> ORGANISM: Homo sapiens

<400> SEQUENCE: 130

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Arg Met Gly Trp Val Arg Gln Ala Pro Gly Lys Gly Leu Glu Trp Val
        35                  40                  45

Ser Tyr Ile Tyr Ser Ser Gly Leu Thr Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Thr Gly Ala Leu Gly Gln Trp Gly Gln Gly Thr Leu Val Thr Val
            100                 105                 110

Ser Ser

<210> SEQ ID NO 131
<211> LENGTH: 107
<212> TYPE: PRT
<213> ORGANISM: Homo sapiens

<400> SEQUENCE: 131

Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Arg Ile Ser Ile Tyr
            20                  25                  30

Leu Asn Trp Tyr Gln Gln Lys Pro Gly Lys Ala Pro Lys Leu Leu Ile
            35                  40                  45

Tyr Ala Ala Asp Asn Leu Gln Ser Gly Val Pro Ser Arg Phe Ser Gly
 50                      55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Asp Ser Ser Pro Arg
                 85                  90                  95

Thr Phe Gly Gln Gly Thr Lys Val Glu Ile Lys
            100                 105
```

<210> SEQ ID NO 132
<211> LENGTH: 119
<212> TYPE: PRT
<213> ORGANISM: Homo sapiens

<400> SEQUENCE: 132

```
Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Ser Gly Tyr
            20                  25                  30

Glu Met Gln Trp Val Arg Gln Ala Pro Gly Lys Gly Leu Glu Trp Val
            35                  40                  45

Ser Ser Ile Val Ser Ser Gly Lys Thr Tyr Tyr Ala Asp Ser Val
 50                      55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Arg Leu Val Trp Asn Asp Leu Asp Tyr Trp Gly Gln Gly
            100                 105                 110

Thr Leu Val Thr Val Ser Ser
            115
```

<210> SEQ ID NO 133
<211> LENGTH: 109
<212> TYPE: PRT
<213> ORGANISM: Homo sapiens

<400> SEQUENCE: 133

```
Asp Ile Gln Met Thr Gln Ser Pro Gly Thr Leu Ser Leu Ser Pro Gly
 1               5                   10                  15

Val Arg Ala Ala Leu Ser Cys Arg Ala Ser Gln Ser Val Ser Ser Ser
            20                  25                  30

Tyr Leu Ala Trp Tyr Gln His Lys Pro Gly Gln Ala Pro Arg Leu Leu
            35                  40                  45

Ile Tyr Gly Ala Ser Ser Arg Ala Thr Gly Ile Pro Asp Arg Phe Ser
 50                      55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Pro Ile Thr Phe Gly Gln Gly Thr Arg Leu Glu Ile Lys
            100                 105
```

```
<210> SEQ ID NO 134
<211> LENGTH: 123
<212> TYPE: PRT
<213> ORGANISM: Homo sapiens

<400> SEQUENCE: 134

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Tyr
            20                  25                  30

Ser Met Thr Trp Val Arg Gln Ala Pro Gly Lys Gly Leu Glu Trp Val
        35                  40                  45

Ser Tyr Ile Ser Pro Ser Gly Gly Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Trp Arg Gly Ser Ser Trp Leu Pro Thr Gly Met Asp Val
            100                 105                 110

Trp Gly Gln Gly Thr Thr Val Thr Val Ser Ser
        115                 120

<210> SEQ ID NO 135
<211> LENGTH: 111
<212> TYPE: PRT
<213> ORGANISM: Homo sapiens

<400> SEQUENCE: 135

Asp Ile Gln Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Thr Phe Gly Gly Gly Thr Lys Val Glu Ile Lys
            100                 105                 110

<210> SEQ ID NO 136
<211> LENGTH: 123
<212> TYPE: PRT
<213> ORGANISM: Homo sapiens

<400> SEQUENCE: 136

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser His Tyr
            20                  25                  30

Arg Met Ile Trp Val Arg Gln Ala Pro Gly Lys Gly Leu Glu Trp Val
        35                  40                  45

Ser Ser Ile Ser Pro Ser Gly Gly Arg Thr Gly Tyr Ala Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Gly Tyr Asp Ser Ser Gly Tyr Tyr Tyr Phe Asp Leu
            100                 105                 110

Trp Gly Arg Gly Thr Leu Val Thr Val Ser Ser
        115                 120
```

<210> SEQ ID NO 137
<211> LENGTH: 111
<212> TYPE: PRT
<213> ORGANISM: Homo sapiens

<400> SEQUENCE: 137

```
Asp Ile Gln Met Thr Gln Ser Pro Asp Thr Leu Ser Leu Ser Pro Gly
 1               5                  10                  15

Glu Ser Ala Thr Leu Ser Cys Arg Ala Ser Glu Ser Ile Ser Leu Asn
             20                  25                  30

Ser Leu Ala Trp Tyr Gln His Lys Pro Gly Gln Pro Pro Arg Leu Leu
         35                  40                  45

Ile His Gly Ala Ser Tyr Arg Ala Ser Gly Ile Pro Leu Arg Phe Ile
     50                  55                  60

Gly Ser Gly Ser Gly Thr Gly Phe Thr Leu Thr Ile Ser Arg Leu Glu
 65                  70                  75                  80

Pro Glu Asp Ser Ala Val Tyr Tyr Cys Gln Gln Tyr Gln Gln Arg Ser
                 85                  90                  95

Ser Pro Ala Leu Thr Phe Gly Gly Gly Thr Lys Val Glu Ile Lys
            100                 105                 110
```

<210> SEQ ID NO 138
<211> LENGTH: 123
<212> TYPE: PRT
<213> ORGANISM: Homo sapiens

<400> SEQUENCE: 138

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Trp Tyr
             20                  25                  30

His Met Ile Trp Val Arg Gln Ala Pro Gly Lys Gly Leu Glu Trp Val
         35                  40                  45

Ser Arg Ile Gly Pro Ser Gly Gly Phe Thr Glu Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Met Tyr Tyr Cys
                 85                  90                  95

Ala Arg Ala Tyr Asp Phe Trp Ser Gly Tyr Pro Ser Ala Phe Asp Ile
            100                 105                 110

Trp Gly Gln Gly Thr Met Val Thr Val Ser Ser
        115                 120
```

<210> SEQ ID NO 139
<211> LENGTH: 106
<212> TYPE: PRT
<213> ORGANISM: Homo sapiens

<400> SEQUENCE: 139

Asp Ile Gln Met Thr Gln Ser Pro Gly Thr Leu Ser Val Ser Pro Gly
1               5                   10                  15

Glu Arg Ala Thr Leu Ser Cys Arg Ala Ser Gln Ser Val Ser Asn Asn
            20                  25                  30

Leu Ala Trp Tyr Gln Gln Arg Pro Gly Gln Ala Pro Arg Leu Leu Ile
        35                  40                  45

Tyr Ser Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Ile Tyr Tyr Cys Gln Gln Ser Tyr Ser Thr Leu Thr
                85                  90                  95

Phe Gly Pro Gly Thr Lys Val Asp Ile Lys
            100                 105

<210> SEQ ID NO 140
<211> LENGTH: 118
<212> TYPE: PRT
<213> ORGANISM: Homo sapiens

<400> SEQUENCE: 140

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Asn Met Gly Trp Val Arg Gln Ala Pro Gly Lys Gly Leu Glu Trp Val
        35                  40                  45

Ser Gly Ile Trp Pro Ser Gly Trp Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Met Ala Val Tyr Tyr Cys
                85                  90                  95

Ala Arg Val Ser Glu Tyr Gly Ser Phe Asp Tyr Trp Gly Gln Gly Thr
            100                 105                 110

Leu Val Thr Val Ser Ser
        115

<210> SEQ ID NO 141
<211> LENGTH: 107
<212> TYPE: PRT
<213> ORGANISM: Homo sapiens

<400> SEQUENCE: 141

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Val Thr Tyr
            20                  25                  30

Leu Ala Trp Tyr Gln Gln Thr Pro Gly Lys Ala Pro Lys Leu Leu Ile
        35                  40                  45

Tyr Ser Ala Ser Thr Leu Gln Ser Glu Val Pro Ser Arg Phe Ser Gly
    50                  55                  60

Ser Gly Ser Gly Thr Asp Phe Thr Leu Ser Ile Ser Ser Leu Gln Pro
65                  70                  75                  80

Glu Asp Phe Ala Thr Tyr Tyr Cys Gln Gln Gly Asn Ser Phe Pro Pro
                85                  90                  95

Thr Phe Gly Gly Gly Thr Lys Val Glu Ile Lys
            100                 105

<210> SEQ ID NO 142
<211> LENGTH: 120
<212> TYPE: PRT
<213> ORGANISM: Homo sapiens

<400> SEQUENCE: 142

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ala Tyr
             20                  25                  30

Gly Met Glu Trp Val Arg Gln Ala Pro Gly Lys Gly Leu Glu Trp Val
         35                  40                  45

Ser Tyr Ile Tyr Pro Ser Gly Gly Trp Thr Gln Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Ile Pro Arg Gly Ala Ser Ala Phe Asp Ile Trp Gly Gln
            100                 105                 110

Gly Thr Met Val Thr Val Ser Ser
        115                 120

<210> SEQ ID NO 143
<211> LENGTH: 107
<212> TYPE: PRT
<213> ORGANISM: Homo sapiens

<400> SEQUENCE: 143

Asn Ile Gln Met Thr Gln Ser Pro Ser Ser Val Ser Ala Ser Val Gly
  1               5                  10                  15

Asp Arg Val Thr Ile Thr Cys Arg Ala Ser Gln Gly Ile Ser Ser Trp
             20                  25                  30

Leu Ala Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr His Cys Gln Gln Ala Asp Ser Phe Pro Phe
                 85                  90                  95

Thr Phe Gly Pro Gly Thr Lys Val Asp Val Lys
            100                 105

<210> SEQ ID NO 144
<211> LENGTH: 117
<212> TYPE: PRT
<213> ORGANISM: Homo sapiens

<400> SEQUENCE: 144

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Gly Tyr
             20                  25                  30

Ser Met Val Trp Val Arg Gln Ala Pro Gly Lys Gly Leu Glu Trp Val

```
                    35                  40                  45
Ser Arg Ile Ser Pro Ser Gly Gly Tyr Thr Asn Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Phe Gly Tyr Gly Met Asp Val Trp Gly Gln Gly Thr Thr
            100                 105                 110

Val Thr Val Ser Ser
            115

<210> SEQ ID NO 145
<211> LENGTH: 109
<212> TYPE: PRT
<213> ORGANISM: Homo sapiens

<400> SEQUENCE: 145

Asp Ile Gln Met Thr Gln Ser Pro Ser Thr Leu Ser Ala Ser Val Gly
  1               5                  10                  15

Asp Arg Val Thr Ile Thr Cys Arg Ala Ser Gln Ser Ile Ser Ser Trp
                 20                  25                  30

Leu Ala Trp Tyr Gln Gln Lys Pro Gly Lys Ala Pro Lys Leu Leu Ile
             35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Ser Tyr Ser Pro
                 85                  90                  95

Met Tyr Thr Phe Gly Gln Gly Thr Lys Leu Glu Ile Lys
            100                 105

<210> SEQ ID NO 146
<211> LENGTH: 123
<212> TYPE: PRT
<213> ORGANISM: Homo sapiens

<400> SEQUENCE: 146

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Gly Tyr
                 20                  25                  30

Asn Met Phe Trp Val Arg Gln Ala Pro Gly Lys Gly Leu Glu Trp Val
             35                  40                  45

Ser Val Ile Val Pro Ser Gly Gly Leu Thr Ser Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Ile Gly Ser Ser Gly Asp Tyr Tyr Gly Met Asp Val
            100                 105                 110

Trp Gly Gln Gly Thr Thr Val Thr Val Ser Ser
            115                 120

<210> SEQ ID NO 147
```

```
<211> LENGTH: 108
<212> TYPE: PRT
<213> ORGANISM: Homo sapiens

<400> SEQUENCE: 147

Asp Ile Gln Met Thr Gln Ser Pro Gly Thr Leu Ser Val Ser Pro Gly
 1               5                  10                  15

Glu Arg Val Thr Leu Ser Cys Arg Ala Ser Gln Ser Val Gly Ser Asn
            20                  25                  30

Leu Ala Trp Tyr Gln Gln Lys Ala Gly Gln Ala Pro Arg Leu Leu Phe
        35                  40                  45

Tyr Asp Ala Ser Thr Arg Ala Thr Gly Ile Pro Asp Arg Phe Ser Gly
 50                  55                  60

Ser Gly Ser Gly Arg Asp Phe Thr Leu Thr Ile Ser Gly Leu His Ser
65                  70                  75                  80

Glu Asp Phe Ala Val Tyr Phe Cys His His Tyr Asp Asp Trp Ser Pro
                85                  90                  95

Gly Thr Phe Gly Gln Gly Thr Lys Val Glu Ile Lys
            100                 105

<210> SEQ ID NO 148
<211> LENGTH: 120
<212> TYPE: PRT
<213> ORGANISM: Homo sapiens

<400> SEQUENCE: 148

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Tyr
            20                  25                  30

Ala Met Phe Trp Val Arg Gln Ala Pro Gly Lys Gly Leu Glu Trp Val
        35                  40                  45

Ser Gly Ile Trp Ser Ser Gly Phe Thr Gln Tyr Ala Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Arg Val Gly Ser Thr Gly Asn Phe Asp Tyr Trp Gly Gln
            100                 105                 110

Gly Thr Leu Val Thr Val Ser Ser
        115                 120

<210> SEQ ID NO 149
<211> LENGTH: 111
<212> TYPE: PRT
<213> ORGANISM: Homo sapiens

<400> SEQUENCE: 149

Asp Ile Gln Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
 50                  55                  60

Asp Arg Phe Ser Gly Ser Gly Ser Gly Thr Asp Phe Thr Leu Lys Ile
```

```
                65                  70                  75                  80
            Ser Arg Val Glu Ala Glu Asp Val Gly Val Tyr Tyr Cys Met Gln Ala
                            85                  90                  95

Leu Gln Thr Leu Thr Phe Gly Pro Gly Thr Lys Val Asp Ile Lys
                        100                 105                 110

<210> SEQ ID NO 150
<211> LENGTH: 124
<212> TYPE: PRT
<213> ORGANISM: Homo sapiens

<400> SEQUENCE: 150

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Tyr
            20                  25                  30

His Met Val Trp Val Arg Gln Ala Pro Gly Lys Gly Leu Glu Trp Val
        35                  40                  45

Ser Ser Ile Val Pro Ser Gly Gly Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Arg Asp Leu Gly Ser Tyr Ser Ser Gly Trp Gly Gly Trp Phe Asp
            100                 105                 110

Pro Trp Gly Gln Gly Thr Leu Val Thr Val Ser Ser
        115                 120

<210> SEQ ID NO 151
<211> LENGTH: 112
<212> TYPE: PRT
<213> ORGANISM: Homo sapiens

<400> SEQUENCE: 151

Asp Ile Gln Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 152
<211> LENGTH: 121
<212> TYPE: PRT
<213> ORGANISM: Homo sapiens

<400> SEQUENCE: 152

Glu Val Gln Leu Leu Glu Ser Gly Gly Gly Leu Val Gln Pro Gly Gly
 1               5                  10                  15
```

```
Ser Leu Arg Leu Ser Cys Ala Ala Ser Gly Phe Thr Phe Ser Pro Tyr
            20                  25                  30

Gly Met Ser Trp Val Arg Gln Ala Pro Gly Lys Gly Leu Glu Trp Val
        35                  40                  45

Ser Tyr Ile Tyr Ser Ser Gly Gly Lys Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Pro Gly Gly Asn Thr Tyr Tyr Phe Asp Tyr Trp Gly
            100                 105                 110

Gln Gly Thr Leu Val Thr Val Ser Ser
        115                 120

<210> SEQ ID NO 153
<211> LENGTH: 108
<212> TYPE: PRT
<213> ORGANISM: Homo sapiens

<400> SEQUENCE: 153

Asp Ile Gln Met Thr Gln Ser Pro Gly Thr Leu Ser Val Ser Pro Gly
1               5                   10                  15

Glu Arg Ala Thr Leu Ser Cys Arg Ala Ser Gln Ser Ile Gly Gly Asn
            20                  25                  30

Leu Ala Trp Tyr Gln Gln Lys Pro Gly Gln Ala Pro Arg Leu Leu Ile
        35                  40                  45

Tyr Tyr Ala Ser Thr Arg Ala Thr Gly Ile Pro Ala Arg Phe Ser Gly
    50                  55                  60

Ser Gly Ser Gly Thr Asp Phe Ala Leu Thr Ile Ser Arg Leu Glu Pro
65                  70                  75                  80

Glu Asp Ser Ala Val Tyr Phe Cys Gln His Arg Ser Asn Trp Pro Pro
                85                  90                  95

Leu Thr Phe Gly Gln Gly Thr Lys Val Glu Val Lys
            100                 105

<210> SEQ ID NO 154
<211> LENGTH: 120
<212> TYPE: PRT
<213> ORGANISM: Homo sapiens

<400> SEQUENCE: 154

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ala Met Gly Trp Val Arg Gln Ala Pro Gly Lys Gly Leu Glu Trp Val
        35                  40                  45

Ser Tyr Ile Ser Pro Ser Gly Gly Met Thr Trp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Arg Ile Phe Asp Tyr Ala Phe Asp Ile Trp Gly Gln
            100                 105                 110

Gly Thr Thr Val Thr Val Ser Ser
```

```
            115                 120

<210> SEQ ID NO 155
<211> LENGTH: 107
<212> TYPE: PRT
<213> ORGANISM: Homo sapiens

<400> SEQUENCE: 155

Asp Ile Gln Met Thr Gln Ser Pro Ala Thr Leu Ser Ala Ser Val Gly
1               5                   10                  15

Asp Arg Val Thr Ile Thr Cys Arg Thr Ser Gln Thr Ile Ser His Tyr
            20                  25                  30

Leu Asn Trp Tyr Gln Gln Lys Pro Gly Arg Ala Pro Lys Leu Leu Ile
        35                  40                  45

Tyr Ala Ile Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Lys Tyr Asn Ser Ala Pro Tyr
                85                  90                  95

Thr Phe Gly Gln Gly Thr Lys Leu Glu Ile Lys
            100                 105

<210> SEQ ID NO 156
<211> LENGTH: 125
<212> TYPE: PRT
<213> ORGANISM: Homo sapiens

<400> SEQUENCE: 156

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Ile Met His Trp Val Arg Gln Ala Pro Gly Lys Gly Leu Glu Trp Val
        35                  40                  45

Ser Gly Ile Ser Pro Ser Gly Gly Ile Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Leu Arg Gly Val Pro Ala Ala Arg Asp Tyr Tyr Tyr Tyr Met
            100                 105                 110

Asp Val Trp Gly Lys Gly Thr Thr Val Thr Val Ser Ser
        115                 120                 125

<210> SEQ ID NO 157
<211> LENGTH: 112
<212> TYPE: PRT
<213> ORGANISM: Homo sapiens

<400> SEQUENCE: 157

Asp Ile Gln Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Thr
            20                  25                  30

Asn Gly Tyr Asn Tyr Leu Asp Trp Tyr Leu Gln Lys Pro Gly Gln Ser
        35                  40                  45
```

Pro Gln Leu Leu Ile Tyr Leu Gly Ser Tyr Arg Ala Ser Gly Val Pro
         50                  55                  60

Asp Arg Phe Ser Gly Gly Ser Gly Thr Asp Phe Thr Leu Lys Ile
65                  70                  75                  80

Ser Arg Val Glu Ala Asp Asp Val Gly Val Tyr Tyr Cys Met Gln Gly
                85                  90                  95

Leu Gln Thr Pro Ile Thr Phe Gly Pro Gly Thr Arg Leu Gly Ile Lys
                100                 105                 110

<210> SEQ ID NO 158
<211> LENGTH: 112
<212> TYPE: PRT
<213> ORGANISM: Homo sapiens

<400> SEQUENCE: 158

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
                20                  25                  30

Ser Met Val Trp Val Arg Gln Ala Pro Gly Lys Gly Leu Glu Trp Val
            35                  40                  45

Ser Tyr Ile Gly Ser Ser Gly Gly Lys Thr Met Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Ala Pro Ser Gly Trp Tyr Tyr Asp Tyr Trp Gly Gln Gly
                100                 105                 110

<210> SEQ ID NO 159
<211> LENGTH: 115
<212> TYPE: PRT
<213> ORGANISM: Homo sapiens

<400> SEQUENCE: 159

Thr Leu Val Thr Val Ser Ser Asp Ile Gln Met Thr Gln Ser Pro Gly
1               5                   10                  15

Thr Leu Ser Leu Ser Pro Gly Glu Arg Ala Thr Leu Ser Cys Arg Ala
                20                  25                  30

Ser Gln Thr Val Ser Ser Ala Tyr Leu Ala Trp Tyr Gln Gln Arg Pro
            35                  40                  45

Gly Gln Ala Pro Arg Leu Leu Ile Tyr Gly Ala Ser Ser Arg Ala Thr
    50                  55                  60

Gly Val Pro Asp Arg Phe Ser Gly Ser Gly Ser Gly Thr Asp Phe Thr
65                  70                  75                  80

Leu Thr Ile Asn Arg Leu Glu Pro Glu Asp Phe Ala Val Tyr Tyr Cys
                85                  90                  95

Gln Gln Phe Gly Val Ser Ser Trp Thr Phe Gly Gln Gly Thr Lys Val
                100                 105                 110

Glu Ile Lys
        115

<210> SEQ ID NO 160
<211> LENGTH: 118
<212> TYPE: PRT
<213> ORGANISM: Homo sapiens

<400> SEQUENCE: 160

```
Glu Val Gln Leu Leu Glu Ser Gly Gly Gly Leu Val Gln Pro Gly Gly
  1               5                  10                 15

Ser Leu Arg Leu Ser Cys Ala Ala Ser Gly Phe Thr Phe Ser Ile Tyr
             20                  25                  30

Asn Met Tyr Trp Val Arg Gln Ala Pro Gly Lys Gly Leu Glu Trp Val
         35                  40                  45

Ser Gly Ile Arg Pro Ser Gly Gly Pro Thr Thr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ala Lys Trp Gly Trp Tyr Phe Asp Leu Trp Gly Arg Gly Thr
            100                 105                 110

Leu Val Thr Val Ser Ser
            115

<210> SEQ ID NO 161
<211> LENGTH: 107
<212> TYPE: PRT
<213> ORGANISM: Homo sapiens

<400> SEQUENCE: 161

Asp Ile Gln Met Thr Gln Ser Pro Ser Ser Leu Ser Ala Ser Val Gly
  1               5                  10                 15

Asp Arg Val Thr Ile Thr Cys Arg Ala Ser Gln Ser Ile Gly Thr Tyr
             20                  25                  30

Leu Asn Trp Tyr Gln Gln Lys Pro Gly Thr Pro Pro Lys Leu Leu Met
         35                  40                  45

Tyr Ala Ala Ser Arg Leu Gln Pro Gly Val Pro Ser Arg Phe Ser Gly
     50                  55                  60

Ser Gly Ser Leu Thr Glu Phe Thr Leu Thr Ile Ser Asn Leu Gln Pro
 65                  70                  75                  80

Glu Asp Phe Ala Ser Tyr Tyr Cys Gln Gln Ser Tyr Ile Ala Pro Pro
                 85                  90                  95

Thr Phe Gly Gly Gly Thr Lys Val Glu Ile Lys
            100                 105

<210> SEQ ID NO 162
<211> LENGTH: 128
<212> TYPE: PRT
<213> ORGANISM: Homo sapiens

<400> SEQUENCE: 162

Glu Val Gln Leu Leu Glu Ser Gly Gly Gly Leu Val Gln Pro Gly Gly
  1               5                  10                 15

Ser Leu Arg Leu Ser Cys Ala Ala Ser Gly Phe Thr Phe Ser Arg Tyr
             20                  25                  30

Val Met Gly Trp Val Arg Gln Ala Pro Gly Lys Gly Leu Glu Trp Val
         35                  40                  45

Ser Tyr Ile Gly Pro Ser Gly Gly Tyr Thr Leu Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95
```

Ala Arg Asp Lys Tyr Tyr Gly Ser Gly Ser Tyr Pro Arg Tyr Tyr Tyr
            100                 105                 110

Tyr Tyr Met Asp Val Trp Gly Lys Gly Thr Thr Val Thr Val Ser Ser
            115                 120                 125

<210> SEQ ID NO 163
<211> LENGTH: 111
<212> TYPE: PRT
<213> ORGANISM: Homo sapiens

<400> SEQUENCE: 163

Asp Ile Gln Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Gly
            20                  25                  30

Asn Gly Tyr Asn Tyr Leu Asp Trp Tyr Leu Gln Lys Pro Gly Gln Ser
        35                  40                  45

Pro Gln Leu Leu Val Tyr Leu Gly Ser Asn Arg Ala Ser Gly Val Pro
    50                  55                  60

Asp Arg Phe Ser Gly Ser Gly Ser Gly Thr Asp Phe Thr Leu Gln Ile
65                  70                  75                  80

Ser Arg Val Glu Ala Glu Asp Val Gly Val Tyr Tyr Cys Met Gln Ala
                85                  90                  95

Leu Gln Thr Pro Thr Phe Gly Gly Gly Thr Lys Val Glu Ile Lys
            100                 105                 110

<210> SEQ ID NO 164
<211> LENGTH: 121
<212> TYPE: PRT
<213> ORGANISM: Homo sapiens

<400> SEQUENCE: 164

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Gly Met Met Trp Val Arg Gln Ala Pro Gly Lys Gly Leu Glu Trp Val
        35                  40                  45

Ser Ser Ile Trp Pro Ser Gly Lys Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Thr Thr Val Trp Trp Asn Tyr Tyr Met Asp Val Trp Gly
            100                 105                 110

Lys Gly Thr Thr Val Thr Val Ser Ser
        115                 120

<210> SEQ ID NO 165
<211> LENGTH: 109
<212> TYPE: PRT
<213> ORGANISM: Homo sapiens

<400> SEQUENCE: 165

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ile Ser Pro
                85                  90                  95

Pro Tyr Ser Phe Gly Gln Gly Thr Lys Leu Glu Ile Lys
                100                 105

<210> SEQ ID NO 166
<211> LENGTH: 118
<212> TYPE: PRT
<213> ORGANISM: Homo sapiens

<400> SEQUENCE: 166

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ile Tyr
            20                  25                  30

Ala Met Gly Trp Val Arg Gln Ala Pro Gly Lys Gly Leu Glu Trp Val
            35                  40                  45

Ser Gly Ile Val Pro Ser Gly Gly Pro Thr Asn Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Ile Met Trp Tyr Gly Gln Phe Asp Tyr Trp Gly Gln Gly Thr
                100                 105                 110

Leu Val Thr Val Ser Ser
            115

<210> SEQ ID NO 167
<211> LENGTH: 107
<212> TYPE: PRT
<213> ORGANISM: Homo sapiens

<400> SEQUENCE: 167

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
            20                  25                  30

Leu Asn Trp Tyr Gln Lys Arg Pro Gly Lys Ala Pro Asn Leu Leu Ile
            35                  40                  45

Tyr Gly Ala Asp Thr Leu Gln Thr Gly Val Pro Ser Arg Phe Ser Gly
 50                  55                  60

Asp Gly Ser Gly Thr Asp Phe Thr Leu Thr Ile Asn Ser Leu Gln Pro
 65                  70                  75                  80

Glu Asp Phe Ala Thr Tyr Tyr Cys Gln Gln Ser Tyr Ser Thr Ser Trp
                85                  90                  95

Thr Phe Gly Gln Gly Thr Lys Val Glu Val Arg
                100                 105

<210> SEQ ID NO 168
<211> LENGTH: 118

```
<212> TYPE: PRT
<213> ORGANISM: Homo sapiens

<400> SEQUENCE: 168

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Gly Tyr
            20                  25                  30

Val Met Ser Trp Val Arg Gln Ala Pro Gly Lys Gly Leu Glu Trp Val
        35                  40                  45

Ser Ser Ile Gly Pro Ser Gly Gly Thr Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Lys Asp Arg Gly Leu Tyr Tyr Phe Asp Tyr Trp Gly Gln Gly Thr
            100                 105                 110

Leu Val Thr Val Ser Ser
        115

<210> SEQ ID NO 169
<211> LENGTH: 113
<212> TYPE: PRT
<213> ORGANISM: Homo sapiens

<400> SEQUENCE: 169

Asp Ile Gln Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Pro Trp Thr Phe Gly Gln Gly Thr Lys Val Glu Ile
            100                 105                 110

Lys

<210> SEQ ID NO 170
<211> LENGTH: 122
<212> TYPE: PRT
<213> ORGANISM: Homo sapiens

<400> SEQUENCE: 170

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Thr Met Ile Trp Val Arg Gln Ala Pro Gly Lys Gly Leu Glu Trp Val
        35                  40                  45

Ser Arg Ile Ser Pro Ser Gly Gly His Thr Glu Tyr Ala Asp Ser Val
    50                  55                  60
```

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly His Tyr Gly Ser Gly Tyr Tyr Ala Ser Leu Asp Tyr Trp
            100                 105                 110

Gly Gln Gly Thr Leu Val Thr Val Ser Ser
            115                 120

<210> SEQ ID NO 171
<211> LENGTH: 112
<212> TYPE: PRT
<213> ORGANISM: Homo sapiens

<400> SEQUENCE: 171

Asp Ile Gln Met Thr Gln Ser Pro Leu Ser Leu Pro Val Thr Pro Gly
1               5                   10                  15

Glu Pro Ala Ser Ile Ser Cys Lys Ser Ser Gln Ser Leu Leu His Phe
            20                  25                  30

Asn Gly Tyr Ser Tyr Leu Asp Trp Tyr Leu Gln Lys Pro Gly Gln Ser
        35                  40                  45

Pro Gln Leu Leu Ile Tyr Leu Ala Ser Asn Arg Ala Ser Gly Val Pro
50                  55                  60

Asp Arg Phe Ser Gly Ser Gly Ser Gly Thr Asp Phe Thr Leu Asn Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Gln Met Lys
            100                 105                 110

<210> SEQ ID NO 172
<211> LENGTH: 120
<212> TYPE: PRT
<213> ORGANISM: Homo sapiens

<400> SEQUENCE: 172

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Ala Met Gln Trp Val Arg Gln Ala Pro Gly Lys Gly Leu Glu Trp Val
        35                  40                  45

Ser Ser Ile Ser Pro Ser Gly Gly Asp Thr Ser Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Ser Gly Thr Gly Tyr Tyr Tyr Met Asp Val Trp Gly Lys
            100                 105                 110

Gly Thr Thr Val Thr Val Ser Ser
            115                 120

<210> SEQ ID NO 173
<211> LENGTH: 112
<212> TYPE: PRT
<213> ORGANISM: Homo sapiens

<400> SEQUENCE: 173

Asn Ile Gln Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Ile Thr Phe Gly Gln Gly Thr Arg Leu Glu Ile Lys
                100                 105                 110

<210> SEQ ID NO 174
<211> LENGTH: 116
<212> TYPE: PRT
<213> ORGANISM: Homo sapiens

<400> SEQUENCE: 174

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ala Met Trp Trp Val Arg Gln Ala Pro Gly Lys Gly Leu Glu Trp Val
        35                  40                  45

Ser Gly Ile Val Pro Ser Gly Gly Leu Thr Thr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val His Asp Ala Phe Asp Ile Trp Gly Gln Gly Thr Met Val
                100                 105                 110

Thr Val Ser Ser
            115

<210> SEQ ID NO 175
<211> LENGTH: 112
<212> TYPE: PRT
<213> ORGANISM: Homo sapiens

<400> SEQUENCE: 175

Asn Ile Gln Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

```
Leu Gln Asn Ser Ile Thr Phe Gly Gln Gly Thr Arg Leu Glu Ile Lys
            100                 105                 110
```

<210> SEQ ID NO 176
<211> LENGTH: 124
<212> TYPE: PRT
<213> ORGANISM: Homo sapiens

<400> SEQUENCE: 176

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Arg Tyr
             20                  25                  30

Ala Met Trp Trp Val Arg Gln Ala Pro Gly Lys Gly Leu Glu Trp Val
         35                  40                  45

Ser Gly Ile Val Pro Ser Gly Leu Thr Thr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg His Glu Val Ser Glu Gln Trp Leu Phe Pro Gly Asn Phe Asp
            100                 105                 110

Tyr Trp Gly Gln Gly Thr Leu Val Thr Val Ser Ser
            115                 120
```

<210> SEQ ID NO 177
<211> LENGTH: 112
<212> TYPE: PRT
<213> ORGANISM: Homo sapiens

<400> SEQUENCE: 177

```
Asn Ile Gln Met Thr Gln Ser Pro Leu Ser Leu Pro Val Thr Leu Gly
  1               5                  10                  15

Gln Pro Ala Ser Ile Ser Cys Arg Ser Ser Gln Ser Leu Val Tyr Ser
             20                  25                  30

Asp Gly Asn Thr Tyr Leu Asn Trp Phe Gln Gln Arg Pro Gly Gln Ser
         35                  40                  45

Pro Arg Arg Leu Ile Tyr Lys Val Ser Asn Arg Asp Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                 85                  90                  95

Thr His Trp Pro Ile Thr Phe Gly Gln Gly Thr Arg Leu Glu Ile Lys
            100                 105                 110
```

<210> SEQ ID NO 178
<211> LENGTH: 124
<212> TYPE: PRT
<213> ORGANISM: Homo sapiens

<400> SEQUENCE: 178

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Arg Tyr
             20                  25                  30

Ala Met Trp Trp Val Arg Gln Ala Pro Gly Lys Gly Leu Glu Trp Val
         35                  40                  45
```

```
Ser Gly Ile Val Pro Ser Gly Gly Leu Thr Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Glu Val Ser Glu Gln Trp Leu Phe Pro Gly Asn Phe Asp
                100                 105                 110

Tyr Trp Gly Gln Gly Thr Leu Val Thr Val Ser Ser
            115                 120

<210> SEQ ID NO 179
<211> LENGTH: 112
<212> TYPE: PRT
<213> ORGANISM: Homo sapiens

<400> SEQUENCE: 179

Asn Ile Gln Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Ile Thr Phe Gly Gln Gly Thr Arg Leu Glu Ile Lys
            100                 105                 110

<210> SEQ ID NO 180
<211> LENGTH: 117
<212> TYPE: PRT
<213> ORGANISM: Homo sapiens

<400> SEQUENCE: 180

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
                20                  25                  30

Gly Met Asp Trp Val Arg Gln Ala Pro Gly Lys Gly Leu Glu Trp Val
            35                  40                  45

Ser Ser Ile Pro Pro Ser Gly Gly Gln Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Gly Leu Trp Ala Phe Asp Ile Trp Gly Gln Gly Thr Met
                100                 105                 110

Val Thr Val Ser Ser
            115

<210> SEQ ID NO 181
<211> LENGTH: 112
```

```
<212> TYPE: PRT
<213> ORGANISM: Homo sapiens

<400> SEQUENCE: 181

Asn Ile Gln Met Thr Gln Ser Pro Leu Ser Leu Pro Val Thr Leu Gly
 1               5                  10                  15

Gln Pro Ala Ser Ile Ser Cys Arg Ser Ser Gln Ser Leu Leu His Ser
             20                  25                  30

Asn Gly Tyr Asn Tyr Leu Asp Trp Tyr Leu Gln Lys Pro Gly Gln Ser
         35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Asn Ser Ile Thr Phe Gly Gln Gly Thr Arg Leu Glu Ile Lys
            100                 105                 110

<210> SEQ ID NO 182
<211> LENGTH: 121
<212> TYPE: PRT
<213> ORGANISM: Homo sapiens

<400> SEQUENCE: 182

Glu Val Gln Leu Leu Glu Phe Gly Gly Gly Leu Val Gln Pro Gly Gly
 1               5                  10                  15

Ser Leu Arg Leu Ser Cys Ala Ala Ser Gly Phe Thr Phe Ser Val Tyr
             20                  25                  30

Ala Met His Trp Val Arg Gln Ala Pro Gly Lys Gly Leu Glu Trp Val
         35                  40                  45

Ser Val Ile Ser Pro Ser Gly Gly Phe Thr Phe Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Val Val Arg Gly Tyr Tyr Tyr Tyr Gly Met Asp Val Trp Gly
            100                 105                 110

Gln Gly Thr Thr Val Thr Val Ser Ser
        115                 120

<210> SEQ ID NO 183
<211> LENGTH: 112
<212> TYPE: PRT
<213> ORGANISM: Homo sapiens

<400> SEQUENCE: 183

Asn Ile Gln Met Thr Gln Ser Pro Leu Ser Leu Pro Val Thr Leu Gly
 1               5                  10                  15

Gln Pro Ala Ser Ile Ser Cys Arg Ser Ser Gln Ser Leu Leu His Ser
             20                  25                  30

Asn Gly Tyr Asn Tyr Leu Asp Trp Tyr Leu Gln Lys Pro Gly Gln Ser
         35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80
```

Ser Arg Val Glu Ala Glu Asp Val Gly Val Tyr Tyr Cys Met Gln Ala
            85                  90                  95

Leu Gln Asn Ser Ile Thr Phe Gly Gln Gly Thr Arg Leu Glu Ile Lys
            100                 105                 110

<210> SEQ ID NO 184
<211> LENGTH: 124
<212> TYPE: PRT
<213> ORGANISM: Homo sapiens

<400> SEQUENCE: 184

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ala Met Trp Trp Val Arg Gln Ala Pro Gly Lys Gly Leu Glu Trp Val
            35                  40                  45

Ser Gly Ile Val Pro Ser Gly Gly Leu Thr Thr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg His Glu Val Ser Glu Gln Trp Leu Phe Pro Gly Asn Phe Asp
            100                 105                 110

Tyr Trp Gly Gln Gly Thr Leu Val Thr Val Ser Ser
            115                 120

<210> SEQ ID NO 185
<211> LENGTH: 112
<212> TYPE: PRT
<213> ORGANISM: Homo sapiens

<400> SEQUENCE: 185

Asn Ile Gln Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
            35                  40                  45

Pro Arg Arg Leu Ile Tyr Lys Val Ser Asn Arg Asp Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
            85                  90                  95

Thr His Trp Pro Ile Thr Phe Gly Gln Gly Thr Arg Leu Glu Ile Lys
            100                 105                 110

<210> SEQ ID NO 186
<211> LENGTH: 123
<212> TYPE: PRT
<213> ORGANISM: Homo sapiens

<400> SEQUENCE: 186

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr

-continued

```
            20                  25                  30
Gly Met Asp Trp Val Arg Gln Ala Pro Gly Lys Gly Leu Glu Trp Val
        35                  40                  45
Ser Ser Ile Ser Pro Ser Gly Gly Gln Thr Lys Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                85                  90                  95
Ala Lys Asp Leu Gly Gly Gly Tyr Tyr Tyr Tyr Gly Met Asp Val
                100                 105                 110
Trp Gly Gln Gly Thr Leu Val Thr Val Ser Ser
            115                 120
```

<210> SEQ ID NO 187
<211> LENGTH: 123
<212> TYPE: PRT
<213> ORGANISM: Homo sapiens

<400> SEQUENCE: 187

```
Glu Val Gln Leu Leu Glu Ser Gly Gly Gly Leu Val Gln Pro Gly Gly
 1               5                  10                  15
Ser Leu Arg Leu Ser Cys Ala Ala Ser Gly Phe Thr Phe Ser Ala Tyr
            20                  25                  30
Gly Met Asp Trp Val Arg Gln Ala Pro Gly Lys Gly Leu Glu Trp Val
        35                  40                  45
Ser Ser Ile Ser Pro Ser Gly Gly Gln Thr Lys Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                85                  90                  95
Ala Lys Asp Leu Gly Gly Gly Tyr Tyr Tyr Tyr Gly Met Asp Val
                100                 105                 110
Trp Gly Gln Gly Thr Leu Val Thr Val Ser Ser
            115                 120
```

<210> SEQ ID NO 188
<211> LENGTH: 112
<212> TYPE: PRT
<213> ORGANISM: Homo sapiens

<400> SEQUENCE: 188

```
Asp Ile Gln Met Thr Gln Ser Pro Leu Ser Leu Pro Val Thr Pro Gly
 1               5                  10                  15
Glu Pro Ala Ser Ile Ser Cys Arg Ser Ser Gln Ser Leu Leu His Ser
            20                  25                  30
Asn Gly Tyr Asn Tyr Leu Asp Trp Tyr Leu Gln Lys Pro Gly Gln Ser
        35                  40                  45
Pro Gln Leu Leu Ile Tyr Leu Gly Ser Asn Arg Ala Ser Gly Val Pro
 50                  55                  60
Asp Arg Phe Ser Gly Ser Gly Ser Gly Thr Asp Phe Thr Leu Lys Ile
 65                  70                  75                  80
Ser Arg Val Glu Ala Glu Asp Val Arg Val Tyr Tyr Cys Met Gln Ala
                85                  90                  95
Leu Gln Asn Ser Ile Thr Phe Gly Gln Gly Thr Arg Leu Glu Ile Lys
                100                 105                 110
```

<210> SEQ ID NO 189
<211> LENGTH: 121
<212> TYPE: PRT
<213> ORGANISM: Homo sapiens

<400> SEQUENCE: 189

Glu Val His Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Val Tyr
            20                  25                  30

Phe Met Ser Trp Val Arg Gln Ala Pro Gly Lys Gly Leu Glu Trp Val
        35                  40                  45

Ser Tyr Ile Gly Pro Ser Gly Gly Phe Thr Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Val Arg Gly Tyr Tyr Tyr Tyr Gly Met Asp Val Trp Gly
            100                 105                 110

Gln Gly Thr Thr Val Thr Val Ser Ser
        115                 120

<210> SEQ ID NO 190
<211> LENGTH: 107
<212> TYPE: PRT
<213> ORGANISM: Homo sapiens

<400> SEQUENCE: 190

Gln Ser Ala Leu Thr Gln Pro Pro Ser Leu Ser Val Ser Pro Gly Gln
 1               5                  10                  15

Thr Ala Thr Ile Thr Cys Ser Gly Asp Lys Leu Gly Asp Lys Tyr Thr
            20                  25                  30

Ser Trp Tyr Gln Gln Arg Pro Gly Gln Ser Pro Val Leu Val Leu Tyr
        35                  40                  45

Lys Asp Asn Lys Arg Pro Ser Gly Ile Pro Gln Arg Phe Ser Gly Ser
    50                  55                  60

Asn Ser Gly Asn Thr Ala Thr Leu Thr Ile Ser Gly Thr Gln Ala Val
65                  70                  75                  80

Asp Glu Ala Asp Tyr Tyr Cys Gln Ala Trp Asp Ser Lys Glu Phe Tyr
                85                  90                  95

Val Phe Gly Thr Gly Thr Lys Val Thr Val Leu
            100                 105

<210> SEQ ID NO 191
<211> LENGTH: 126
<212> TYPE: PRT
<213> ORGANISM: Homo sapiens

<400> SEQUENCE: 191

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ile Tyr
            20                  25                  30

Lys Met His Trp Val Arg Gln Ala Pro Gly Lys Gly Leu Glu Trp Val
        35                  40                  45

Ser Ser Ile Val Ser Ser Gly Gly Ala Thr Gln Tyr Ala Asp Ser Val

```
                50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                     85                  90                  95

Ala Arg Val Gly Trp Val Leu Arg Phe Leu Glu Trp Leu Pro Asp Ser
                100                 105                 110

Phe Asp Tyr Trp Gly Gln Gly Thr Leu Val Thr Val Ser Ser
                115                 120                 125

<210> SEQ ID NO 192
<211> LENGTH: 106
<212> TYPE: PRT
<213> ORGANISM: Homo sapiens

<400> SEQUENCE: 192

Gln Tyr Glu Leu Thr Gln Pro Pro Ser Val Ser Val Ser Pro Gly Gln
  1               5                  10                  15

Thr Ala Ile Ile Thr Cys Ser Gly Asp Arg Leu Gly Asp Lys Tyr Ala
                 20                  25                  30

Ser Trp Tyr Gln Gln Lys Pro Gly Gln Ser Pro Val Leu Val Ile Tyr
             35                  40                  45

Gln Asp Thr Lys Arg Pro Ser Gly Ile Pro Glu Arg Phe Ser Gly Ser
 50                  55                  60

Asn Ser Gly Asp Thr Ala Thr Leu Thr Ile Ser Gly Thr Gln Ala Met
 65                  70                  75                  80

Asp Asp Ala Asp Tyr Tyr Cys His Ser Trp Asp Ser Arg Thr Gly Ile
                 85                  90                  95

Phe Gly Gly Gly Thr Lys Leu Thr Val Leu
                100                 105

<210> SEQ ID NO 193
<211> LENGTH: 131
<212> TYPE: PRT
<213> ORGANISM: Homo sapiens

<400> SEQUENCE: 193

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Lys Tyr
                 20                  25                  30

Asn Met His Trp Val Arg Gln Ala Pro Gly Lys Gly Leu Glu Trp Val
             35                  40                  45

Ser Ser Ile Ser Ser Ser Gly Gly Asn Thr Asp Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                 85                  90                  95

Ala Arg Val Phe Pro Phe Arg Asp Gly Tyr Asn Tyr Trp Phe Gly Gly
                100                 105                 110

Asp Ser Arg Asp Ala Phe Asp Ile Trp Gly Gln Gly Thr Met Val Thr
                115                 120                 125

Val Ser Ser
        130

<210> SEQ ID NO 194
```

```
<211> LENGTH: 106
<212> TYPE: PRT
<213> ORGANISM: Homo sapiens

<400> SEQUENCE: 194

Gln Ser Ala Leu Thr Gln Pro Pro Ser Val Ser Val Ser Pro Gly Gln
 1               5                  10                  15

Thr Ala Ser Ile Thr Cys Ser Ala Asp Lys Leu Gly Asp Arg Tyr Ala
            20                  25                  30

Ser Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Ala Val
                85                  90                  95

Phe Gly Gly Gly Thr Lys Leu Thr Val Leu
            100                 105

<210> SEQ ID NO 195
<211> LENGTH: 126
<212> TYPE: PRT
<213> ORGANISM: Homo sapiens

<400> SEQUENCE: 195

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Tyr
            20                  25                  30

Pro Met Ile Trp Val Arg Gln Ala Pro Gly Lys Gly Leu Glu Trp Val
        35                  40                  45

Ser Gly Ile Ser Pro Ser Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Arg Gly Lys Val Val Pro Ala Ala Met Pro Tyr Tyr Tyr Tyr Gly
            100                 105                 110

Met Asp Val Trp Gly Gln Gly Thr Thr Val Thr Val Ser Ser
        115                 120                 125

<210> SEQ ID NO 196
<211> LENGTH: 106
<212> TYPE: PRT
<213> ORGANISM: Homo sapiens

<400> SEQUENCE: 196

Gln Ser Ala Leu Thr Gln Pro Pro Ser Val Ser Val Ser Pro Gly Gln
 1               5                  10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
```

-continued

```
                65                  70                  75                  80
Asp Glu Ala Asp Tyr Tyr Cys Gln Ala Trp Asp Ser Ser Thr Ala Val
                    85                  90                  95

Phe Gly Gly Gly Thr Lys Leu Thr Val Leu
                100                 105

<210> SEQ ID NO 197
<211> LENGTH: 126
<212> TYPE: PRT
<213> ORGANISM: Homo sapiens

<400> SEQUENCE: 197

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

His Met Gly Trp Val Arg Gln Ala Pro Gly Lys Gly Leu Glu Trp Val
            35                  40                  45

Ser Arg Ile Gly Pro Ser Gly Gly Trp Thr Thr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Tyr Asp Phe Trp Ser Gly Tyr Pro Leu Gly Tyr Gly
                100                 105                 110

Met Asp Val Trp Gly Gln Gly Thr Thr Val Thr Val Ser Ser
            115                 120                 125

<210> SEQ ID NO 198
<211> LENGTH: 108
<212> TYPE: PRT
<213> ORGANISM: Homo sapiens

<400> SEQUENCE: 198

Asp Ile Gln Met Thr Gln Ser Pro Gly Thr Leu Ser Val Ser Leu Gly
1               5                   10                  15

Glu Arg Ala Thr Leu Ser Cys Arg Ala Ser Gln Ser Val Ser Ser Arg
                20                  25                  30

Phe Leu Ala Trp Tyr Gln Gln Lys Pro Gly Gln Ala Pro Arg Leu Leu
            35                  40                  45

Met Tyr Gly Ala Ser Ser Arg Ala Thr Gly Ile Pro Asp Arg Ile Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Thr
                85                  90                  95

Ile Thr Phe Gly Gln Gly Thr Arg Leu Glu Ile Lys
                100                 105

<210> SEQ ID NO 199
<211> LENGTH: 125
<212> TYPE: PRT
<213> ORGANISM: Homo sapiens

<400> SEQUENCE: 199

Glu Val Gln Leu Leu Glu Ser Gly Gly Gly Leu Val Gln Pro Gly Gly
1               5                   10                  15
```

Ser Leu Arg Leu Ser Cys Ala Ala Ser Gly Phe Thr Phe Ser Met Tyr
            20                  25                  30

Arg Met Met Trp Val Arg Gln Ala Pro Gly Lys Gly Leu Glu Trp Val
                35                  40                  45

Ser Tyr Ile Arg Pro Ser Gly Gly Asn Thr Gly Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Gly Gly Ile Thr Ile Phe Gly Val Val Ile Pro Ala Phe
            100                 105                 110

Asp Ile Trp Gly Gln Gly Thr Thr Val Thr Val Ser Ser
            115                 120                 125

<210> SEQ ID NO 200
<211> LENGTH: 106
<212> TYPE: PRT
<213> ORGANISM: Homo sapiens

<400> SEQUENCE: 200

Gln Ser Glu Leu Thr Gln Pro Pro Ser Val Ser Val Ser Pro Gly Gln
 1               5                  10                  15

Thr Ala Ser Ile Thr Cys Ser Gly Asp Lys Leu Gly Asn Lys Tyr Ile
            20                  25                  30

Ser Trp Tyr Gln Gln Lys Ala Gly Gln Ser Pro Met Val Val Met Tyr
                35                  40                  45

Gln Asp Asp Lys Arg Pro Ser Gly Ile Pro Glu Arg Phe Ser Gly Ser
 50                  55                  60

Asn Ser Gly Asn Thr Ala Thr Leu Thr Ile Thr Gly Thr Gln Thr Val
 65                  70                  75                  80

Asp Glu Ala Asp Tyr Phe Cys Gln Thr Arg Asp Phe Ser Ser Val Ile
                85                  90                  95

Phe Gly Gly Gly Thr Lys Leu Thr Val Leu
            100                 105

<210> SEQ ID NO 201
<211> LENGTH: 116
<212> TYPE: PRT
<213> ORGANISM: Homo sapiens

<400> SEQUENCE: 201

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Trp Tyr
            20                  25                  30

Met Met Trp Trp Val Arg Gln Ala Pro Gly Lys Gly Leu Glu Trp Val
                35                  40                  45

Ser Ser Ile Arg Ser Ser Gly Gly Lys Thr Pro Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Asp Pro Tyr Gly Met Asp Val Trp Gly Gln Gly Thr Thr Val
            100                 105                 110

Thr Val Ser Ser

<210> SEQ ID NO 202
<211> LENGTH: 106
<212> TYPE: PRT
<213> ORGANISM: Homo sapiens

<400> SEQUENCE: 202

Gln Tyr Glu Leu Thr Gln Pro Pro Ser Val Ser Val Ser Pro Gly Gln
1               5                   10                  15

Thr Ala Ser Ile Thr Cys Ser Gly Asp Arg Leu Gly Asp Lys Tyr Ala
            20                  25                  30

Ser Trp Tyr Gln Gln Lys Pro Gly Gln Ser Pro Val Leu Val Ile Tyr
        35                  40                  45

Gln Asp Thr Lys Arg Pro Ser Gly Ile Pro Glu Arg Phe Ser Gly Ser
    50                  55                  60

Asn Ser Gly Ser Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Val Val
                85                  90                  95

Phe Gly Gly Gly Thr Lys Leu Thr Val Leu
            100                 105

<210> SEQ ID NO 203
<211> LENGTH: 129
<212> TYPE: PRT
<213> ORGANISM: Homo sapiens

<400> SEQUENCE: 203

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asn Met Leu Trp Val Arg Gln Ala Pro Gly Lys Gly Leu Glu Trp Val
        35                  40                  45

Ser Ser Ile Ser Pro Ser Gly Glu Thr Met Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Pro Thr Tyr Tyr Gly Asp Phe Leu Asn Gly Glu Tyr Tyr
            100                 105                 110

Tyr Tyr Gly Met Asp Val Trp Gly Gln Gly Thr Thr Val Thr Val Ser
        115                 120                 125

Ser

<210> SEQ ID NO 204
<211> LENGTH: 106
<212> TYPE: PRT
<213> ORGANISM: Homo sapiens

<400> SEQUENCE: 204

Gln Ser Ala Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Phe Trp Tyr Gln Gln Lys Pro Gly Gln Ser Pro Val Leu Val Ile Tyr

```
                35                  40                  45
Gln Asp Ser Lys Arg Pro Ser Gly Ile Pro Glu Arg Phe Ser Gly Ser
 50                  55                  60

Asn Ser Gly Asn Thr Ala Thr Leu Thr Ile Ser Gly Ala Gln Ala Met
 65                  70                  75                  80

Asp Glu Ala Asp Tyr Tyr Cys Gln Thr Trp Asp Ser Gly Thr Met Val
                 85                  90                  95

Phe Gly Gly Gly Thr Lys Leu Thr Val Leu
            100                 105
```

<210> SEQ ID NO 205
<211> LENGTH: 125
<212> TYPE: PRT
<213> ORGANISM: Homo sapiens

<400> SEQUENCE: 205

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Pro Tyr
                 20                  25                  30

Gln Met Tyr Trp Val Arg Gln Ala Pro Gly Lys Gly Leu Glu Trp Val
             35                  40                  45

Ser Ser Ile Tyr Ser Ser Gly Lys Thr Ala Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Met Tyr Tyr Cys
                 85                  90                  95

Ala Arg Ala Pro Arg Gly Trp Glu Ser Tyr Tyr Tyr Tyr Gly Met
            100                 105                 110

Asp Val Trp Gly Gln Gly Thr Thr Val Thr Val Ser Ser
            115                 120                 125
```

<210> SEQ ID NO 206
<211> LENGTH: 108
<212> TYPE: PRT
<213> ORGANISM: Homo sapiens

<400> SEQUENCE: 206

```
Asp Ile Gln Met Thr Gln Ser Pro Ala Thr Leu Ser Leu Ser Pro Gly
  1               5                  10                  15

Glu Arg Ala Thr Leu Ser Cys Arg Ala Ser Gln Ser Val Gly Ser Tyr
                 20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Met
                 85                  90                  95

Leu Thr Phe Gly Gly Gly Thr Lys Val Glu Ile Lys
            100                 105
```

<210> SEQ ID NO 207
<211> LENGTH: 125
<212> TYPE: PRT
<213> ORGANISM: Homo sapiens

<400> SEQUENCE: 207

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Glu Met Ile Trp Val Arg Gln Ala Pro Gly Lys Gly Leu Glu Trp Val
        35                  40                  45

Ser Arg Ile Ser Pro Ser Gly Gly Asn Thr Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Arg Asp Lys Gly Ser Gly Trp Arg Arg Tyr Tyr Tyr Gly Met
            100                 105                 110

Asp Val Trp Gly Gln Gly Thr Thr Val Thr Val Ser Ser
            115                 120                 125

<210> SEQ ID NO 208
<211> LENGTH: 108
<212> TYPE: PRT
<213> ORGANISM: Homo sapiens

<400> SEQUENCE: 208

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Asn Asn
            20                  25                  30

Asp Leu Ala Trp Tyr Gln Arg Pro Gly Gln Ala Pro Arg Phe Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Pro Thr Phe Gly Gly Gly Thr Lys Val Glu Ile Lys
            100                 105

<210> SEQ ID NO 209
<211> LENGTH: 124
<212> TYPE: PRT
<213> ORGANISM: Homo sapiens

<400> SEQUENCE: 209

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Arg Met Val Trp Val Arg Gln Ala Pro Gly Lys Gly Leu Glu Trp Val
        35                  40                  45

Ser Ser Ile Ser Pro Ser Gly Trp Thr Ile Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys

```
                85                  90                  95
Ala Arg Thr Leu Phe Tyr Tyr Asp Asp Ser His Asp Lys Tyr Phe Asp
            100                 105                 110

Arg Trp Gly Gln Gly Thr Leu Val Thr Val Ser Ser
        115                 120

<210> SEQ ID NO 210
<211> LENGTH: 108
<212> TYPE: PRT
<213> ORGANISM: Homo sapiens

<400> SEQUENCE: 210

Asp Ile Gln Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Asn Tyr
            20                  25                  30

Leu Ala Trp Tyr Gln Gln Lys Pro Gly Gln Ala Pro Arg Leu Leu Ile
        35                  40                  45

Tyr Ser Thr Ser Tyr Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Trp Thr Phe Gly Gln Gly Thr Lys Val Glu Ile Lys
            100                 105

<210> SEQ ID NO 211
<211> LENGTH: 119
<212> TYPE: PRT
<213> ORGANISM: Homo sapiens

<400> SEQUENCE: 211

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Ala Met Val Trp Val Arg Gln Ala Pro Gly Lys Gly Leu Glu Trp Val
        35                  40                  45

Ser Val Ile Gly Ser Gly Gly Gly Thr Tyr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Ser Ile Thr Gln Gly Trp Phe Asp Pro Trp Gly Gln Gly
            100                 105                 110

Thr Leu Val Thr Val Ser Ser
        115

<210> SEQ ID NO 212
<211> LENGTH: 108
<212> TYPE: PRT
<213> ORGANISM: Homo sapiens

<400> SEQUENCE: 212

Asp Ile Gln Met Thr Gln Ser Pro Ala Thr Leu Ser Val Ser Pro Gly
1               5                   10                  15
```

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Met
            35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Leu Thr Phe Gly Gly Gly Thr Lys Val Glu Ile Lys
            100                 105

<210> SEQ ID NO 213
<211> LENGTH: 123
<212> TYPE: PRT
<213> ORGANISM: Homo sapiens

<400> SEQUENCE: 213

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
                20                  25                  30

Asp Met Asn Trp Val Arg Gln Ala Pro Gly Lys Gly Leu Glu Trp Val
            35                  40                  45

Ser Val Ile Val Pro Ser Gly Gly Leu Thr Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Gly Tyr Ser Ser Arg Ser Ala Gly Met Asp Val
            100                 105                 110

Trp Gly Gln Gly Thr Thr Val Thr Val Ser Ser
            115                 120

<210> SEQ ID NO 214
<211> LENGTH: 108
<212> TYPE: PRT
<213> ORGANISM: Homo sapiens

<400> SEQUENCE: 214

Asp Ile Gln Met Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Ser Tyr
                20                  25                  30

Leu Ala Trp Tyr Gln Gln Lys Pro Gly Gln Ala Pro Arg Leu Leu Ile
            35                  40                  45

Tyr His Ala Ser Asn Arg Ala Thr Gly Ile Pro Ala Arg Phe Ser Gly
    50                  55                  60

Ser Gly Ser Gly Thr Asp Phe Thr Leu Thr Ile Thr Ser Leu Glu Pro
65                  70                  75                  80

Glu Asp Phe Ala Val Tyr Tyr Cys Gln Gln Arg Ser Asn Ser Pro Pro
                85                  90                  95

Trp Thr Phe Gly Gln Gly Thr Lys Val Glu Met Lys
            100                 105

```
<210> SEQ ID NO 215
<211> LENGTH: 120
<212> TYPE: PRT
<213> ORGANISM: Homo sapiens

<400> SEQUENCE: 215

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Asp Tyr
             20                  25                  30

Lys Met Met Trp Val Arg Gln Ala Pro Gly Lys Gly Leu Glu Trp Val
         35                  40                  45

Ser Ser Ile Gly Ser Ser Gly Gly Pro Thr Trp Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Arg Leu Ala Tyr Ser Ser Gly Trp Tyr Asp Asp Tyr Trp Gly Gln
            100                 105                 110

Gly Thr Leu Val Thr Val Ser Ser
            115                 120

<210> SEQ ID NO 216
<211> LENGTH: 107
<212> TYPE: PRT
<213> ORGANISM: Homo sapiens

<400> SEQUENCE: 216

Asp Ile Gln Met Thr Gln Ser Pro Ala Thr Leu Ser Leu Ser Pro Gly
  1               5                  10                  15

Glu Arg Ala Thr Leu Ser Cys Arg Ala Ser Gln Ser Ile Gly Arg Tyr
             20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Lys Trp Pro Pro
             85                  90                  95

Thr Phe Gly Gln Gly Thr Lys Val Glu Ile Lys
            100                 105

<210> SEQ ID NO 217
<211> LENGTH: 124
<212> TYPE: PRT
<213> ORGANISM: Homo sapiens

<400> SEQUENCE: 217

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ala Tyr
             20                  25                  30

Lys Met Ser Trp Val Arg Gln Ala Pro Gly Lys Gly Leu Glu Trp Val
         35                  40                  45

Ser Ser Ile Ser Pro Ser Gly Gly Gly Thr His Tyr Ala Asp Ser Val
 50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Leu Tyr Tyr Cys
                 85                  90                  95

Ala Lys Asp Met Gly Gly Ile Ala Ala Arg Gln Ala Gly Gly Phe Gly
            100                 105                 110

Tyr Trp Gly Gln Gly Thr Leu Val Thr Val Ser Ser
        115                 120

<210> SEQ ID NO 218
<211> LENGTH: 109
<212> TYPE: PRT
<213> ORGANISM: Homo sapiens

<400> SEQUENCE: 218

Asp Ile Gln Met Thr Gln Ser Pro Val Thr Leu Ser Leu Ser Pro Gly
  1               5                  10                  15

Glu Arg Ala Thr Leu Ser Cys Arg Ala Ser Gln Ser Tyr Ile Ser Tyr
             20                  25                  30

Leu Ala Trp Tyr Gln Gln Lys Ser Gly Gln Ala Pro Arg Leu Leu Ile
         35                  40                  45

Tyr Asp Thr Ser Asn Arg Ala Thr Gly Ile Pro Ala Arg Phe Ser Gly
 50                  55                  60

Ser Gly Ser Gly Ser Asp Phe Thr Leu Thr Ile Asn Ser Leu Glu Pro
 65                  70                  75                  80

Glu Asp Val Ala Val Tyr Tyr Cys Gln Gln Arg Ser Asn Trp Pro Pro
                 85                  90                  95

Glu Phe Thr Phe Gly Gln Gly Thr Arg Leu Glu Ile Lys
            100                 105

<210> SEQ ID NO 219
<211> LENGTH: 119
<212> TYPE: PRT
<213> ORGANISM: Homo sapiens

<400> SEQUENCE: 219

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Val Tyr
             20                  25                  30

Thr Met Tyr Trp Val Arg Gln Ala Pro Gly Lys Gly Leu Glu Trp Val
         35                  40                  45

Ser Trp Ile Ser Pro Ser Gly Gly Ser Thr Val Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ala Ser Arg Thr Thr Pro Gly Gly Phe Asp Val Trp Gly Gln Gly
            100                 105                 110

Thr Met Val Thr Val Ser Ser
        115

<210> SEQ ID NO 220
<211> LENGTH: 107
<212> TYPE: PRT
<213> ORGANISM: Homo sapiens

<400> SEQUENCE: 220
```

Asp Ile Gln Met Thr Gln Ser Pro Ser Val Ser Ala Ser Val Gly
1               5                   10                  15

Asp Arg Val Thr Ile Thr Cys Arg Ala Ser Gln Asp Ile Asn Ile Trp
            20                  25                  30

Leu Ala Trp Tyr Gln Leu Lys Pro Gly Glu Ala Pro Lys Leu Leu Ile
            35                  40                  45

His Ser Ala Ser Thr Leu Gln Ser Gly Val Pro Ser Arg Phe Ser Gly
50                  55                  60

Ser Gly Ser Gly Thr Asp Phe Ile Phe Thr Ile Ser Ser Leu Gln Pro
65                  70                  75                  80

Glu Asp Tyr Ala Thr Tyr His Cys Gln Gln Ile Asn Thr Phe Pro Pro
            85                  90                  95

Thr Phe Gly Gly Gly Thr Lys Val Asp Ile Lys
            100                 105

<210> SEQ ID NO 221
<211> LENGTH: 117
<212> TYPE: PRT
<213> ORGANISM: Homo sapiens

<400> SEQUENCE: 221

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Glu Tyr
            20                  25                  30

Ala Met Glu Trp Val Arg Gln Ala Pro Gly Lys Gly Leu Glu Trp Val
            35                  40                  45

Ser Tyr Ile Tyr Ser Ser Gly Gly Phe Thr Ile Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Asp Gly Ser Asp Ala Phe Asp Ile Trp Gly Gln Gly Thr Met
            100                 105                 110

Val Thr Val Ser Ser
        115

<210> SEQ ID NO 222
<211> LENGTH: 112
<212> TYPE: PRT
<213> ORGANISM: Homo sapiens

<400> SEQUENCE: 222

Asn Ile Gln Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
            85                  90                  95

```
Leu Gln Asn Ser Ile Thr Phe Gly Gln Gly Thr Arg Leu Glu Ile Lys
            100                 105                 110
```

<210> SEQ ID NO 223
<211> LENGTH: 123
<212> TYPE: PRT
<213> ORGANISM: Homo sapiens

<400> SEQUENCE: 223

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Val Tyr
            20                  25                  30

Ala Met His Trp Val Arg Gln Ala Pro Gly Lys Gly Leu Glu Trp Val
        35                  40                  45

Ser Val Ile Ser Pro Ser Gly Gly Phe Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Tyr Ser Trp Gly Tyr Tyr Tyr Tyr Met Asp Val
            100                 105                 110

Trp Gly Lys Gly Thr Thr Val Thr Val Ser Ser
            115                 120
```

<210> SEQ ID NO 224
<211> LENGTH: 112
<212> TYPE: PRT
<213> ORGANISM: Homo sapiens

<400> SEQUENCE: 224

```
Asn Ile Gln Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Asn Ser Ile Thr Phe Gly Gln Gly Thr Arg Leu Glu Ile Lys
            100                 105                 110
```

<210> SEQ ID NO 225
<211> LENGTH: 123
<212> TYPE: PRT
<213> ORGANISM: Homo sapiens

<400> SEQUENCE: 225

```
Glu Val Gln Leu Leu Glu Ser Gly Gly Gly Leu Val Gln Pro Gly Gly
 1               5                  10                  15

Ser Leu Arg Phe Ser Cys Ala Ala Ser Gly Phe Thr Phe Ser Val Tyr
            20                  25                  30

Ala Met His Trp Val Arg Gln Ala Pro Gly Lys Gly Leu Glu Trp Val
        35                  40                  45
```

Ser Val Ile Ser Pro Ser Gly Gly Phe Thr Phe Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Gly Gly Tyr Ser Trp Gly Tyr Tyr Tyr Tyr Met Asp Val
            100                 105                 110

Trp Gly Lys Gly Thr Thr Val Thr Val Ser Ser
            115                 120

<210> SEQ ID NO 226
<211> LENGTH: 112
<212> TYPE: PRT
<213> ORGANISM: Homo sapiens

<400> SEQUENCE: 226

Asn Ile Gln Met Thr Gln Ser Pro Leu Ser Leu Pro Val Thr Leu Gly
  1               5                  10                  15

Gln Pro Ala Ser Ile Ser Cys Arg Ser Ser Gln Gly Leu Val Tyr Ser
             20                  25                  30

Asp Gly Asn Thr Tyr Leu Asn Trp Phe Gln Gln Arg Pro Gly Gln Ser
             35                  40                  45

Pro Arg Arg Leu Ile Tyr Lys Val Ser Asn Arg Asp Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                85                  90                  95

Thr His Trp Pro Ile Thr Phe Gly Gln Gly Thr Arg Leu Glu Ile Lys
            100                 105                 110

<210> SEQ ID NO 227
<211> LENGTH: 124
<212> TYPE: PRT
<213> ORGANISM: Homo sapiens

<400> SEQUENCE: 227

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Arg Tyr
             20                  25                  30

Ala Met Trp Trp Val Arg Gln Ala Pro Gly Lys Gly Leu Glu Trp Val
             35                  40                  45

Ser Gly Ile Val Pro Ser Gly Gly Leu Thr Thr Tyr Ala Asp Ser Val
 50                  55                  60

Lys Gly Arg Phe Thr Ile Ser Arg Asp Asn Ser Lys Asp Thr Leu Tyr
 65                  70                  75                  80

Leu Gln Met Asn Ser Leu Arg Ala Glu Asp Thr Ala Val Tyr Tyr Cys
                85                  90                  95

Ala Arg His Glu Val Ser Glu Gln Trp Leu Phe Pro Gly Asn Phe Asp
            100                 105                 110

Tyr Trp Gly Gln Gly Thr Leu Val Thr Val Ser Ser
            115                 120

<210> SEQ ID NO 228
<211> LENGTH: 107

```
<212> TYPE: PRT
<213> ORGANISM: Homo sapiens

<400> SEQUENCE: 228

Asn Ile Gln Met Thr Gln Ser Pro Ser Val Ser Ala Ser Val Gly
  1               5                  10                  15

Asp Arg Val Thr Ile Thr Cys Arg Ala Ser Gln Gly Val Ser Thr Trp
             20                  25                  30

Leu Ala Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Ala Tyr Asn Phe Pro Leu
                 85                  90                  95

Thr Phe Gly Gly Gly Thr Lys Val Glu Ile Glu
            100                 105

<210> SEQ ID NO 229
<211> LENGTH: 116
<212> TYPE: PRT
<213> ORGANISM: Homo sapiens

<400> SEQUENCE: 229

Glu Val Gln Leu Leu Glu Ser Gly Gly Leu Val Gln Pro Gly Gly
  1               5                  10                  15

Ser Leu Arg Leu Ser Cys Ala Ala Ser Gly Phe Thr Phe Ser Arg Tyr
             20                  25                  30

Val Met Gly Trp Val Arg Gln Ala Pro Gly Lys Gly Leu Glu Trp Val
         35                  40                  45

Ser Tyr Ile Ser Pro Ser Gly Gly Trp Thr Trp Tyr Ala Asp Phe Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Val His Asp Ala Phe Asp Ile Trp Gly Gln Gly Thr Met Val
            100                 105                 110

Thr Val Ser Ser
        115

<210> SEQ ID NO 230
<211> LENGTH: 112
<212> TYPE: PRT
<213> ORGANISM: Homo sapiens

<400> SEQUENCE: 230

Asn Ile Gln Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu His Ser
             20                  25                  30

Asn Gly Tyr Asn Tyr Leu Asp Trp Tyr Leu Gln Lys Pro Gly Gln Ser
         35                  40                  45

Pro Gln Leu Leu Ile Tyr Leu Gly Ser Asn Arg Ala Ser Gly Val Pro
 50                  55                  60

Asp Arg Phe Ser Gly Ser Gly Ser Gly Thr Asp Phe Thr Leu Lys Ile
 65                  70                  75                  80
```

```
Ser Arg Val Glu Ala Glu Asp Val Gly Val Tyr Tyr Cys Met Gln Ala
                85                  90                  95

Leu Gln Asn Ser Ile Thr Phe Gly Gln Gly Thr Arg Leu Glu Ile Lys
            100                 105                 110
```

<210> SEQ ID NO 231
<211> LENGTH: 123
<212> TYPE: PRT
<213> ORGANISM: Homo sapiens

<400> SEQUENCE: 231

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Val Tyr
            20                  25                  30

Ala Met His Trp Val Arg Gln Ala Pro Gly Lys Gly Leu Glu Trp Val
        35                  40                  45

Ser Val Ile Ser Pro Ser Gly Gly Phe Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Tyr Ser Trp Gly Tyr Tyr Tyr Tyr Met Asp Val
            100                 105                 110

Trp Gly Lys Gly Thr Met Val Thr Val Ser Ser
        115                 120
```

<210> SEQ ID NO 232
<211> LENGTH: 112
<212> TYPE: PRT
<213> ORGANISM: Homo sapiens

<400> SEQUENCE: 232

```
Asn Ile Gln Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Thr Glu Asp Val Gly Val Tyr Tyr Cys Met Gln Ala
                85                  90                  95

Leu Gln Asn Ser Ile Thr Phe Gly Gln Gly Thr Arg Leu Glu Ile Lys
            100                 105                 110
```

<210> SEQ ID NO 233
<211> LENGTH: 138
<212> TYPE: PRT
<213> ORGANISM: Homo sapiens

<400> SEQUENCE: 233

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Val Tyr
```

-continued

```
                 20                  25                  30
Ala Met His Trp Val Arg Gln Ala Pro Gly Lys Gly Leu Glu Trp Val
            35                  40                  45

Ser Val Ile Ser Pro Ser Gly Gly Phe Thr Phe Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Val His Asp Ala Phe Asp Ile Trp Gly Gln Gly Thr Met Val
            100                 105                 110

Thr Phe Lys Arg Gly Arg Thr Ser Ser Pro Ser Arg Gly Arg Arg
            115                 120                 125

Thr Lys Thr His Leu Arg Arg Gly Ser Glu
            130                 135

<210> SEQ ID NO 234
<211> LENGTH: 107
<212> TYPE: PRT
<213> ORGANISM: Homo sapiens

<400> SEQUENCE: 234

Asn Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Val Ser Thr Trp
            20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Ala Tyr Asn Phe Pro Leu
                85                  90                  95

Thr Phe Gly Gly Gly Thr Lys Val Glu Ile Lys
            100                 105

<210> SEQ ID NO 235
<211> LENGTH: 116
<212> TYPE: PRT
<213> ORGANISM: Homo sapiens

<400> SEQUENCE: 235

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Tyr
            20                  25                  30

Val Met Gly Trp Val Arg Gln Ala Pro Gly Lys Gly Leu Glu Trp Val
            35                  40                  45

Ser Tyr Ile Ser Pro Ser Gly Trp Thr Trp Tyr Ala Asp Phe Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Val His Asp Ala Phe Asp Ile Trp Gly Gln Gly Thr Met Val
            100                 105                 110
```

```
Thr Val Ser Ser
        115

<210> SEQ ID NO 236
<211> LENGTH: 107
<212> TYPE: PRT
<213> ORGANISM: Homo sapiens

<400> SEQUENCE: 236

Asn Ile Gln Met Thr Gln Ser Pro Ser Ser Val Ser Ala Ser Val Gly
  1               5                  10                  15

Asp Arg Val Thr Ile Thr Cys Arg Ala Ser Gln Gly Val Ser Thr Trp
             20                  25                  30

Leu Ala Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Ala Tyr Asn Phe Pro Leu
                 85                  90                  95

Thr Phe Gly Gly Gly Thr Lys Val Glu Ile Lys
            100                 105

<210> SEQ ID NO 237
<211> LENGTH: 116
<212> TYPE: PRT
<213> ORGANISM: Homo sapiens

<400> SEQUENCE: 237

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser His Tyr
             20                  25                  30

Val Met Gly Trp Val Arg Gln Ala Pro Gly Lys Gly Leu Glu Trp Val
         35                  40                  45

Ser Tyr Ile Ser Pro Ser Gly Gly Trp Thr Trp Tyr Ala Asp Phe Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Val His Asp Ala Phe Asp Ile Trp Gly Gln Gly Thr Met Val
            100                 105                 110

Thr Val Ser Arg
        115

<210> SEQ ID NO 238
<211> LENGTH: 112
<212> TYPE: PRT
<213> ORGANISM: Homo sapiens

<400> SEQUENCE: 238

Asn Ile Gln Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu His Ser
             20                  25                  30

Asn Gly Tyr Asn Tyr Leu Asp Trp Tyr Leu Gln Lys Pro Gly Gln Ser
```

```
                35                  40                  45
Pro Gln Leu Leu Ile Tyr Leu Gly Ser Asn Arg Ala Ser Gly Val Pro
 50                  55                  60

Asp Arg Phe Gly Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Asn Ser Ile Thr Phe Gly Gln Gly Thr Arg Leu Glu Ile Lys
                100                 105                 110

<210> SEQ ID NO 239
<211> LENGTH: 123
<212> TYPE: PRT
<213> ORGANISM: Homo sapiens

<400> SEQUENCE: 239

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Val Tyr
                 20                  25                  30

Ala Met His Trp Val Arg Gln Ala Pro Gly Lys Gly Leu Glu Trp Val
                 35                  40                  45

Ser Val Ile Ser Pro Ser Gly Gly Phe Thr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Gly Tyr Ser Trp Gly Tyr Tyr Tyr Tyr Met Asp Val
                100                 105                 110

Trp Gly Lys Gly Thr Thr Val Thr Val Ser Ser
            115                 120

<210> SEQ ID NO 240
<211> LENGTH: 112
<212> TYPE: PRT
<213> ORGANISM: Homo sapiens

<400> SEQUENCE: 240

Gln Tyr Glu Leu Thr Gln Pro Ala Ser Val Ser Gly Ser Pro Gly Gln
  1               5                  10                  15

Ser Ile Thr Ile Ser Cys Thr Gly Thr Ser Ser Asp Val Gly Gly Tyr
                 20                  25                  30

Asn Tyr Val Ser Trp Tyr Gln Gln His Pro Gly Lys Ala Pro Lys Leu
                 35                  40                  45

Met Ile Tyr Glu Val Ser Asn Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                 85                  90                  95

Ser Thr Leu Phe Tyr Val Phe Gly Thr Gly Thr Lys Val Thr Val Arg
                100                 105                 110

<210> SEQ ID NO 241
<211> LENGTH: 123
<212> TYPE: PRT
<213> ORGANISM: Homo sapiens
```

<400> SEQUENCE: 241

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Gly Met Asp Trp Val Arg Gln Ala Pro Gly Lys Gly Leu Glu Trp Val
        35                  40                  45

Ser Ser Ile Ser Pro Ser Gly Gly Gln Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Gly Gly Gly Tyr Tyr Tyr Tyr Gly Met Asp Val
            100                 105                 110

Trp Gly Gln Gly Thr Leu Val Thr Val Ser Ser
            115                 120

<210> SEQ ID NO 242
<211> LENGTH: 112
<212> TYPE: PRT
<213> ORGANISM: Homo sapiens

<400> SEQUENCE: 242

Asn Ile Gln Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Asn Ser Ile Thr Phe Gly Gln Gly Thr Arg Leu Glu Ile Lys
            100                 105                 110

<210> SEQ ID NO 243
<211> LENGTH: 123
<212> TYPE: PRT
<213> ORGANISM: Homo sapiens

<400> SEQUENCE: 243

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Val Tyr
            20                  25                  30

Ala Met His Trp Val Arg Gln Ala Pro Gly Lys Gly Leu Glu Trp Val
        35                  40                  45

Ser Val Thr Ser Pro Ser Gly Phe Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys

```
                85                  90                  95
Ala Arg Gly Gly Tyr Ser Trp Gly Tyr Tyr Tyr Tyr Met Asp Val
            100                 105                 110

Trp Gly Lys Gly Thr Thr Val Thr Val Ser Ser
        115                 120

<210> SEQ ID NO 244
<211> LENGTH: 112
<212> TYPE: PRT
<213> ORGANISM: Homo sapiens

<400> SEQUENCE: 244

Asn Ile Gln Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu His Ser
             20                  25                  30

Asn Gly Tyr Asn Tyr Leu Asp Trp Tyr Leu Gln Lys Pro Gly Gln Ser
         35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Asn Ser Ile Thr Phe Gly Gln Gly Thr Arg Leu Glu Ile Lys
            100                 105                 110

<210> SEQ ID NO 245
<211> LENGTH: 123
<212> TYPE: PRT
<213> ORGANISM: Homo sapiens

<400> SEQUENCE: 245

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Val Tyr
             20                  25                  30

Ala Met His Trp Val Arg Gln Ala Pro Gly Lys Gly Leu Glu Trp Val
         35                  40                  45

Ser Ser Ile Ser Pro Ser Gly Gly Gln Thr Lys Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Gly Tyr Ser Trp Gly Tyr Tyr Tyr Tyr Met Asp Val
            100                 105                 110

Trp Gly Lys Gly Thr Thr Val Thr Val Ser Ser
        115                 120

<210> SEQ ID NO 246
<211> LENGTH: 112
<212> TYPE: PRT
<213> ORGANISM: Homo sapiens

<400> SEQUENCE: 246

Asn Ile Gln Met Thr Gln Ser Pro Leu Ser Leu Pro Val Thr Pro Gly
  1               5                  10                  15
```

-continued

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Asn Ser Ile Thr Phe Gly Pro Gly Thr Arg Leu Glu Ile Lys
            100                 105                 110

<210> SEQ ID NO 247
<211> LENGTH: 123
<212> TYPE: PRT
<213> ORGANISM: Homo sapiens

<400> SEQUENCE: 247

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Val Tyr
                20                  25                  30

Ala Met His Trp Val Arg Gln Ala Pro Gly Lys Gly Leu Glu Trp Val
            35                  40                  45

Ser Val Ile Ser Pro Ser Gly Gly Phe Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Tyr Ser Trp Gly Tyr Tyr Tyr Tyr Met Asp Val
            100                 105                 110

Trp Gly Lys Gly Thr Thr Val Thr Val Ser Ser
            115                 120

<210> SEQ ID NO 248
<211> LENGTH: 112
<212> TYPE: PRT
<213> ORGANISM: Homo sapiens

<400> SEQUENCE: 248

Gln Tyr Glu Leu Thr Gln Pro Ala Pro Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Phe Tyr Val Phe Gly Thr Gly Thr Lys Val Thr Val Leu
            100                 105                 110

<210> SEQ ID NO 249
<211> LENGTH: 123
<212> TYPE: PRT
<213> ORGANISM: Homo sapiens

<400> SEQUENCE: 249

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ala Tyr
            20                  25                  30

Gly Met Asp Trp Val Arg Gln Ala Pro Gly Lys Gly Leu Glu Trp Val
        35                  40                  45

Ser Ser Ile Ser Pro Ser Gly Gly Gln Thr Lys Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Gly Gly Gly Tyr Tyr Tyr Tyr Gly Met Asp Val
            100                 105                 110

Trp Gly Gln Gly Thr Leu Val Thr Val Ser Ser
        115                 120
```

<210> SEQ ID NO 250
<211> LENGTH: 112
<212> TYPE: PRT
<213> ORGANISM: Homo sapiens

<400> SEQUENCE: 250

```
Gln Tyr Glu Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Phe Tyr Val Phe Gly Thr Gly Thr Lys Val Thr Val Leu
            100                 105                 110
```

<210> SEQ ID NO 251
<211> LENGTH: 123
<212> TYPE: PRT
<213> ORGANISM: Homo sapiens

<400> SEQUENCE: 251

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ala Tyr
            20                  25                  30

Gly Met Asp Trp Val Arg Gln Ala Pro Gly Arg Gly Leu Glu Trp Val
        35                  40                  45

Ser Ser Ile Ser Pro Ser Gly Gly Gln Thr Lys Tyr Ala Asp Ser Val
50                  55                  60
```

-continued

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Lys Asp Leu Gly Gly Gly Tyr Tyr Tyr Tyr Gly Met Asp Val
            100                 105                 110

Trp Gly Gln Gly Thr Leu Val Thr Val Ser Ser
        115                 120

<210> SEQ ID NO 252
<211> LENGTH: 112
<212> TYPE: PRT
<213> ORGANISM: Homo sapiens

<400> SEQUENCE: 252

Asn Ile Gln Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu His Ser
             20                  25                  30

Asn Gly Tyr Asn Tyr Leu Asp Trp Tyr Leu Gln Lys Pro Gly Gln Ser
         35                  40                  45

Pro Gln Leu Leu Ile Tyr Leu Gly Ser Asn Arg Ala Ser Gly Val Pro
 50                  55                  60

Asp Arg Phe Ser Gly Ser Gly Ser Gly Thr Gly Phe Thr Leu Lys Ile
 65                  70                  75                  80

Ser Arg Val Glu Ala Glu Asp Val Gly Val Tyr Tyr Cys Met Gln Ala
             85                  90                  95

Leu Gln Asn Ser Ile Thr Phe Gly Gln Gly Thr Arg Leu Glu Ile Lys
            100                 105                 110

<210> SEQ ID NO 253
<211> LENGTH: 123
<212> TYPE: PRT
<213> ORGANISM: Homo sapiens

<400> SEQUENCE: 253

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Val Tyr
             20                  25                  30

Ala Met His Trp Val Arg Gln Ala Pro Gly Lys Gly Leu Glu Trp Val
         35                  40                  45

Ser Val Ile Ser Pro Ser Gly Gly Phe Thr Phe Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Arg Gly Gly Tyr Ser Trp Gly Tyr Tyr Tyr Tyr Met Asp Val
            100                 105                 110

Trp Gly Lys Gly Thr Thr Val Thr Val Ser Ser
        115                 120

<210> SEQ ID NO 254
<211> LENGTH: 112
<212> TYPE: PRT
<213> ORGANISM: Homo sapiens

<400> SEQUENCE: 254

Asn Ile Gln Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Arg Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Ile Thr Phe Gly Gln Gly Thr Arg Leu Glu Ile Lys
                100                 105                 110

<210> SEQ ID NO 255
<211> LENGTH: 124
<212> TYPE: PRT
<213> ORGANISM: Homo sapiens

<400> SEQUENCE: 255

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ala Met Trp Trp Val Arg Gln Ala Pro Gly Lys Gly Leu Glu Trp Val
        35                  40                  45

Ser Gly Ile Val Pro Ser Gly Gly Leu Thr Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Glu Val Ser Glu Gln Trp Leu Phe Pro Gly Asn Phe Asp
                100                 105                 110

Tyr Trp Gly Gln Gly Thr Leu Val Thr Val Ser Ser
        115                 120

<210> SEQ ID NO 256
<211> LENGTH: 112
<212> TYPE: PRT
<213> ORGANISM: Homo sapiens

<400> SEQUENCE: 256

Gln Tyr Glu Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

```
Ser Thr Leu Phe Tyr Val Phe Gly Thr Gly Thr Lys Val Thr Val Leu
            100                 105                 110
```

<210> SEQ ID NO 257
<211> LENGTH: 123
<212> TYPE: PRT
<213> ORGANISM: Homo sapiens

<400> SEQUENCE: 257

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ala Tyr
            20                  25                  30

Gly Met Asp Trp Val Arg Gln Ala Pro Gly Lys Gly Leu Glu Trp Val
        35                  40                  45

Ser Ser Ile Ser Pro Ser Gly Gly Gln Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Lys Ser Leu Arg Ala Glu Asp Thr Ala Val Tyr Tyr Cys
                85                  90                  95

Ala Lys Asp Leu Gly Gly Gly Tyr Tyr Tyr Tyr Gly Met Asp Val
            100                 105                 110

Trp Gly Gln Gly Thr Leu Val Thr Val Ser Ser
        115                 120
```

<210> SEQ ID NO 258
<211> LENGTH: 112
<212> TYPE: PRT
<213> ORGANISM: Homo sapiens

<400> SEQUENCE: 258

```
Asp Ile Arg Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Asn Ser Ile Thr Phe Gly Gln Gly Thr Arg Leu Glu Ile Lys
            100                 105                 110
```

<210> SEQ ID NO 259
<211> LENGTH: 123
<212> TYPE: PRT
<213> ORGANISM: Homo sapiens

<400> SEQUENCE: 259

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Val Tyr
            20                  25                  30

Ala Met His Trp Val Arg Gln Ala Pro Gly Lys Gly Leu Glu Trp Val
        35                  40                  45
```

Ser Val Ile Ser Pro Ser Gly Gly Phe Thr Phe Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Gly Gly Tyr Ser Trp Gly Tyr Tyr Tyr Tyr Met Asp Val
            100                 105                 110

Trp Gly Lys Gly Thr Thr Val Thr Val Ser Ser
            115                 120

<210> SEQ ID NO 260
<211> LENGTH: 107
<212> TYPE: PRT
<213> ORGANISM: Homo sapiens

<400> SEQUENCE: 260

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro Ile
                85                  90                  95

Thr Phe Gly Gln Gly Thr Arg Leu Glu Ile Lys
            100                 105

<210> SEQ ID NO 261
<211> LENGTH: 126
<212> TYPE: PRT
<213> ORGANISM: Homo sapiens

<400> SEQUENCE: 261

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Trp Tyr
            20                  25                  30

Met Met Met Trp Val Arg Gln Ala Pro Gly Lys Gly Leu Glu Trp Val
        35                  40                  45

Ser Tyr Ile Tyr Pro Ser Gly Gly Thr Leu Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Gly Gly Tyr Asp Tyr Val Trp Gly Ser Tyr Arg Pro Tyr Tyr
            100                 105                 110

Phe Asp Tyr Trp Gly Gln Gly Thr Leu Val Thr Val Ser Ser
        115                 120                 125

<210> SEQ ID NO 262
<211> LENGTH: 107

```
<212> TYPE: PRT
<213> ORGANISM: Homo sapiens

<400> SEQUENCE: 262

Asp Ile Gln Met Thr Gln Ser Pro Ser Thr Leu Ser Thr Ser Val Gly
1               5                   10                  15

Asp Arg Val Thr Ile Thr Cys Arg Ala Ser Gln Ser Ile Ser Thr Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Ile Leu Thr Ile Ser Ser Leu Gln Pro
65                  70                  75                  80

Glu Asp Phe Ala Thr Tyr Tyr Cys Leu Gln His Asn Ser Tyr Pro Phe
                85                  90                  95

Thr Phe Gly Pro Gly Thr Lys Val Asp Ile Lys
            100                 105

<210> SEQ ID NO 263
<211> LENGTH: 107
<212> TYPE: PRT
<213> ORGANISM: Homo sapiens

<400> SEQUENCE: 263

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Arg Ile Asn Asn Tyr
            20                  25                  30

Leu Asn Trp Tyr Gln Gln Thr Pro Gly Asn Ala Pro Lys Leu Leu Ile
        35                  40                  45

Tyr Ala Ala Ser Thr Leu Gln Asp Gly Val Pro Ser Arg Phe Ser Gly
50                  55                  60

Ser Gly Phe Gly Thr Asp Phe Thr Leu Thr Ile Ser Ser Leu Gln Pro
65                  70                  75                  80

Glu Asp Ile Ala Thr Tyr Phe Cys Gln Gln Ser Phe Asn Ile Pro Ile
                85                  90                  95

Thr Phe Gly Gln Gly Thr Arg Leu Glu Ile Lys
            100                 105

<210> SEQ ID NO 264
<211> LENGTH: 112
<212> TYPE: PRT
<213> ORGANISM: Homo sapiens

<400> SEQUENCE: 264

Gln Tyr Glu Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95
```

```
Ser Thr Leu Phe Tyr Val Phe Gly Thr Gly Thr Lys Val Thr Val Pro
            100                 105                 110

<210> SEQ ID NO 265
<211> LENGTH: 123
<212> TYPE: PRT
<213> ORGANISM: Homo sapiens

<400> SEQUENCE: 265

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ala Tyr
             20                  25                  30

Gly Met Asp Trp Val Arg Gln Ala Pro Gly Lys Gly Leu Glu Trp Val
         35                  40                  45

Ser Ser Ile Ser Pro Ser Gly Gly Gln Thr Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Leu Gly Gly Gly Tyr Tyr Tyr Tyr Tyr Gly Met Asp Val
            100                 105                 110

Trp Gly Gln Gly Thr Thr Val Thr Val Ser Ser
            115                 120

<210> SEQ ID NO 266
<211> LENGTH: 112
<212> TYPE: PRT
<213> ORGANISM: Homo sapiens

<400> SEQUENCE: 266

Gln Tyr Glu Leu Thr Gln Pro Ala Ser Val Ser Gly Ser Pro Gly Gln
  1               5                  10                  15

Ser Ile Thr Ile Ser Cys Thr Gly Thr Ser Ser Asp Val Gly Gly Tyr
             20                  25                  30

Asn Tyr Val Ser Trp Tyr Gln Gln His Pro Gly Lys Ala Pro Lys Leu
         35                  40                  45

Met Ile Tyr Glu Val Ser Asn Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                 85                  90                  95

Ser Thr Leu Phe Tyr Val Phe Gly Thr Gly Thr Lys Val Thr Val Leu
            100                 105                 110

<210> SEQ ID NO 267
<211> LENGTH: 123
<212> TYPE: PRT
<213> ORGANISM: Homo sapiens

<400> SEQUENCE: 267

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ala Tyr
             20                  25                  30

Gly Met Asp Trp Val Arg Gln Ala Pro Gly Lys Gly Leu Glu Trp Val
```

```
                        35                  40                  45
Ser Ser Ile Ser Pro Ser Gly Gly Arg Thr Lys Tyr Ala Asp Ser Val
         50                  55                  60

Lys Gly Arg Phe Thr Ile Ser Arg Asp Asn Ser Lys Asn Thr Leu Tyr
 65              70                  75                      80

Leu Gln Met Asn Ser Leu Arg Ala Glu Asp Thr Ala Val Tyr Tyr Cys
                 85                  90                  95

Ala Lys Asp Leu Gly Gly Tyr Tyr Tyr Tyr Tyr Gly Met Asp Val
             100                 105                 110

Trp Gly Gln Gly Thr Leu Val Thr Val Ser Ser
             115                 120

<210> SEQ ID NO 268
<211> LENGTH: 122
<212> TYPE: PRT
<213> ORGANISM: Homo sapiens

<400> SEQUENCE: 268

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Ser Ala Tyr
             20                  25                  30

Gly Met Asp Trp Val Arg Gln Ala Pro Gly Lys Gly Leu Glu Trp Val
             35                  40                  45

Ser Ile Ser Pro Ser Gly Gly Arg Thr Lys Tyr Ala Asp Ser Val Lys
         50                  55                  60

Gly Arg Phe Thr Ile Ser Arg Asp Asn Ser Lys Asn Thr Leu Tyr Leu
 65              70                  75                      80

Gln Met Asn Ser Leu Arg Ala Glu Asp Thr Ala Val Tyr Tyr Cys Ala
                 85                  90                  95

Lys Asp Leu Gly Gly Gly Tyr Tyr Tyr Tyr Gly Met Asp Val Trp
             100                 105                 110

Gly Gln Gly Thr Leu Val Thr Val Ser Ser
             115                 120
```